(12) United States Patent  
Jakob et al.

(10) Patent No.: US 12,344,605 B2  
(45) Date of Patent: *Jul. 1, 2025

(54) SUBSTITUTED PYRROLIDINE AMIDES II

(71) Applicant: GRUENENTHAL GMBH, Aachen (DE)

(72) Inventors: Florian Jakob, Aachen (DE); Jo Alen, Averbode (BE); Sebastian Krueger, Aachen (DE); Markus Schade, Aachen (DE); Daniela Friebe, Duesseldorf (DE); Stephanie Hennen, Aachen (DE)

(73) Assignee: Gruenenthal GmbH, Aachen (DE)

( * ) Notice: Subject to any disclaimer, the term of this patent is extended or adjusted under 35 U.S.C. 154(b) by 761 days.

This patent is subject to a terminal disclaimer.

(21) Appl. No.: 17/568,979

(22) Filed: Jan. 5, 2022

(65) Prior Publication Data

US 2022/0127264 A1 Apr. 28, 2022

Related U.S. Application Data

(63) Continuation of application No. 16/223,925, filed on Dec. 18, 2018, now abandoned.

(30) Foreign Application Priority Data

Dec. 18, 2017 (EP) .................................. 17208180

(51) Int. Cl.
| | | |
|---|---|---|
| *C07D 471/04* | (2006.01) | |
| *A61P 11/06* | (2006.01) | |
| *A61P 19/02* | (2006.01) | |
| *A61P 29/00* | (2006.01) | |
| *C07D 401/14* | (2006.01) | |
| *C07D 403/04* | (2006.01) | |
| *C07D 403/14* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |

(52) U.S. Cl.
CPC ............ *C07D 471/04* (2013.01); *A61P 11/06* (2018.01); *A61P 19/02* (2018.01); *A61P 29/00* (2018.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 417/14* (2013.01)

(58) Field of Classification Search
CPC .. C07D 471/04; C07D 401/14; C07D 403/04; C07D 403/14; C07D 405/14; C07D 409/14; C07D 413/14; C07D 417/14; A61P 11/06; A61P 19/02; A61P 29/00

See application file for complete search history.

(56) References Cited

U.S. PATENT DOCUMENTS 10,626,106 B2 * 4/2020 Jakob ...................... A61P 19/02

FOREIGN PATENT DOCUMENTS

WO WO-2008063116 A1 * 5/2008 ................ A61P 1/04

OTHER PUBLICATIONS

Office Action mailed Oct. 8, 2024 in connection with U.S. Appl. No. 17/422,257.

* cited by examiner

*Primary Examiner* — Jonathan S Lau  
*Assistant Examiner* — Sarah Grace Scrivener  
(74) *Attorney, Agent, or Firm* — Norris McLaughlin, P.A.

(57) ABSTRACT

The invention relates to compounds according to general formula (I),

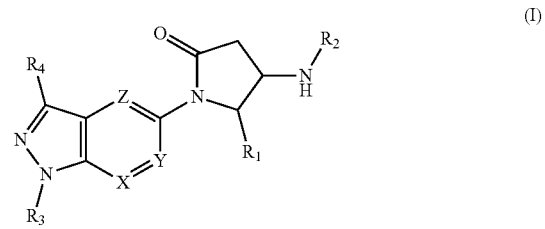

which act as modulators of the glucocorticoid receptor and can be used in the treatment and/or prophylaxis of disorders which are at least partially mediated by the glucocorticoid receptor.

19 Claims, No Drawings

SUBSTITUTED PYRROLIDINE AMIDES II

This application is a continuation of U.S. Nonprovisional application Ser. No. 16/223,925, filed Dec. 18, 2018, pending, which, in turn, claims foreign priority benefit of European Application No. 17 208 180.4, filed Dec. 18, 2017, the disclosures of which patent applications are incorporated herein by reference The invention relates to compounds according to general formula (I)

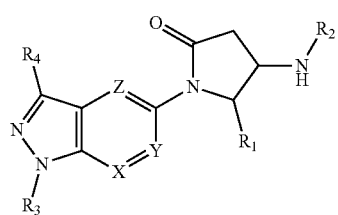

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases such as asthma, rheumatoid arthritis, inflammatory bowel disease, chronic obstructive pulmonary disease, acute respiratory distress syndrome, cystic fibrosis, osteoarthritis, polymyalgia rheumatica and giant cell arteritis is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. el al, Clin Exp Rheumatol. 2015 July-August; 33(4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., JAMA. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known e.g. from WO 2007/122165, WO 2008/076048 and WO 2008/043789, WO 2009/035067, WO 2009/142571, WO 2016/046260, and WO 2017/034006.

It was an object of the invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter as described herein.

It was surprisingly found that the compounds according to the invention are highly potent modulators of the glucocorticoid receptor.

The invention relates to a compound according to general formula (I),

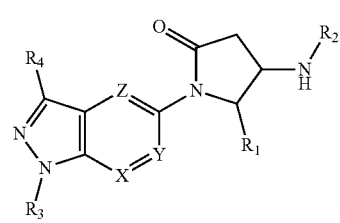

wherein $R_1$ represents —$C_{1-10}$-alkyl; —$C_{3-10}$-cycloalkyl; —$C_{1-6}$-alkylene-$C_{3-10}$-cycloalkyl; 3 to 7 membered heterocycloalkyl; —$C_{1-6}$-alkylene-(3 to 7 membered heterocycloalkyl); aryl; —$C_{1-6}$-alkylene-aryl; 5 or 6-membered heteroaryl; or —$C_{1-6}$-alkylene-(5 or 6-membered heteroaryl);

$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)-aryl; —C(=O)—$C_{1-6}$-alkylene-aryl; —C(=O)-(5 or 6-membered heteroaryl); —C(=O)—$C_{1-6}$-alkylene-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-aryl; —S(=O)$_{1-2}$—$C_{1-6}$-alkylene-aryl; —S(=O)$_{1-2}$-(5 or 6-membered heteroaryl); or —S(=O)$_{1-2}$—$C_{1-6}$-alkylene-(5 or 6-membered heteroaryl);

$R_3$ represents —$C_{1-10}$-alkyl; —$C_{3-10}$-cycloalkyl; —$C_{1-6}$-alkylene-$C_{3-10}$-cycloalkyl; aryl; —$C_{1-6}$-alkylene-aryl;

—C(═O)—$C_{1-10}$-alkyl; —C(═O)—$C_{3-10}$-cycloalkyl; —C(═O)—$C_{1-6}$-alkylene-$C_{3-10}$-cycloalkyl; —C(═O)-aryl; —C(═O)—$C_{1-6}$-alkylene-aryl; —S(═O)$_{1-2}$—$C_{1-10}$-alkyl; —S(═O)$_{1-2}$—$C_{3-10}$-cycloalkyl; —S(═O)$_{1-2}$—$C_{1-6}$-alkylene-$C_{3-10}$-cycloalkyl; —S(═O)$_{1-2}$-aryl; or —S(═O)$_{1-2}$—$C_{1-6}$-alkylene-aryl;

$R_4$ represents —H; —F; —Cl; —Br; —I; —CN; —$CF_3$; —$CF_2H$; —$CFH_2$ or cyclopropyl;

X represents N or $CR_5$; wherein $R_5$ represents —H; —F; —Cl; —Br; —I; —CN; —$C_{1-10}$-alkyl or —$C_{3-16}$-cycloalkyl;

Y represents N or $CR_6$; wherein $R_6$ represents —H; —F; —Cl; —Br; —I; —CN; —$C_{1-10}$-alkyl or —$C_{3-10}$-cycloalkyl;

Z represents N or $CR_7$; wherein $R_7$ represents —H; —F; —Cl; —Br; —I; —CN; —$C_{1-10}$-alkyl or —$C_{3-10}$-cycloalkyl;

wherein —$C_{1-10}$-alkyl, —$C_{1-4}$-alkyl and —$C_{1-6}$-alkylene- in each case independently from one another is linear or branched, saturated or unsaturated;

wherein —$C_{1-10}$-alkyl, —$C_{1-4}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(═O)—$C_{1-6}$-alkyl; —C(═O)—OH; —C(═O)—O$C_{1-6}$-alkyl; —C(═O)—$NH_2$; —C(═O)—NH($C_{1-6}$-alkyl); —C(═O)—N($C_{1-6}$-alkyl)$_2$; —OH; ═O; —$OCF_3$; —$OCF_2H$; —$OCFH_2$; —$OCF_2Cl$; —$OCFCl_2$; —O—$C_{1-6}$-alkyl; —O—C(═O)—$C_{1-6}$-alkyl; —O—C(═O)—O—$C_{1-6}$-alkyl; —O—(CO)—NH($C_{1-6}$-alkyl); —O—C(═O)—N($C_{1-6}$-alkyl)$_2$; —O—S(═O)$_2$—$NH_2$; —O—S(═O)$_2$—NH($C_{1-6}$-alkyl); —O—S(═O)$_2$—N($C_{1-6}$-alkyl)$_2$; —$NH_2$; —NH($C_{1-6}$-alkyl); —N($C_{1-6}$-alkyl)$_2$; —NH—C(═O)—$C_{1-6}$-alkyl; —NH—C(═O)—O—$C_{1-6}$-alkyl; —NH—C(═O)—$NH_2$; —NH—C(═O)—NH($C_{1-6}$-alkyl); —NH—C(═O)—N($C_{1-6}$-alkyl)$_2$; —N($C_{1-6}$-alkyl)-C(═O)—$C_{1-6}$-alkyl; —N($C_{1-6}$-alkyl)-C(═O)—O—$C_{1-6}$-alkyl; —N($C_{1-6}$-alkyl)-C(═O)—$NH_2$; —N($C_{1-6}$-alkyl)-C(═O)—NH($C_{1-6}$-alkyl); —N($C_{1-6}$-alkyl)-C(═O)—N($C_{1-6}$-alkyl)$_2$; —NH—S(═O)$_2$OH; NH—S(═O)$_2$—$C_{1-6}$-alkyl; —NH—S(═O)$_2$—O—$C_{1-6}$-alkyl; —NH—S(═O)$_2$—$NH_2$; —NH—S(═O)$_2$—NH($C_{1-6}$-alkyl); S(═O)$_2$N($C_{1-6}$-alkyl)$_2$; —N($C_{1-6}$-alkyl)-S(═O)$_2$—OH; —N($C_{1-6}$-alkyl)-S(═O)$_2$—$C_{1-6}$-alkyl; —N(C alkyl)-S(═O)$_2$—O—$C_{1-6}$-alkyl; —N($C_{1-6}$-alkyl)-S(═O)$_2$—$NH_2$; —N($C_{1-6}$-alkyl)-S(═O)$_2$—NH($C_{1-6}$-alkyl); —N($C_{1-6}$-alkyl)-S(═O)$_2$—N($C_{1-6}$-alkyl)$_2$; —$SCF_3$; —$SCF_2H$; —$SCFH_2$; —S—$C_{1-6}$-alkyl; —S(═O)—$C_{1-6}$-alkyl; —S(═O)$_2$—$C_{1-6}$-alkyl; —S(═O)$_2$—OH; —S(═O)$_2$—O—$C_{1-6}$-alkyl; —S(═O)$_2$—$NH_2$; —S(═O)$_2$—NH($C_{1-6}$-alkyl); —S(═O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(═O)—$C_{3-6}$-cycloalkyl; —C(═O)-(3 to 6-membered heterocycloalkyl); —C(═O)-phenyl; —C(═O)-(5 or 6-membered heteroaryl); —S(═O)$_2$—($C_{3-6}$-cycloalkyl); —S(═O)$_2$-(3 to 6-membered heterocycloalkyl); —S(═O)$_2$-phenyl or —S(═O)$_2$-(5 or 6-membered heteroaryl);

wherein aryl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(═O)—$C_{1-6}$-alkyl; —C(═O)—OH; —C(═O)—O$C_{1-6}$-alkyl; —C(═O)—NH(OH); —C(═O)—$NH_2$; —C(═O)—NH($C_{1-6}$-alkyl); —C(═O)—N($C_{1-6}$-alkyl)$_2$; —OH; ═O; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —O-(3 to 6-membered heterocycloalkyl); —$NH_2$; —NH($C_{1-6}$-alkyl); —N($C_{1-6}$-alkyl)$_2$; —NH—C(═O)—$C_{1-6}$-alkyl; —N($C_{1-6}$-alkyl)-C(═O)—$C_{1-6}$-alkyl; —NH—C(═O)—$NH_2$; —NH—C(═O)—NH($C_{1-6}$-alkyl); —NH—C(═O)—N($C_{1-6}$-alkyl)$_2$; —N($C_{1-6}$-alkyl)-C(═O)—NH($C_{1-6}$-alkyl); —N($C_{1-6}$-alkyl)-C(═O)—N($C_{1-6}$-alkyl)$_2$; —NH—S(═O)$_2$—$C_{1-6}$-alkyl; —$SCF_3$; —S—$C_{1-6}$-alkyl; —S(═O)—$C_{1-6}$-alkyl; —S(═O)$_2$—$C_{1-6}$-alkyl; —S(═O)$_2$—$NH_2$; —S(═O)$_2$—NH($C_{1-6}$-alkyl); —S(═O)$_2$—N($C_{1-6}$-alkyl)$_2$; —$C_{3-6}$-cycloalkyl; —$C_{1-4}$-alkylene-$C_{3-6}$-cycloalkyl; 3 to 6-membered heterocycloalkyl; —$C_{1-4}$-alkylene-(3 to 6-membered heterocycloalkyl); phenyl or 5 or 6-membered heteroaryl;

in the form of the free compound or a physiologically acceptable salt thereof.

In a preferred embodiment, the compound according to the invention is present in form of the free compound. For the purpose of specification, "free compound" preferably means that the compound according to the invention is not present in form of a salt. Methods to determine whether a chemical substance is present as the free compound or as a salt are known to the skilled artisan such as $^{14}$N or $^{15}$N solid state NMR, x-ray diffraction, x-ray powder diffraction, IR, Raman, XPS. $^1$H-NMR recorded in solution may also be used to consider the presence of protonation.

In another preferred embodiment, the compound according to the invention is present in form of a physiologically acceptable salt. For the purposes of this specification, the term "physiologically acceptable salt" preferably refers to a salt obtained from a compound according to the invention and a physiologically acceptable acid or base.

According to the invention, the compound according to the invention may be present in any possible form including solvates, cocrystals and polymorphs. For the purposes of this specification, the term "solvate" preferably refers to an adduct of (i) a compound according to the invention and/or a physiologically acceptable salt thereof with (ii) distinct molecular equivalents of one or more solvents.

Further, the compound according to the invention may be present in form of the racemate, enantiomers, diastereomers, tautomers or any mixtures thereof.

The invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C. Isotopic isomers of a compound of the invention can generally be prepared by conventional procedures known to a person skilled in the art.

According to the invention, the terms "—$C_{1-10}$-alkyl", "—$C_{1-8}$-alkyl", "—$C_{1-6}$-alkyl" and "—$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, —$C_{1-10}$-alkyl, —$C_{1-8}$-alkyl, —$C_{1-6}$-alkyl and —$C_{1-4}$-alkyl are saturated. In another preferred embodiment, —$C_{1-10}$-alkyl, —$C_{1-8}$-alkyl, —$C_{1-6}$-alkyl and —$C_{1-4}$-alkyl are not saturated. According to this embodiment, —$C_{1-10}$-alkyl, —$C_{1-8}$-alkyl, —$C_{1-6}$-alkyl and —$C_{1-4}$-alkyl comprise at least one C═C double bond (a C═C-bond) or at least one C—C triple bond (a C≡C-bond). In still another preferred embodiment, —$C_{1-10}$-alkyl, —$C_{1-8}$-alkyl, —$C_{1-6}$-alkyl and —$C_{1-4}$-alkyl are (i) saturated or (ii) not saturated, wherein —$C_{1-10}$-alkyl, —$C_{1-8}$-alkyl, —$C_{1-6}$-alkyl and —$C_{1-4}$-alkyl comprise at least one, preferably one, C—C triple bond (a C≡C-bond).

Preferred —$C_{1-10}$-alkyl groups are selected from methyl, ethyl, ethenyl (vinyl), n-propyl, 2-propyl, 1-propynyl, 2-propynyl, propenyl (—$CH_2CH═CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2CH═CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl.

Preferred —$C_{1-8}$-alkyl groups are selected from methyl, ethyl, ethenyl (vinyl), n-propyl, 2-propyl, 1-propynyl, 2-propynyl, propenyl (—$CH_2CH═CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2CH═CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl.

Preferred —$C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2$—CH═$CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred —$C_{1-6}$-alkyl groups are selected from $C_{1-4}$-alkyl groups.

Preferred —$C_{1-4}$-alkyl groups are selected from methyl, ethyl, ethenyl (vinyl), n-propyl, 2-propyl, 1-propynyl, 2-propynyl, propenyl (—$CH_2CH═CH_2$, —CH═CH—$CH_3$, —C(═$CH_2$)—$CH_3$), n-butyl, 1-butynyl, 2-butynyl, 1-butenyl, 2-butenyl, isobutyl, sec-butyl, tert-butyl and 3-methylbut-1-ynyl.

Further according to the invention, the terms "—$C_{1-6}$-alkylene-"; "—$C_{1-4}$-alkylene-" and "—$C_{1-2}$-alkylene-" relate to a linear or branched, preferably linear, and preferably saturated aliphatic residues which are preferably selected from the group consisting of methylene (—$CH_2$—), ethylene (—$CH_2CH_2$—), propylene (—$CH_2CH_2CH_2$— or —C($CH_3$)$_2$—), butylene (—$CH_2CH_2CH_2CH_2$—), pentylene (—$CH_2CH_2CH_2CH_2CH_2$—) and hexylene (—$CH_2CH_2CH_2CH_2CH_2CH_2$—); more preferably methylene (—$CH_2$—) and ethylene (—$CH_2CH_2$—) and most preferably methylene (—$CH_2$—). Preferably, —$C_{1-6}$-alkylene- is selected from —$C_{1-4}$-alkylene-, more preferably from —$C_{1-2}$-alkylene-.

Still further according to the invention, the terms "—$C_{3-10}$-cycloalkyl" and "—$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted.

Preferably, —$C_{3-10}$-cycloalkyl and —$C_{3-6}$-cycloalkyl are saturated. The —$C_{3-10}$-cycloalkyl and —$C_{3-6}$-cycloalkyl can be bound to the respective superordinate general structure via any desired and possible ring member of the cycloalkyl group. The —$C_{3-10}$-cycloalkyl and —$C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, —$C_{3-10}$-cycloalkyl and —$C_{3-6}$-cycloalkyl can be singly or multiply bridged such as, for example, in the case of adamantyl, bicyclo[2.2.1]heptyl or bicyclo[2.2.2]octyl. However, preferably, —$C_{3-10}$-cycloalkyl and —$C_{3-6}$-cycloalkyl are neither condensed with further ring systems nor bridged. More preferably, —$C_{3-10}$-cycloalkyl and —$C_{3-6}$-cycloalkyl are neither condensed with further ring systems nor bridged and are saturated. Preferred —$C_{3-10}$-cycloalkyl groups are selected from the group consisting of cyclopropyl, cyclobutyl, cyclopentyl, cyclohexyl, cyclopentenyl, cyclohexenyl, cycloheptyl, cyclooctyl, cyclononyl, cyclodecyl, adamantly, cyclopentenyl, cyclohexenyl, cycloheptenyl, cyclooctenyl, bicyclo[2.2.1]heptyl and bicyclo[2.2.2]octyl. Particularly preferred —$C_{3-10}$-cycloalkyl groups are selected from —$C_{3-6}$-cycloalkyl groups.

Preferred —$C_{3-6}$-cycloalkyl groups are selected from the group consisting of cyclopropyl, cyclobutyl, cyclopentyl, cyclohexyl, cyclopentenyl and cyclohexenyl. Particularly preferred —$C_{3-6}$-cycloalkyl groups are selected from the group consisting of cyclopropyl, cyclobutyl, cyclopentyl and cyclohexyl, most preferably cyclopropyl.

According to the invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{1-4}$-alkyl) such as N($CH_3$), wherein the carbon atoms of the ring can be unsubstituted or mono- or polysubstituted.

Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, tetrahydrofuranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups.

Preferred 3 to 6-membered heterocycloalkyl groups are selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. Particularly preferred 3 to 6-membered heterocycloalkyl groups are selected from the group consisting of tetrahydropyranyl, oxetanyl, oxiranyl, and tetrahydrofuranyl.

According to the invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo[b][1,4]oxazin-3(4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl.

Preferably, aryl is selected from the group consisting of phenyl, 1H-benzo[d]imidazolyl, 2H-benzo[b][1,4]oxazin-3(4H)-onyl, 2,3-dihydro-1H-indenyl, tetrahydronaphthalenyl, isochroman, 1,3-dihydroisobenzofuranyl, 1-naphthyl, 2-naphthyl, fluorenyl and anthracenyl, each of which can be respectively unsubstituted or mono- or polysubstituted. In another preferred embodiment, aryl is not condensed with any further ring system. A particularly preferred aryl is phenyl, unsubstituted or mono- or polysubstituted.

According to the invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the superordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system.

Preferably, the 5- to 6-membered heteroaryl is selected from the group consisting of pyridyl (i.e. 2-pyridyl, 3-pyridyl, 4-pyridyl), pyridone (pyridinone), pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl). As pyridones can be regarded as pyridines that are substituted with =O, for the purpose of the specification the definition of pyridines that may optionally be substituted with =O covers pyridones.

The compounds according to the invention are defined by substituents, for example by $R_2$, $R_3$ and $R_4$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R_1$=—$C_{1-10}$-alkyl ($1^{st}$ generation substituent), then the —$C_{1-10}$-alkyl can for its part be substituted, for example with a —NH($C_{1-6}$-alkyl) ($2^{nd}$ generation substituent). This produces the functional group $R_1$=(—$C_{1-10}$-alkyl-NH—$C_{1-6}$-alkyl). The —NH—$C_{1-6}$-alkyl can then for its part be resubstituted, for example with —Cl ($3^{rd}$ generation substituent). Overall, this produces the functional group $R_1$=$C_{1-10}$-alkyl, wherein the —$C_{1-6}$-alkyl of the —NH—$C_{1-6}$-alkyl is substituted by —Cl.

However, in a preferred embodiment, the $3^{rd}$ generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R_2$ and $R_3$ denote —$C_{1-6}$-alkyl, then —$C_{1-6}$-alkyl can e.g. represent ethyl for $R_2$ and can represent methyl for $R_3$.

In connection with the terms "—$C_{1-10}$-alkyl", "—$C_{1-6}$-alkyl", "—$C_{1-4}$-alkyl", "—$C_{3-10}$-cycloalkyl", "—$C_{3-6}$-cycloalkyl", "3 to 7 membered heterocycloalkyl", "3 to 6-membered heterocycloalkyl", "—$C_{1-6}$-alkylene-", "—$C_{1-4}$-alkylene-" and "—$C_{1-2}$-alkylene-", the term "substituted" refers in the sense of the invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of —$CF_3$, —$CH_2CF_3$ or disubstituted as in the case of 1,1-difluorocyclohexyl, or at various points, as in the case of —CH(OH)—CH=CH—$CHCl_2$ or 1-chloro-3-fluorocyclohexyl. The multiple substitution can be carried out using the same or using different substituents.

In relation to the terms "aryl", "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the invention, preferably —$C_{1-10}$-alkyl, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl, —$C_{1-6}$-alkylene-, —$C_{1-4}$-alkylene- and —$C_{1-2}$-alkylene- in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; —NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$—N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl and —S(=O)$_2$-(5 or 6-membered heteroaryl).

Preferred substituents of —$C_{1-10}$-alkyl, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl, —$C_{1-6}$-alkylene- and —$C_{1-4}$-alkylene- are selected from the group consisting of —F; —Cl; —Br; —I; —CN; —$C_{1-6}$-alkyl; —$CF_3$; —$CF_2H$; —$CFH_2$; —C(=O)—$NH_2$; —C(=O)—NH($C_{1-6}$-alkyl); —C(=O)—N($C_{1-6}$-alkyl)$_2$; —OH; —$OCF_3$; —$OCF_2H$; —$OCFH_2$; —O—$C_{1-6}$-alkyl; —$NH_2$; —NH($C_{1-6}$-alkyl); —N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —$C_{3-6}$-cycloalkyl; 3 to 6-membered heterocycloalkyl; phenyl and 5 or 6-membered heteroaryl; and particularly preferably —F, —CN, —$CH_3$, —$CH_2CH_3$, —$CF_3$; —$CF_2H$; —$CFH_2$; —C(=O)—$NH_2$; —C(=O)—NH($CH_3$); —C(=O)—N($CH_3$)$_2$; —OH, —$NH_2$, —$OCH_3$, —$SCH_3$, —S(=O)$_2$($CH_3$), —S(=O)($CH_3$), —N($CH_3$)$_2$, cyclopropyl and oxetanyl. According to this embodiment, —$C_{1-10}$-alkyl, —$C_{1-6}$-alkyl, —$C_{1-4}$-alkyl, —$C_{3-10}$-cycloalkyl, —$C_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or monosubstituted or disubstituted with a substituent selected from the group consisting of —F; —Cl; —Br; —I; —CN; —$C_{1-6}$-alkyl; —$CF_3$; —$CF_2H$; —$CFH_2$; —C(=O)—$NH_2$; —C(=O)—NH($C_{1-6}$-alkyl); —C(=O)—N($C_{1-6}$-alkyl)$_2$; —OH; —$OCF_3$; —$OCF_2H$; —$OCFH_2$; —O—$C_{1-6}$-alkyl; —$NH_2$; —NH($C_{1-6}$-alkyl); —N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —$C_{3-6}$-cycloalkyl; 3 to 6-membered heterocycloalkyl; phenyl and 5 or 6-membered heteroaryl. Preferably, —$C_{1-6}$-alkylene- groups and —$C_{1-4}$-alkylene- groups are unsubstituted.

According to the invention, preferably aryl, phenyl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; $C_{1-4}$-alkylene-$CF_2H$; —$C_{1-4}$-alkylene-$CFH_2$; —C(=O)—$C_{1-6}$-alkyl; —C(=O)—OH; —C(=O)—O$C_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; =O; —OH; —$OCF_3$;

—OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; 3 to 6-membered heterocycloalkyl; —C$_{1-4}$-alkylene-(3 to 6-membered heterocycloalkyl); phenyl or 5 or 6-membered heteroaryl.

Preferred substituents of aryl, phenyl and 5 or 6-membered heteroaryl are selected from the group consisting of —F; —Cl; —Br; —I; —CN; —C$_{1-6}$-alkyl; —CF$_3$; —CF$_2$H; —CFH$_2$; —C$_{1-4}$-alkylene-CF$_3$; —C$_{1-4}$-alkylene-CF$_2$H; —C$_{1-4}$-alkylene-CFH$_2$; —OH; —OCF$_3$; —OCF$_2$H; —OCFH$_2$; —O—C$_{1-6}$-alkyl; —O—C$_{3-6}$-cycloalkyl and —C$_{3-6}$-cycloalkyl; and particularly preferably of —F; —Cl; —Br; —CN; —CH$_3$; —CH$_2$CH$_3$; —CF$_3$; —CF$_2$H; —CFH$_2$; —CH$_2$—CF$_3$; =O; —OH; —OCF$_3$; —OCF$_2$H; —OCFH$_2$; —O—CH$_3$; —O-cyclopropyl and cyclopropyl. According to this embodiment, aryl, phenyl and 5 or 6-membered heteroaryl are preferably each independently from one another unsubstituted, mono- di- or trisubstituted, more preferably unsubstituted or monosubstituted or disubstituted with a substituent selected from the group consisting of —F; —Cl; —Br; —I; —CN; —C$_{1-6}$-alkyl; —CF$_3$; —CF$_2$H; —CFH$_2$; —C$_{1-4}$-alkylene-CF$_3$; —C$_{1-4}$-alkylene-CF$_2$H; —C$_{1-4}$-alkylene-CFH$_2$; =O; —OH; —OCF$_3$; —OCF$_2$H; —OCFH$_2$; —O—C$_{1-6}$-alkyl; —O—C$_{3-6}$-cycloalkyl and —C$_{3-6}$-cycloalkyl. A particularly preferred substituted 5 or 6-membered heteroaryl is N-methyl-2-oxo-pyridyl.

In a preferred embodiment, the compound according to the invention has a stereochemistry according to general formula (II), (III), (IV) or (V)

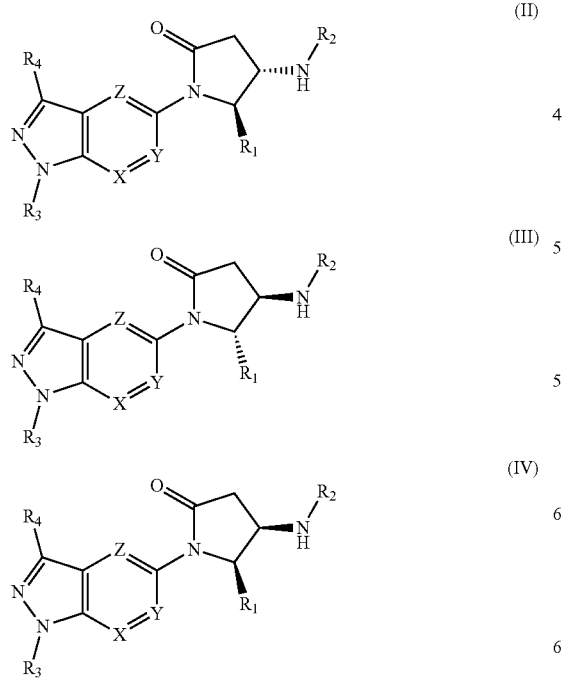

In a preferred embodiment, the compound according to the invention has a stereochemistry according to general formula (II) or (III), such that the residues —R$_1$ and —NH—R$_2$ on the pyrrolidone ring are oriented trans. Preferably, the compound according to the invention has a stereochemistry according to general formula (II). Preferably, the compound according to the invention has a stereochemistry according to general formula (III). The stereochemistry according to general formula (II) is particularly preferred.

In another preferred embodiment, the compound according to the invention has a stereochemistry according to general formula (IV) or (V), such that the residues —R$_1$ and —NH—R$_2$ on the pyrrolidone ring are oriented cis. Preferably, the compound according to the invention has a stereochemistry according to general formula (IV). Preferably, the compound according to the invention has a stereochemistry according to general formula (V).

In the compound of the invention according to any of general formulas (I), (II), (III), (IV) or (V), R$_1$ represents —C$_{1-10}$-alkyl; —C$_{3-10}$-cycloalkyl; —C$_{1-6}$-alkylene-C$_{3-10}$-cycloalkyl; 3 to 7 membered heterocycloalkyl; —C$_{1-6}$-alkylene-(3 to 7 membered heterocycloalkyl); aryl; —C$_{1-6}$-alkylene-aryl; 5 or 6-membered heteroaryl; or —C$_{1-6}$-alkylene-(5 or 6-membered heteroaryl).

In a preferred embodiment, R$_1$ represents —C$_{3-10}$-cycloalkyl; —C$_{1-6}$-alkylene-C$_{3-10}$-cycloalkyl; aryl; or 5 or 6-membered heteroaryl.

In particularly preferred embodiments, R$_1$ represents
(i) cyclopropyl, unsubstituted;
(ii) —CH$_2$-cyclopropyl, unsubstituted;
(iii) phenyl, unsubstituted or mono- or disubstituted with substituents independently of one another selected from the group consisting of —F, —Cl, —Br, —CH$_3$, —CF$_3$, —CN, cyclopropyl, and —OCH$_3$, wherein phenyl is optionally annealed to a dioxolane ring by a substituent —O—CH$_2$CH$_2$—O—; or
(iv) pyridyl, unsubstituted or mono- or disubstituted with substituents independently of one another selected from the group consisting of —F, —Cl, —Br, —CH$_3$, —CF$_3$, —CN, and —OCH$_3$.

In the compound of the invention according to any of general formulas (I), (II), (III), (IV) or (V), R$_2$ represents —C(=O)—C$_{1-10}$-alkyl; —C(=O)—C$_{3-10}$-cycloalkyl; —C(=O)—C$_{1-6}$-alkylene-C$_{3-10}$-cycloalkyl; —C(=O)-(3 to 7 membered heterocycloalkyl); —C(=O)—C$_{1-6}$-alkylene-(3 to 7 membered heterocycloalkyl); —C(=O)-aryl; —C(=O)—C$_{1-6}$-alkylene-aryl; —C(=O)-(5 or 6-membered heteroaryl); —C(=O)—C$_{1-6}$-alkylene-(5 or 6-membered heteroaryl); —S(=O)$_{1-2}$—C$_{1-10}$-alkyl; —S(=O)$_{1-2}$—C$_{3-10}$-cycloalkyl; —S(=O)$_{1-2}$—C$_{1-6}$-alkylene-C$_{3-10}$-cycloalkyl; —S(=O)$_{1-2}$-(3 to 7 membered heterocycloalkyl); —S(=O)$_{1-2}$—C$_{1-6}$-alkylene-(3 to 7 membered heterocycloalkyl); —S(=O)$_{1-2}$-aryl; —S(=O)$_{1-2}$—C$_{1-6}$-alkylene-aryl; —S(=O)$_{1-2}$-(5 or 6-membered heteroaryl); or —S(=O)$_{1-2}$—C$_{1-6}$-alkylene-(5 or 6-membered heteroaryl).

In a preferred embodiment, $R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)-(5 or 6-membered heteroaryl); —S(=O)$_2$—$C_{1-10}$-alkyl; —S(=O)$_2$—$C_{3-10}$-cycloalkyl; —S(=O)$_2$—$C_{1-6}$-alkylene-$C_{3-10}$-cycloalkyl or —S(=O)$_2$-(5 or 6-membered heteroaryl).

In particularly preferred embodiments, $R_2$ represents
(i) —C(=O)—$C_{1-10}$-alkyl, unsubstituted or mono- or disubstituted with substituents independently of one another selected from the group consisting of —F, —Cl, and —Br;
(ii) —C(=O)-cyclopropyl, unsubstituted or mono- or disubstituted with substituents independently of one another selected from the group consisting of —F, —Cl, —Br, —CH$_3$, —CF$_3$, —CN, and —OCH$_3$;
(iii) —C(=O)-cyclobutyl, unsubstituted or mono- or disubstituted with substituents independently of one another selected from the group consisting of —F, —Cl, —Br, —CH$_3$, —CF$_3$, —CN and —OCH$_3$;
(iv) —C(=O)-2-tetrahydrofuranyl, unsubstituted;
(v) —C(=O)-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$;
(vi) unsubstituted;
(vii) —S(=O)$_2$-cyclopropyl, unsubstituted;
(viii) —S(=O)$_2$—CH$_2$-cyclopropyl, unsubstituted; or
(ix) —S(=O)$_2$-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

In the compound of the invention according to any of general formulas (I), (II), (III), (IV) or (V), $R_3$ represents —$C_{1-10}$-alkyl; —$C_{3-10}$-cycloalkyl; —$C_{1-6}$-alkylene-$C_{3-10}$-cycloalkyl; aryl; —$C_{1-6}$-alkylene-aryl; —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-aryl; —C(=O)—$C_{1-6}$-alkylene-aryl; —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-aryl; or —S(=O)$_{1-2}$—$C_{1-6}$-alkylene-aryl.

In a preferred embodiment, $R_3$ represents —$C_{1-10}$-alkyl; —$C_{3-10}$-cycloalkyl; —$C_{1-6}$-alkylene-$C_{3-10}$-cycloalkyl; aryl; —$C_{1-6}$-alkylene-aryl.

In particularly preferred embodiments, $R_3$ represents
(i) unsubstituted or mono- or disubstituted with substituents independently of one another selected from the group consisting of —F, —Cl, and —Br;
(ii) -cyclohexyl, unsubstituted or mono- or disubstituted with substituents independently of one another selected from the group consisting of —F, —Cl, and —Br;
(iii) —CH$_2$-cyclopropyl, unsubstituted;
(iv) —CH$_2$-cyclohexyl, unsubstituted or mono- or disubstituted with substituents independently of one another selected from the group consisting of —F, —Cl, and —Br;
(v) phenyl, unsubstituted or mono- or disubstituted with substituents independently of one another selected from the group consisting of —F, —Cl, —Br, —CH$_3$, —CF$_3$, —CN, and —OCH$_3$; or
(vi) —CH$_2$-phenyl, unsubstituted or mono- or disubstituted with substituents independently of one another selected from the group consisting of —F, —Cl, —Br, —CH$_3$, —CF$_3$, —CN, and —OCH$_3$.

In the compound of the invention according to any of general formulas (I), (II), (III), (IV) or (V), $R_4$ represents —H; —F; —Cl; —Br; —I; —CN; —CH$_3$; —CF$_3$; —CF$_2$H; —CFH$_2$ or cyclopropyl.

In a preferred embodiment, $R_4$ represents —H.

In the compound of the invention according to any of general formulas (I), (II), (III), (IV) or (V), X represents N or CR$_5$; wherein $R_5$ represents —H; —F; —Cl; —Br; —I; —CN; —$C_{1-10}$-alkyl or —$C_{3-10}$-cycloalkyl.

In a preferred embodiment, X represents N or CH.

In the compound of the invention according to any of general formulas (I), (II), (III), (IV) or (V), Y represents N or CR$_6$; wherein $R_6$ represents —H; —F; —Cl; —Br; —I; —CN; —$C_{1-10}$-alkyl or —$C_{3-10}$-cycloalkyl.

In a preferred embodiment, Y represents N or CH.

In the compound of the invention according to any of general formulas (I), (II), (III), (IV) or (V), Z represents N or CR$_7$; wherein $R_7$ represents —H; —F; —Cl; —Br; —I; —CN; —$C_{1-10}$-alkyl or —$C_{3-10}$-cycloalkyl.

In a preferred embodiment, Z represents N or CH.

In particularly preferred embodiments,
(i) X represents CR$_5$, preferably CH; Y represents CR$_6$, preferably CH; and Z represents CR$_7$, preferably CH; or
(ii) X represents N; Y represents CR$_6$, preferably CH; and Z represents CR$_7$, preferably CH; or
(iii) X represents CR$_5$, preferably CH; Y represents N; and Z represents CR$_7$, preferably CH; or
(iv) X represents CR$_5$, preferably CH; Y represents CR$_6$, preferably CH; and Z represents N; or
(v) X represents N; Y represents N; and Z represents CR$_7$, preferably CH; or
(vi) X represents N; Y represents CR$_6$, preferably CH; and Z represents N; or
(vii) X represents CR$_5$, preferably CH; Y represents N; and Z represents N; or
(viii) X represents N; Y represents N; and Z represents N.

In particularly preferred embodiments of the invention according to any of general formulas (I), (II), (III), (IV) or (V),
$R_1$ represents phenyl, unsubstituted or mono- or disubstituted with substituents independently of one another selected from the group consisting of —F, —Cl, —Br, —CH$_3$, —CF$_3$, —CN, and —OCH$_3$; and/or
$R_2$ represents —C(=O)—$C_{1-6}$-alkyl; —C(=O)-cyclopropyl; or —C(=O)-cyclobutyl, unsubstituted or mono- or disubstituted with substituents independently of one another selected from the group consisting of —F, —Cl, and —Br; and/or
$R_3$ represents fluoro-phenyl.

In a preferred embodiment, the compound according to the invention is selected from the group consisting of
1   2,2-difluoro-N-[rac-(2R,3S)-2-(2,3-dihydro-1,4-benzodioxin-6-yl)-1-[1-(4-fluorophenyl)indazol-5-yl]-5-oxo-pyrrolidin-3-yl]propanamide
2   2,2-difluoro-N-[(2R,3S)-1-[1-(4-fluorophenyl)indazol-5-yl]-5-oxo-2-phenyl-pyrrolidin-3-yl]propanamide
3   2,2-difluoro-N-[rac-(2R,3S)-1-[1-(4-fluorophenyl)indazol-5-yl]-5-oxo-2-phenyl-pyrrolidin-3-yl]propanamide 4  2,2-difluoro-N-[(2R,3S)-1-[1-(4-fluorophenyl)indazol-5-yl]-2-(2-methoxy-4-pyridyl)-5-oxo-pyrrolidin-3-yl]propanamide
5  2,2-difluoro-N-[rac-(2R,3S)-2-(2,4-difluorophenyl)-1-[1-(4-fluorophenyl)indazol-5-yl]-5-oxo-pyrrolidin-3-yl]propanamide
6  2,2-difluoro-N-[rac-(2R,3S)-1-[1-(3,4-difluorophenyl)indazol-5-yl]-5-oxo-2-phenyl-pyrrolidin-3-yl]propanamide
7  2,2-difluoro-N-[rac-(2R,3S)-1-[1-(4-fluorophenyl)indazol-5-yl]-2-(3-methoxyphenyl)-5-oxo-pyrrolidin-3-yl]propanamide
8  N-[rac-(2R,3S)-1-[1-(4-fluorophenyl)indazol-5-yl]-5-oxo-2-phenyl-pyrrolidin-3-yl]cyclopropanecarboxamide
9  N-[rac-(2R,3S)-1-[1-(4-fluorophenyl)indazol-5-yl]-5-oxo-2-phenyl-pyrrolidin-3-yl]cyclopropanesulfonamide
10  N-[rac-(2R,3S)-1-[1-(4-fluorophenyl)indazol-5-yl]-2-(3-methoxyphenyl)-5-oxo-pyrrolidin-3-yl]cyclopropanesulfonamide
11  2,2-difluoro-N-[rac-(2R,3S)-2-(4-fluorophenyl)-1-[1-(4-fluorophenyl)indazol-5-yl]-5-oxo-pyrrolidin-3-yl]propanamide
12  N-[(2R,3S)-2-(3-chlorophenyl)-1-[1-(4-fluorophenyl)indazol-5-yl]-5-oxo-pyrrolidin-3-yl]-2,2-difluoro-propanamide
13  1-methyl-N-[rac-(2R,3S)-2-(4-fluorophenyl)-1-[1-(4-fluorophenyl)indazol-5-yl]-5-oxo-pyrrolidin-3-yl]cyclopropanecarboxamide
14  1-fluoro-N-[rac-(2R,3S)-2-(3-fluorophenyl)-1-[1-(4-fluorophenyl)indazol-5-yl]-5-oxo-pyrrolidin-3-yl]cyclopropanecarboxamide
15  N-[rac-(2R,3S)-2-(3-fluorophenyl)-1-[1-(4-fluorophenyl)indazol-5-yl]-5-oxo-pyrrolidin-3-yl]-1-(trifluoromethyl)cyclopropanecarboxamide
16  N-[rac-(2R,3S)-2-(3-fluorophenyl)-1-[1-(4-fluorophenyl)indazol-5-yl]-5-oxo-pyrrolidin-3-yl]methanesulfonamide
17  N-[rac-(2R,3S)-1-[1-(4-fluorophenyl)indazol-5-yl]-2-(3-methoxyphenyl)-5-oxo-pyrrolidin-3-yl]-1-(trifluoromethyl)cyclopropanecarboxamide
18  1-methyl-N-[rac-(2R,3S)-2-(3-fluorophenyl)-1-[1-(4-fluorophenyl)indazol-5-yl]-5-oxo-pyrrolidin-3-yl]cyclopropanecarboxamide
19  N-[rac-(2R,3S)-2-(3-fluorophenyl)-1-[1-(4-fluorophenyl)indazol-5-yl]-5-oxo-pyrrolidin-3-yl]cyclobutanecarboxamide
20  2,2-difluoro-N-[(2S,3R)-2-(4-fluoro-3-methoxy-phenyl)-1-[1-(4-fluorophenyl)indazol-5-yl]-5-oxo-pyrrolidin-3-yl]propanamide
21  2,2-difluoro-N-[(2R,3S)-2-(4-fluoro-3-methoxy-phenyl)-1-[1-(4-fluorophenyl)indazol-5-yl]-5-oxo-pyrrolidin-3-yl]propanamide
22  1-methyl-N-[rac-(2R,3S)-1-[1-(4-fluorophenyl)indazol-5-yl]-2-(3-methoxyphenyl)-5-oxo-pyrrolidin-3-yl]cyclopropanecarboxamide
23  1-fluoro-N-[rac-(2R,3S)-1-[1-(4-fluorophenyl)indazol-5-yl]-2-(3-methoxyphenyl)-5-oxo-pyrrolidin-3-yl]cyclopropanecarboxamide
24  2,2-difluoro-N-[(2S,3R)-2-(2-fluorophenyl)-1-[1-(4-fluorophenyl)indazol-5-yl]-5-oxo-pyrrolidin-3-yl]propanamide
25  2,2-difluoro-N-[rac-(2R,3S)-1-[1-(3-fluorophenyl)indazol-5-yl]-5-oxo-2-phenyl-pyrrolidin-3-yl]propanamide
26  2,2-difluoro-N-[rac-(2R,3S)-2-(3,5-difluorophenyl)-1-[1-(4-fluorophenyl)indazol-5-yl]-5-oxo-pyrrolidin-3-yl]propanamide
27  2,2-difluoro-N-[rac-(2R,3S)-5-oxo-2-phenyl-1-(1-phenylindazol-5-yl)pyrrolidin-3-yl]propanamide
28  N-[(2R,3S)-2-(2-fluorophenyl)-1-[1-(4-fluorophenyl)indazol-5-yl]-5-oxo-pyrrolidin-3-yl]cyclopropanecarboxamide
29  2,2-difluoro-N-[rac-(2R,3S)-1-[1-(4-cyanophenyl)indazol-5-yl]-5-oxo-2-phenyl-pyrrolidin-3-yl]propanamide
30  2,2-difluoro-N-[rac-(2R,3S)-1-[1-(3-cyanophenyl)indazol-5-yl]-5-oxo-2-phenyl-pyrrolidin-3-yl]propanamide
31  2,2-difluoro-N-[rac-(2R,3S)-2-(3-chlorophenyl)-1-[1-(4-fluorophenyl)indazol-5-yl]-5-oxo-pyrrolidin-3-yl]propanamide
32  N-[rac-(2R,3S)-2-(3-chlorophenyl)-1-[1-(4-fluorophenyl)indazol-5-yl]-5-oxo-pyrrolidin-3-yl]cyclobutanecarboxamide
33  2,2-difluoro-N-[(2R,3S)-2-(2-fluorophenyl)-1-[1-(4-fluorophenyl)indazol-5-yl]-5-oxo-pyrrolidin-3-yl]propanamide
34  N-[(2S,3R)-2-(4-fluoro-3-methoxy-phenyl)-1-[1-(4-fluorophenyl)indazol-5-yl]-5-oxo-pyrrolidin-3-yl]cyclopropanecarboxamide
36  2,2-difluoro-N-[rac-(2S,3S)-2-cyclopropyl-1-[1-(4-fluorophenyl)indazol-5-yl]-5-oxo-pyrrolidin-3-yl]propanamide
37  1-cyclopropyl-N-[rac-(2R,3S)-2-(3-chlorophenyl)-1-[1-(4-fluorophenyl)indazol-5-yl]-5-oxo-pyrrolidin-3-yl]methanesulfonamide
38  2,2-difluoro-N-[(2S,3R)-1-[1-(4-fluorophenyl)indazol-5-yl]-2-(o-tolyl)-5-oxo-pyrrolidin-3-yl]propanamide
39  N-[(2S,3R)-1-[1-(4-fluorophenyl)indazol-5-yl]-5-oxo-2-phenyl-pyrrolidin-3-yl]cyclopropanecarboxamide
42  2,2-difluoro-N-[(2S,3R)-2-(2-fluoro-5-methoxy-phenyl)-1-[1-(4-fluorophenyl)indazol-5-yl]-5-oxo-pyrrolidin-3-yl]propanamide
43  N-[(2S,3R)-2-(2-fluoro-5-methoxy-phenyl)-1-[1-(4-fluorophenyl)indazol-5-yl]-5-oxo-pyrrolidin-3-yl]cyclopropanecarboxamide
45  1:1 mixture of (1S,2S)-2-fluoro-N-[(2R,3S)-2-(4-fluorophenyl)-1-[1-(4-fluorophenyl)indazol-5-yl]-5-oxo-pyrrolidin-3-yl]cyclopropanecarboxamide and (1S,2S)-2-fluoro-N-[(2S,3R)-2-(4-fluorophenyl)-1-[1-(4-fluorophenyl)indazol-5-yl]-5-oxo-pyrrolidin-3-yl]cyclopropanecarboxamide
46  rac-(1S,2R)-2-fluoro-N-[rac-(2R,3S)-1-[1-(4-fluorophenyl)indazol-5-yl]-2-(3-methoxyphenyl)-5-oxo-pyrrolidin-3-yl]cyclopropanecarboxamide
48  2,2-difluoro-N-[rac-(2S,3R)-2-cyclopropyl-1-[1-(4-fluorophenyl)indazol-5-yl]-5-oxo-pyrrolidin-3-yl]propanamide
49  N-[(2R,3S)-1-[1-(4-fluorophenyl)indazol-5-yl]-2-(2-methoxy-4-pyridyl)-5-oxo-pyrrolidin-3-yl]cyclopropanecarboxamide
51  N-[rac-(2R,3S)-2-(4-fluorophenyl)-1-[1-(4-fluorophenyl)indazol-5-yl]-5-oxo-pyrrolidin-3-yl]cyclopropanesulfonamide
52  2-methyl-N-[rac-(2R,3S)-2-(3-fluorophenyl)-1-[1-(4-fluorophenyl)indazol-5-yl]-5-oxo-pyrrolidin-3-yl]cyclopropanecarboxamide
53  N-[(2R,3S)-1-[1-(4-fluorophenyl)indazol-5-yl]-2-(o-tolyl)-5-oxo-pyrrolidin-3-yl]cyclopropanecarboxamide
54  N-[rac-(2R,3S)-2-(4-fluorophenyl)-1-[1-(4-fluorophenyl)indazol-5-yl]-5-oxo-pyrrolidin-3-yl]cyclopropanecarboxamide
55  N-[rac-(2R,3S)-1-[1-(4-fluorophenyl)indazol-5-yl]-2-(3-methoxyphenyl)-5-oxo-pyrrolidin-3-yl]cyclopropanecarboxamide
56  1:1 mixture of (1R,2R)-2-fluoro-N-[(2R,3S)-2-(4-fluorophenyl)-1-[1-(4-fluorophenyl)indazol-5-yl]-5-oxo-pyrrolidin-3-yl]cyclopropanecarboxamide and (1R,2R)-2- fluoro-N-[(2S,3R)-2-(4-fluorophenyl)-1-[1-(4-fluorophenyl)indazol-5-yl]-5-oxo-pyrrolidin-3-yl]cyclopropanecarboxamide 61  N-[rac-(2R,3S)-2-(3-fluorophenyl)-1-[1-(4-fluorophenyl)indazol-5-yl]-5-oxo-pyrrolidin-3-yl]cyclopropanecarboxamide 62  N-[(2R,3S)-2-(2-fluoro-5-methoxy-phenyl)-1-[1-(4-fluorophenyl)indazol-5-yl]-5-oxo-pyrrolidin-3-yl]cyclopropanecarboxamide 63  1:1 mixture of (1R,2R)-2-fluoro-N-[(2R,3S)-1-[1-(4-fluorophenyl)indazol-5-yl]-2-(3-methoxyphenyl)-5-oxo-pyrrolidin-3-yl]cyclopropanecarboxamide and (1R,2R)-2-fluoro-N-[(2S,3R)-1-[1-(4-fluorophenyl)indazol-5-yl]-2-(3-methoxyphenyl)-5-oxo-pyrrolidin-3-yl]cyclopropanecarboxamide 65  N-[(2R,3S)-1-[1-(4-fluorophenyl)indazol-5-yl]-5-oxo-2-phenyl-pyrrolidin-3-yl]cyclopropanecarboxamide 66  N-[rac-(2R,3S)-2-(3-fluorophenyl)-1-[1-(4-fluorophenyl)indazol-5-yl]-5-oxo-pyrrolidin-3-yl]acetamide 67  N-[rac-(2R,3S)-2-(3-chlorophenyl)-1-[1-(4-fluorophenyl)indazol-5-yl]-5-oxo-pyrrolidin-3-yl]cyclopropanecarboxamide 68  2,2-difluoro-N-[rac-(2R,3S)-2-(3-fluorophenyl)-1-[1-(4-fluorophenyl)indazol-5-yl]-5-oxo-pyrrolidin-3-yl]propanamide 69  2,2-difluoro-N-[(2R,3S)-2-(2-fluoro-5-methoxy-phenyl)-1-[1-(4-fluorophenyl)indazol-5-yl]-5-oxo-pyrrolidin-3-yl]propanamide 70  1-fluoro-N-[rac-(2R,3S)-2-(4-fluorophenyl)-1-[1-(4-fluorophenyl)indazol-5-yl]-5-oxo-pyrrolidin-3-yl]cyclopropanecarboxamide 71  N-[rac-(2R,3S)-2-(4-fluorophenyl)-1-[1-(4-fluorophenyl)indazol-5-yl]-5-oxo-pyrrolidin-3-yl]-1-(trifluoromethyl)cyclopropanecarboxamide 72  2,2-difluoro-N-[(2R,3S)-1-[1-(4-fluorophenyl)indazol-5-yl]-2-(o-tolyl)-5-oxo-pyrrolidin-3-yl]propanamide 73  1-fluoro-N-[(2R,3S)-1-[1-(4-fluorophenyl)indazol-5-yl]-5-oxo-2-phenyl-pyrrolidin-3-yl]cyclopropanecarboxamide 74  N-[(2R,3S)-1-[1-(4-fluorophenyl)indazol-5-yl]-5-oxo-2-phenyl-pyrrolidin-3-yl]-1-methyl-cyclopropanecarboxamide 75  2,2-difluoro-N-[rac-(2R,3S)-1-[1-(4,4-difluorocyclohexyl)indazol-5-yl]-5-oxo-2-phenyl-pyrrolidin-3-yl]propanamide 76  2,2-difluoro-N-[rac-(2R,3S)-1-(1-cyclohexylindazol-5-yl)-5-oxo-2-phenyl-pyrrolidin-3-yl]propanamide 77  2,2-difluoro-N-[rac-(2R,3S)-2-(2-fluoro-5-methoxy-phenyl)-1-(1-methylindazol-5-yl)-5-oxo-pyrrolidin-3-yl]propanamide 78  2,2-difluoro-N-[rac-(2R,3S)-1-[1-(2,2-difluoroethyl)indazol-5-yl]-2-(2-fluoro-5-methoxy-phenyl)-5-oxo-pyrrolidin-3-yl]propanamide 79  2,2-difluoro-N-[rac-(2R,3S)-1-[1-[(2-fluorophenyl)methyl]indazol-5-yl]-5-oxo-2-phenyl-pyrrolidin-3-yl]propanamide 80  2,2-difluoro-N-[rac-(2R,3S)-1-[1-[(3-fluorophenyl)methyl]indazol-5-yl]-5-oxo-2-phenyl-pyrrolidin-3-yl]propanamide 81  2,2-difluoro-N-[rac-(2R,3S)-1-[1-[(4-fluorophenyl)methyl]indazol-5-yl]-5-oxo-2-phenyl-pyrrolidin-3-yl]propanamide 82  2,2-difluoro-N-[rac-(2R,3S)-1-[1-(cyclopropylmethyl)indazol-5-yl]-5-oxo-2-phenyl-pyrrolidin-3-yl]propanamide 84  2,2-difluoro-N-[rac-(2R,3S)-1-[1-[(4,4-difluorocyclohexyl)methyl]indazol-5-yl]-5-oxo-2-phenyl-pyrrolidin-3-yl]propanamide 85  2,2-difluoro-N-[rac-(2R,3S)-2-(4-fluorophenyl)-1-[1-[(2-fluorophenyl)methyl]indazol-5-yl]-5-oxo-pyrrolidin-3-yl]propanamide 86  2,2-difluoro-N-[rac-(2R,3S)-2-(4-fluorophenyl)-1-[1-[(4-fluorophenyl)methyl]indazol-5-yl]-5-oxo-pyrrolidin-3-yl]propanamide 87  2,2-difluoro-N-[rac-(2R,3S)-2-(4-fluorophenyl)-1-[1-[(3-fluorophenyl)methyl]indazol-5-yl]-5-oxo-pyrrolidin-3-yl]propanamide 88  N-[(2R,3S)-2-benzyl-1-(1-(4-fluorophenyl)-1H-indazol-5-yl)-5-oxopyrrolidin-3-yl]-2,2-difluoropropanamide 89  2,2-difluoro-N-[rac-(2R,3S)-2-ethyl-1-[1-(4-fluorophenyl)indazol-5-yl]-5-oxopyrrolidin-3-yl]propanamide 90  2,2-difluoro-N-[rac-(2R,3R)-2-(cyclopropylmethyl)-1-[1-(4-fluorophenyl)indazol-5-yl]-5-oxopyrrolidin-3-yl]propanamide 91  2-cyclopropyl-N-[(2S,3R)-1-(1-(4-fluorophenyl)-1H-indazol-5-yl)-5-oxo-2-phenylpyrrolidin-3-yl]acetamide 92  N-[(2R,3S)-1-(1-(4-fluorophenyl)-1H-indazol-5-yl)-5-oxo-2-phenylpyrrolidin-3-yl]-1-methyl-1H-pyrazole-3-carboxamide 93  N-[(2R,3S)-1-(1-(4-fluorophenyl)-1H-indazol-5-yl)-5-oxo-2-phenylpyrrolidin-3-yl]-1H-imidazole-2-carboxamide 94  N-[(2R,3S)-1-(1-(4-fluorophenyl)-1H-indazol-5-yl)-5-oxo-2-phenylpyrrolidin-3-yl]-2-methyloxazole-5-carboxamide 95  N-[(2R,3S)-1-(1-(4-fluorophenyl)-1H-indazol-5-yl)-5-oxo-2-phenylpyrrolidin-3-yl]-5-methylthiazole-4-carboxamide 96  N-[(2R,3S)-1-(1-(4-fluorophenyl)-1H-indazol-5-yl)-5-oxo-2-phenylpyrrolidin-3-yl]pyrimidine-2-carboxamide 97  N-[(2R,3S)-1-(1-(4-fluorophenyl)-1H-indazol-5-yl)-5-oxo-2-phenylpyrrolidin-3-yl]nicotinamide 98  N-[(2R,3S)-1-(1-(4-fluorophenyl)-1H-indazol-5-yl)-5-oxo-2-phenylpyrrolidin-3-yl]oxetane-3-carboxamide 99  N-[(2R,3S)-1-(1-(4-fluorophenyl)-1H-indazol-5-yl)-5-oxo-2-phenylpyrrolidin-3-yl]thiazole-5-sulfonamide 100 N-[rac-(2R,3R)-2-(5-chlorothiophen-2-yl)-1-[1-(4-fluorophenyl)indazol-5-yl]-5-oxopyrrolidin-3-yl]cyclopropanesulfonamide 101  2,2-difluoro-N-[rac-(2R,3S)-1-[1-(4-fluorophenyl)pyrazolo[3,4-b]pyridin-5-yl]-5-oxo-2-phenylpyrrolidin-3-yl]propanamide 102  2,2-difluoro-N-[rac-(2R,3S)-1-[1-(4-fluorophenyl)pyrazolo[3,4-c]pyridin-5-yl]-5-oxo-2-phenylpyrrolidin-3-yl]propanamide 103  2,2-difluoro-N-[rac-(2R,3S)-1-[1-(4-fluorophenyl)pyrazolo[4,3-b]pyridin-5-yl]-5-oxo-2-phenylpyrrolidin-3-yl]propanamide in each case in the form of the free compound or a physiologically acceptable salt thereof.

The compounds according to the invention can be synthesized by standard reactions in the field of organic chemistry known to the person skilled in the art or in a manner as described herein (cf. Reaction Schemes below) or analogously. The reaction conditions in the synthesis routes described herein are known to the skilled person and are for some cases also exemplified in the Examples described herein.

Reaction scheme 1

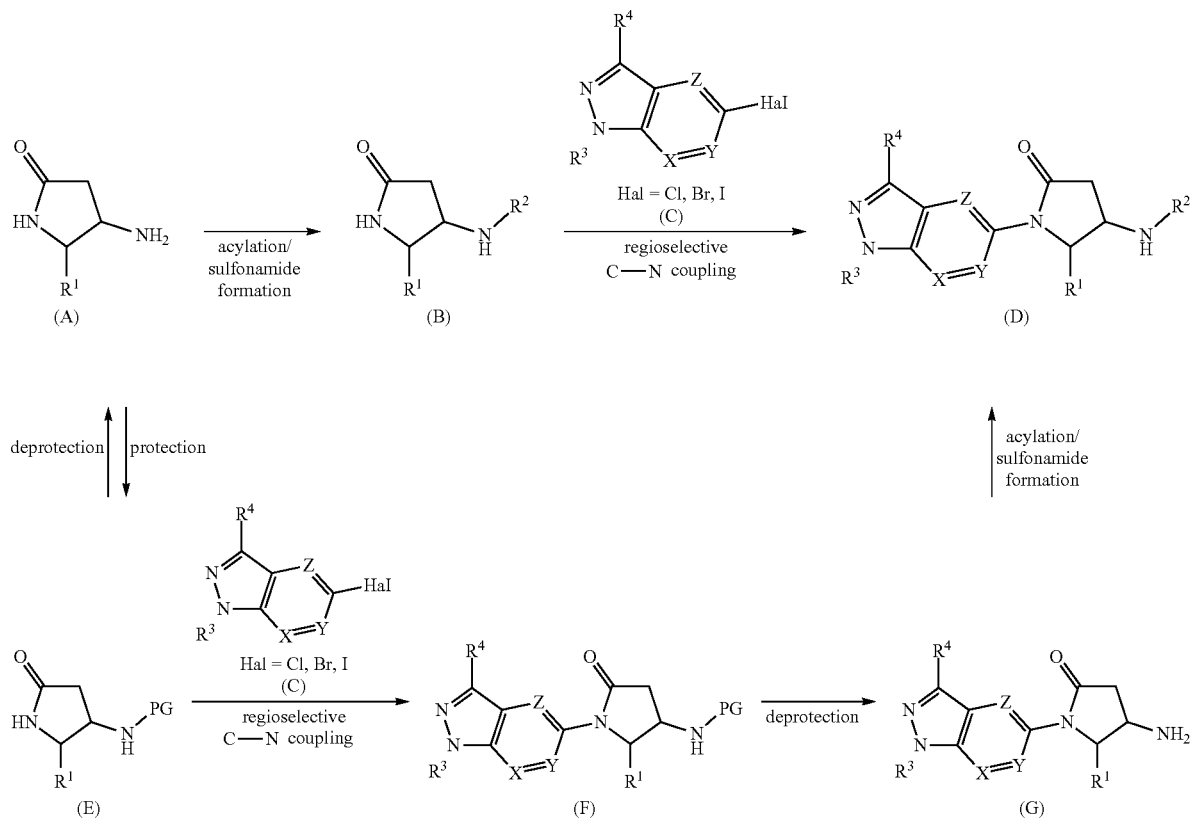

Substituted indazole moieties in compounds of formula (D) and formula (F) are introduced by subjecting lactam (B) or lactam (E) in a regioselective metal catalyzed C—N coupling reaction with corresponding indazole halides (C), preferred with corresponding indazole iodides. Metal catalyzed C—N coupling reactions are generally known in the art (*Current Organic Synthesis*, 2011, 8, 53). Favorable C—N coupling reactions are palladium and copper catalyzed cross-coupling reactions (*Chem. Rev.*, 2016, 116, 12564; *Chem. Soc. Rev.*, 2014, 43, 3525; *Chem. Sci.*, 2010, 1, 13). Regioselective C—N couplings with arylhalides are known in the art (*Chem. Sci.*, 2011, 2, 27; *J. Am. Chem. Soc.*, 2001, 123, 7727).

Primary amines (A) and (G) are converted to corresponding amides and sulfonamides (acylation and sulfonamide formation) (B) and (D) using commercially available acids (activation of acids using e.g. HATU) or acid chlorides under standard amide coupling reaction conditions (*March's Advanced Organic Chemistry*, 2007, 6th Edition, page 1427-1474).

Introduction of different orthogonal protecting groups PG (e.g. Boc, Cbz) to convert (A) to (E) as well as deprotection of compounds of formula (E) to (A) is well described in the literature (T. W. Green, P. G. M. Wuts, *Protective Groups in Organic Synthesis*, Wiley-Interscience, New York, 1999).

Reaction scheme 1.1
Compounds (A) and (E) can be synthesized according to procedures which are described in the literature.

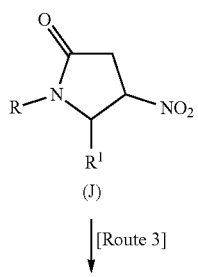

[Route 3]

-continued

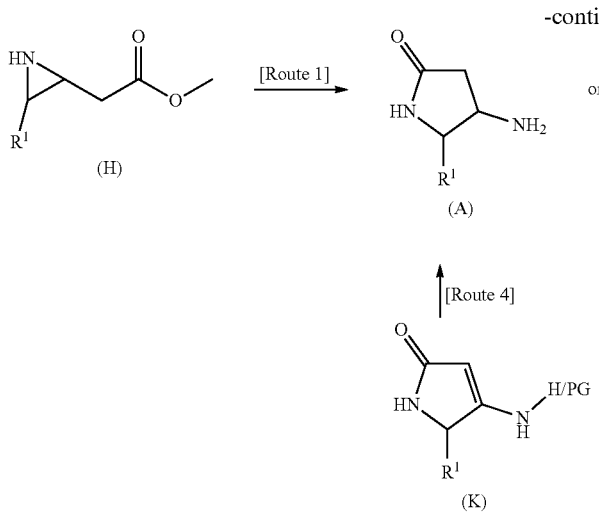
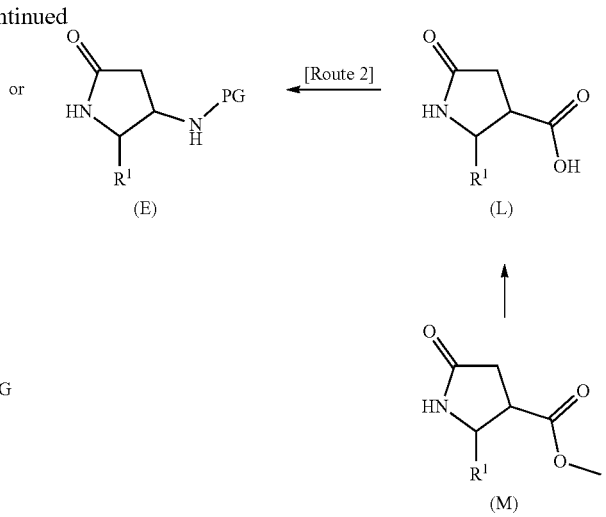

Route 1: Compounds of formula (A) and (E) can be synthesized starting from compounds of formula (H) (*J. Org. Chem.*, 2010, 76, 948).

Route 2: Synthesis of compounds of formula (M) and (L) is described in the literature (*J. Org. Chem.*, 2007, 72, 5016; *Org. Lett.*, 2007, 9, 4077; *J. Org. Chem.*, 2012, 77, 160). Compounds of formula (A) and (E) can be synthesized using Curtius rearrangement as key step to convert carboxylic acid (L) to corresponding primary amine (A) or (E). Curtius rearrangement is well known in the art (*Tetrahedron Letters*, 2010, 385).

Route 3: Synthesis of compounds of formula (J) is described in the literature (Org. Lett., 2009, 11, 4512; *ACS Sustainable Chem. Eng.*, 2015, 3, 1873). Reduction of highly functionalized lactams (J) gives an alternate route for synthesis of compounds of formula (A) and (E). Reduction of nitro groups is well known in the art (*March's Advanced Organic Chemistry*, 2007, 6th Edition, page 1815f).

Route 4: Synthesis of compounds of formula (K) is described in the literature (*J. Heterocyclic Chem.*, 2014, 51, E25). Reduction of highly functionalized lactams (K) gives an alternate route for synthesis of compounds of formula (A) and (E). Reduction of enamides/imines is well known in the art (*March's Advanced Organic Chemistry*, 2007, 6th Edition, page 1053f and page 1811f).

Reaction scheme 2

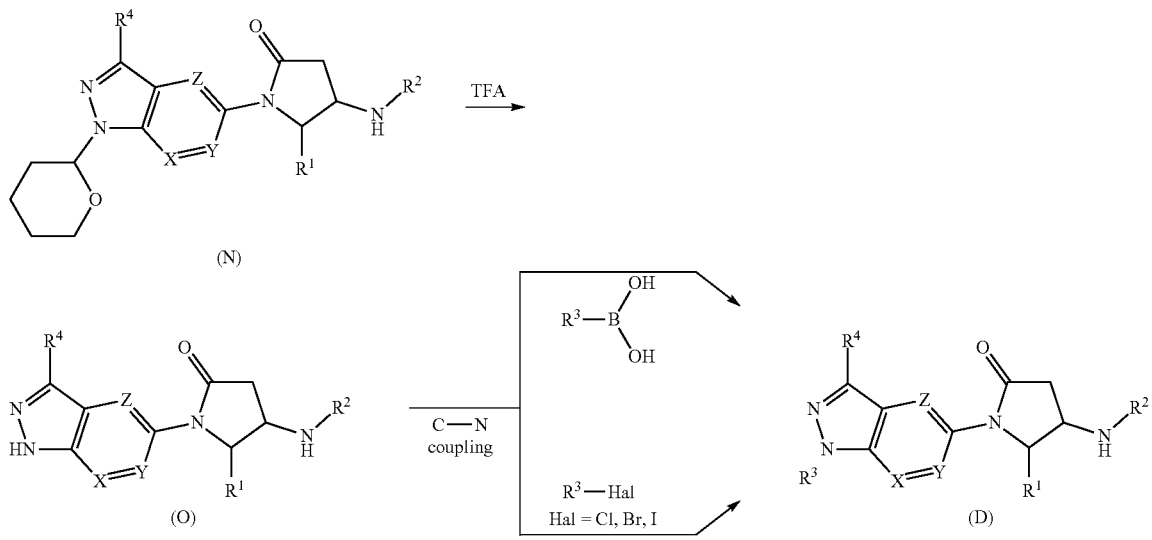

Compounds of formula (D) can be synthesized via regioselective C—N coupling of compound (O). Suitable C—N coupling reactions for N—H containing heterocycles are known in the art (Synthesis, 2011, 829; *Chem. Sci.*, 2011, 2, 27; Beilstein *J. Org. Chem.*, 2011, 7, 59; *J. Org. Chem.*, 2004, 69, 5578). Compound of formula (O) is synthesized via deprotection of compound (N) under acidic conditions.

The compounds according to the invention can be produced in the manner described here or in an analogous manner.

In a preferred embodiment, the compounds according to the invention are modulators of the glucocorticoid receptor.

In the sense of the invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 µM ($10 \cdot 10^{-6}$ mol/L) or at most 10 µM; more preferably at most 1 µM; still more preferably at most 500 nM ($10^{-9}$ mol/L); yet more preferably at most 300 nM; even more preferably at most 100 nM; most preferably at most 10 nM; and in particular at most 1 nM. In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor fragments used are capable of binding the ligand (e.g. beclomethasone) to identify molecules that compete for binding with glucocorticoid receptor ligands. In more detail, the glucocorticoid receptor ligand binding domain is fused to the DNA binding domain (DBD) of the transcriptionfactor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calculated. Engagement of molecules which induce gene expression via glucocortocoid receptor binding to the DNA leads to expression of the luciferase gene under the control of the fusion protein GAL4 DBD-GR and therefore to a dose dependent increase of the luminescence signal. Binding of molecules which repress beclomethasone-induced gene expression of the luciferase gene under the control of the fusion protein GAL4 DBD-GR leads to a dose dependent reduction of the luminescence signal.

In a preferred embodiment, the compound according to the invention exhibits in a cellular target engagement assay for agonistic or antagonistic potency on the glucocorticoid receptor an EC50 or IC50 value on the glucocorticoid receptor of at most 1 µM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Preferably, the compounds according to the invention are useful as selective modulators of the glucocorticoid receptor.

Therefore, the compounds according to the invention are preferably useful for the in vivo treatment or prevention of diseases in which participation of the glucocorticoid receptor is implicated.

The invention therefore further relates to a compound according to the invention for use in the modulation of glucocorticoid receptor activity.

Therefore, another aspect of the invention relates to a compound according to the invention for use in the treatment and/or prophylaxis of a disorder which is mediated at least in part by the glucocorticoid receptor. Still another aspect of the invention relates to a method of treatment of a disorder which is mediated at least in part by the glucocorticoid receptor comprising the administration of a therapeutically effective amount of a compound according to the invention to a subject in need thereof, preferably a human.

A further aspect of the invention relates to the use of a compound according to the invention as medicament.

Another aspect of the invention relates to a pharmaceutical dosage form comprising a compound according to the invention. Preferably, the pharmaceutical dosage form comprises a compound according to the invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical dosage form according to the invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the invention is preferably prepared with the aid of conventional means, devices, methods and processes known in the art. The amount of the compound according to the invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the invention are administered per kg of the patient's body weight.

The glucocorticoid receptor is believed to have potential to modify a variety of diseases or disorders in mammals such as humans. These include in particular inflammatory diseases, asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and Crohn's disease.

Further diseases and disorders that are believed to be modulated by the glucocorticoid receptor include endocrine disorders, preferably selected from primary or secondary adrenocortical insufficiency, congenital adrenal hyperplasia, hypercalcemia associated with cancer, and nonsuppurative thyroiditis; rheumatic disorders; preferably selected from psoriatic arthritis, rheumatoid arthritis, juvenile rheumatoid arthritis, ankylosing spondilitis, acute and subacute bursistis, acute nonspecific tenosynovitis, acute gouty arthritis, post-traumatic osteoarthritis, synovitis of osteoarthritis and epicondylitis; collagen diseases, preferably selected from systemic lupus erythematosus, systemic dermatomyositis (polymyositis) and acute rheumatic carditis; dermatologic diseases, preferably selected from pemphigus, bullous dermatitis herpetiformis, severe erythema multiforme (Stevens-Johnson syndrome), exfoliative dermatitis, mycosis fungoides, psoriasis and seborrheic dermatitis; allergic states, preferably selected from seasonal or perennial allergic rhinitis, bronchial asthma, contact dermatitis, atopic dermatitis, serum sickness and drug hypersensitivity reactions; ophthalmis diseases, preferably selected from allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis; respiratory diseases, preferably selected from symptomatic sarcoidosis, Loeffler's syndrome, berylliosis, fulminating or disseminated pulmonary tubercolosis when used concurrently with antituberculous chemotherapy, aspiration pneumonitis; hematologic disorders, preferably selected from idiopathic thrombocytopenic purpura, secondary thrombocytopenia, acquired (autoimmune) hemolytic anemia, erythroblastopenia (RBC anemia), congenital (erythroid) hypoplastic anemia; neoplastic diseases, preferably selected from leukemias and lyphomas, acute leukemia of childhood; gastrointestinal diseases, preferably selected from ulcerative colitis and regional enteritis.

Another aspect of the invention relates to a compound according to the invention for use in the treatment and/or prophylaxis of pain and/or inflammation; more preferably inflammatory pain.

Another aspect of the invention relates to a compound according to the invention for use in the treatment and/or prophylaxis of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

Still another aspect of the invention relates to a compound according to the invention for use in the treatment and/or prophylaxis of endocrine disorders, preferably selected from primary or secondary adrenocortical insufficiency, congenital adrenal hyperplasia, hypercalcemia associated with cancer, and nonsuppurative thyroiditis; rheumatic disorders; preferably selected from psoriatic arthritis, rheumatoid arthritis, juvenile rheumatoid arthritis, ankylosing spondilitis, acute and subacute bursistis, acute nonspecific tenosynovitis, acute gouty arthritis, post-traumatic osteoarthritis, synovitis of osteoarthritis and epicondylitis; collagen diseases, preferably selected from systemic lupus erythematosus, systemic dermatomyositis (polymyositis) and acute rheumatic carditis; dermatologic diseases, preferably selected from pemphigus, bullous dermatitis herpetiformis, severe erythema multiforme (Stevens-Johnson syndrome), exfoliative dermatitis, mycosis fungoides, psoriasis and seborrheic dermatitis; allergic states, preferably selected from seasonal or perennial allergic rhinitis, bronchial asthma, contact dermatitis, atopic dermatitis, serum sickness and drug hypersensitivity reactions; ophthalmis diseases, preferably selected from allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis; respiratory diseases, preferably selected from symptomatic sarcoidosis, Loeffler's syndrome, berylliosis, fulminating or disseminated pulmonary tubercolosis when used concurrently with antituberculous chemotherapy, aspiration pneumonitis; hematologic disorders, preferably selected from idiopathic thrombocytopenic purpura, secondary thrombocytopenia, acquired (autoimmune) hemolytic anemia, erythroblastopenia (RBC anemia), congenital (erythroid) hypoplastic anemia; neoplastic diseases, preferably selected from leukemias and lyphomas, acute leukemia of childhood; gastrointestinal diseases, preferably selected from ulcerative colitis and regional enteritis.

A further aspect of the invention relates to a method of treatment of pain and/or inflammation; more preferably inflammatory pain. Still a further aspect of the invention relates to a method of treatment of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

The following examples further illustrate the invention but are not to be construed as limiting its scope.

The following abbreviations are used in the descriptions of the experiments: AcOH=acetic acid; Attaphos=bis(di-tert-butyl(4 dimethylaminophenyl)phosphine)dichloropalladium(II); Cbz=carboxybenzyl; DCM=dichloromethane; DEA=diethylamine; DIPEA=N,N-diisopropylethylamine; DMAP=4-(dimethylamino)-pyridine; DMF=N,N-dimethylformamid; DMSO=dimethylsulfoxid; DPPA=diphenyl phosphoryl azide; dppf=1,1'; bis(diphenylphosphanyl)ferrocene; EA=ethyl acetate; EtOAc=ethyl acetate; EtOH=ethanol; HATU=1-[bis(dimethylamino)methylene]-1H-1,2,3-triazolo[4,5-b]pyridinium 3-oxid hexafluorophosphate; h=hour; LDA=lithiumdiisopropylamide; LiHMDS=lithium bis(trimethylsilyl)amide; MeOH=methanol; min=minute; n-BuLi=n-butyllithium; sat.=saturated; RT=room temperature; Rt=retention time; tert=tertiary; TEA=triethylamine; TFA=trifluoro acetic acid; THF=tetrahydrofuran; p-TSA=para-toluene sulfonic acid; TMSCl=trimethylsilyl chloride.

Synthesis of trans-4-amino-5-(3-chlorophenyl)pyrrolidin-2-one (Intermediate A1)

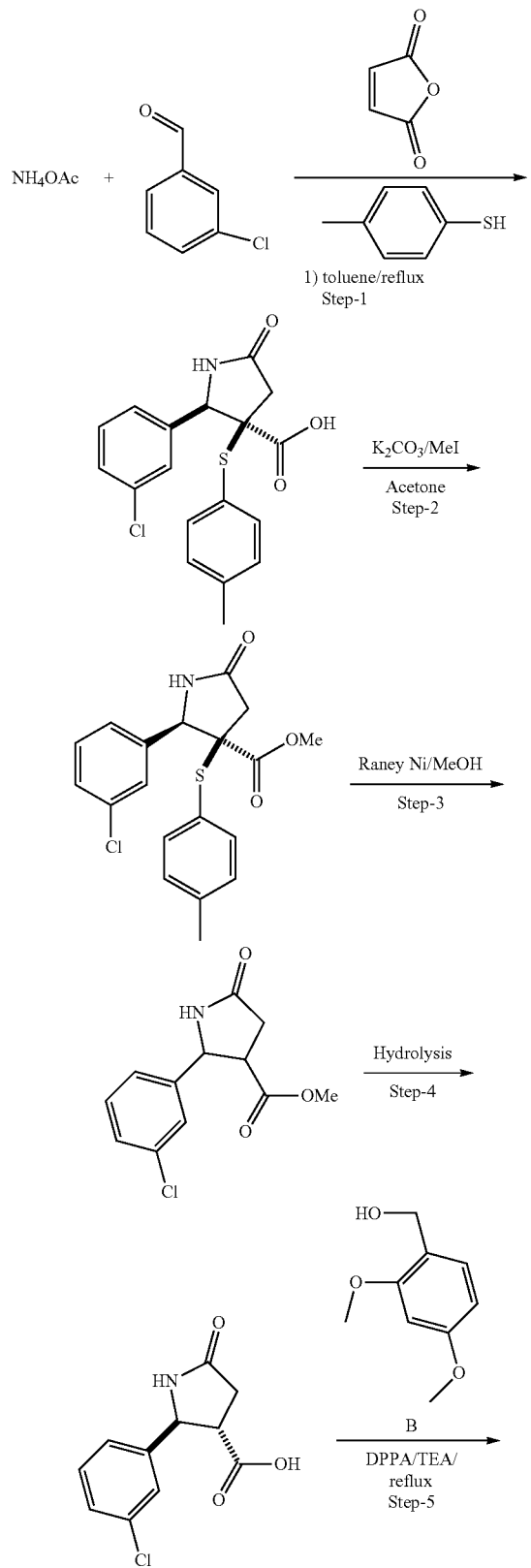

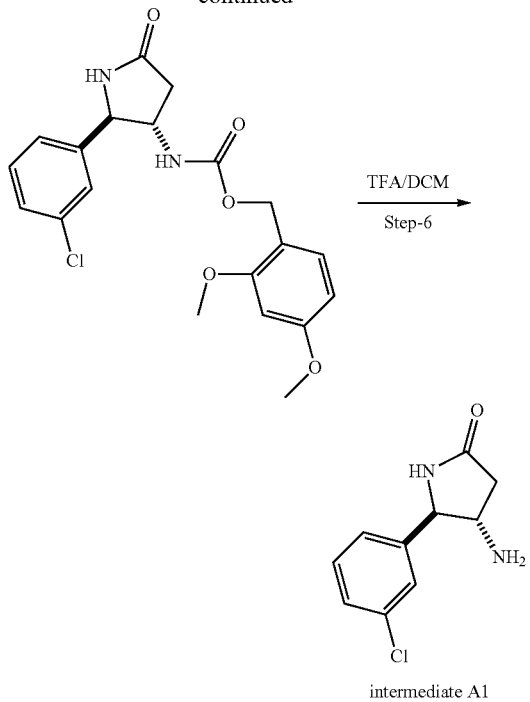

intermediate A1

Step 1: Maleic anhydride (9.8 g, 100 mmol, 1.0 eq), p-thiocresol (12.4 g, 100 mmol, 1.0 eq), ammonium acetate (7.8 g, 100 mmol, 1.0 eq), 3-chlorobenzaldehyde (11.5 mL, 100 mmol, 1.0 eq) and toluene (100 mL) were put in a sealed tube. The reaction mixture was stirred at RT for 1 h and then stirred at 150° C. for 16 h. After cooling to RT, the solvent was evaporated under reduced pressure, and the residue was basified with sat. NaHCO$_3$ solution and was extracted with DCM. The aqueous layer was acidified with 2N HCl under ice cooling and the crude product was extracted twice with EtOAc. The combined organic layers were washed with brine, dried over Na$_2$SO$_4$, filtered and concentrated to get the crude 2-(3-chlorophenyl)-5-oxo-3-(p-tolylthio)pyrrolidine-3-carboxylic acid (10.0 g).

Step 2: To a stirred solution of crude 2-(3-chlorophenyl)-5-oxo-3-(p-tolylthio)pyrrolidine-3-carboxylic acid (10.0 g, 27.7 mmol, 1.0 eq) in acetone (100 mL), potassium carbonate (15.3 g, 110.8 mmol, 4.0 eq) and methyl iodide (7.0 mL, 110.8 mmol, 4.0 eq) were added at 0° C. and the reaction mixture was stirred for 16 h at RT. The solvent was removed under reduced pressure, and the residue was partitioned between DCM and water. The aqueous layer was extracted twice with DCM. The combined organic layers were washed with brine, dried over Na$_2$SO$_4$, filtered and concentrated. The crude product was purified by column chromatography (100-200 silica gel, 50% EtOAc:hexanes) to give methyl 2-(3-chlorophenyl)-5-oxo-3-(p-tolylthio)pyrrolidine-3-carboxylate as an off white solid (4.0 g, 38%).

Step 3: To a stirred solution of methyl 2-(3-chlorophenyl)-5-oxo-3-(p-tolylthio)pyrrolidine-3-carboxylate (10.0 g, 26.66 mmol, 1.0 eq) in EtOH:THF (100 mL, 2:1), Raney Nickel (2.5 g) was added and the reaction mixture was stirred for 2 h at RT After completion, the reaction mixture was filtered through a celite bed and the celite bed was then washed 2-3 times with EtOAc.

The combined organic layers were concentrated and the crude product was purified by column chromatography (100-200 silica gel, 50% EtOAc:hexanes) to give methyl 2-(3-chlorophenyl)-5-oxopyrrolidine-3-carboxylate as an off white solid (6.0 g, 89%) (syn:anti, 1:1 mixture).

Step 4: To a stirred solution of methyl 2-(3-chlorophenyl)-5-oxopyrrolidine-3-carboxylate (3.0 g, 11.85 mmol, 1.0 eq) in MeOH (50 mL) was added 2 N NaOH solution (10 mL) and the reaction mixture was stirred at 80° C. for 2 h. After completion of the reaction (monitored by LCMS), the reaction mixture was concentrated and acidified with 2N HCl solution and the crude product was then extracted with 30% isopropanol-DCM. The combined organic layers were dried over Na$_2$SO$_4$ and concentrated under reduced pressure to get trans-2-(3-chlorophenyl)-5-oxopyrrolidine-3-carboxylic acid (2.5 g, 88%).

Step 5: To a stirred solution of trans-2-(3-chlorophenyl)-5-oxopyrrolidine-3-carboxylic acid (2.0 g, 8.36 mmol, 1.0 eq) in benzene:THF (100 mL, 4:1) were added TEA (2.35 mL, 16.73 mmol, 2.0 eq) and DPPA (2.35 ml, 10.8 mmol, 1.3 eq) and the reaction mixture was stirred at RT for 2 h. Then 2,4-dimethoxybenzyl alcohol (1.8 g, 10.87 mmol, 1.3 eq) was added to the reaction mixture and the reaction mixture was heated to reflux for 16 h. After completion, the reaction mixture was concentrated under reduced pressure to get the crude which was extracted with water and EtOAc. The combined organic layers were dried over Na$_2$SO$_4$ and concentrated under reduced pressure to get the crude product which was purified by column chromatography (100-200 mesh silica gel; 2% MeOH-DCM; R$_f$-value-0.5) to afford trans-2,4-dimethoxybenzyl (2-(3-chlorophenyl)-5-oxopyrrolidin-3-yl)carbamate (1.5 g, 44%).

Step 6: To a stirred solution of trans-2,4-dimethoxybenzyl (2-(3-chlorophenyl)-5-oxopyrrolidin-3-yl)carbamate (0.5 g, 1.23 mmol, 1.0 eq) in DCM (10 mL) was added TFA (2 mL) at 0° C., and the reaction was stirred for 3 h at RT After completion, the reaction mixture was diluted with EtOAc and washed with sat·NaHCO$_3$ solution. The combined organic layers were dried over Na$_2$SO$_4$ and concentrated to get the desired trans-4-amino-5-(3-chlorophenyl)pyrrolidin-2-one as a white solid (0.25 g, 96%).

Synthesis of
trans-4-amino-5-phenylpyrrolidin-2-one
(Intermediate A2)

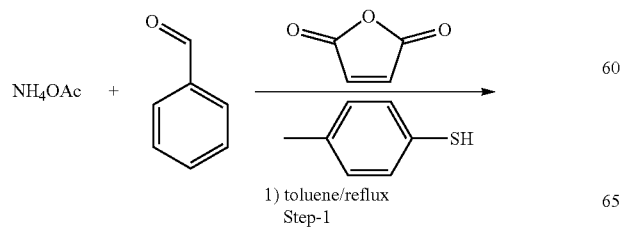

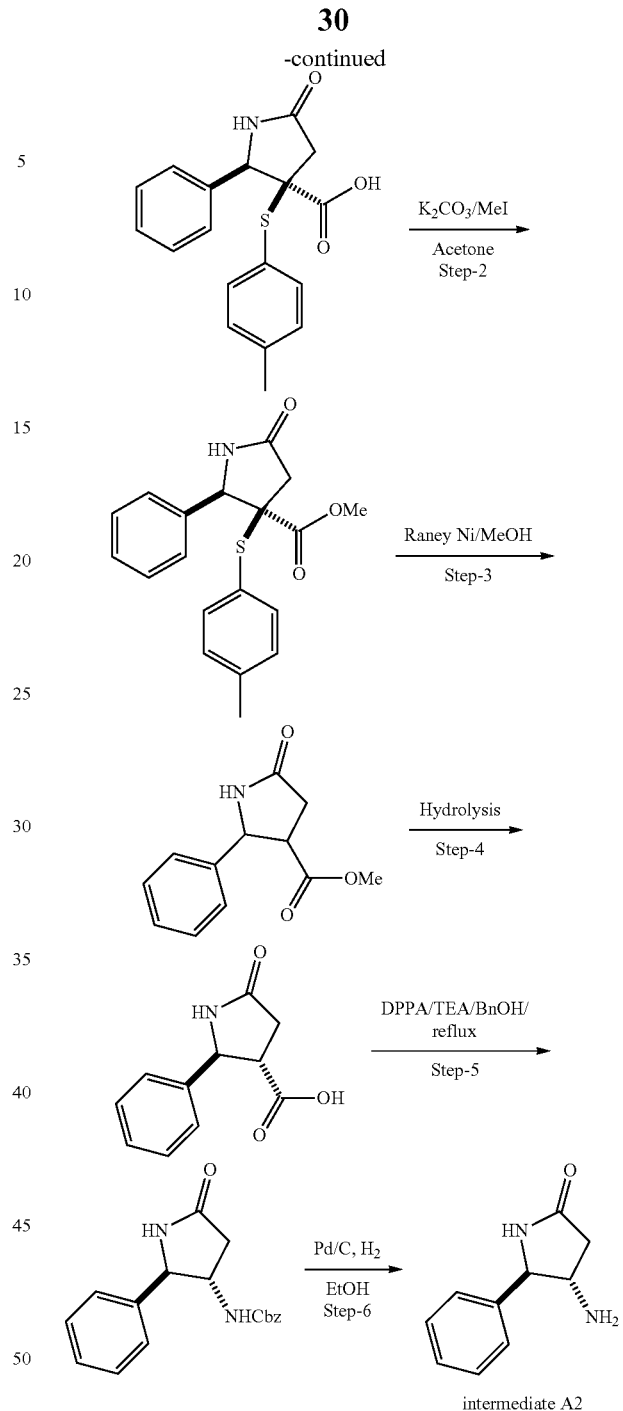

intermediate A2

Step 1: Maleic anhydride (9.8 g, 100 mmol, 1.0 eq), p-thiocresol (12.4 g, 100 mmol, 1.0 eq), ammonium acetate (7.8 g, 100 mmol, 1.0 eq) and benzaldehyde (10 mL, 100 mmol, 1.0 eq) were put in a sealed tube and 100 ml toluene was added. The reaction mixture was stirred at RT for 1 h and then stirred at 150° C. for 16 h. After cooling to RT, the solvent was evaporated under reduced pressure, and the residue was basified with sat·NaHCO$_3$ solution and was extracted with DCM. The aqueous layer was acidified with 2N HCl under ice cooling and the crude product was extracted twice with EtOAc. The combined organic layers were washed with brine, dried over Na$_2$SO$_4$, filtered and concentrated to get the crude 5-oxo-2-phenyl-3-(p-tolylthio)pyrrolidine-3-carboxylic acid (10.0 g, crude).

Step 2: To a stirred solution of crude 5-oxo-2-phenyl-3-(p-tolylthio)pyrrolidine-3-carboxylic acid (10.0 g, 30.58 mmol, 1.0 eq) in acetone (100 mL), potassium carbonate (16.8 g, 122.32 mmol, 4.0 eq) and methyl iodide (7.6 ml, 122.32 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over $Na_2SO_4$, filtered, and concentrated. The crude product was purified by column chromatography (100-200 silica gel, 50% EtOAc:hexanes) to give methyl 5-oxo-2-phenyl-3-(p-tolylthio)pyrrolidine-3-carboxylate (4.0 g, 38%) as an off-white solid.

Step 3: To a stirred solution of methyl 5-oxo-2-phenyl-3-(p-tolylthio)pyrrolidine-3-carboxylate (4.0 g, 11.73 mmol, 1.0 eq) in EtOH:THF (100 mL, 2:1), Raney Nickel (1 g) was added and the reaction mixture was stirred for 2 h at RT After completion, the reaction mixture was filtered through a celite bed and the celite bed was washed 2-3 times with EtOAc. The combined organic layers were concentrated and the crude was purified by column chromatography (100-200 silica gel, 50% EtOAc:hexanes) to afford methyl 5-oxo-2-phenylpyrrolidine-3-carboxylate (2.2 g, 88%, syn:anti, 1:1 mixture) as an off-white solid.

Step 4: To a stirred solution of methyl 5-oxo-2-phenylpyrrolidine-3-carboxylate (1.0 g, 4.56 mmol, 1.0 eq) in MeOH (25 mL) was added 2 N NaOH solution (5 mL) and the reaction mixture was stirred at 80° C. for 2 h. After completion of the reaction (monitored by LCMS), the reaction mixture was concentrated and acidified with 2N HCl solution and was extracted with 30% isopropanol-DCM. The combined organic layers were dried over $Na_2SO_4$ and were concentrated under reduced pressure to get the desired trans-5-oxo-2-phenylpyrrolidine-3-carboxylic acid (0.8 g, 85%).

Step 5: To a stirred solution of trans-5-oxo-2-phenylpyrrolidine-3-carboxylic acid (0.5 g, 2.43 mmol, 1.0 eq) in benzene:THF (25 mL, 4:1) was added TEA (0.68 ml, 4.87 mmol, 2.0 eq) and DPPA (0.68 ml, 3.17 mmol, 1.3 eq) and the reaction mixture was stirred at RT for 2 h. Then benzyl alcohol (0.33 mL, 3.17 mmol, 1.3 eq) was added and the reaction mixture was heated to reflux for 16 h. After completion, the reaction mixture was concentrated under reduced pressure to get the crude compound which was extracted with water and EtOAc. The combined organic layers were dried over $Na_2SO_4$ and concentrated under reduced pressure to get the crude product which was purified by column chromatography (100-200 mesh silica gel; 2% MeOH-DCM; $R_f$-value-0.5) to afford trans-benzyl (5-oxo-2-phenylpyrrolidin-3-yl)carbamate (0.38 g, 50%).

Step 6: To a stirred solution of trans-benzyl (5-oxo-2-phenylpyrrolidin-3-yl)carbamate (1.7 g, 5.48 mmol, 1.0 eq) in MeOH (20 mL, 2:1), Pd/C (0.058 g, 0.548 mmol, 0.1 eq) was added, and the reaction was stirred with a hydrogen balloon for 2 h at RT. After completion, the reaction mixture was filtered through a celite bed and the celite bed was washed 2-3 times with EtOAc. The combined organic layers were concentrated to get the desired trans-4-amino-5-phenylpyrrolidin-2-one as brown gum (0.9 g, 93%).

Synthesis of (4S,5R)-4-amino-5-phenylpyrrolidin-2-one (Intermediate A2-ent2)

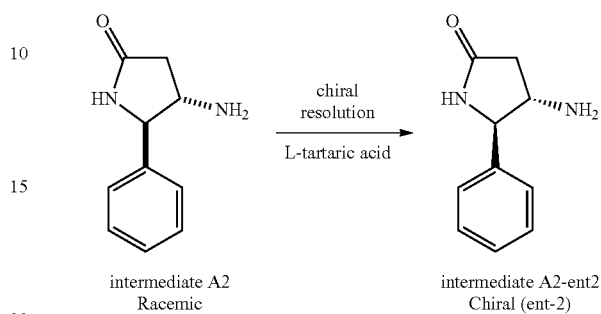

intermediate A2
Racemic intermediate A2-ent2
Chiral (ent-2)

To a stirred solution of trans-4-amino-5-phenyl-pyrrolidin-2-one (Intermediate A2) (10.0 g, 0.056 mol) in EtOH (180 mL) and acetonitrile (200 mL) was added L-tartaric acid (8.5 g, 0.056 mol) at RT. The resulting suspension was stirred at 90° C. for 1 h. To this refluxing suspension was slowly added water (110 mL). The resulting reaction mixture was maintained at 90° C. and was stirred for 4 h. The resulting clear solution was slowly cooled to RT and was allowed to stand at RT for 24 h. The solid thus precipitated was collected by filtration and washed with EtOH (100 mL) to afford 7.5 g of chiral (ent-2) as the corresponding L-tartrate salt. This solid material was treated with 1N aq. NaOH solution at RT. The resulting basic aqueous solution was then extracted with 10% MeOH in DCM (100 mL x 5-6 times) to afford (4S,5R)-4-amino-5-phenyl-pyrrolidin-2-one (3 g, 60%) as a white solid (intermediate A2-ent2).

Enantiomeric excess (ee) determined by chiral HPLC (Column Name: Chiralpak IA (4.6×250 mm), 5 μm; Mobile Phase: Hexane/EtOH/IP amine: 80/20/0.1; Flow Rate: 1.0 ml/min; RT=25.0 min): ee=99.7%

Specific Rotation: [+29.9°] at 25° C., C=1% in EtOH.

Synthesis of (4R,5S)-4-amino-5-phenylpyrrolidin-2-one (Intermediate A2-ent1)

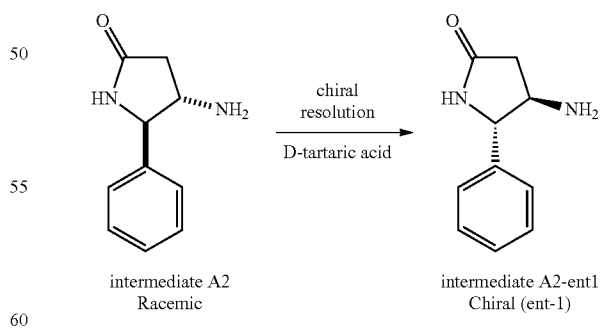

intermediate A2
Racemic intermediate A2-ent1
Chiral (ent-1)

To a stirred solution of trans-4-amino-5-phenyl-pyrrolidin-2-one (intermediate A2) (7.0 g, 39.77 mmol) in EtOH (126 mL) and acetonitrile (140 mL) was added D-tartaric acid (5.96 g, 39.77 mmol) at RT. The resulting suspension was stirred at 90° C. for 1 h. To this refluxing suspension was slowly added water (77 mL). The resulting reaction mixture was maintained at 90° C. for 4 h. The resulting clear solution was slowly cooled to RT and was allowed to stand at RT for 24 h. The solid thus precipitated was collected by filtration and washed with EtOH (70 mL) to afford 5.2 g of chiral (ent-1) as the corresponding D-tartrate salt as an off-white solid. (4R,5S)-4-amino-5-phenylpyrrolidin-2-one (2R,3R)-2,3-dihydroxysuccinate (5.2 g) was treated with 1N NaOH solution at RT. The resulting basic aqueous solution was then extracted with 10% MeOH in DCM (4×50 mL) to afford (4R,5S)-4-amino-5-phenylpyrrolidin-2-one (2.4 g, 34%) as a white solid.

Enantiomeric excess (ee) determined by chiral HPLC (Column Name: Chiralpak IA (4.6×250 mm), 5 μm; Mobile Phase: Hexane/EtOH/IP amine: 80/20/0.1; Flow Rate: 1.0 ml/min; RT=17.65 min): ee=99.1%

Specific Rotation: [−34.5°] at 25° C., C=1.0% in EtOH.

Synthesis of trans-4-amino-5-(2,4-difluorophenyl) pyrrolidin-2-one (Intermediate A3)

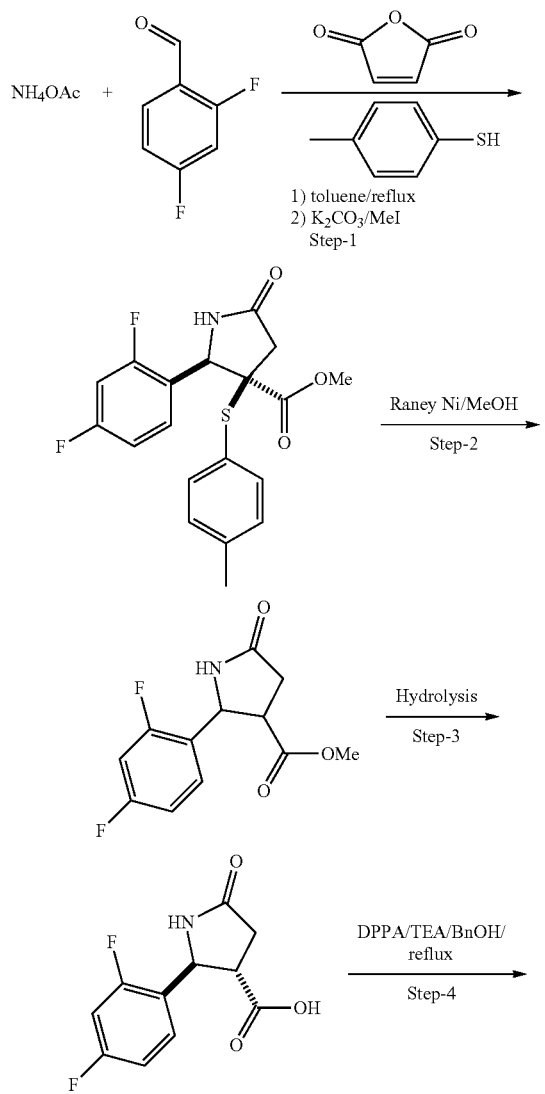

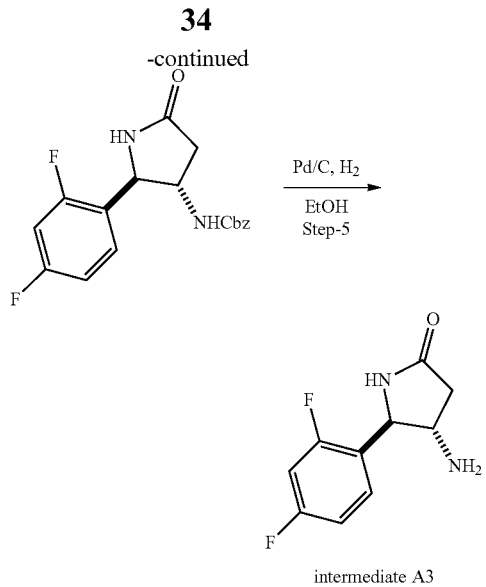

intermediate A3

Step 1: Maleic anhydride (28.9 g, 295.7 mmol, 1.0 eq), p-thiocresol (36.6 g, 295.7 mmol, 1.0 eq), ammonium acetate (22.7 g, 295.7 mmol, 1.0 eq), and 2,4-difluorobenzaldehyde (42.0 g, 295.7 mmol, 1.0 eq) were put in a sealed tube and 100 mL toluene was added. The reaction mixture was stirred at RT for 1 h and was then stirred at 150° C. for 16 h. After cooling to RT, the solvent was evaporated under reduced pressure, and the residue was basified with sat. NaHCO₃ solution and was extracted with DCM. The aqueous layer was acidified with 2N HCl under ice cooling and was then extracted twice with EtOAc. The combined organic layers were washed with brine, dried over Na₂SO₄, filtered, and concentrated to get the crude 3-((2,4-difluorophenyl)thio)-5-oxo-2-phenylpyrrolidine-3-carboxylic acid (120.0 g).

Step 2: To a stirred solution of crude 3-((2,4-difluorophenyl)thio)-5-oxo-2-phenylpyrrolidine-3-carboxylic acid (107.0 g, crude) in acetone (600 mL), potassium carbonate (162.7 g, 1170 mmol, 4.0 eq) and methyl iodide (73.3 mL, 1170 mmol, 4.0 eq) were added at 0° C., and the reaction mixture was stirred for 16 h at RT. The solvent was removed under reduced pressure, and the residue was partitioned between DCM and water. The aqueous layer was extracted twice with DCM. The combined organic layers were washed with brine, dried over Na₂SO₄, filtered and concentrated. The crude product was purified by column chromatography (100-200 silica gel, 50% EtOAc:hexanes) which gave methyl 3-((2,4-difluorophenyl)thio)-5-oxo-2-phenylpyrrolidine-3-carboxylate as an off white solid (6.0 g, 5%).

Step 3: To a stirred solution of methyl 3-((2,4-difluorophenyl)thio)-5-oxo-2-phenylpyrrolidine-3-carboxylate (6.0 g, 15.9 mmol, 1.0 eq) in EtOH:THF (225 mL, 2:1), Raney Nickel (60.0 g) was added and the reaction was stirred for 2 h at RT. After completion, the reaction mixture was filtered through a celite bed and the celite bed was washed 2-3 times with EtOAc. The combined organic layers were concentrated and the crude product was purified by column chromatography (100-200 silica gel, 50% EtOAc:hexanes) which gave methyl 2-(2,4-difluorophenyl)-5-oxopyrrolidine-3-carboxylate (2.8 g, 69%, syn:anti 1:1) as an off white solid.

Step 4: To a stirred solution of methyl 2-(2,4-difluorophenyl)-5-oxopyrrolidine-3-carboxylate (2.0 g, 7.84 mmol, 1.0 eq) in MeOH (47 mL) was added 2 N NaOH solution (12 mL) and the reaction mixture was stirred at 70° C. for 3 h. After completion of the reaction (monitored by LCMS), the reaction mixture was concentrated and acidified with 2N HCl solution and was then extracted with 30% isopropanol-DCM. The combined organic layers were dried over $Na_2SO_4$ and were concentrated under reduced pressure to get the desired trans-2-(2,4-difluorophenyl)-5-oxopyrrolidine-3-carboxylic acid (1.8 g, 95%).

Step 5: To a stirred solution of trans-2-(2,4-difluorophenyl)-5-oxopyrrolidine-3-carboxylic acid (1.8 g, 7.46 mmol, 1.0 eq) in benzene:THF (60 mL, 4:1) was added TEA (2.07 mL, 14.93 mmol, 2.0 eq) and DPPA (2.1 mL, 9.7 mmol, 1.3 eq) and the reaction mixture was stirred at ambient temperature for 2 h. Then benzyl alcohol (1.0 ml, 9.7 mmol, 1.3 eq) was added and the reaction mixture was heated to reflux for 16 h. After completion, the reaction mixture was concentrated under reduced pressure to get the crude which was extracted with water and EtOAc. The combined organic layers were dried over $Na_2SO_4$ and were concentrated under reduced pressure to get the crude product which was purified by flash column chromatography (100-200 mesh silica gel; 2% MeOH-DCM; $R_f$-value-0.5) to afford trans-benzyl (2-(2,4-difluorophenyl)-5-oxopyrrolidin-3-yl)carbamate (1.2 g, 46%) as an off-white solid.

Step 6: To a stirred solution of trans-benzyl (2-(2,4-difluorophenyl)-5-oxopyrrolidin-3-yl)carbamate (1.2 g, 3.46 mmol, 1.0 eq) in MeOH (15 mL), Pd/C (0.12 g, 10% w/w) was added, and the reaction was stirred with a hydrogen balloon for 2 h at RT. After completion, the reaction mixture was filtered through a celite bed and the celite bed was washed 2-3 times with EtOAc. The combined organic layers were concentrated to get the desired trans-4-amino-5-(2,4-difluorophenyl)pyrrolidin-2-one (0.85 g) as an off-white solid.

Synthesis of trans-4-amino-5-(2,3-dihydrobenzo[b][1,4]dioxin-6-yl)pyrrolidin-2-one (Intermediate A4)

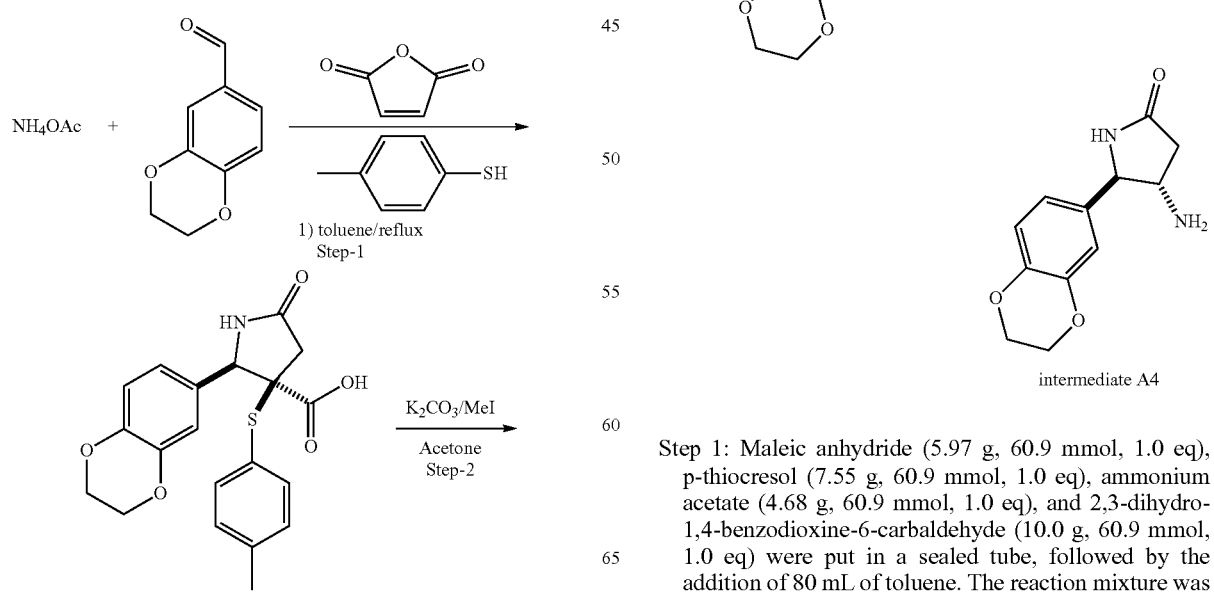

intermediate A4

Step 1: Maleic anhydride (5.97 g, 60.9 mmol, 1.0 eq), p-thiocresol (7.55 g, 60.9 mmol, 1.0 eq), ammonium acetate (4.68 g, 60.9 mmol, 1.0 eq), and 2,3-dihydro-1,4-benzodioxine-6-carbaldehyde (10.0 g, 60.9 mmol, 1.0 eq) were put in a sealed tube, followed by the addition of 80 mL of toluene. The reaction mixture was stirred at RT for 1 h and was then heated to 150° C. for 16 h. After cooling to RT, the solvent was evaporated under reduced pressure, and the residue was basified with sat. NaHCO$_3$ solution and was extracted with DCM. The aqueous layer was acidified with 2N HCl under ice cooling and was extracted twice with EtOAc. The combined organic layers were washed with brine, dried over Na$_2$SO$_4$, filtered and concentrated to get the crude 2-(2,3-dihydrobenzo[b][1,4]dioxin-6-yl)-5-oxo-3-(p-tolylthio)pyrrolidine-3-carboxylic acid (2.20 g).

Step 2: To a stirred solution of crude 2-(2,3-dihydrobenzo[b][1,4]dioxin-6-yl)-5-oxo-3-(p-tolylthio)pyrrolidine-3-carboxylic acid (2.2 g, 5.707 mmol, 1.0 eq) in acetone (100 mL), potassium carbonate (3.2 g, 22.831 mmol, 4.0 eq) and methyl iodide (1.42 mL, 22.831 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over Na$_2$SO$_4$, filtered and concentrated. The crude product was purified by column chromatography (100-200 silica gel, 50% EtOAc:hexanes) which gave methyl 2-(2,3-dihydrobenzo[b][1,4]dioxin-6-yl)-5-oxo-3-(p-tolylthio)pyrrolidine-3-carboxylate as an off white solid (0.9 g, 41%).

Step 3: To a stirred solution of methyl 2-(2,3-dihydrobenzo[b][1,4]dioxin-6-yl)-5-oxo-3-(p-tolylthio)pyrrolidine-3-carboxylate (0.9 g, 2.253 mmol, 1.0 eq) in EtOH:THF (60 mL, 2:1), Raney Nickel (1.0 g) was added, and the reaction was stirred for 2 h at RT. After completion, the reaction mixture was filtered through a celite bed and the celite bed was washed 2-3 times with EtOAc. The combined organic layers were concentrated and the crude remains were purified by column chromatography (100-200 silica gel, 50% EtOAc:hexanes) which gave methyl 2-(2,3-dihydrobenzo[b][1,4]dioxin-6-yl)-5-oxopyrrolidine-3-carboxylate (0.6 g, 96%, syn:anti, 1:1) as an off white solid.

Step 4: To a stirred solution of methyl 2-(2,3-dihydrobenzo[b][1,4]dioxin-6-yl)-5-oxopyrrolidine-3-carboxylate (0.7 g, 2.524 mmol, 1.0 eq) in MeOH (15 mL) was added a 2 N NaOH solution (3.7 mL) and the reaction mixture was stirred at 80° C. for 2 h. After completion of the reaction (monitored by LCMS), the reaction mixture was concentrated and acidified with 2N HCl solution and was then extracted with 30% isopropanol-DCM. The organic layer was dried over anhydrous Na$_2$SO$_4$ and concentrated under reduced pressure to get the desired trans-2-(2,3-dihydrobenzo[b][1,4]dioxin-6-yl)-5-oxopyrrolidine-3-carboxylic acid (0.5 g, 75%).

Step 5: To a stirred solution of trans-2-(2,3-dihydrobenzo[b][1,4]dioxin-6-yl)-5-oxopyrrolidine-3-carboxylic acid (0.3 g, 1.139 mmol, 1.0 eq) in benzene: THF (15 mL, 4:1) were added TEA (0.31 mL, 4.87 mmol, 2.0 eq) and DPPA (0.32 mL, 1.48 mmol, 1.3 eq) and the reaction mixture was stirred at RT for 2 h. Then benzyl alcohol (3 mL) was added and the reaction mixture was heated to reflux for 16 h. After completion, the reaction mixture was concentrated under reduced pressure to give the crude which was extracted with water and EtOAc. The organic layer was dried over anhydrous Na$_2$SO$_4$ and concentrated under reduced pressure to get the crude product which was purified by column chromatography (100-200 mesh silica gel; 2% MeOH-DCM; R$_f$-value-0.5) to afford trans-benzyl (-2-(2,3-dihydrobenzo[b][1,4]dioxin-6-yl)-5-oxopyrrolidin-3-yl)carbamate (0.2 g, 47%).

Step 6: To a stirred solution of trans-benzyl (-2-(2,3-dihydrobenzo[b][1,4]dioxin-6-yl)-5-oxopyrrolidin-3-yl)carbamate (0.32 g, 0.869 mmol, 1.0 eq) in MeOH: THF (20 mL, 2:1), Pd/C (50.0 mg) was added and the reaction was stirred with a hydrogen balloon for 2 h at RT. After completion, the reaction mixture was filtered through a celite bed and the celite bed was washed 2-3 times with EtOAc. The combined organic layer was concentrated to get the desired trans-4-amino-5-(2,3-dihydrobenzo[b][1,4]dioxin-6-yl)pyrrolidin-2-one (0.2 g, 98%) as brown gum.

Synthesis of trans-4-amino-5-(3-fluorophenyl)pyrrolidin-2-one (Intermediate A5)

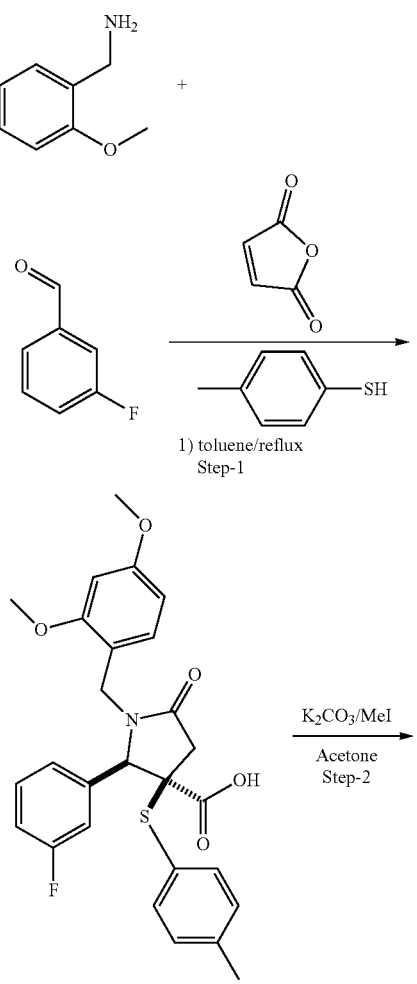

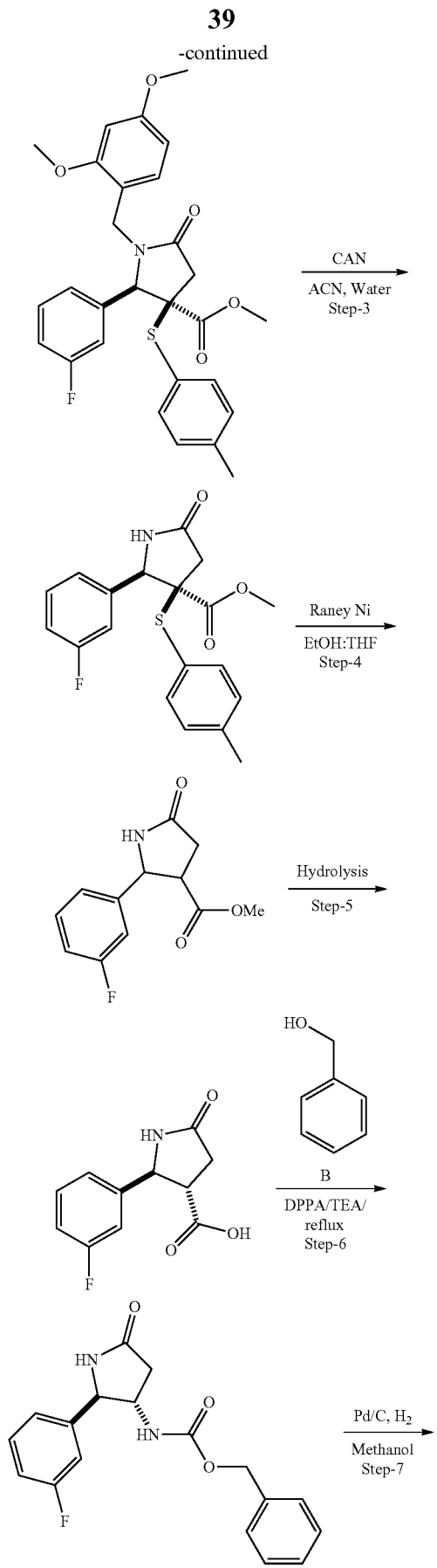

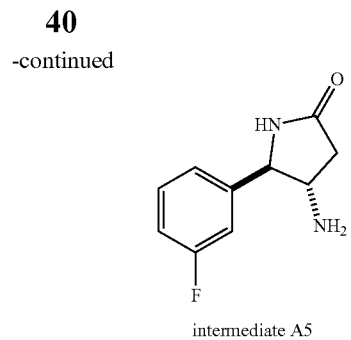

intermediate A5

Step 1: Maleic anhydride (19.7 g, 201.61 mmol, 1.0 eq), p-thiocresol (25.0 g, 201.61 mmol, 1.0 eq), 2,4-dimethoxybenzylamine (33.6 g, 201.61 mmol, 1.0 eq), and 3-fluorobenzaldehyde (25.0 g, 201.61 mmol, 1.0 eq) were put in a round-bottom flask followed by the addition of 250 mL toluene. The reaction mixture was refluxed for 16 h with vigorous stirring. After completion of the reaction (monitored by TLC), the reaction mixture was cooled to RT and the solvent was evaporated under reduced pressure to afford crude 1-(2,4-dimethoxybenzyl)-2-(3-fluorophenyl)-5-oxo-3-(p-tolylthio)pyrrolidine-3-carboxylic acid (89.0 g, 89%) as a gummy liquid which was used in the next step without further purification.

Step 2: To a stirred solution of 1-(2,4-dimethoxybenzyl)-2-(3-fluorophenyl)-5-oxo-3-(p-tolylthio)pyrrolidine-3-carboxylic acid (99.7 g, 201.4 mmol, 1.0 eq) in acetone (1 L), potassium carbonate (111.3 g, 805.6 mmol, 4.0 eq) and methyl iodide (51.0 mL, 805.6 mmol, 4.0 eq) were added at 0° C. and the reaction was stirred for 16 h at RT. After completion of the reaction (monitored by TLC), the solvent was removed under reduced pressure and the residue was partitioned between EtOAc and water. The aqueous layer was extracted twice with EtOAc. The combined organic layers were washed with brine, dried over $Na_2SO_4$, filtered, and concentrated. The crude product was purified by column chromatography (100-200 silica gel, 40% EtOAc in hexane) to afford methyl 1-(2,4-dimethoxybenzyl)-2-(3-fluorophenyl)-5-oxo-3-(p-tolylthio)pyrrolidine-3-carboxylate (79.0 g, 77%) as an off white solid.

Step 3: To a stirred solution of methyl 1-(2,4-dimethoxybenzyl)-2-(3-fluorophenyl)-5-oxo-3-(p-tolylthio)pyrrolidine-3-carboxylate (78.0 g, 153.2 mmol, 1.0 eq) in acetonitrile (500 mL), was added CAN (251.9 g, 459.6 mmol, 3.0 eq) dissolved in water dropwise at 0° C. through an addition funnel. The reaction mixture was then stirred at RT for 16 h. After completion of the reaction (monitored by TLC), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) to afford methyl 2-(3-fluorophenyl)-5-oxo-3-(p-tolylthio)pyrrolidine-3-carboxylate (47.0 g, 85%) as an off white solid.

Step 4: To a stirred solution of methyl 2-(3-fluorophenyl)-5-oxo-3-(p-tolylthio)pyrrolidine-3-carboxylate (30.0 g, 83.5 mmol, 1.0 eq) in EtOH:THF (500 mL:500 mL, 1:1), Raney Nickel (20.0 g) was added and the reaction was stirred under a hydrogen atmosphere for 16 h at RT. After completion (monitored by TLC) the reaction mixture was filtered through a celite bed and the celite bed was and washed 4-5 times with THF. The filtrate was concentrated to afford methyl 2-(3-fluorophenyl)-5-oxopyrrolidine-3-carboxylate (15.2 g, 77%, syn:anti mixture) as a white solid.

Step 5: To a stirred solution of methyl 2-(3-fluorophenyl)-5-oxopyrrolidine-3-carboxylate (16.0 g, 67.4 mmol, 1.0 eq) in MeOH (320 mL) was added 2 N NaOH solution (75 mL) and the reaction mixture was stirred at 80° C. for 16 h. After completion of the reaction (monitored by TLC) the reaction mixture was concentrated and acidified with 2N HCl solution to get a solid which was filtered off and was washed with diethyl ether, and was then dried under vacuum to afford trans-2-(3-fluorophenyl)-5-oxopyrrolidine-3-carboxylic acid (9.3 g, 62%).

Step 6: To a stirred solution of trans-2-(3-fluorophenyl)-5-oxopyrrolidine-3-carboxylic acid (13.0 g, 58.3 mmol, 1.0 eq) in toluene (130 mL) was added TEA (8.5 mL, 61.2 mmol, 1.05 eq) and DPPA (19.3 g, 70.0 mmol, 1.2 eq) and the reaction mixture was stirred at 90° C. for 30 min. Then benzyl alcohol (12.6 g, 116.6 mmol, 2.0 eq) was added and the reaction mixture was heated to reflux for 16 h. After completion (monitored by TLC), the reaction mixture was concentrated under reduced pressure. The residue was then diluted with EtOAc (100 mL), washed with water (2×100 mL), dried over anhydrous $Na_2SO_4$ and concentrated under reduced pressure to get the crude product which was purified by column chromatography (230-400 mesh silica gel; 0-2% MeOH in DCM) to afford trans-benzyl (2-(3-fluorophenyl)-5-oxopyrrolidin-3-yl)carbamate (7.0 g, 37%).

Step 7: To a stirred solution of trans-benzyl (2-(3-fluorophenyl)-5-oxopyrrolidin-3-yl)carbamate (7.0 g, 21.3 mmol, 1.0 eq) in MeOH (50 mL) and THF (20 mL), Pd—C (1.5 g, 14.9 mmol, 0.7 eq) was added and the reaction mixture was stirred with a hydrogen balloon for 2 h at RT. After completion (monitored by TLC), the reaction mixture was filtered through a celite bed and the celite bed was washed 2-3 times with THF. The filtrate was concentrated to get the desired trans-4-amino-5-(3-fluorophenyl)pyrrolidin-2-one (3.8 g, 92%) as a brown gum.

Synthesis of trans-4-amino-5-(2-fluorophenyl)pyrrolidin-2-one (Intermediate A6)

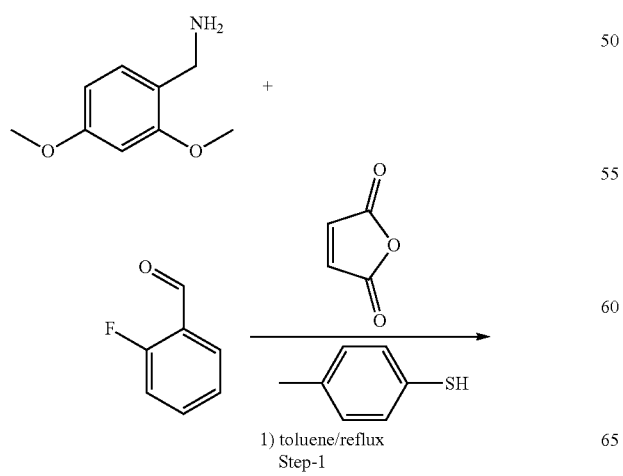

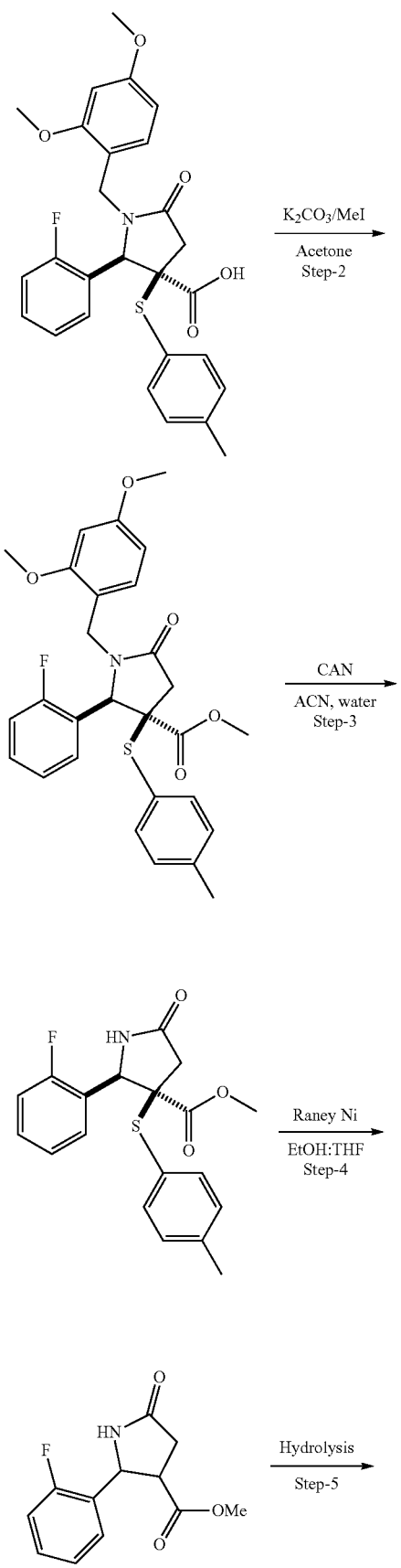

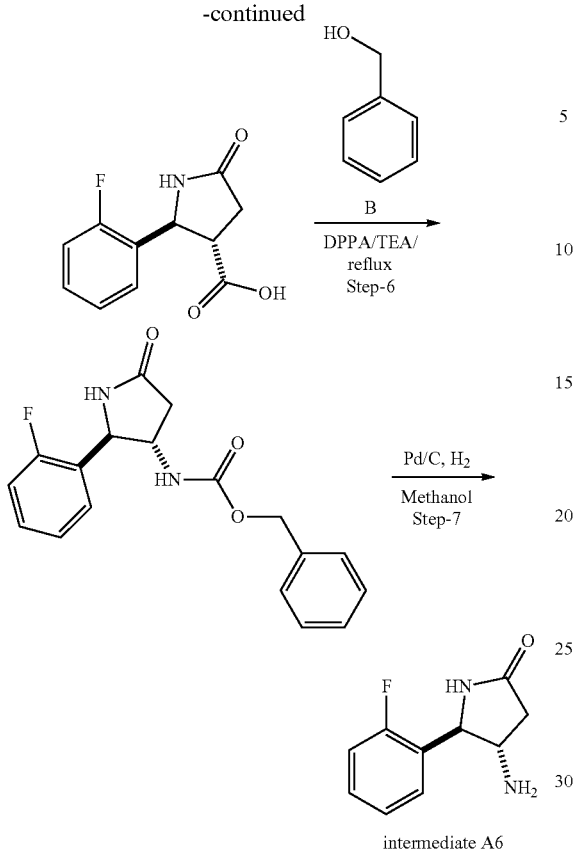

intermediate A6

Step 1: Maleic anhydride (19.7 g, 201.4 mmol, 1.0 eq), p-thiocresol (25.0 g, 201.4 mmol, 1.0 eq), 2,4 dimethoxybenzylamine (33.6 g, 201.4 mmol, 1.0 eq), and 2-fluorobenzaldehyde (25.0 g, 201.4 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2,4-dimethoxybenzyl)-2-(2-fluorophenyl)-5-oxo-3-(p-tolylthio)pyrrolidine-3-carboxylic acid as a gummy liquid (95.0 g, 95%) which was used in the next step without further purification.

Step 2: To a stirred solution of crude 1-(2,4-dimethoxybenzyl)-2-(2-fluorophenyl)-5-oxo-3-(p-tolylthio)pyrrolidine-3-carboxylic acid (95.0 g, 191.7 mmol, 1.0 eq) in acetone (1 L), potassium carbonate (111.3 g, 805.0 mmol, 4.2 eq) and methyl iodide (50.0 mL, 805.0 mmol, 4.2 eq) were added at 0° C., and the reaction mixture was stirred at RT for 16 h. After completion of the reaction (monitored by TLC; TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford the desired methyl 1-(2,4-dimethoxybenzyl)-2-(2-fluorophenyl)-5-oxo-3-(p-tolylthio)pyrrolidine-3-carboxylate as an off white solid (55.0 g, 56%).

Step 3: To a stirred solution of methyl 1-(2,4-dimethoxybenzyl)-2-(2-fluorophenyl)-5-oxo-3-(p-tolylthio)pyrrolidine-3-carboxylate (55.0 g, 108.0 mmol, 1.0 eq) in acetonitrile (300 mL), CAN (178.0 g, 324.0 mmol, 3.0 eq) in water (300 mL) was added dropwise at 0° C. through an addition funnel. The reaction mixture was then stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) which gave methyl 2-(2-fluorophenyl)-5-oxo-3-(p-tolylthio)pyrrolidine-3-carboxylate as an off white solid (15.0 g, 39%).

Step 4: To a stirred solution of methyl 2-(2-fluorophenyl)-5-oxo-3-(p-tolylthio)pyrrolidine-3-carboxylate (15.0 g, 41.7 mmol, 1.0 eq) in EtOH:THF (300:300 mL, 1:1), Raney Nickel (15 g) was added, and the reaction was stirred under a hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF. The filtrate was concentrated to afford methyl 2-(2-fluorophenyl)-5-oxopyrrolidine-3-carboxylate as a white solid (9.0 g, 91%; syn:anti mixture).

Step 5: To a stirred solution of methyl 2-(2-fluorophenyl)-5-oxopyrrolidine-3-carboxylate (9.0 g, 37.9 mmol, 1.0 eq) in MeOH (180 mL) was added 2 N NaOH solution (40 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to get a solid which was filtered off and was then washed with diethyl ether and dried under vacuum to afford trans-2-(2-fluorophenyl)-5-oxopyrrolidine-3-carboxylic acid (7.0 g, 83%).

Step 6: To a stirred solution of trans-2-(2-fluorophenyl)-5-oxopyrrolidine-3-carboxylic acid (7.0 g, 31.4 mmol, 1.00 eq) in Toluene (80 mL) was added TEA (4.6 mL, 33.0 mmol, 1.05 eq) and DPPA (10.4 g, 37.7 mmol, 1.2 eq) and the reaction mixture was stirred at 90° C. for 30 min. Then benzyl alcohol (6.8 g, 62.8 mmol, 2.0 eq) was added and the reaction mixture was heated to reflux for 16 h. After completion (monitored by TLC, TLC system 5% MeOH in DCM, Rf-0.3), the reaction mixture was concentrated under reduced pressure and was then diluted with EtOAc (100 mL), washed with water (2×100 mL), dried over $Na_2SO_4$ and concentrated under reduced pressure to get the crude product which was purified by column chromatography (230-400 mesh silica gel; 0-2% MeOH in DCM) to afford trans-benzyl (2-(2-fluorophenyl)-5-oxopyrrolidin-3-yl)carbamate (4.7 g, 46%).

Step 7: To a stirred solution of trans-benzyl (2-(2-fluorophenyl)-5-oxopyrrolidin-3-yl)carbamate (4.7 g, 14.3 mmol, 1.0 eq) in MeOH:THF (20 mL, 2:1), Pd/C (2.0 g, 10% moist) was added, and the reaction was stirred with a hydrogen balloon for 2 h at RT. After completion, (monitored by TLC, TLC system 5% MeOH in DCM, $R_f$-0.2), the reaction mixture was filtered through a celite bed and the celite bed was washed 2-3 times with THF. The filtrate was concentrated to get the desired trans-4-amino-5-(2-fluorophenyl)pyrrolidin-2-one as a brown gum (2.5 g, 90%).

Synthesis of trans-4-amino-5-(4-fluoro-3-methoxy-phenyl)pyrrolidin-2-one (Intermediate A7)

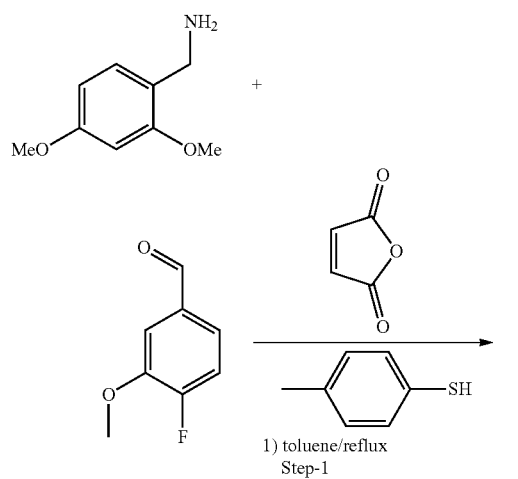

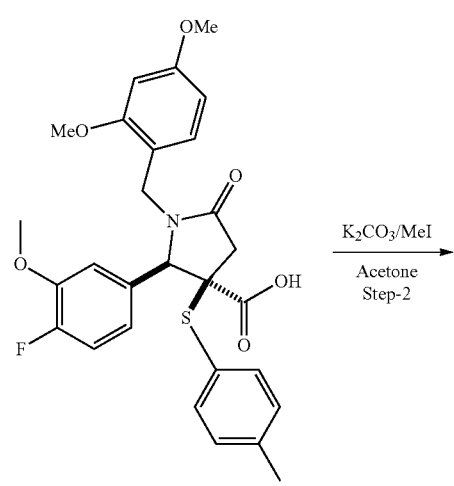

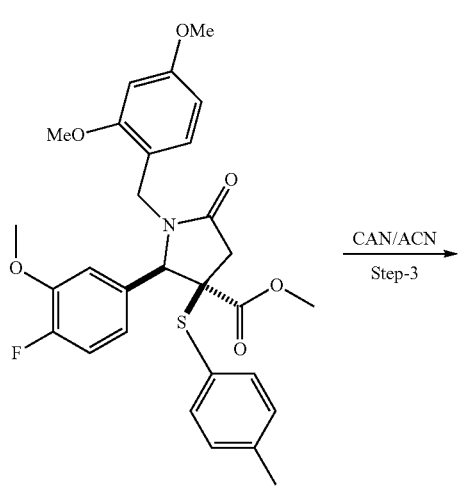

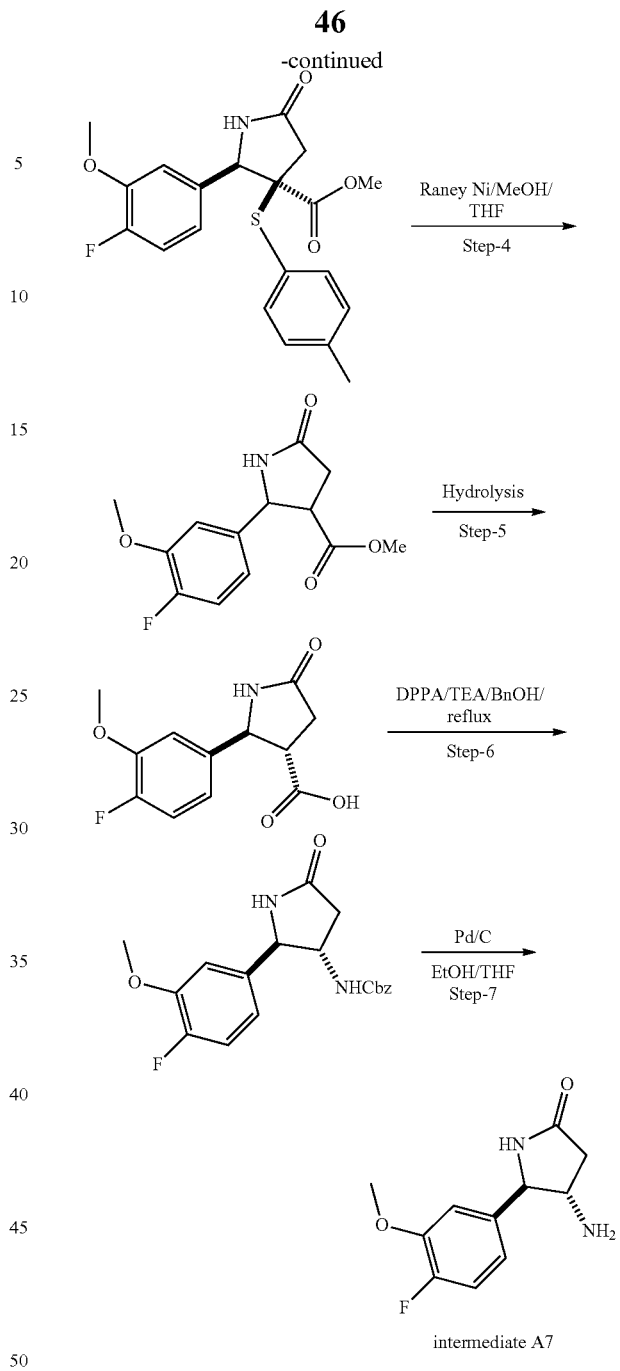

intermediate A7

Step 1: Maleic anhydride (14.6 g, 149.7 mmol, 1.0 eq), p-thiocresol (18.5 g, 149.7 mmol, 1.0 eq), 2,4-dimethoxy benzyl amine (25.0 g, 149.7 mmol, 1.0 eq), and 4-fluoro-3-methoxy benzaldehyde (23.0 g, 149.7 mmol, 1.0 eq) were dissolved in 500 mL toluene in a two neck round bottom flask fitted with a dean stark trap and a condenser. The reaction mixture was then heated to 150° C. for 16 h. After cooling to RT, the solvent was evaporated under reduced pressure to get the crude 1-(2,4-dimethoxybenzyl)-2-(4-fluoro-3-methoxyphenyl)-5-oxo-3-(p-tolylthio)-pyrrolidine-3-carboxylic acid which was taken to the next step without further purification.

Step 2: To a stirred solution of crude 1-(2,4-dimethoxybenzyl)-2-(4-fluoro-3-methoxyphenyl)-5-oxo-3-(p-tolylthio)pyrrolidine-3-carboxylic acid (max. 149.7 mmol, 1.0 eq) in acetone (500 mL), potassium carbonate (82.0 g, 598.0 mmol, 4.0 eq) and methyl iodide (37.5 mL, 598.0 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over $Na_2SO_4$, filtered and concentrated. The crude product was purified by column chromatography (100-200 silica gel, 50% EtOAc:hexanes) which gave methyl 1-(2,4-dimethoxybenzyl)-2-(4-fluoro-3-methoxyphenyl)-5-oxo-3-(p-tolylthio)pyrrolidine-3-carboxylate (72.0 g, 88%) as an off white solid.

Step 3: To a stirred solution of methyl 1-(2,4-dimethoxybenzyl)-2-(4-fluoro-3-methoxyphenyl)-5-oxo-3-(p-tolylthio)pyrrolidine-3-carboxylate (70.0 g, 129.0 mmol, 1.0 eq) in acetonitrile:water (500 mL 1:1), CAN was added at 0° C. and the reaction was stirred for 16 h at RT. The solvent was removed under reduced pressure, and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 50% EtOAc:hexanes) which gave methyl 2-(4-fluoro-3-methoxyphenyl)-5-oxo-3-(p-tolylthio)pyrrolidine-3-carboxylate (25.0 g, 50%) as an off white solid.

Step 4: To a stirred solution of methyl 2-(4-fluoro-3-methoxyphenyl)-5-oxo-3-(p-tolylthio)pyrrolidine-3-carboxylate (15.0 g, 64.3 mmol, 1.0 eq) in EtOH:THF (300 mL, 2:1), Raney Nickel (5.0 g) was added, and the reaction was stirred for 2 h at RT. After completion, the reaction mixture was filtered through a celite bed and washed 2-3 times with EtOAc. The combined organic layers were concentrated and the crude product was purified by column chromatography (100-200 silica gel, 50% EtOAc:hexanes) which gave methyl 2-(4-fluoro-3-methoxyphenyl)-5-oxopyrrolidine-3-carboxylate (10.0 g, 98%, syn:anti, 1:1 mixture) as an off white solid.

Step 5: To a stirred solution of methyl 2-(4-fluoro-3-methoxyphenyl)-5-oxopyrrolidine-3-carboxylate (10.0 g, 37.5 mmol, 1.0 eq) in MeOH (250 mL) was added 2 N NaOH solution (50 mL) and the reaction mixture was stirred at 80° C. for 2 h. After completion of the reaction (monitored by LCMS), the reaction mixture was concentrated, acidified with 2N HCl solution and then extracted with 30% isopropanol-DCM. The combined organic layers were dried over anhydrous $Na_2SO_4$ and concentrated under reduced pressure to get the desired trans-2-(4-fluoro-3-methoxyphenyl)-5-oxopyrrolidine-3-carboxylic acid (8.0 g, 84%).

Step 6: To a stirred solution of trans-2-(4-fluoro-3-methoxyphenyl)-5-oxopyrrolidine-3-carboxylic acid (2.0 g, 7.90 mmol, 1.0 eq) in benzene:THF (100 mL, 4:1) was added TEA (2.2 mL, 15.81 mmol, 2.0 eq) and DPPA (2.2 mL, 10.27 mmol, 1.3 eq) and the reaction mixture was stirred at RT for 2 h. Then benzyl alcohol (1.0 mL, 10.27 mmol, 1.3 eq) was added to the reaction mixture and heated to reflux for 16 h. After completion, the reaction mixture was concentrated under reduced pressure to get the crude which was extracted with water and EtOAc. Organic layer was dried over anhydrous $Na_2SO_4$ and concentrated under reduced pressure to get the crude product which was purified by column chromatography (100-200 mesh silica gel; 2% MeOH-DCM; $R_f$-value-0.5) to afford trans-benzyl (2-(4-fluoro-3-methoxyphenyl)-5-oxopyrrolidin-3-yl) carbamate (1.4 g, 50%).

Step 7: To a stirred solution of trans-benzyl (2-(4-fluoro-3-methoxyphenyl)-5-oxopyrrolidin-3-yl)carbamate (7 g, 19.55 mmol, 1 eq) in MeOH:THF (20 mL, 2:1), Pd—C (0.7 g) was added, and the reaction was stirred for 2 h at RT. After completion, the reaction mixture was filtered through celite bed and washed 2-3 times with EtOAc. The combined organic layer was concentrated to get trans-4-amino-5-(4-fluoro-3-methoxyphenyl)pyrrolidin-2-one (4 g, 91%) as brown gum.

Synthesis of trans-4-amino-5-(4-fluorophenyl)pyrrolidin-2-one (Intermediate A8)

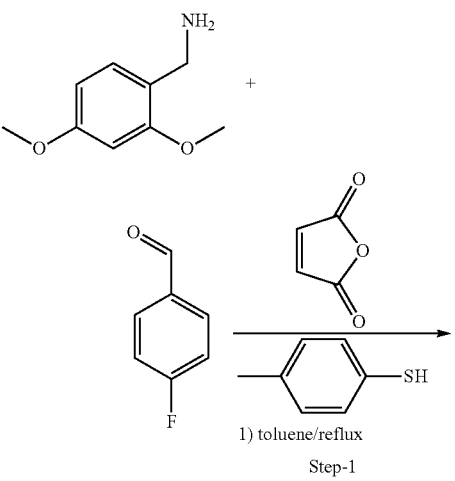

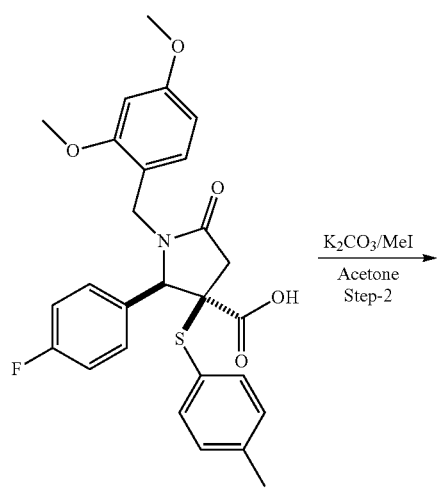

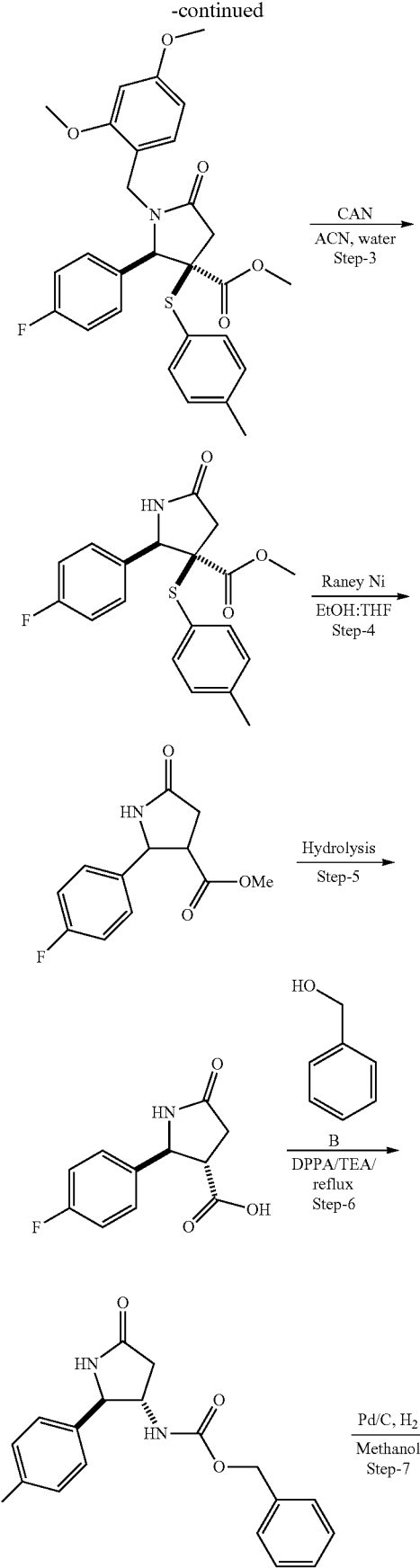

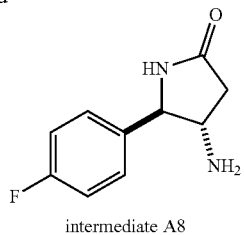

intermediate A8

Step 1: Maleic anhydride (19.7 g, 201.6 mmol, 1.0 eq), p-thiocresol (25.0 g, 201.6 mmol, 1.0 eq), 2,4 dimethoxybenzylamine (33.6 g, 201.6 mmol, 1.0 eq), and 4-fluorobenzaldehyde (25.0 g, 201.6 mmol, 1.0 eq) were taken up in 250 mL toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to give crude 1-(2,4-dimethoxybenzyl)-2-(4-fluorophenyl)-5-oxo-3-(p-tolylthio) pyrrolidine-3-carboxylic acid (92.0 g, 92%) as a gummy liquid, which was used in the next step without further purification.

Step 2: To a stirred solution of crude 1-(2,4-dimethoxybenzyl)-2-(4-fluorophenyl)-5-oxo-3-(p-tolylthio)pyrrolidine-3-carboxylic acid (92.0 g, 201.4 mmol, 1.0 eq) in acetone (1 L), potassium carbonate (111.3 g, 805.6 mmol, 4.0 eq) and methyl iodide (50.0 mL, 805.6 mmol, 4.0 eq) were added at 0° C. and the reaction was stirred for 16 h at RT. After completion of the reaction (monitored by TLC), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford methyl 1-(2,4-dimethoxybenzyl)-2-(4-fluorophenyl)-5-oxo-3-(p-tolylthio) pyrrolidine-3-carboxylate (79.0 g, 84%) as an off white solid.

Step 3: To a stirred solution of methyl 1-(2,4-dimethoxybenzyl)-2-(4-fluorophenyl)-5-oxo-3-(p-tolylthio)pyrrolidine-3-carboxylate (92.0 g, 180.7 mmol, 1.0 eq) in acetonitrile, CAN (297.0 g, 542.1 mmol, 3.0 eq) in water was added dropwise to the reaction mixture at 0° C. through an addition funnel. The reaction was then stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) which gave methyl 2-(4-fluorophenyl)-5-oxo-3-(p-tolylthio)pyrrolidine-3-carboxylate (41.0 g, 63%) as an off white solid.

Step 4: To a stirred solution of methyl 2-(4-fluorophenyl)-5-oxo-3-(p-tolylthio)pyrrolidine-3-carboxylate (13.0 g, 36.2 mmol, 1.0 eq) in EtOH:THF (260:130 mL, 2:1), Raney Nickel (13.0 g) was added and the reaction mixture was stirred under a hydrogen atmosphere for 16 h at RT. After completion of the reaction (monitored by TLC), the reaction mixture was filtered through a celite bed and the celite bed was washed 4-5 times with THF. The filtrate was concentrated to give methyl 2-(4-fluorophenyl)-5-oxopyrrolidine-3-carboxylate (6.7 g, 78%, syn:anti mixture) as a white solid.

Step 5: To a stirred solution of methyl 2-(4-fluorophenyl)-5-oxopyrrolidine-3-carboxylate (10.0 g, 42.2 mmol, 1.0 eq) in MeOH (200 mL) was added 2N NaOH solution (48 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to obtain a solid which was filtered and washed with diethyl ether, followed by drying under vacuum to afford trans 2-(4-fluorophenyl)-5-oxopyrrolidine-3-carboxylic acid (6.4 g, 68%).

Step 6: To a stirred solution of trans 2-(4-fluorophenyl)-5-oxopyrrolidine-3-carboxylic acid (5.0 g, 22.4 mmol, 1.00 eq) in toluene (50 mL) was added TEA (3.3 mL, 23.5 mmol, 1.05 eq) and DPPA (7.4 g, 26.9 mmol, 1.20 eq) and the reaction mixture was heated to 90° C. for 30 min. Then benzyl alcohol (4.8 g, 44.8 mmol, 2.00 eq) was added and the reaction mixture was heated to reflux for 16 h. After completion (monitored by TLC), the reaction mixture was concentrated under reduced pressure. The residue was then diluted with EtOAc (100 mL), washed with water (2×100 mL), dried over $Na_2SO_4$ and finally concentrated under reduced pressure to get the crude product which was purified by column chromatography (230-400 mesh silica gel; 0-2% MeOH in DCM) to afford trans-benzyl (2-(4-fluorophenyl)-5-oxopyrrolidin-3-yl)carbamate (4.1 g, 56%).

Step 7: To a stirred solution of trans-benzyl (2-(4-fluorophenyl)-5-oxopyrrolidin-3-yl)carbamate (2.0 g, 6.1 mmol, 1.0 eq) in MeOH (50 mL) and THF (20 mL), Pd/C (0.3 g, 3.0 mmol, 0.5 eq) was added and the reaction was stirred with a hydrogen balloon for 2 h at RT. After completion (monitored by TLC), the reaction mixture was filtered through a celite bed and the celite bed was washed 2-3 times with THF. The filtrate was concentrated to get the desired trans4-amino-5-(4-fluorophenyl)pyrrolidin-2-one (1.1 g, 93%) as a brown gum.

Synthesis of trans-4-amino-5-(2-methoxypyridin-4-yl)pyrrolidin-2-one (Intermediate A9)

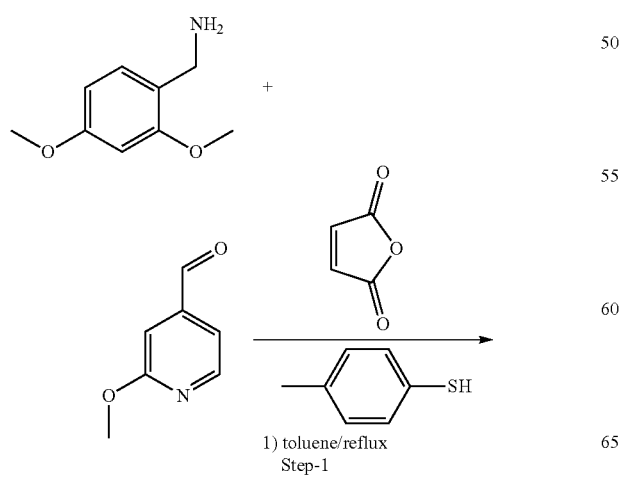

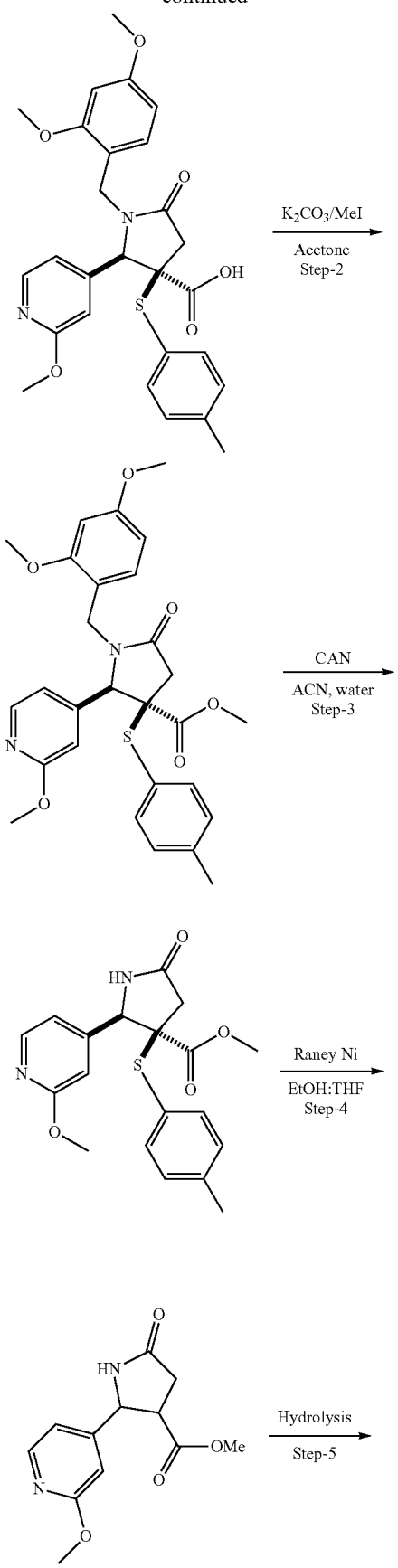

-continued

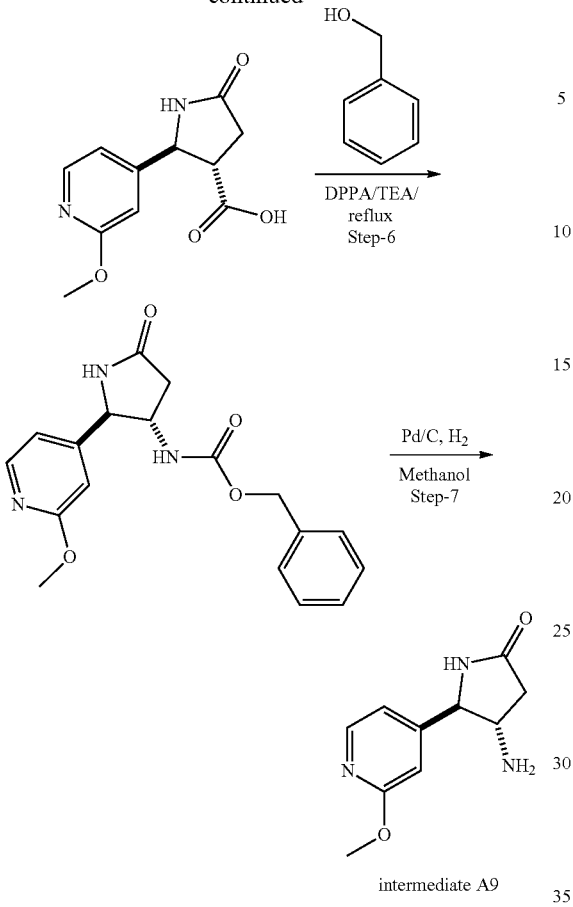

intermediate A9

Step 1: Maleic anhydride (17.2 g, 175.0 mmol, 1.0 eq), p-thiocresol (21.7 g, 175.0 mmol, 1.0 eq), 2,4-dimethoxybenzylamine (29.2 g, 175.0 mmol, 1.0 eq), and 2-methoxypyridine-4-carbaldehyde (24.0 g, 175.0 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2,4-dimethoxybenzyl)-2-(2-methoxypyridin-4-yl)-5-oxo-3-(p-tolylthio)pyrrolidine-3-carboxylic acid as a gummy liquid (80.0 g) which was used in the next step without further purification.

Step 2: To a stirred solution of 1-(2,4-dimethoxybenzyl)-2-(2-methoxypyridin-4-yl)-5-oxo-3-(p-tolylthio)pyrrolidine-3-carboxylic acid (57.0 g, 112.1 mmol, 1.0 eq) in acetone (300 mL), potassium carbonate (61.9 g, 448.3 mmol, 4.0 eq) and methyl iodide (28.0 mL, 448.3 mmol, 4.0 eq) were added at 0° C., and the reaction was stirred at RT for 16 h. After completion of the reaction (monitored by TLC, TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford methyl 1-(2,4-dimethoxybenzyl)-2-(2-methoxypyridin-4-yl)-5-oxo-3-(p-tolylthio)pyrrolidine-3-carboxylate as an off white solid (35.0 g, 60%).

Step 3: To a stirred solution of methyl 1-(2,4-dimethoxybenzyl)-2-(2-methoxypyridin-4-yl)-5-oxo-3-(p-tolylthio)pyrrolidine-3-carboxylate (60.0 g, 114.8 mmol, 1.0 eq) in acetonitrile (300 mL), CAN (188.8 g, 344.4 mmol, 3.0 eq) in water (300 mL) was added dropwise at 0° C. through an addition funnel and the reaction mixture was then stirred at RT for 16 h. After completion of the reaction (monitored by TLC, TLC system 70% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) to give methyl 2-(2-methoxypyridin-4-yl)-5-oxo-3-(p-tolylthio)pyrrolidine-3-carboxylate as an off white solid (12.0 g, 28%).

Step 4: To a stirred solution of methyl 2-(2-methoxypyridin-4-yl)-5-oxo-3-(p-tolylthio)pyrrolidine-3-carboxylate (11.4 g, 30.6 mmol, 1.0 eq) in EtOH:THF (50:100 mL, 1:2), Raney Nickel (18 g) was added, and the reaction was stirred under a hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF. The filtrate was concentrated to afford methyl 2-(2-methoxypyridin-4-yl)-5-oxopyrrolidine-3-carboxylate as a white solid (7.1 g, 93%, syn:anti mixture).

Step 5: To a stirred solution of methyl 2-(2-methoxypyridin-4-yl)-5-oxopyrrolidine-3-carboxylate (0.7 g, 2.8 mmol, 1 eq) in MeOH (10 mL) was added 2N NaOH solution (6 mL) and the reaction mixture was stirred at 80° C. for 16 h. After completion of the reaction (monitored by TLC, TLC system 5% MeOH in DCM, $R_f$-0.1), the reaction mixture was concentrated and acidified with 2N HCl solution to get a solid which was filtered off and was washed with diethyl ether. After drying under vacuum trans-2-(2-methoxypyridin-4-yl)-5-oxopyrrolidine-3-carboxylic acid was obtained (0.4 g, 61%).

Step 6: To a stirred solution of trans-2-(2-methoxypyridin-4-yl)-5-oxopyrrolidine-3-carboxylic acid (0.37 g, 1.58 mmol, 1.00 eq) in toluene (20 mL) was added TEA (0.30 mL, 1.66 mmol, 1.05 eq) and DPPA (0.40 mL, 1.89 mmol, 1.20 eq) and the reaction mixture was stirred at 90° C. for 30 min. Then benzyl alcohol (0.40 mL, 3.16 mmol, 2.00 eq) was added to the reaction mixture and heated to reflux for 16 h. After completion, (monitored by TLC, TLC system 5% MeOH in DCM, Rf-0.3), the reaction mixture was concentrated under reduced pressure. The residue was then diluted with EtOAc (100 mL), washed with water (2×100 mL), dried over $Na_2SO_4$ and concentrated under reduced pressure to get the crude product which was purified by column chromatography (230-400 mesh silica gel; 0-2% MeOH in DCM) to afford trans-benzyl (2-(2-methoxypyridin-4-yl)-5-oxopyrrolidin-3-yl)carbamate (0.20 g, 37%).

Step 7: To a stirred solution of trans-benzyl (2-(2-methoxypyridin-4-yl)-5-oxopyrrolidin-3-yl)carbamate (0.2 g, 24.0 mmol, 1.0 eq) in MeOH:THF (20 mL, 2:1), Pd/C (0.2 g, 10%, moist) was added and the reaction was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get trans-4-amino-5-(2-methoxypyridin-4-yl) pyrrolidin-2-one as a brown gum (0.1 g, 82%).

Synthesis of trans-4-amino-5-(o-tolyl)pyrrolidin-2-one (Intermediate A10)

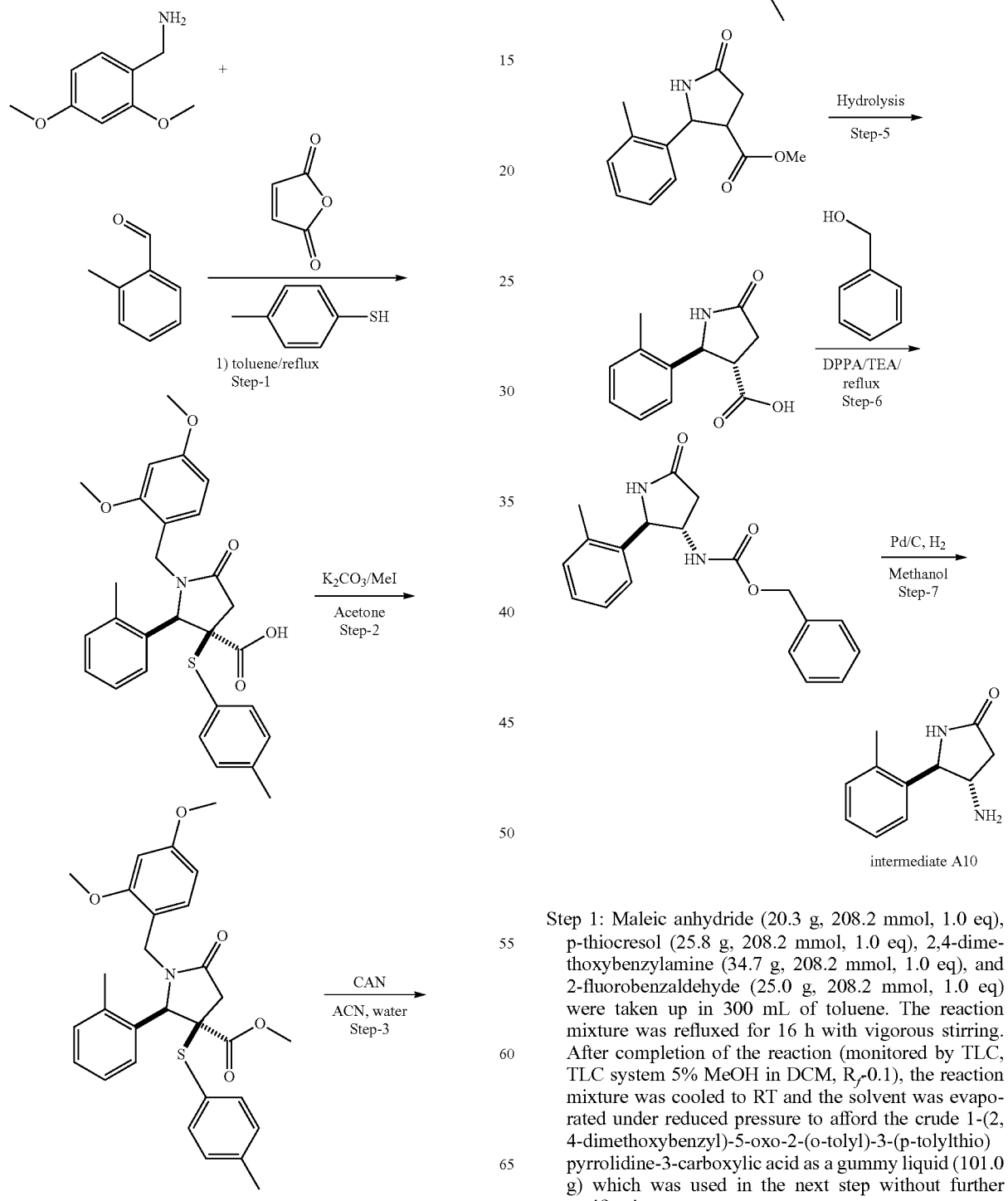

intermediate A10

Step 1: Maleic anhydride (20.3 g, 208.2 mmol, 1.0 eq), p-thiocresol (25.8 g, 208.2 mmol, 1.0 eq), 2,4-dimethoxybenzylamine (34.7 g, 208.2 mmol, 1.0 eq), and 2-fluorobenzaldehyde (25.0 g, 208.2 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was evaporated under reduced pressure to afford the crude 1-(2, 4-dimethoxybenzyl)-5-oxo-2-(o-tolyl)-3-(p-tolylthio) pyrrolidine-3-carboxylic acid as a gummy liquid (101.0 g) which was used in the next step without further purification.

Step 2: To a stirred solution of crude 1-(2,4-dimethoxybenzyl)-5-oxo-2-(o-tolyl)-3-(p-tolylthio)pyrrolidine-3-carboxylic acid (101.0 g, 208.2 mmol, 1.0 eq) in acetone (1 L), potassium carbonate (115.0 g, 832.8 mmol, 4.0 eq) and methyl iodide (52.0 mL, 832.8 mmol, 4.0 eq) were added at 0° C. and the reaction was stirred at RT for 16 h. After completion of the reaction (monitored by TLC, TLC system 30% EtOAc in hexane, $R_f$-0.3) the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford methyl 1-(2,4-dimethoxybenzyl)-5-oxo-2-(o-tolyl)-3-(p-tolylthio)pyrrolidine-3-carboxylate as an off white solid (80.0 g, 76%).

Step 3: To a stirred solution of methyl 1-(2,4-dimethoxybenzyl)-5-oxo-2-(o-tolyl)-3-(p-tolylthio)pyrrolidine-3-carboxylate (80.0 g, 158.0 mmol, 1.0 eq) in acetonitrile (300 mL), CAN (260.0 g, 475.0 mmol, 3.0 eq) in water (300 mL) was added dropwise to the reaction mixture at 0° C. through an addition funnel and the reaction mixture was stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) which gave methyl 5-oxo-2-(o-tolyl)-3-(p-tolylthio)pyrrolidine-3-carboxylate as an off white solid (21.5 g, 38%).

Step 4: To a stirred solution of methyl 5-oxo-2-(o-tolyl)-3-(p-tolylthio)pyrrolidine-3-carboxylate (21.5 g, 60.5 mmol, 1.0 eq) in EtOH:THF (300:300 mL, 1:1), Raney Nickel (~18 g) was added, and the reaction was stirred under a hydrogen atmosphere for 16 h at RT. After completion, (monitored by TLC, TLC system 70% EtOAc in hexane, $R_f$-0.4) the reaction mixture was filtered through a celite bed and the celite bed was washed 4-5 times with THF. The filtrate was concentrated to afford methyl 5-oxo-2-(o-tolyl)pyrrolidine-3-carboxylate as a white solid (11.5 g, 82%, syn:anti mixture).

Step 5: To a stirred solution of methyl 5-oxo-2-(o-tolyl)pyrrolidine-3-carboxylate (11.5 g, 49.3 mmol, 1.0 eq) in MeOH (400 mL) was added 2N NaOH solution (80 mL) and the reaction mixture was stirred at 80° C. for 16 h. After completion of the reaction (monitored by TLC, TLC system 5% MeOH in DCM, $R_f$-0.1), the reaction mixture was concentrated and acidified with 2N HCl solution to get a solid which was filtered off and was washed with diethyl ether. Drying under vacuum then afforded trans-5-oxo-2-(o-tolyl)pyrrolidine-3-carboxylic acid (8.5 g, 79%).

Step 6: To a stirred solution of trans-5-oxo-2-(o-tolyl)pyrrolidine-3-carboxylic acid (8.5 g, 38.0 mmol, 1.00 eq) in toluene (110 mL) were added TEA (5.5 mL, 39.9 mmol, 1.05 eq) and DPPA (10.5 g, 45.0 mmol, 1.20 eq) and the reaction mixture was stirred at 90° C. for 30 min. After 30 min, benzyl alcohol (8.4 g, 77.0 mmol, 2.00 eq) was added and the reaction mixture was heated to reflux for 16 h. After completion (monitored by TLC, TLC system 5% MeOH in DCM, Rf-0.3), the reaction mixture was concentrated under reduced pressure. The residue was then diluted with EtOAc (100 mL), washed with water (2×100 mL), dried over anhydrous $Na_2SO_4$ and was then concentrated under reduced pressure to get the crude product which was purified by column chromatography (230-400 mesh silica gel; 0-2% MeOH in DCM) to afford trans-benzyl (5-oxo-2-(o-tolyl)pyrrolidin-3-yl)carbamate (8.0 g, 65%).

Step 7: To a stirred solution of trans-benzyl (5-oxo-2-(o-tolyl)pyrrolidin-3-yl)carbamate (8.0 g, 24.0 mmol, 1.0 eq) in MeOH:THF (20 mL, 2:1), Pd/C (2.0 g, 10%, moist) was added, and the reaction mixture was stirred with a hydrogen balloon for 2 h at RT. After completion, (monitored by TLC, TLC system 5% MeOH in DCM, $R_f$-0.2), the reaction mixture was filtered through a celite bed and the celite bed was washed 2-3 times with THF. The filtrate was concentrated to get the desired trans-4-amino-5-(o-tolyl)pyrrolidin-2-one as brown gum (4.5 g, 99%).

Synthesis of trans-4-amino-5-(2-fluoro-5-methoxyphenyl)pyrrolidin-2-one (Intermediate A11)

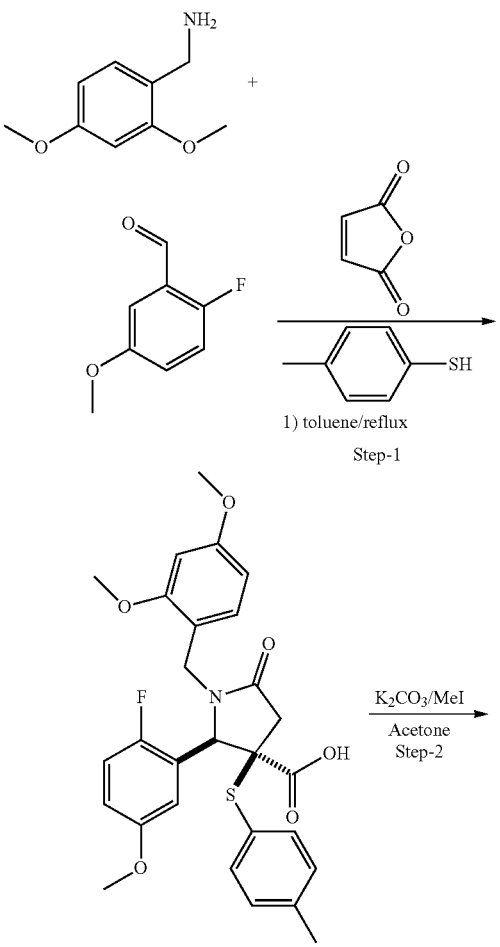

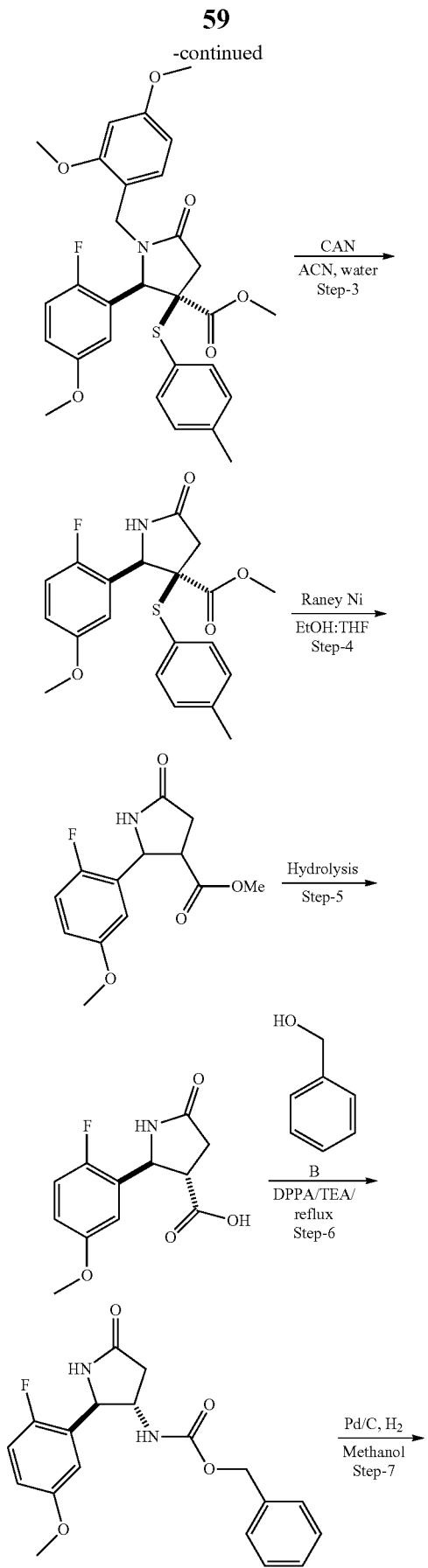

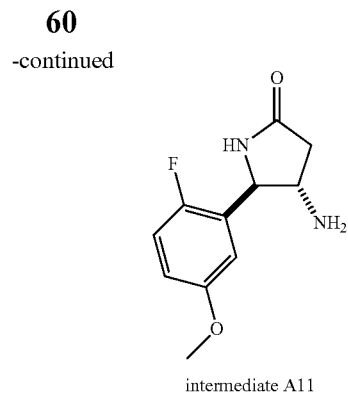

intermediate A11

Step 1: Maleic anhydride (14.6 g, 149.7 mmol, 1.0 eq), p-thiocresol (18.5 g, 149.7 mmol, 1.0 eq), 2,4-dimethoxybenzylamine (25.0 g, 149.7 mmol, 1.0 eq), and 2-fluoro-5-methoxybenzaldehyde (23.0 g, 149.7 mmol, 1.0 eq) were taken up in 300 mL of toluene. The reaction mixture was refluxed for 16 h with vigorous stirring. After completion of the reaction (monitored by TLC, TLC system 5% MeOH in DCM, $R_f$-0.1), the reaction mixture was cooled to RT and the solvent was then evaporated under reduced pressure to afford the crude product as a gummy liquid (75.0 g, 96%) which was used in the next step without further purification.

Step 2: To a stirred solution of crude 1-(2,4-dimethoxybenzyl)-2-(2-fluoro-5-methoxyphenyl)-5-oxo-3-(p-tolylthio)pyrrolidine-3-carboxylic acid (75.0 g, 142.9 mmol, 1.0 eq) in acetone (1 L), potassium carbonate (78.9 g, 571.4 mmol, 4.0 eq) and methyl iodide (35.0 mL, 571.4 mmol, 4.0 eq) were added at 0° C., and the reaction mixture was stirred at RT for 16 h. After completion of the reaction (monitored by TLC, TLC system 30% EtOAc in hexane, $R_f$-0.3), the solvent was removed under reduced pressure and the residue was partitioned between EtOAc and water. The aqueous layer was extracted twice with EtOAc. The combined organic layers were washed with brine, dried over $Na_2SO_4$, filtered and concentrated. The crude product was purified by column chromatography (100-200 silica gel, 40% EtOAc in hexane) to afford the desired methyl 1-(2,4-dimethoxybenzyl)-2-(2-fluoro-5-methoxyphenyl)-5-oxo-3-(p-tolylthio)pyrrolidine-3-carboxylate (45.0 g, 58%) as an off white solid.

Step 3: To a stirred solution of methyl 1-(2,4-dimethoxybenzyl)-2-(2-fluoro-5-methoxyphenyl)-5-oxo-3-(p-tolylthio)pyrrolidine-3-carboxylate (45.0 g, 83.5 mmol, 1.0 eq) in acetonitrile, CAN (137.3 g, 250.4 mmol, 3.0 eq) in water was added dropwise through an addition funnel to the reaction mixture at 0° C. and the reaction mixture was stirred at RT for 16 h. After completion of the reaction (monitored by TLC, TLC system 50% EtOAc in hexane, Rf-0.3), the reaction mixture was diluted with water and extracted twice with EtOAc. The combined organic layers were washed with brine, dried over $Na_2SO_4$, filtered and concentrated. The crude product was purified by column chromatography (230-400 silica gel, 40-50% EtOAc:hexane) to give methyl 2-(2-fluoro-5-methoxyphenyl)-5-oxo-3-(p-tolylthio)pyrrolidine-3-carboxylate (17.0 g, 52%) as an off white solid.

Step 4: To a stirred solution of methyl 2-(2-fluoro-5-methoxyphenyl)-5-oxo-3-(p-tolylthio)pyrrolidine-3-carboxylate (17.0 g, 43.7 mmol, 1.0 eq) in EtOH:THF (300:300 mL, 1:1), Raney Nickel (17 g) was added and the reaction mixture was stirred under a hydrogen hydrogen atmosphere for 16 h at RT. After completion, (monitored by TLC, TLC system 70% EtOAc in hexane, Rf-0.4) the reaction mixture was filtered through a celite bed and the celite bed was washed 4-5 times with THF. The filtrate was concentrated to afford the desired methyl 2-(2-fluoro-5-methoxyphenyl)-5-oxopyrrolidine-3-carboxylate (9.0 g, 77%, syn:anti mixture) as a white solid.

Step 5: To a stirred solution of methyl 2-(2-fluoro-5-methoxyphenyl)-5-oxopyrrolidine-3-carboxylate (9.0 g, 33.7 mmol, 1 eq) in MeOH (180 mL) was added 2 N NaOH solution (36 mL) and the reaction mixture was stirred at 80° C. for 16 h. After completion of the reaction (monitored by TLC, TLC system 5% MeOH in DCM, Rf-0.1), the reaction mixture was concentrated and acidified with 2N HCl solution to obtain a solid which was filtered off and then washed with diethyl ether. Drying under vacuum afforded trans-2-(2-fluoro-5-methoxyphenyl)-5-oxopyrrolidine-3-carboxylic acid (7.9 g, 93%).

Step 6: To a stirred solution of trans-2-(2-fluoro-5-methoxyphenyl)-5-oxopyrrolidine-3-carboxylic acid (7.9 g, 31.2 mmol, 1.00 eq) in toluene (80 mL) were added TEA (4.6 mL, 32.8 mmol, 1.05 eq) and DPPA (10.3 g, 37.46 mmol, 1.20 eq) and the reaction mixture was stirred at 90° C. for 30 min. After 30 min, benzyl alcohol (6.7 g, 62.4 mmol, 2.00 eq) was added and the reaction mixture was heated to reflux for 16 h. After completion, (monitored by TLC, TLC system 5% MeOH in DCM, Rf-0.3), the reaction mixture was concentrated under reduced pressure. The residue was then diluted with EtOAc (100 mL), washed with water (2×100 mL), dried over Na$_2$SO$_4$ and concentrated under reduced pressure to get the crude product which was purified by column chromatography (230-400 mesh silica gel; 0-2% MeOH in DCM) to afford benzyl (trans-2-(2-fluoro-5-methoxyphenyl)-5-oxopyrrolidin-3-yl)carbamate (1.5 g, 13%).

Step 7: To a stirred solution of benzyl (trans-2-(2-fluoro-5-methoxyphenyl)-5-oxopyrrolidin-3-yl)carbamate (1.5 g, 4.2 mmol, 1.0 eq) in MeOH:THF (20 mL, 2:1), Pd/C (0.3 g, 0.548 mmol, 0.1 eq) was added, and the reaction mixture was stirred with a hydrogen balloon for 2 h at RT. After completion, (monitored by TLC, TLC system 5% MeOH in DCM, Rf-0.2), the reaction mixture was filtered through a celite bed and the celite bed was washed 2-3 times with THF. The filtrate was concentrated to get the desired trans-4-amino-5-(2-fluoro-5-methoxyphenyl)pyrrolidin-2-one (0.9 g, 96%) as a brown gum.

Synthesis of tert-butyl (trans-2-cyclopropyl-5-oxopyrrolidin-3-yl)carbamate (Intermediate A12-Boc) and tert-butyl (cis-2-cyclopropyl-5-oxopyrrolidin-3-yl)carbamate (Intermediate A13-Boc)

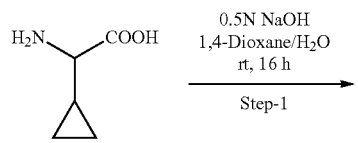

0.5N NaOH
1,4-Dioxane/H$_2$O
rt, 16 h
Step-1

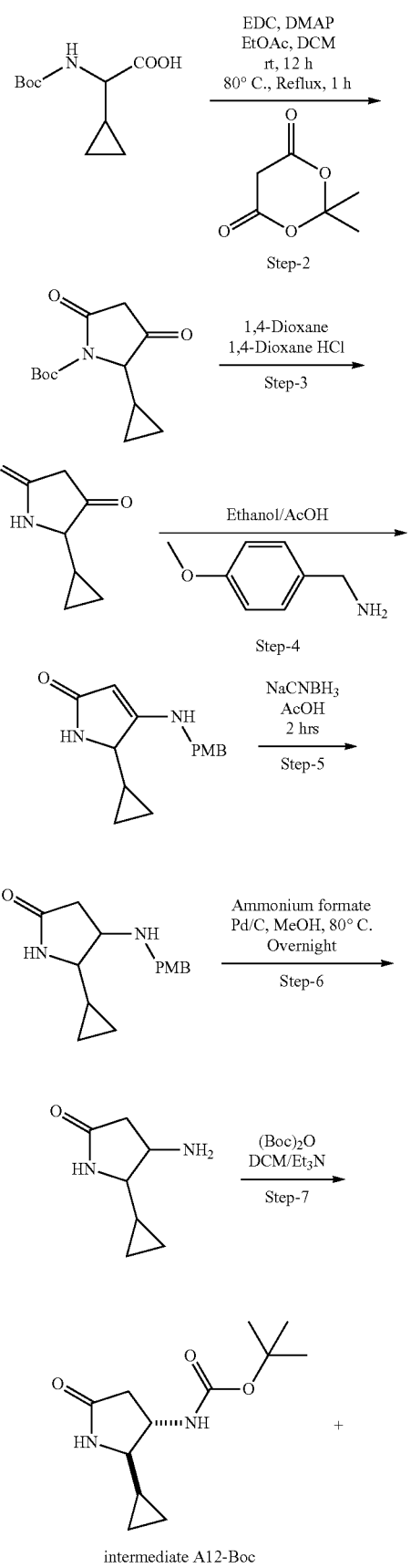

intermediate A12-Boc

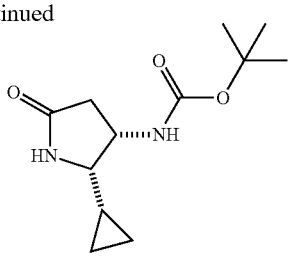

intermediate A13-Boc

Step 1: To a stirred solution of 2-amino-2-cyclopropylacetic acid (40.0 g, 347.4 mmol), 0.5N NaOH aqueous solution (240 mL) and 1,4-dioxane (200 mL) was added di-tert-butyl-di-carbonate (83.3 g, 382.1 mmol) at 0° C. Then the reaction mixture was allowed to warm up to ambient temperature and was stirred for 16 h. The reaction mixture was acidified with 5% $KHSO_4$ solution after completion of the reaction. The aqueous layer was extracted with EtOAc, the combined organic layers were then washed with brine, dried over sodium sulfate and concentrated under reduced pressure to afford 2-((tert-butoxycarbonyl)amino)-2-cyclopropylacetic acid (40.0 g) as a yellow sticky liquid.

Step 2: To a stirred solution of 2-((tert-butoxycarbonyl)amino)-2-cyclopropylacetic acid (78.5 g, 365.1 mmol) and DCM (785 mL) were added Meldrum's acid (59.9 g, 401.6 mmol) and DMAP (62.4 g, 511.1 mmol) at 0° C. The reaction mixture was allowed to stir at this temperature for 30 min. To this reaction mixture was added EDC·HCl (98.0 g, 511.1 mmol) and the reaction mixture was stirred at ambient temperature for 12 h. The reaction mixture was diluted with EtOAc. The organic layer was washed with 5% citric acid, water and brine. The organic layer was then heated to 75° C. for 1 h, concentrated under reduced pressure. The obtained residue was triturated with diethyl ether to afford tert-butyl 2-cyclopropyl-3,5-dioxopyrrolidine-1-carboxylate (33.1 g, 38%) as an off white solid.

Step 3: To a stirred solution of tert-butyl 2-cyclopropyl-3,5-dioxopyrrolidine-1-carboxylate (40.0 g, 167.3 mmol) in 1,4-dioxane (200 mL) was added 1,4-dioxane·HCl (200 mL) at 0° C. The reaction mixture was then stirred at ambient temperature for 3 h. The reaction mixture was then concentrated under reduced pressure to afford 5-cyclopropylpyrrolidine-2,4-dione (30.0 g) as an off white solid.

Step 4: To a stirred solution of 5-cyclopropylpyrrolidine-2,4-dione (30.0 g, 215.8 mmol) in a mixture of ethanol (270 mL) and acetic acid (30 mL) was added (4-methoxyphenyl)methanamine (29.6 g, 215.8 mmol) under nitrogen atmosphere. The reaction was then heated to 80° C. for 12 hours. The reaction mixture was concentrated under reduced pressure, the obtained residue was basified with 1N NaOH, causing precipitation. The precipitated solid was filtered off and was then dried under reduced pressure to afford a light yellow solid.

$^1$H NMR (DMSO-$d_6$) δ: 7.17 (d, 2H), 6.98 (q, 1H), 6.83 (d, 2H), 6.66-6.58 (m, 1H), 4.17 (s, 1 h) 4.06 (d, 2H), 3.64 (s, 3H), 0.96 (td, 1H), 0.46 (dq, 1H), 0.37 (p, 1H), 0.21 (dt, 1H), 0.12 (dd, 1H).

Step 5: To a stirred solution of 5-cyclopropyl-4-((4-methoxybenzyl)amino)-1,5-dihydro-2H-pyrrol-2-one (17.0 g, 65.9 mmol) and acetic acid (170 mL) was added sodium cyano borohydride (24.8 g, 395.3 mmol) at 0° C. and the reaction was stirred for 1 h at this temperature. The reaction mixture was then concentrated under reduced pressure; the obtained residue was basified with 1N NaOH and extracted with EtOAc. The combined organic layers were washed with water and brine and were then dried over sodium sulfate and concentrated under reduced pressure to get the crude product which was used in the next step without further purification.

Step 6: To a stirred solution of 5-cyclopropyl-4-((4-methoxybenzyl)amino)pyrrolidin-2-one (3.8 g, 14.6 mmol) and MeOH (38 mL) were added 2N HCl (4.0 mL), ammonium formate (18.4 g, 292.3 mmol) and 10% palladium on carbon (3.8 g) The reaction mixture was then heated to 80° C. for 12 h. The reaction mixture was then filtered through a celite bed and the filtrate was concentrated under reduced pressure to afford 4-amino-5-cyclopropylpyrrolidin-2-one (5.8 g) as a yellow sticky solid.

Step 7: To a stirred solution of trans-4-amino-5-cyclopropylpyrrolidin-2-one (5.8 g, 40.25 mmol) and DCM (25 mL) were added TEA (17.2 mL, 123.17 mmol) and Boc anhydride (9.8 g, 45.17 mmol) at 0° C. The reaction mixture was then stirred at RT overnight. The reaction mixture was then diluted with DCM. The organic layer was washed with water and brine, dried over sodium sulfate and concentrated under reduced pressure. The obtained residue was purified by column chromatography using neutral aluminium oxide and 1% MeOH and $CHCl_3$ as an eluent to afford an off-white solid which was further purified by preparative HPLC to afford tert-butyl (trans-2-cyclopropyl-5-oxopyrrolidin-3-yl)carbamate (0.42 g) and tert-butyl (cis-2-cyclopropyl-5-oxopyrrolidin-3-yl)carbamate (1.4 g) as off-white solids.

tert-butyl (trans-2-cyclopropyl-5-oxopyrrolidin-3-yl) carbamate (Intermediate C12-Boc)

$^1$H NMR (DMSO-$d_6$) δ: 7.78 (s, 1H), 7.20 (d, 1H), 3.87 (p, 1H), 2.79 (dd, 1H), 2.46 (d, 1H), 2.01 (dd, 1H), 0.82 (dt, 1H), 0.38 (dd, 2H), 0.26 (dd, 1H), 0.13-0.07 (m, 1H).

tert-butyl (cis-2-cyclopropyl-5-oxopyrrolidin-3-yl) carbamate (Intermediate C13-Boc)

$^1$H NMR (DMSO-$d_6$) δ: 7.84 (s, 1H), 7.25 (d, 1H), 4.18 (q, 1H), 2.88 (t, 1H), 2.25 (d, 2H), 1.38 (s, 9H), 0.74 (dt, 1H), 0.38 (dt, 2H), 0.09 (d, 2H).

Synthesis of tert-butyl ((2R,3R)-2-(cyclopropylmethyl)-5-oxopyrrolidin-3-yl)carbamate (Intermediate $C_{1-4}$-Boc)

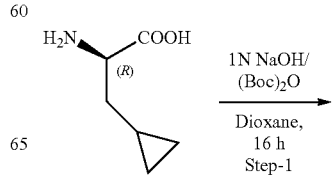

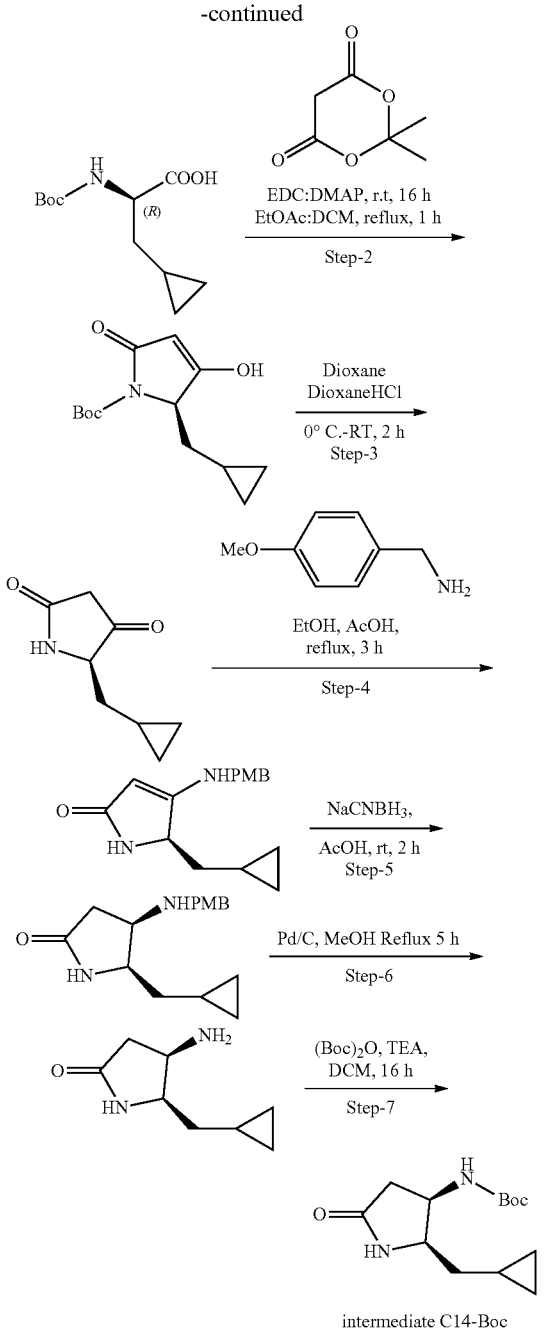

Step 1: To a stirred solution of (R)-2-amino-3-cyclopropylpropanoic acid (20.0 g, 154.9 mmol) in 1,4-dioxane (100 mL) was added 0.5N NaOH aqueous solution (120 mL) and di-tert-butyl-di-carbonate (40.6 g, 185.8 mmol) at 0° C., stirring was then continued at RT for 16 h. The solvent was then concentrated under reduced pressure, the resulting residue was acidified with 2N HCl solution. The remains were extracted with EtOAc, washed with water and brine. The organic layer was then dried over Na$_2$SO$_4$ and concentrated in vacuo to afford (R)-2-((tert-butoxy-carbonyl)amino)-3-cyclopropylpropanoic acid as an off white solid (25.0 g).

Step 2: To a stirred solution of (R)-2-((tert-butoxycarbonyl)amino)-3-cyclopropylpropanoic acid (20.0 g, 87.2 mmol) in DCM (200 mL) were added Meldrum's acid (13.8 g, 96.0 mmol) and DMAP (14.9 g, 122.1 mmol) at 0° C. After 30 min EDC·HCl (23.4 g, 122.1 mmol) was added at 0° C., the reaction mixture was then allowed to stir at ambient temperature for 20 h. The reaction mixture was diluted with EtOAc (50 ml), washed with cold 5% KHSO$_4$ solution and brine. The organic layer was dried over Na$_2$SO$_4$ and the solvent was distilled off under reduced pressure The remains were diluted with ethyl acetate (50 mL), and were refluxed for 1 h at 65° C. Removal of the solvent under reduced pressure afforded tert-butyl (R)-2-(cyclopropylmethyl)-3-hydroxy-5-oxo-2,5-dihydro-1H-pyrrole-1-carboxylate (27.0 g) as a yellow solid.

$^1$H NMR (DMSO-d$_6$) δ: 12.3 (s, 1H), 6 8.31 (s, 1H), 6 4.89 (s, 1H), 4.4-4.38 (m, 1H), 4.05-3.99 (m, 1H), 1.77-1.73 (m, 1H), 1.38 (s, 9H), 0.45-0.44 (m, 1H), 0.23-0.22 (m, 2H), 0.2-0.1 (m, 2H).

Step 3: To a stirred solution of tert-butyl (R)-2-(cyclopropylmethyl)-3,5-dioxopyrrolidine-1-carboxylate (10.0 g, 65.4 mmol) in 1,4-dioxane (270 mL) was added 4M HCl in 1,4-dioxane (135 mL) at 0° C. under a nitrogen atmosphere and the reaction mixture was allowed to stir for 2 h at ambient temperature. The reaction mixture was then concentrated under vacuum and the obtained residue was triturated with diethyl ether to get (R)-5-(cyclopropylmethyl)pyrrolidine-2,4-dione (18.0 g) as a white gummy solid.

Step 4: To a stirred solution of (R)-5-(cyclopropylmethyl)pyrrolidine-2,4-dione (10.0 g, 65.4 mmol) in EtOH: AcOH (100 mL, 9:1 w/v) was added (4-methoxyphenyl) methanamine (13.4 g, 98.0 mmol) at 0° C. and the reaction mixture was stirred to 80° C. under a nitrogen atmosphere for 1 h. The reaction mixture was concentrated under reduced pressure and the obtained residue was triturated with 1N NaOH to get (R)-5-(cyclopropylmethyl)-4-((4-methoxybenzyl)amino)-1,5-dihydro-2H-pyrrol-2-one (5.0 g, 23%) as an off white solid.

Step 5: To a stirred solution of (R)-5-(cyclopropylmethyl)-4-((4-methoxybenzyl)amino)-1,5-dihydro-2H-pyrrol-2-one (5.0 g, 18.4 mmol) in AcOH (50 mL) was added NaCNBH$_3$ (3.4 g, 55.1 mmol) at 0° C. and the reaction mixture was then stirred at ambient temperature under a nitrogen atmosphere for 2 h. The reaction mixture was then concentrated under reduced pressure. The obtained residue was basified with 1N NaOH at 0° C. leading to precipitation. The solid was filtered off and dried in vacuo to afford the crude product which was purified by combiflash (using MeOH:DCM (0-5%)) to afford (4R,5R)-5-(cyclopropylmethyl)-4-((4-methoxybenzyl)-amino)pyrrolidin-2-one (5.0 g).

Step 6: To a solution of (4R,5R)-5-(cyclopropylmethyl)-4-((4-methoxybenzyl)amino)pyrrolidin-2-one (7.0 g, 25.5 mmol) in MeOH (210 mL), were added HCOONH$_4$ (32.1 g, 510.3 mmol) and 10% Pd/C (7.0 g) at ambient temperature under a nitrogen atmosphere and the reaction mixture was then heated to 75° C. for 2 h. The reaction mixture was then filtered through celite and the obtained filtrate was concentrated under reduced pressure to afford (4R,5R)-4-amino-5-(cyclopropylmethyl)pyrrolidin-2-one (3.9 g).

Step 7: To a solution of (4R,5R)-4-amino-5-(cyclopropylmethyl)pyrrolidin-2-one (3.9 g, 25.5 mmol) in DCM (39 mL), TEA (4.5 g, 44.6 mmol) and (Boc)$_2$O (6.1 g, 28.0 mmol) were added at 0° C. The mixture was stirred at ambient temperature for 16 h, then the reaction mixture was diluted with DCM and washed consecutively with 5% citric acid solution and brine. The solvent was removed under reduced pressure to afford the crude product as an off white solid which was washed with diethyl ether (2×1 mL), filtered and the solid was dried in vacuo to afford tert-butyl ((2S,3S)-2-(2,3-dihydrobenzo[b][1,4]dioxin-6-yl)-5-oxopyrrolidin-3-yl)carbamate as a white solid (2.6 g, 40%).

$^1$H NMR (DMSO-$d_6$) δ 7.8 (s, 1H), 7.3-7.2 (m, 1H), 4.26-4.21 (m, 1H) 3.70-3.60 (m, 1H), 3.4 (s, 2H), 2.46-2.40 (m, 1H), 1.38 (s, 9H), 0.45-0.44 (m, 1H), 0.23-0.22 (m, 2H), 0.20-0.10 (m, 2H).

Synthesis of (trans)-4-amino-5-(3,5-difluorophenyl)pyrrolidin-2-one (Intermediate A15)

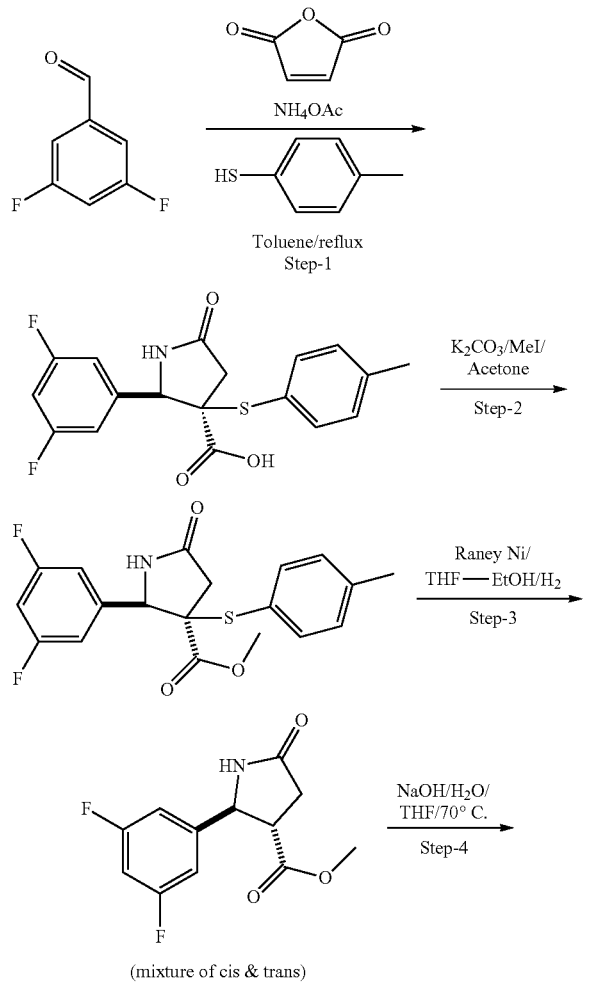

(mixture of cis & trans)

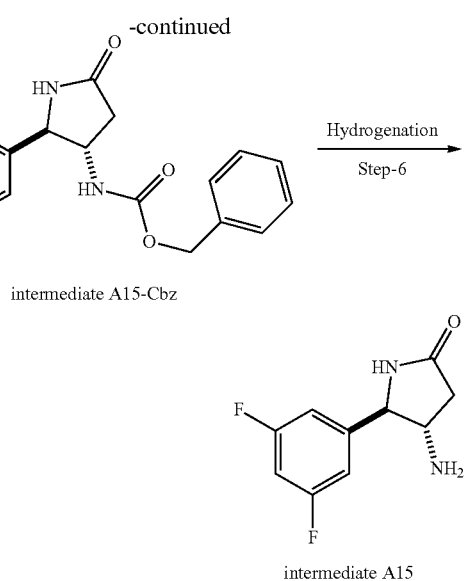

intermediate A15-Cbz intermediate A15

Step 1: A solution of 3,5-difluorobenzaldehyde (100.0 g, 0.7 mol, 1.0 eq), 4-methyl-benzenethiol (87.4 g, 0.7 mol, 1 eq), maleic anhydride (69.0 g, 0.7 mol, 1.0 eq) and ammonium acetate (54.2 g, 0.7 mol, 1.0 eq) in toluene (2.5 L) was stirred at ambient temperature for 2 hours, followed by heating to 140° C. in an autoclave for 16 hours. After complete disappearance of the starting material (monitored by LCMS), the reaction mixture was cooled to ambient temperature and was concentrated under reduced pressure to afford 2-(3,5-difluoro-phenyl)-5-oxo-3-p-tolylsulfanyl-pyrrolidine-3-carboxylic acid (266 g crude material) as a brown gum.

Step 2: To a suspension of 2-(3,5-difluoro-phenyl)-5-oxo-3-p-tolylsulfanyl-pyrrolidine-3-carboxylic acid (266.0 g, 0.73 mol, 1.0 eq) in acetone (2.61) was added $K_2CO_3$ (405.1 g, 2.93 mol, 4.0 eq) followed by methyl iodide (273.7 mL, 4.39 mol, 6.0 eq) and the resulting suspension was stirred at ambient temperature for 48 hours. The reaction mixture was then filtered and the filtrate was concentrated under reduced pressure. The crude residue was purified by column chromatography (silica 100-200 mesh and 40% ethyl acetate/hexane as eluent) to afford 2-(3,5-difluoro-phenyl)-5-oxo-3-p-tolylsulfanyl-pyrrolidine-3-carboxylic acid methyl ester (24.0 g, 9% over two steps) as a brown solid.

Step 3: To a solution of 2-(3,5-difluoro-phenyl)-5-oxo-3-p-tolylsulfanyl-pyrrolidine-3-carboxylic acid methyl ester (20.0 g, 0.053 mol, 1.0 eq) in an ethanol:THF mixture (360 mL, 2:1) was added Raney Nickel (10 g). The resulting suspension was reacted in a Parr shaker at 40 psi of hydrogen pressure for 4 h. After completion of the reaction (monitored by LCMS), the reaction mixture was filtered over a bed of celite and the celite bed was washed with ethanol (2×150 ml). The combined filtrates were concentrated under reduced pressure to afford 2-(3,5-difluoro-phenyl)-5-oxo-pyrrolidine-3 carboxylic acid methyl ester (9 g crude material) as a brown gum.

Step 4: To a suspension of 2-(3,5-difluoro-phenyl)-5-oxo-pyrrolidine-3-carboxylic acid methyl ester (13.0 g, 0.05 mol, 1.0 eq) in MeOH (130 mL) was added 2N NaOH (75 mL, 0.15 mol, 3.0 eq) at 0° C. and the resulting suspension was then stirred at 80° C. for 6 hours. After completion of the reaction (monitored by LCMS), the reaction mixture was concentrated and the residue was diluted with water and washed with ethyl acetate (2×150 ml). The aqueous basic mixture was acidified to pH 4 with 6N HCl. The precipitated solids were filtered, dried and triturated with ethyl acetate and diethyl ether to afford trans-5-oxo-2-(3,5-difluorophenyl)pyrrolidine-3-carboxylic acid (4.1 g) as an off-white solid.

Step 5: To a stirred solution of trans-5-oxo-2-(3,5-difluorophenyl)pyrrolidine-3-carboxylic acid (4.6 g, 0.019 mol, 1.0 eq) in a mixture of benzene (60 mL) and THF (23 mL) was added DPPA (5.43 ml, 0.025 mol, 1.3 eq) followed by DIPEA (4.96 ml, 0.029 mol, 1.5 eq) at ambient temperature. The resulting reaction mixture was stirred at ambient temperature for 2 hours, followed by the addition of benzyl alcohol (5.2 g, 0.048 mol, 2.5 eq) and the reaction mixture was heated at 90° C. for 16 hours. After completion of the reaction (monitored by TLC), the reaction mixture was concentrated. The crude residue was purified by column chromatography (silica 100-200 mesh, 10% EA-Hexane as eluent), followed by trituration using MTBE to afford trans-benzyl (5-oxo-2-(3,5-difluorophenyl)pyrrolidin-3-yl)carbamate (intermediate A15-Cbz) (1.2 g, 18%) as an off-white solid.

Step 6: Trans-benzyl-N-(5-oxo-2-(3,5-difluorophenyl)pyrrolidin-3-yl)carbamate (611.0 mg, 1.764 mmol, 1.0 eq) was dissolved in EtOH/EtOAc/AcOH (35 mL, 24/2/1, v/v/v) and is hydrogenated using a flow hydrogenation apparatus (Pd/C as catalyst, H₂ pressure below 10 bar). The inlet flask is rinsed repeatedly with the solvent mixture described above. The solvent is then removed under reduced pressure, and the remains are purified using ion exchange chromatography (DSC-SCX). N-trans-(5-oxo-2-(3,5-difluorophenyl)pyrrolidin-3-yl)amine (intermediate A15) is obtained in 99% yield (370.1 mg).

Synthesis of benzyl (trans-2-(3-methoxyphenyl)-5-oxopyrrolidin-3-yl)carbamate (Intermediate A16-Cbz)

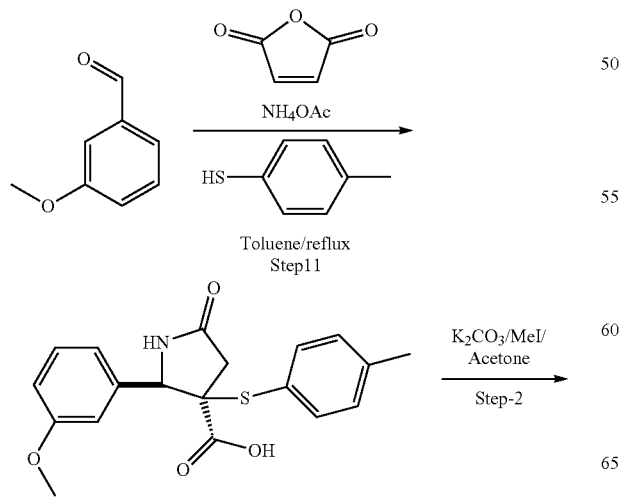

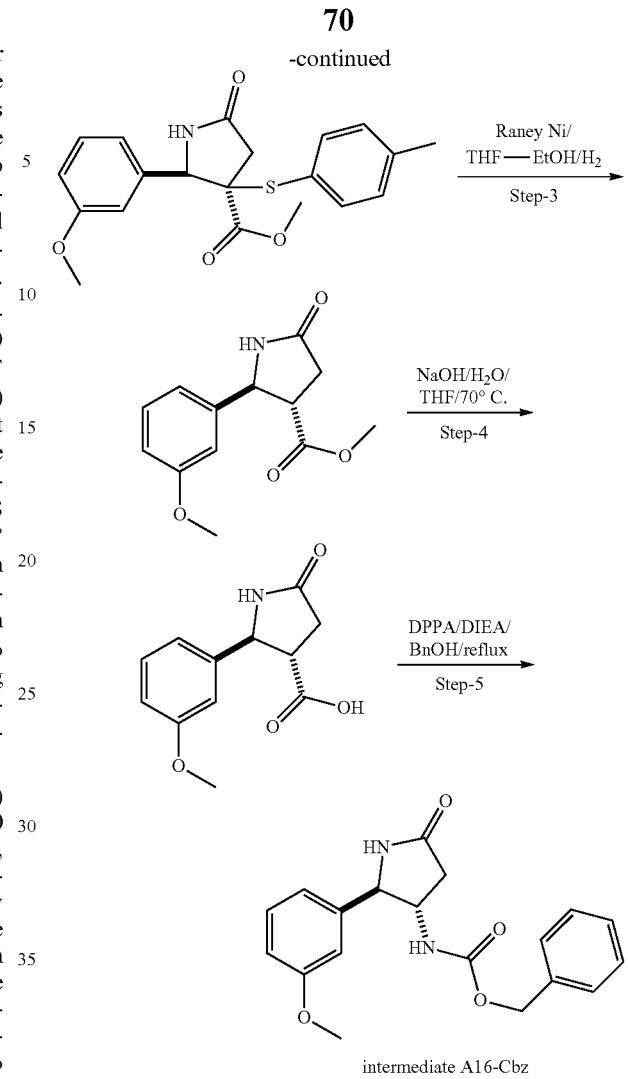

intermediate A16-Cbz

Step 1: A solution of 3-methoxy-benzaldehyde (100.0 g, 0.73 mol, 1.0 eq), 4-methyl-benzenethiol (91.2 g, 0.73 mol, 1.0 eq), maleic anhydride (72.0 g, 0.73 mol, 1.0 eq) and ammonium acetate (56.2 g, 0.73 mol, 1.0 eq) in Toluene (2.5 L) was stirred at ambient temperature for 2 hours, followed by heating to 140° C. in an autoclave for 16 hours. After completion of the reaction (monitored by LCMS), the reaction mixture was cooled to ambient temperature and was concentrated under reduced pressure to afford 2-(3-methoxy-phenyl)-5-oxo-3-p-tolylsulfanyl-pyrrolidine-3-carboxylic acid (262 g crude material) as a brown gum.

Step 2: To a suspension of 2-(3-methoxy-phenyl)-5-oxo-3-p-tolylsulfanyl-pyrrolidine-3-carboxylic acid (262.0 g, 0.73, 1.0 eq) in acetone (2.6 L), was added K₂CO₃ (405.7 g, 2.93 mol, 4.0 eq), followed by methyl iodide (274.1 mL, 4.40 mol, 6.0 eq) and the resulting suspension was stirred at ambient temperature for 48 hours. The reaction mixture was filtered and the filtrate was concentrated under reduced pressure. The crude residue was purified by column chromatography (silica 100-200 mesh and 15% ethyl acetate/hexane as eluent) to afford 2-(3-methoxy-phenyl)-5-oxo-3-p-tolylsulfanyl-pyrrolidine-3-carboxylic acid methyl ester (42.0 g, 15% over 2 steps) as a brown solid.

Step 3: To a solution of 2-(3-methoxy-phenyl)-5-oxo-3-p-tolylsulfanyl-pyrrolidine-3-carboxylic acid methyl ester (40.0 g, 0.053 mol, 1.0 eq) in an ethanol:THF mixture (670 mL, 2:1), was added Raney Nickel (40 g) and the resulting suspension was stirred under hydrogen pressure (using a hydrogen balloon) for 16 hours. After completion of the reaction (monitored by LCMS), the reaction mixture was filtered over a bed of celite and the celite bed was washed with ethanol (2×150 ml). The combined filtrates were concentrated under reduced pressure to afford 2-(3-methoxy-phenyl)-5-oxo-pyrrolidine-3-carboxylic acid methyl ester (20.0 g, 77%) as a brown gum.

Step 4: To a suspension of 2-(3-methoxy-phenyl)-5-oxo-pyrrolidine-3-carboxylic acid methyl ester (20.0 g, 0.08 mol, 1.0 eq) in MeOH (480 mL) was added 2N NaOH (240 mL) at 0° C. and the resulting suspension was stirred at 80° C. for 66 hours. After completion of the reaction (monitored by LCMS), the reaction mixture was concentrated and the residue was diluted with water and washed with ethyl acetate (2×250 mL). The basic aqueous layer was acidified to pH 4 with 6N HCl. The precipitated solids were filtered, dried, triturated with ethyl acetate and diethyl ether to afford trans-5-oxo-2-(3-methoxyphenyl)pyrrolidine-3-carboxylic acid (9.5 g, 50%) as an off-white solid.

Step 5: To a stirred solution of trans-5-oxo-2-(3-methoxyphenyl)pyrrolidine-3-carboxylic acid (8.3 g, 0.035 mol, 1.0 eq) in a mixture of benzene (250 mL) and THF (80 mL) was added DPPA (9.9 ml, 0.046 mol, 1.3 eq) followed by TEA (9.8 ml, 0.705 mol, 20.0 eq) at ambient temperature. The resulting reaction mixture was stirred at ambient temperature for 2 hours, then benzyl alcohol (4.8 ml, 0.046 mol, 1.3 eq) was added and the reaction mixture was heated to 90° C. for 16 hours. After completion of the reaction (monitored by TLC), the reaction mixture was concentrated and the crude residue was purified by column chromatography (silica 100-200 mesh, 10% EA-Hexane as eluent), followed by trituration using MTBE to afford benzyl (trans-2-(3-methoxyphenyl)-5-oxopyrrolidin-3-yl)carbamate (intermediate A16-Cbz) (5.6 g, 46%) as an off-white solid.

Synthesis of tert-butyl ((2R,3S)-2-benzyl-5-oxopyrrolidin-3-yl)carbamate (Intermediate A17-Boc ent1)

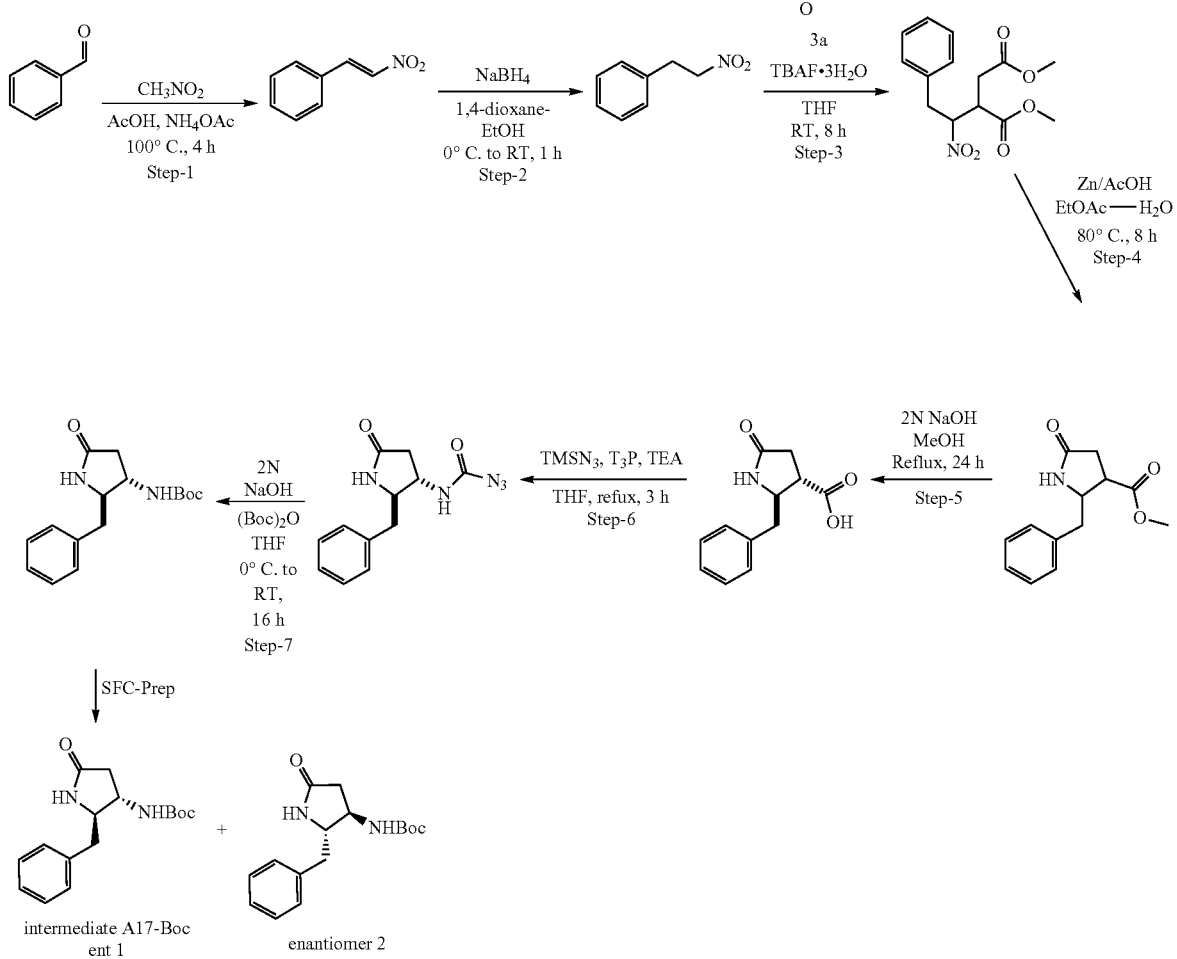

Step 1: Benzaldehyde (150 g, 1.41 mol) was added to a stirred solution of nitromethane (300 mL), acetic acid (20 mL) and ammonium acetate (11 g, 0.14 mol) at ambient temperature under argon atmosphere. The solution was then heated to 110° C. for 4 h. The reaction mixture was then cooled and diluted with water (1000 mL) and extracted with EtOAc (3×500 mL). The combined organic layers were washed with water and brine. The separated organic layer was then concentrated to obtain the crude product. This crude product was purified by column chromatography (silica gel, eluent EtOAc/hexane 5:95) to afford 130 g (62%) of (E)-(2-nitrovinyl)benzene as a pale yellow solid. (TLC system: 10% ethyl acetate in pet-ether; Rf: 0.6).

Step 2: To a stirred solution of NaBH$_4$ (43 g, 1.13 mol) in EtOH (300 mL) and 1,4-dioxane (1000 mL) was added a solution of (E)-(2-nitrovinyl)benzene in 1,4-dioxane (1000 mL) at 0° C. The resulting reaction mixture was stirred at ambient temperature for 30 minutes. The reaction mixture was then quenched with saturated NH$_4$Cl solution and the mixture was then extracted with EtOAc (500 mL×3). The combined organic layers were washed with brine (500 mL), dried over anhydrous Na$_2$SO$_4$, filtered and the filtrate was concentrated to obtain the crude product. This crude product was purified by column chromatography (silica gel, eluent EtOAc/hexane 2:98) to afford 100 g (77%) of (2-nitroethyl)benzene as a brown liquid (TLC system: 5% ethyl acetate in pet-ether; Rf: 0.5).

Step 3: To a stirred mixture of (2-nitroethyl)benzene (140 g, 0.927 mol) and dimethyl maleate (116 mL, 0.97 mol) was added TBAF·3H$_2$O (58 g, 0.185 mol) at 0° C. The reaction mixture was then allowed to stir at 25° C. for 16 h. The reaction mixture was diluted with EtOAc (1000 mL), washed with water and brine, dried over anhydrous Na$_2$SO$_4$, and concentrated under reduced pressure to give a brown liquid. Flash column chromatography of this material (eluent hexane/EtOAc 90:10) gave dimethyl 2-(1-nitro-2-phenylethyl)succinate (200 g, 73%) as a brown liquid. (TLC system: 30% ethyl acetate in pet-ether; Rf: 0.4).

Step 4: To a stirred solution of dimethyl 2-(1-nitro-2-phenylethyl)succinate (100 g, 0.33 mol) in EtOAc (2 L), were added acetic acid (150 mL), water (50 mL) and zinc (110 g, 1.69 mol, lot wise). The reaction mixture was heated to 80° C. for 16 h. After completion of the reaction, the reaction mixture was cooled and filtered, and the filtrate was diluted with EtOAc and water. The layers were separated, and the separated organic layer was washed with water and sat. NaHCO$_3$ solution and was then concentrated under reduced pressure to give 50 g (65%) of methyl 2-benzyl-5-oxopyrrolidine-3-carboxylate as a brown liquid. (TLC: 50% EtOAc in pet ether; Rf: 0.3).

Step 5: To a stirred solution of methyl 2-benzyl-5-oxopyrrolidine-3-carboxylate (50 g, 0.214 mol) in methanol (500 mL) at ambient temperature was added 2 N NaOH solution and the mixture was heated to reflux under N$_2$ atmosphere for 24 h. The mixture was then concentrated under reduced pressure to give a residue, which was diluted with water (100 mL), acidified with sat. KHSO$_4$ solution and was then extracted with EtOAc (3×300 mL). The combined organic layers were washed with brine and concentrated to give 38 g (82%) of trans-2-benzyl-5-oxopyrrolidine-3-carboxylic acid as brown liquid. (TLC system: 20% MeOH/DCM; Rf: 0.1).

Step 6: To a stirred solution of trans-2-benzyl-5-oxopyrrolidine-3-carboxylic acid (12 g, 54.79 mmol) in THF (120 mL) were added 50% T$_3$P (35 mL, 54.79) and TEA (23 mL, 164.3 mmol) and the resulting mixture was stirred at ambient temperature for 10 min, prior to the addition of TMSN$_3$ (14.5 mL, 109.56) and the resulting mixture was heated to reflux for 3 h. The reaction mixture was cooled to ambient temperature, diluted with water (50 mL) and extracted with EtOAc (3×100 mL). The separated organic layer was washed with brine and concentrated to give the crude product. This crude product was purified by column chromatography (silicagel, eluent MeOH/CH$_2$Cl$_2$ 2:98) to afford 3.0 g (21%) of (trans-2-benzyl-5-oxopyrrolidin-3-yl)carbamoyl azide as a brown solid (TLC system: 100% EA; Rf: 0.5).

Step 7: A solution of (trans-2-benzyl-5-oxopyrrolidin-3-yl)carbamoyl azide (3.0 g, 11.58 mmol) in THF (30 mL) was added drop wise to 30 mL of 2 N NaOH solution at 0° C. The resulting reaction mixture was stirred at ambient temperature for 30 min and monitored by TLC, prior to the addition of Boc anhydride (6 mL) at ambient temperature and the stirring was continued for 16 h. The reaction mixture was diluted with water (30 mL) and extracted with EtOAc (3×50 mL). The separated organic layer was washed with brine and concentrated to give the crude product. The crude product was triturated with 50% EtOAc in pet-ether to afford 2.1 g (63%) of tert-butyl (trans-2-benzyl-5-oxopyrrolidin-3-yl)carbamate as an off-white solid which was separated by SFC to give individual enantiomers.

Chiral, preparative SFC was conducted as follows: column: Chiralpak IG (4.6×150 mm) 3 µm, co-solvent:methanol (40%), total flow: 3 g/minute, ABPR: 1500 psi, temperature 30° C. Retention times: enantiomer 1 (intermediate A17-Boc end): 1.329 minutes, enantiomer 2: 1.965 minutes.

Synthesis of trans {1-[1-(4-Fluoro-phenyl)-1H-indazol-5-yl]-5-oxo-2-ethyl-pyrrolidin-3-yl}-carbamic acid benzyl ester (Intermediate A18-Cbz)

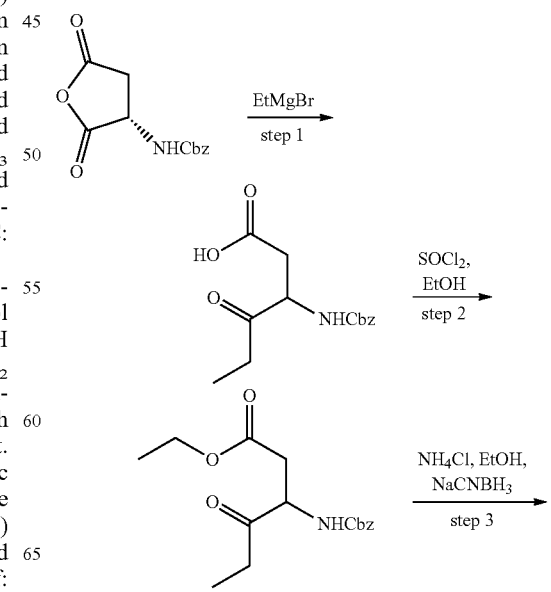

-continued

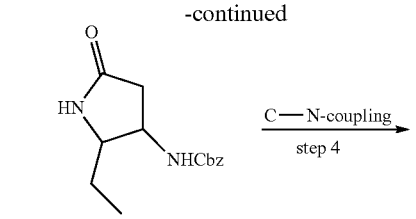

C—N-coupling
step 4

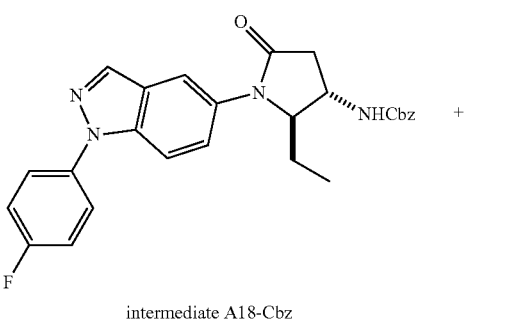

intermediate A18-Cbz

+

[structure with indazole-pyrrolidinone-NHCbz, 4-fluorophenyl]

Step 1: Benzyl N-[(3S)-2,5-dioxotetrahydrofuran-3-yl] carbamate (500.0 mg, 2.006 mmol, 1.0 eq) was weighed out into a Schlenk flask, a stir bar was added, the flask was sealed and sparged with nitrogen. Then THF (20 mL) was added, followed by cooling of the reaction mixture to 78° C. Then, ethylmagnesiumbromide (3.2 mL of a 1 M solution in THF, 1.6 eq.) was added dropwise over two minutes, and the mixture was stirred at that temperature for 2 hours. Then, 7 mL of 10% citric acid was added at 78° C. The mixture was allowed to warm to ambient temperature. $Et_2O$ was then added as well as water. The layers were separated, and the aqueous layer was extracted two more times with $Et_2O$. The combined organic layers were washed with brine, dried over $MgSO_4$, and the solvent was removed under reduced pressure to yield a colorless oil (638 mg, containing 3-(Benzyloxycarbonylamino)-4-oxo-hexanoic acid and byproducts) which was used without further purification in the next step.

Step 2: 3-(Benzyloxycarbonylamino)-4-oxo-hexanoic acid (638 mg from step 1, used crude with all non-volatile byproducts) was dissolved in ethanol (20 mL). A stir bar was added, the flask was sealed with a septum, and was sparged with nitrogen. The reaction mixture was cooled to 0° C. Then, thionyl chloride (0.14 mL, 1.9 mmol) was added, and the mixture was stirred at ambient temperature for 16 hours. The solvent was evaporated under reduced pressure, and the crude material was then purified via silica gel chromatography to yield 438.1 mg of a clear oil containing ethyl 3-(((benzyloxy)carbonyl)amino)-4-oxohexanoate. The desired compound is accompanied by the an inseparable byproduct.

Step 3: Sodium cyanoborohydride (53.8 mg, 0.855 mmol, 0.6 eq.) and ammonium acetate (1099.0 mg, 14.250 mmol, 10.0 eq) were weighed out into a flask, a stir bar was added, the flask was sealed and sparged with nitrogen. Then, ethyl-3-(benzyloxycarbonylamino)-4-oxo-hexanoate (438 mg from step 2, used crude with all non-volatile byproducts) in ethanol (5.0 mL) was added, and the mixture was heated to 50° C. for one hour. The solvent was then removed, and the remains were taken up in EtOAc and water. The layers were separated, and the aqueous phase was extracted two more times with EtOAc. The combined organic layers were then dried over $MgSO_4$, the solvent was removed and the crude material was purified via silica gel chromatography to yield 125.0 mg (33%) of benzyl (2-ethyl-5-oxopyrrolidin-3-yl)carbamate.

Step 4: Benzyl N-(2-ethyl-5-oxo-pyrrolidin-3-yl)carbamate (285.0 mg, 1.087 mmol, 1.0 eq.), 1-(4-fluorophenyl)-5-iodo-indazole (404.1 mg, 1.120 mmol, 1.1 eq.), $K_3PO_4$ (461.2 mg, 2.173 mmol, 2.0 eq.) and copper iodide (165.5 mg, 0.869 mmol, 0.8 eq.) were weighed out into a microwave vial. A stir bar was added, the vial was sealed and sparged with nitrogen. Then, 1,4-dioxane (10.8 mL) and trans-N,N'-dimethylcyclohexane-1,2-diamine (0.108 mmol, 15.4 mg, 0.1 eq.) were added and the mixture was stirred at 90° C. for 16 hours. The reaction mixture was then cooled to ambient temperature, sat. $NaHCO_3$ solution and DCM were added, and the mixture was filtered through a hydrophobic frit. The organic solvent was then removed under reduced pressure, and the crude material was purified via silica gel chromatography to yield 160.0 mg (31%) of trans-{1-[1-(4-Fluoro-phenyl)-1H-indazol-5-yl]-5-oxo-2-ethyl-pyrrolidin-3-yl}-carbamic acid benzyl ester and 70.0 mg (14%) of cis-{1-[1-(4-Fluorophenyl)-1H-indazol-5-yl]-5-oxo-2-ethyl-pyrrolidin-3-yl}-carbamic acid benzyl ester.

Synthesis of benzyl (trans-2-(5-chlorothiophen-2-yl)-5-oxopyrrolidin-3-yl)carbamate (Intermediate A19-Cbz)

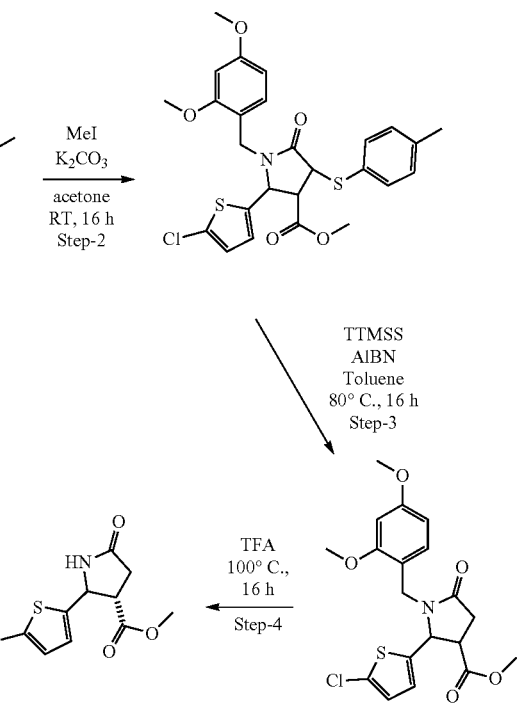

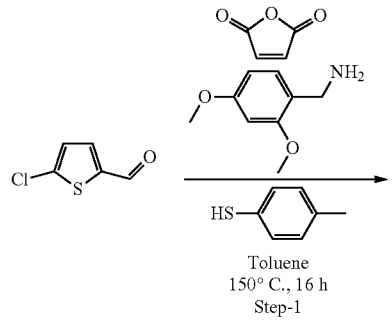

intermediate A19-Cbz

Step 1: To a suspension of 5-chlorothiophene-2-carbaldehyde (60 g, 409.30 mmol), p-thiocresol (50.7 g, 409.30 mmol) and maleic anhydride (40.13 g, 409.30 mmol) in toluene (1 L) was added (2,4-dimethoxyphenyl)methan-amine (68.81 g, 409.30 mmol) at ambient temperature. The resulting mixture was refluxed using a Dean-Stark trap for 16 h and was then concentrated. The crude product was purified via silica-gel (100-200 mesh) column chromatography using 50% EtOAc in pet-ether as an eluent to afford 110 g (52%) of 2-(5-chlorothiophen-2-yl)-1-(2,4-dimethoxybenzyl)-5-oxo-3-(p-tolylthio)pyrrolidine-3-carboxylic acid as a brown solid (TLC system: EtOAc/pet ether (3:7), $R_f$: 0.1).

Step 2: To a suspension of 2-(5-chlorothiophen-2-yl)-1-(2,4-dimethoxybenzyl)-5-oxo-3-(p-tolylthio)pyrrolidine-3-carboxylic acid (95 g, 183.7 mmol) and $K_2CO_3$ (101.4 g, 735 mmol) in acetone (1.2 L) was added methyl iodide (47.4 mL, 735 mmol) at 0° C. The resulting mixture was allowed to stir at ambient temperature for 16 h, was then filtered and the filtrate was concentrated. The crude product was purified via silicagel (100-200 mesh) column chromatography using 5-10% EtOAc in pet-ether as an eluent to afford 79 g (81%) of methyl 2-(5-chlorothiophen-2-yl)-1-(2,4-dimethoxybenzyl)-5-oxo-3-(p-tolylthio)pyrrolidine-3-carboxylate as a colorless gummy liquid (TLC system: EtOAc/pet ether (3:7), $R_f$: 0.44).

Step 3: To a solution of methyl 2-(5-chlorothiophen-2-yl)-1-(2,4-dimethoxybenzyl)-5-oxo-3-(p-tolylthio)pyrrolidine-3-carboxylate (33 g, 62.14 mmol) in toluene (700 mL) were added AIBN (5.09 g, 31.07 mmol) and tristrimethylsilyl silane (30.9 g, 124.29 mmol). The resulting mixture was refluxed for 16 h and was then concentrated. The crude product was triturated with pet ether; the resulting solid was filtered off and dried under vacuum to give 20 g (80%) of methyl 2-(5-Chlorothiophen-2-yl)-1-(2,4-dimethoxybenzyl)-5-oxopyrrolidine-3-carboxylate as an off white solid (TLC system: EtOAc/pet ether (5:5), $R_f$: 0.5).

Step 4: A solution of methyl 2-(5-Chlorothiophen-2-yl)-1-(2,4-dimethoxybenzyl)-5-oxopyrrolidine-3-carboxylate (10 g, 24.44 mmol) in TFA (100 mL) was stirred at 80° C. for 16 h. The reaction mass was concentrated. The residue was basified with sat. $NaHCO_3$ to pH 8, and extracted with EtOAc (2×500 mL). The combined organic layers were washed with brine (500 mL), dried over $Na_2SO_4$, and concentrated. The residue was triturated with n-pentane to give 5 g of crude product of methyl 2-(5-chlorothiophen-2-yl)-5-oxopyrrolidine-3-carboxylate as an off white solid (TLC system: EtOAc/pet ether (5:5), $R_f$: 0.5).

Step 5: A mixture of methyl 2-(5-chlorothiophen-2-yl)-5-oxopyrrolidine-3-carboxylate (5 g, 19.3 mmol) and 2 N NaOH (15 mL) in methanol (100 mL) was stirred at 80° C. for 4 h. The reaction mixture was then concentrated and triturated with diethyl ether twice. The residue was taken up in cold water (100 mL) and acidified with 6 N HCl to pH 2 followed by extraction with EtOAc (2×500 mL). The combined organic layers were then dried over $Na_2SO_4$ and concentrated to afford 3.7 g (78%) of trans-5-oxo-2-(5-chlorothiophen-2-yl)pyrrolidine-3-carboxylic acid as a solid (TLC system: EtOAc/pet-ether (6:4), $R_f$: 0.1).

Step 6: To a solution of trans-5-oxo-2-(5-chlorothiophen-2-yl)pyrrolidine-3-carboxylic acid (12 g, 48.97 mmol) in benzene-THF (240 mL and 120 mL) were added DPPA (13.6 mL, 63.66 mmol) and triethylamine (8.8 mL, 63.66 mmol). The resulting mixture was stirred at ambient temperature for 3 h, prior to the addition of benzyl alcohol (6.6 mL, 63.66 mmol). The resulting mixture was then heated to 80° C. for 16 h. The reaction mixture was cooled to ambient temperature, diluted with water (500 mL) and extracted with EtOAc (2×500 mL). The combined organic layers were dried over $Na_2SO_4$ and concentrated. The crude product was purified via silica-gel (100-200 mesh) column chromatography using 40-50% EtOAc in pet-ether as an eluent to afford 6.3 g (36%) of benzyl (trans-2-(5-chlorothiophen-2-yl)-5-oxopyrrolidin-3-yl)carbamate as an off white solid (TLC system: EtOAc/pet-ether (6:4), $R_f$: 0.4).

Synthesis of trans-N-(1-(1H-indazol-5-yl)-5-oxo-2-phenylpyrrolidin-3-yl)-2,2-difluoropropanamide (Intermediate B1)

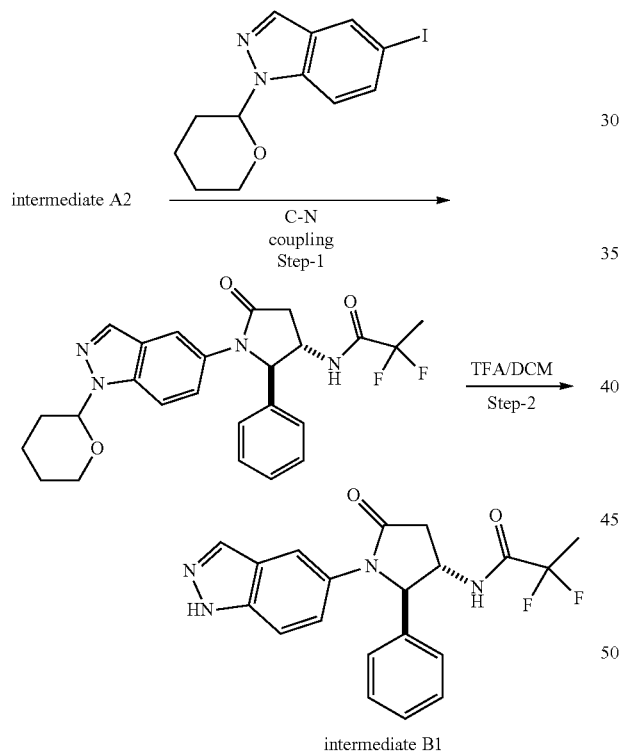

intermediate B1

Step 1: A stirred solution of intermediate A2 (1.2 g, 4.477 mmol, 1.0 eq), 5-iodo-1-(tetrahydro-2H-pyran-2-yl)-1H-indazole (1.8 g, 5.373 mmol, 1.2 eq) and $K_3PO_4$ (1.9 g, 8.955 mmol, 2.0 eq) in 1,4-dioxane (20 mL) was degassed with argon for 30 min. Then trans-N,N'-dimethylcyclohexane-1,2-diamine (0.3 g, 1.791 mmol, 0.4 eq) and CuI (0.2 g, 0.985 mmol, 0.2 eq) were added and the reaction mixture was stirred for 16 h at 90° C. in a sealed tube. After completion of the reaction (monitored by TLC, TLC system 5% MeOH in DCM, Rf-0.5), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the desired trans-2,2-difluoro-N-(5-oxo-2-phenyl-1-(1-(tetrahydro-2H-pyran-2-yl)-1H-indazol-5-yl)pyrrolidin-3-yl)propanamide (1.5 g, 72%).

Step 2: To a stirred solution of trans-2,2-difluoro-N-(5-oxo-2-phenyl-1-(1-(tetrahydro-2H-pyran-2-yl)-1H-indazol-5-yl)pyrrolidin-3-yl)propanamide (1.5 g, 3.20 mmol, 1.0 eq) in DCM (20 mL), TFA (15 mL) was added at 0° C. and the reaction was stirred for 16 h at ambient temperature. After completion of the reaction, (monitored by TLC, TLC system 5% MeOH in DCM, Rf-0.3), the reaction mixture was concentrated and basified with $NaHCO_3$ solution. The aqueous phase was extracted with DCM (3×100 mL). The combined organic layers were dried over $Na_2SO_4$, filtered and concentrated to afford trans-N-(1-(1H-indazol-5-yl)-5-oxo-2-phenylpyrrolidin-3-yl)-2,2-difluoropropanamide (1.1 g, 89%) as a solid.

Synthesis of 1-(4,4-difluorocyclohexyl)-5-iodo-1H-indazole (Intermediate C1)

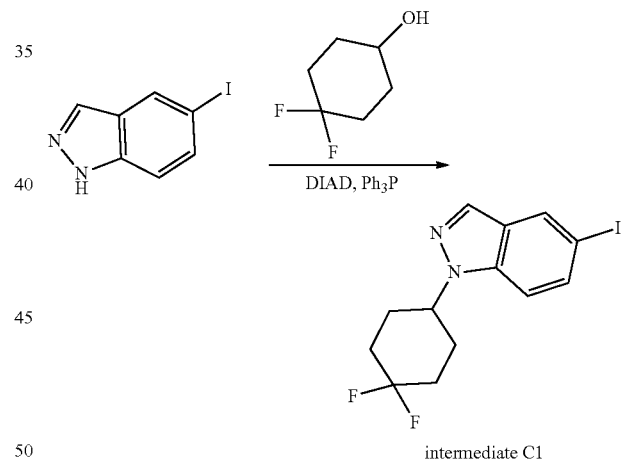

intermediate C1

To a stirred solution of 5-iodo-1H-indazole (1.00 g, 4.09 mmol, 1.0 eq) in THF (20 mL), DIAD (1.2 mL, 6.15 mmol, 1.5 eq) and $Ph_3P$ (1.60 g, 6.15 mmol, 1.5 eq) were added at 0° C. Then, 4,4-difluoro-cyclohexanol (0.84 g, 6.15 mmol, 1.5 eq) was added at 0° C. and the reaction mixture was stirred at ambient temperature for 16 h in the following. After completion of the reaction (monitored by TLC, TLC system 20% EtOAc in hexane, Rf-0.3), the reaction mixture was diluted with EtOAc (35 mL), washed with ice cold water (3×25 mL), dried over $Na_2SO_4$ and concentrated under reduced pressure to get the crude product as a mixture of regioisomers which was purified and separated by column chromatography (230-400 mesh silica gel; 0 to 20% EtOAc in hexane) to afford 1-(4,4-difluorocyclohexyl)-5-iodo-1H-indazole (0.10 g, 7%).

Synthesis of 1-cyclohexyl-5-iodo-1H-indazole (Intermediate C2)

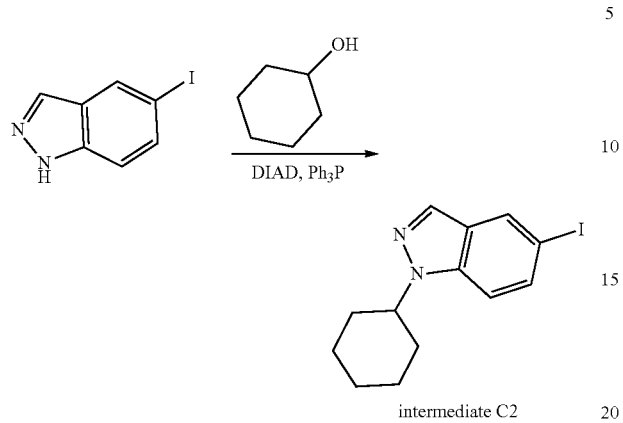

intermediate C2

Starting from cyclohexanol, intermediate C2 was synthesized in analogy to the synthetic procedure described for intermediate C1.

Synthesis of 1-(2-fluorobenzyl)-5-iodo-1H-indazole (Intermediate C3)

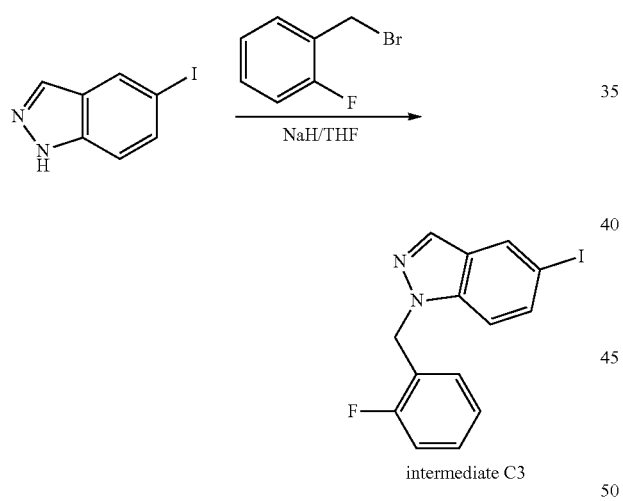

intermediate C3

To a stirred solution of 5-iodo-1H-indazole (1.00 g, 4.099 mmol, 1.0 eq) in THF (10 mL) NaH (0.24 g, 4.917 mmol, 1.2 eq) was added at 0° C. under a $N_2$ atmosphere. After 10 min, 1-(bromomethyl)-2-fluorobenzene (0.93 g, 4.917 mmol, 1.2 eq) was added at ambient temperature. The reaction mixture was stirred for 1 h at ambient temperature. After completion of the reaction (monitored by TLC, 20% EtOAc in hexane, Rf-0.6) the reaction mixture was quenched with ice cold water (20 mL) and extracted with EtOAc (3×20 ml), dried over $Na_2SO_4$ and was then concentrated under reduced pressure. The crude product was purified by column chromatography (using 230-400 silica gel) to separate the two isomers. The major isomer was the desired 1-(2-fluorobenzyl)-5-iodo-1H-indazole which was confirmed by $^1$H-NMR to afford intermediate C3 (0.57 g, 40%).

Synthesis of 1-(3-fluorobenzyl)-5-iodo-1H-indazole (Intermediate C4)

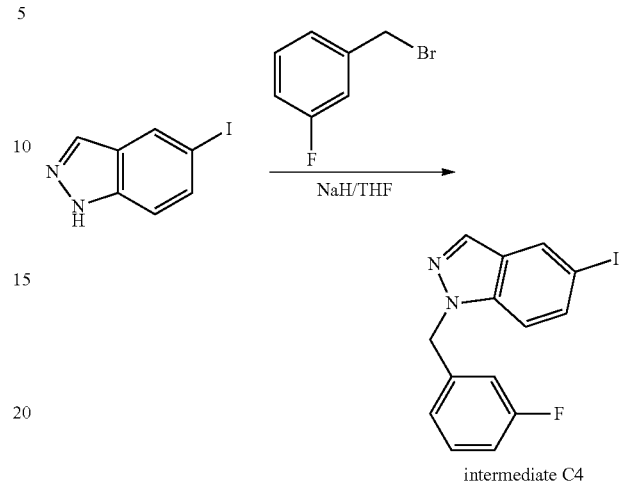

intermediate C4

To a stirred solution of 5-iodo-1H-indazole (1.00 g, 4.099 mmol, 1.0 eq) in THF (20 mL) NaH (0.24 g, 4.917 mmol, 1.2 eq) was added at 0° C. under a $N_2$ atmosphere. After 10 min, 1-(bromomethyl)-3-fluorobenzene (0.93 g, 4.917 mmol, 1.2 eq) was added. The reaction mixture was stirred for 1 h at ambient temperature. After completion of the reaction (monitored by TLC, 20% EtOAc in hexane, Rf-0.6), the reaction mixture was quenched with ice cold water (20 mL) and extracted with EtOAc (3×20 ml), dried over $Na_2SO_4$ and was then concentrated. The crude product was purified by column chromatography (using 230-400 silica gel) to separate the two isomers. The major isomer was the desired 1-(3-fluorobenzyl)-5-iodo-1H-indazole which was confirmed by $^1$H-NMR to afford intermediate C4 (0.61 g, 42%).

Synthesis of 1-(4-fluorobenzyl)-5-iodo-1H-indazole (Intermediate C5)

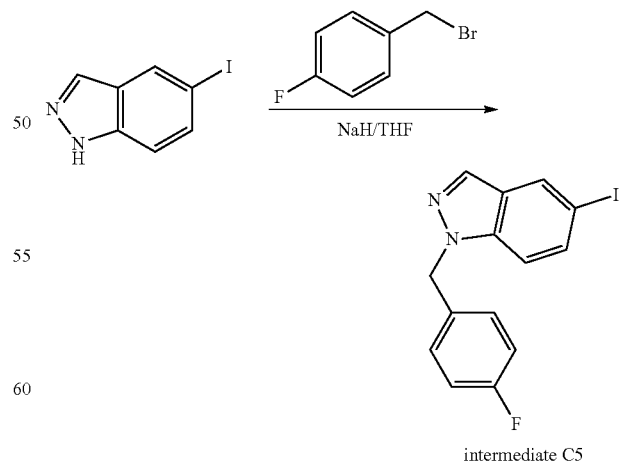

intermediate C5

To a stirred solution of 5-iodo-1H-indazole (1.00 g, 4.099 mmol, 1.0 eq) in THF (10 mL) NaH (0.24 g, 4.9174 mmol, 1.2 eq) was added at 0° C. under a $N_2$ atmosphere. After 10 min, 1-(bromomethyl)-4-fluorobenzene (0.93 g, 4.917 mmol, 1.2 eq) was added. The reaction mixture was stirred for 1 h at ambient temperature. After completion of the reaction (monitored by TLC, 20% EtOAc in hexane, Rf-0.6), the reaction mixture was quenched with ice cold water (20 mL) and extracted with EtOAc (3×20 mL), dried over $Na_2SO_4$ and was then concentrated to give the crude product which was purified by column chromatography (using 230-400 silica gel) to separate the two isomers. The major isomer was the desired 1-(4-fluorobenzyl)-5-iodo-1H-indazole which was confirmed by $^1$H-NMR to afford intermediate C5 (0.54 g, 37%).

Synthesis of 1-(cyclopropylmethyl)-5-iodo-1H-indazole (Intermediate C6)

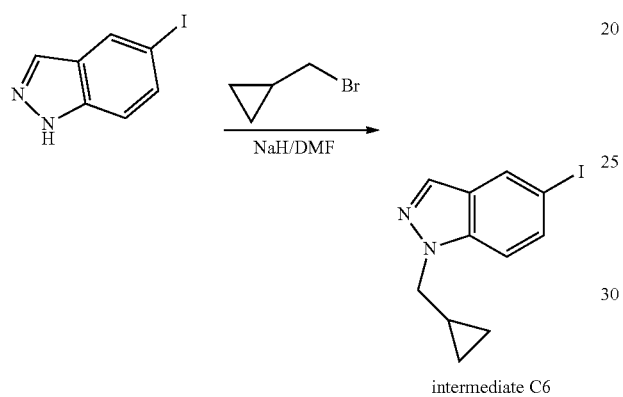

intermediate C6

To an ice cooled stirred solution of 5-iodo-1H-indazole (1.00 g, 4.09 mmol, 1.0 eq) in DMF (20 mL), NaH (0.23 g, 4.91 mmol, 1.2 eq, 50% by wt) was added and the reaction mixture was stirred for 15 min. Bromomethyl-cyclopropane (0.43 ml, 4.50 mmol, 1.1 eq) was dissolved in DMF (10 mL) and was then added dropwise at 0° C. The reaction mixture was then heated to 100° C. for 16 h. The reaction mixture was next diluted with EtOAc and washed with water. The combined organic layers were concentrated under reduced pressure to get the crude product which was purified by column chromatography (100-200 mesh silica gel; 50% EtOAc/Hexane; $R_f$-value-0.5) to separate the two isomers. The major isomer was the desired 1-(cyclopropylmethyl)-5-iodo-1H-indazole which was confirmed by $^1$H-NMR to afford intermediate C6 (0.60 g, 50%).

Synthesis of 1-((4,4-difluorocyclohexyl)methyl)-5-iodo-1H-indazole (Intermediate C7)

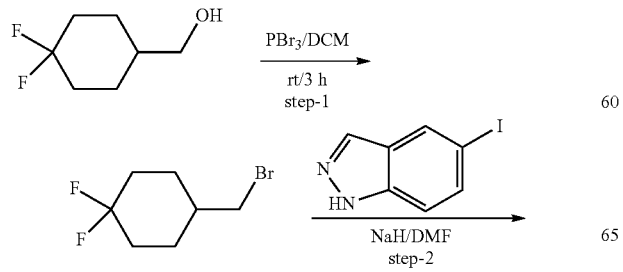

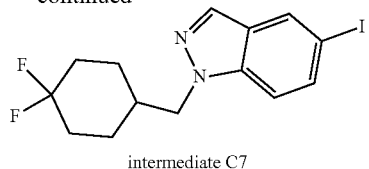

intermediate C7

Step 1: To a stirred solution of (4,4-difluorocyclohexyl)methanol (2.00 g, 14.372 mmol, 1.0 eq) in DCM (20 mL), $PBr_3$ (1.63 mL, 17.247 mmol, 1.2 eq) was added at 0° C. and the reaction mixture was then stirred at ambient temperature for 2 h. After completion of the reaction (monitored by TLC, TLC system 5% MeOH in DCM, Rf-0.3), the reaction was quenched with $NaHCO_3$ solution (150 mL), extracted with DCM (3×150 mL), dried over $Na_2SO_4$ and concentrated to get 4-(bromomethyl)-1,1-difluorocyclohexane (2.80 g, 96%).

Step 2: To a stirred solution of 5-iodo-1H-indazole (0.83 g, 5.396 mmol, 0.8 eq) in DMF (15 mL) NaH (0.25 mg, 3.396 mmol, 1.2 eq, 50% by wt) was added at 0° C., followed by the addition of 4-(bromomethyl)-1,1-difluorocyclohexane (0.90 g, 4.245 mmol, 1.0 eq) and the reaction mixture was stirred at ambient temperature for 16 h. After completion of the reaction (monitored by TLC, TLC system 5% MeOH/DCM, Rf-0.4), the reaction mixture was quenched with ice cold water (50 mL), extracted with EtOAc (3×50 mL), washed with brine (50 mL), dried over $Na_2SO_4$ and was then concentrated under reduced pressure to get the crude product which was purified by column chromatography (230-400 mesh silica gel; 0 to 3% MeOH-DCM) to separate the two isomers. The major isomer was the desired 1-((4,4-difluorocyclohexyl)methyl)-5-iodo-1H-indazole which was confirmed by $^1$H-NMR to afford intermediate C7 (0.54 g, 32%).

Synthesis of 5-bromo-1-(4-fluorophenyl)-1H-pyrazolo[3,4-b]pyridine (Intermediate C8)

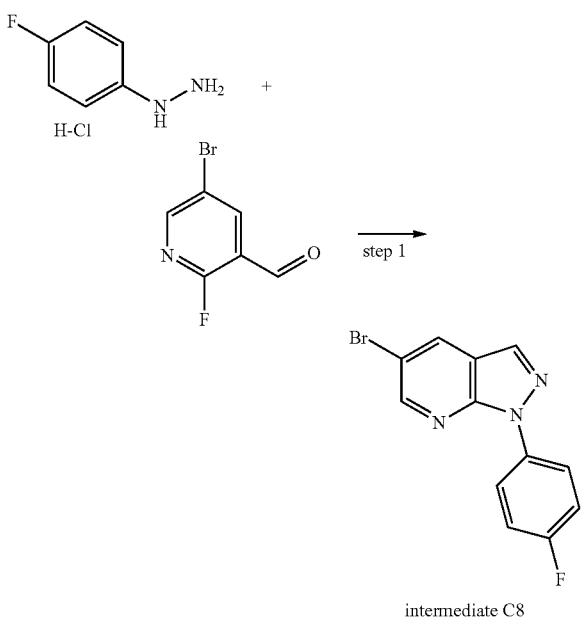

intermediate C8

Step 1: A mixture of 5-bromo-2-fluoro-pyridine-3-carbaldehyde (200.0 mg, 0.980 mmol, 1.0 eq.) and (4-fluorophenyl)hydrazine hydrochloride (159.4 mg 0.980 mmol, 1.0 eq.) in NMP (3.0 mL) was stirred at ambient temperature for two hours, before caesium carbonate (958.3 mg, 2.941 mmol, 3.0 eq.) was added and the mixture was heated to 115° C. for 1 hour. The mixture was cooled to ambient temperature, and was diluted with water/EtOAc. The layers were separated, and the aqueous layer was extracted two more times with EtOAc. The combined organic layers were then washed with brine and were dried over $MgSO_4$. The solvent was removed under reduced pressure and the remains were purified using silica gel chromatography to obtain 184.4 mg (64%) of 5-bromo-1-(4-fluorophenyl)-1H-pyrazolo[3,4-b]pyridine.

Synthesis of 5-bromo-1-(4-fluorophenyl)-1H-pyrazolo[3,4-c]pyridine (Intermediate C9)

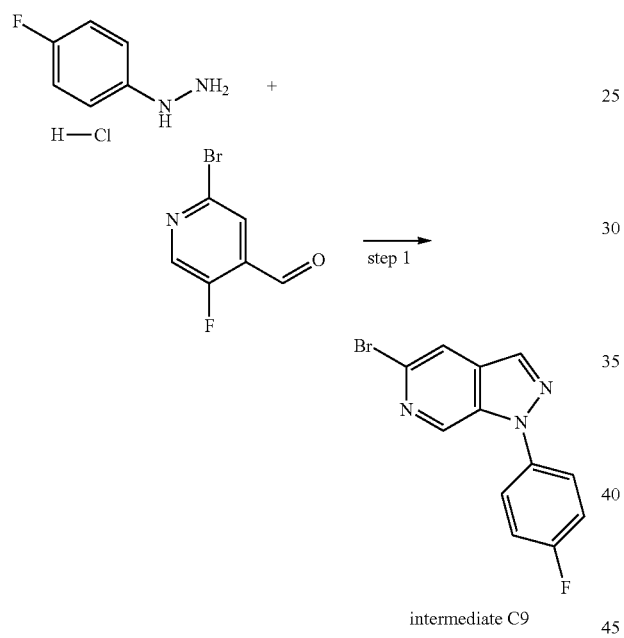

intermediate C9

5-bromo-1-(4-fluorophenyl)-1H-pyrazolo[3,4-c]pyridine was prepared in analogy to 5-bromo-1-(4-fluorophenyl)-1H-pyrazolo[3,4-b]pyridine, using 2-bromo-5-fluoroisonicotinaldehyde instead of 5-bromo-2-fluoro-pyridine-3-carbaldehyde. Yield: 47%

Synthesis of (trans)-4-amino-5-(2,3-dihydrobenzo[b][1,4]dioxin-6-yl)-1-(1-(4-fluorophenyl)-1H-indazol-5-yl)pyrrolidin-2-one (Intermediate D1)

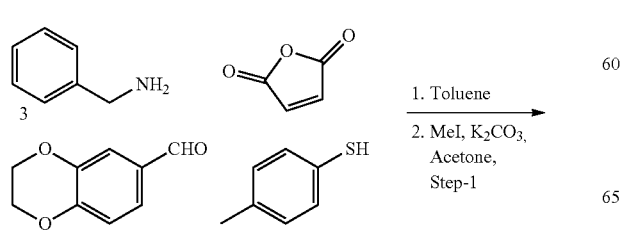

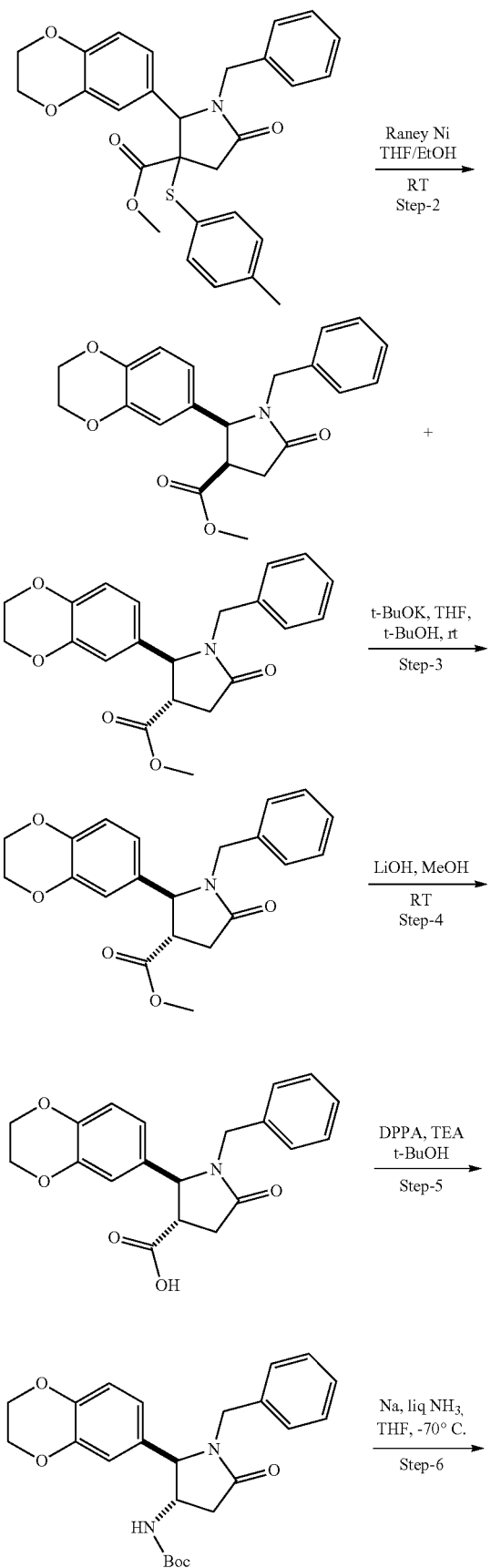

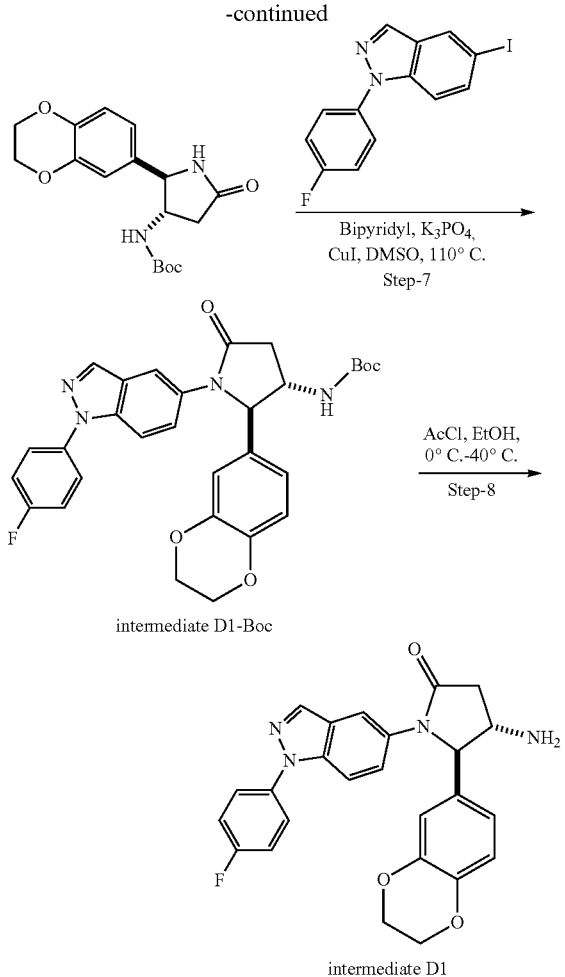

intermediate D1-Boc intermediate D1

Step 1: To a stirred solution of furan-2,5-dione (2.98 g, 30.46 mmol, 1.0 eq), 4-methylbenzenethiol (3.78 g, 30.46 mmol, 1.0 eq) and 2,3-dihydrobenzo[b][1,4]dioxine-6-carbaldehyde (5.00 g, 30.46 mmol, 1.0 eq) in dry toluene (100 mL) was added benzyl amine (3.25 g, 30.46 mmol, 1.0 eq) at ambient temperature under a $N_2$ atmosphere and the reaction mixture was stirred at 111° C. for 24 hours. After completion of the reaction (monitored by TLC), the solvent was removed in vacuo and the residue was dissolved in acetone (100 mL), followed by the addition of $K_2CO_3$ (16.81 g, 121.83 mmol, 4.0 eq) and methyl iodide (17.29 g, 121.83 mmol, 4.0 eq) at 0° C. The reaction mixture was slowly warmed to ambient temperature and was stirred overnight. After the solvent was removed under reduced pressure, water was added and extraction with EtOAc was performed. The organic layer was washed with water and brine, dried over $Na_2SO_4$ and concentrated under reduced pressure. The crude residue was purified by column chromatography (silicagel, 10-50% EtOAc in hexane) to afford methyl 1-benzyl-2-(2,3-dihydrobenzo[b][1,4]dioxin-6-yl)-5-oxo-3-(p-tolylthio)pyrrolidine-3-carboxylate as a pale yellow liquid. (3.0 g, 21%).

Step 2: To a stirred solution of methyl 1-benzyl-2-(2,3-dihydrobenzo[b][1,4]dioxin-6-yl)-5-oxo-3-(p-tolylthio)pyrrolidine-3-carboxylate (7.0 g, 14.31 mmol, 1.0 eq) in a 1:2 mixture of THF:EtOH (656 mL) was added Raney Nickel (49.0 g) at room temperature under a $N_2$ atmosphere and the reaction mixture was stirred at ambient temperature for 48 hours. The reaction mixture was filtered through celite, and the solvent was removed in vacuo. The reaction mixture was then diluted with water and extracted with EtOAc. The organic layer was washed with water and brine, dried over $Na_2SO_4$ and concentrated under reduced pressure to afford the product as a racemic mixture of methyl-1-benzyl-2-(2,3-dihydrobenzo[b][1,4]dioxin-6-yl)-5-oxopyrrolidine-3-carboxylate as a white solid. (5.0 g, 53%).

Step 3: To a stirred solution of methyl-1-benzyl-2-(2,3-dihydrobenzo[b][1,4]dioxin-6-yl)-5-oxopyrrolidine-3-carboxylate (12.0 g, 32.66 mmol, 1.0 eq) in a 1:1 mixture of t-butyl alcohol and THF (1.2 L), was added KOtBu (1.1 g, 10.19 mmol, 0.3 eq) at room temperature under $N_2$ atmosphere and then the reaction mixture was stirred at ambient temperature overnight. The solvent was then removed in vacuo, and the crude product was used in the next step without purification. (Yield: 12 g crude material).

Step 4: To a stirred solution of methyl trans-5-oxo-2-(2,3-dihydrobenzo[b][1,4]dioxin-6-yl)pyrrolidine-3-carboxylate (5.0 g, 8.98 mmol, 1.0 eq) in MeOH (50 mL), 1M LiOH (15.71 ml, 15.72 mmol, 1.75 eq) was added at room temperature under a $N_2$ atmosphere and then the reaction mixture was stirred at room temperature for 6 hours. After completion of the reaction (monitored by TLC), the solvent was removed in vacuo. The reaction mixture was cooled to 0° C. and diluted with water. Adjustment of the pH to 4 with 1N HCl, caused a solid to slowly precipitate out. This precipitate was filtered and dried in vacuo to afford trans-5-oxo-2-(2,3-dihydrobenzo[b][1,4]dioxin-6-yl)pyrrolidine-3-carboxylic acid as a white solid. (3.3 g).

Step 5: To a stirred solution of trans-5-oxo-2-(2,3-dihydrobenzo[b][1,4]dioxin-6-yl)pyrrolidine-3-carboxylic acid (8.0 g, 22.64, mmol, 1.0 eq) in t-BuOH (50.3 g, 679.17 mmol, 30.0 eq), TEA (2.7 g, 27.17 mmol, 1.2 eq) and DPPA (7.5 g, 27.17 mmol, 1.2 eq) were added at 0° C. under a $N_2$ atmosphere and then the reaction mixture was stirred at 82° C. for 1 hour, followed by heating to 100° C. for 5 hours. The reaction progress was monitored by TLC and upon completion, the solvent was removed in vacuo. The reaction mixture was cooled to ambient temperature, diluted with saturated $NaHCO_3$ and extracted with EtOAc. The organic layer was washed with water and brine, dried over $Na_2SO_4$ and concentrated under reduced pressure. The crude residue was purified using column chromatography (silicagel, 10-40% EtOAc in hexane) to afford tert-butyl ((trans)-1-benzyl-2-(2,3-dihydrobenzo[b][1,4]dioxin-6-yl)-5-oxopyrrolidin-3-yl)carbamate as a white solid. (6.0 g, 63%).

Step 6: In a round-bottom flask containing tert-butyl ((trans)-1-benzyl-2-(2,3-dihydrobenzo[b][1,4]dioxin-6-yl)-5-oxopyrrolidin-3-yl)carbamate (2.0 g, 4.71 mmol, 1.0 eq) in dry THF (81.4 ml), anhydrous ammonia was condensed at −70° C., sodium (2 g) was added to the reaction mixture. Stirring was continued at the same temperature for 30 minutes. At −70° C., solid $NH_4Cl$ was added to the reaction mixture, which was then slowly warmed to 0° C. The residue was treated with saturated $NH_4Cl$ solution, warmed to room temperature and extracted with dichloromethane (3×30 mL). The organic extracts were dried over anhydrous Na₂SO₄ and concentrated under reduced pressure. The crude residue was purified by column chromatography (silicagel, 0-70% EtOAc in hexane) to afford tert-butyl ((trans)-2-(2,3-dihydrobenzo[b][1,4]dioxin-6-yl)-5-oxopyrrolidin-3-yl)carbamate as a white solid (0.65 g, 41%).

Step 7: To a sealed vial containing tert-butyl ((trans)-2-(2,3-dihydrobenzo[b][1,4]dioxin-6-yl)-5-oxopyrrolidin-3-yl)carbamate (100 mg, 0.30 mmol, 1.00 eq), 2,2'-bipyridyl (33 mg, 0.21 mmol, 0.70 eq) and potassium phosphate (130 mg, 0.60 mmol, 2.00 eq) were added dimethylsulfoxid (2.1 mL) and 1-(4-fluorophenyl)-5-iodo-indazole (150 mg, 0.45 mmol, 1.50 eq) and the mixture was degassed under a nitrogen atmosphere. After ca. 2 min, copper(I)iodide (2.3 mg, 0.01 mmol, 0.04 eq) was added and the sealed vial was degassed once more. The resulting mixture was stirred overnight at 110° C. Then, DCM and a saturated sodium bicarbonate solution were added, the phases were separated via a hydrophobic frit, and the organic solvent was removed under reduced pressure. The crude residue was purified by column chromatography, followed by preparative HPLC to afford tert-butyl ((trans)-1-(1-(4-fluorophenyl)-1H-indazol-5-yl)-2-(2,3-dihydrobenzo[b][1,4]dioxin-6-yl)-5-oxopyrrolidin-3-yl)carbamate (22 mg, 13%).

Step 8: A solution of tert-butyl ((trans)-1-(1-(4-fluorophenyl)-1H-indazol-5-yl)-2-(2,3-dihydrobenzo[b][1,4]dioxin-6-yl)-5-oxopyrrolidin-3-yl)carbamate (21.0 mg, 0.039 mmol, 1.0 eq) in ethanol (0.45 ml) was cooled to 0° C., and acetylchloride (0.014 mL, 0.193 mmol, 5.0 eq) was added dropwise. Then, the ice bath was removed, and the reaction mixture was stirred at 40° C. for 3 hours. Then, the mixture was allowed to cool to ambient temperature, and was stirred overnight. The solvent was then removed under reduced pressure to yield crude (trans)-4-amino-5-(2,3-dihydrobenzo[b][1,4]dioxin-6-yl)-1-(1-(4-fluorophenyl)-1H-indazol-5-yl)pyrrolidin-2-one (Intermediate D1, 15.0 mg, 81%).

Synthesis of (trans)-4-Amino-1-[1-(4-fluoro-phenyl)-1H-indazol-5-yl]-5-phenyl-pyrrolidine-2-one (Intermediate D2)

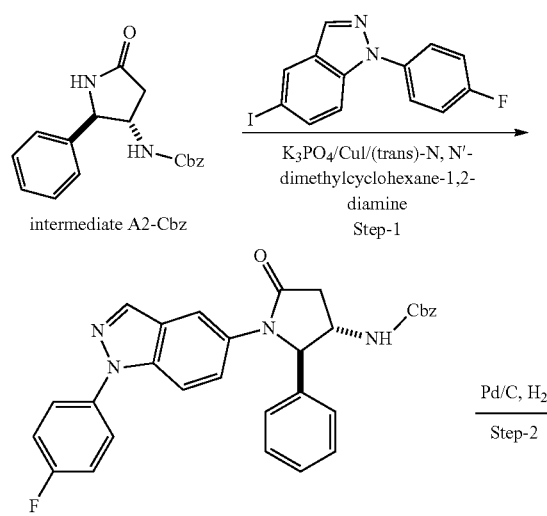

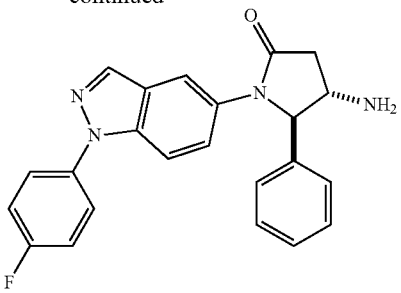

intermediate D2

Step 1: To a stirred solution of benzyl N-[(trans)-2-phenyl-5-oxo-pyrrolidin-3-yl]carbamate (intermediate A2-Cbz)(1.0 g, 3.22 mmol, 1.0 eq) and 1-(4-fluorophenyl)-5-iodo-1H-indazole (1.1 g, 3.22 mmol, 1.0 eq) in 1,4-dioxane (80 mL) in a sealed tube was added potassium phosphate (1.4 g, 6.44 mmol, 2.0 eq) followed by trans-N,N'-dimethylcyclohexane-1,2-diamine (1.02 ml, 0.644 mmol, 0.2 eq). The reaction mixture was degassed under an argon atmosphere for 30 minutes. CuI (61.3 mg, 0.322 mmol, 0.1 eq) was added and the reaction was heated to 90° C. for 16 hours (monitored by LCMS). The reaction mixture was filtered through a bed of celite and the celite bed was washed with ethyl acetate (500 mL), the combined filtrate was concentrated under reduced pressure and was purified by column chromatography (100-200 silica gel, 30-40% ethyl acetatehexane as eluent) to afford trans {1-[1-(4-Fluoro-phenyl)-1H-indazol-5-yl]-5-oxo-2-phenyl-pyrrolidin-3-yl}-carbamic acid benzyl ester (0.70 g, 42%)

Step 2: To a stirred solution of trans {1-[1-(4-Fluorophenyl)-1H-indazol-5-yl]-5-oxo-2-phenyl-pyrrolidin-3-yl}-carbamic acid benzyl ester (18.0 g, 34.58 mmol) in THF (800 mL) was added 10% Pd/C (50% moist, 40 g) and the reaction mixture was then stirred under a H₂ balloon until completion (monitored by TLC). The reaction mixture was filtered through a celite bed and the celite bed was washed with THF. The filtrate was concentrated and triturated with DCM-pentane to afford trans 4-amino-1-[1-(4-fluoro-phenyl)-1H-indazol-5-yl]-5-phenyl-pyrrolidine-2-one as an off-grey solid (10.8 g, 81%).

The racemic intermediate D2 can be separated by chiral HPLC using the following conditions: column: CHIRALPAK AD-H (4.6×2500) mm, mobile Phase: MeOH (100%), temperature: 40° C.

Using those conditions, intermediate D2-ent1 (retention time: 6.15 minutes) and intermediate D2-ent2 (retention time: 9.31 minutes) can be obtained.

Synthesis of (trans)-4-amino-5-(3-chlorophenyl)-1-(1-(4-fluorophenyl)-1H-indazol-5-yl)pyrrolidin-2-one (Intermediate D6)

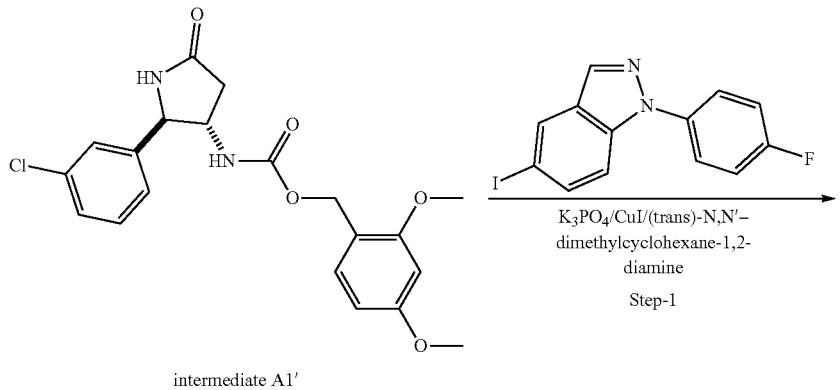

intermediate A1'

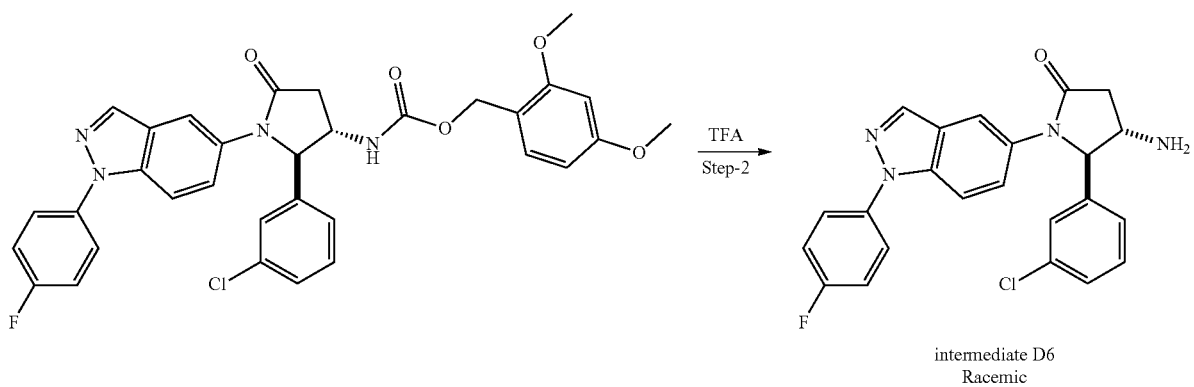

intermediate D6
Racemic

Step 1: (2,4-dimethoxyphenyl)methyl N-[(trans)-2-(3-chlorophenyl)-5-oxo-pyrrolidin-3-yl]carbamate (intermediate A1', 500 mg, 1.235 mmol, 1.00 eq), 1-(4-fluorophenyl)-5-iodo-indazole (438 mg, 1.297 mmol, 1.05 eq), potassium phosphate (524 mg, 2.470 mmol, 2.00 eq) and CuI (12 mg, 0.062 mmol, 0.05 eq) were weighed into a vial. The reaction mixture was then degassed under a nitrogen atmosphere. Then, 1,4-dioxane (5 mL) and trans-N,N'-dimethylcyclohexane-1,2-diamine (14 mg, 0.124 mmol, 0.1 eq) were added, and the reaction mixture was heated to 115° C. overnight. The reaction mixture was filtered through a bed of celite and the celite bed was washed with DCM and the combined filtrates were concentrated under reduced pressure. The crude residue was purified by column chromatography (silicagel, cHex/EtOAc) to afford trans {1-[1-(4-Fluoro-phenyl)-1H-indazol-5-yl]-5-oxo-2-(3-chlorophenyl)pyrrolidin-3-yl}-carbamic acid 2,4-dimethoxybenzyl ester (590 mg, 78%).

Step 2: A solution of trans {1-[1-(4-Fluoro-phenyl)-1H-indazol-5-yl]-5-oxo-2-(3-chlorophenyl)pyrrolidin-3-yl}-carbamic acid 2,4-dimethoxybenzyl ester (590 mg, 0.959 mmol, 1.0 eq) was stirred at ambient temperature. After completion of the reaction (monitored by LCMS), the reaction mixture is cooled to 0° C. and was quenched with saturated sodium bicarbonate solution. Extraction with DCM is then followed by washing of the combined organic layers with saturated sodium bicarbonate solution and drying over magnesium sulfate. After filtration, the solution is concentrated under reduced pressure to afford (trans)-4-amino-5-(3-chlorophenyl)-1-(1-(4-fluorophenyl)-1H-indazol-5-yl)pyrrolidin-2-one (intermediate D6, 338 mg, 84%).

Synthesis of (4S,5R)-4-amino-5-benzyl-1-(1-(4-fluorophenyl)-1H-indazol-5-yl)pyrrolidin-2-one (Intermediate D8)

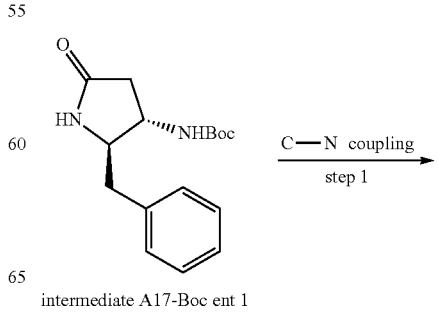

intermediate A17-Boc ent 1

C—N coupling
step 1

-continued

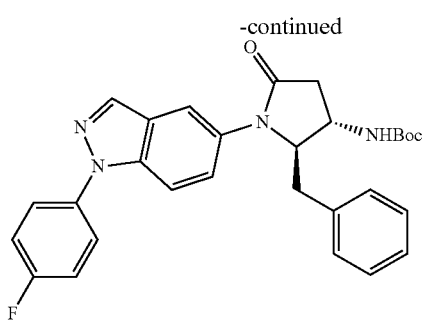

Synthesis of cis-4-amino-5-(cyclopropylmethyl)-1-(1-(4-fluorophenyl)-1H-indazol-5-yl)pyrrolidin-2-one Intermediate D9)

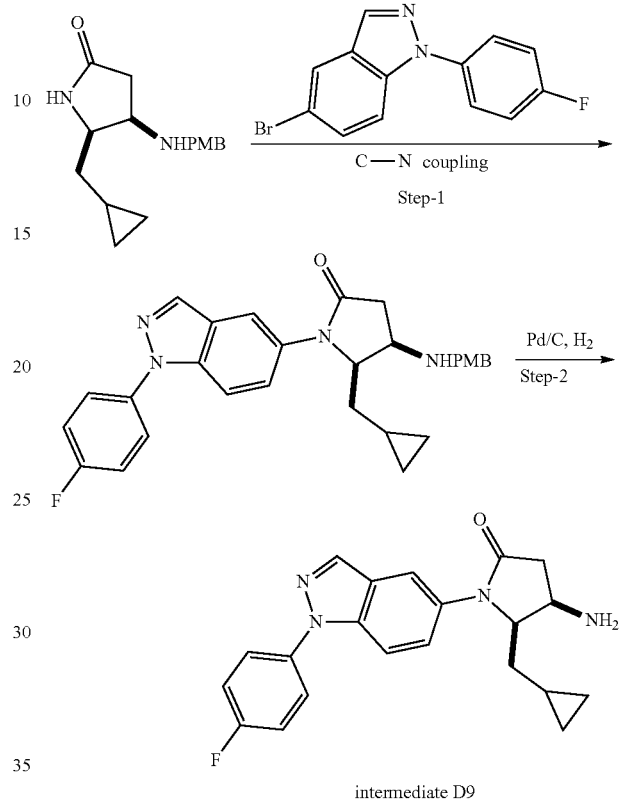

intermediate D8

Step 1: Tert-butyl ((2R,3S)-2-benzyl-5-oxopyrrolidin-3-yl)carbamate (300 mg, 1.033 mmol, 1.0 eq.), 1-(4-fluorophenyl)-5-iodo-indazole (366.8 mg, 1.085 mmol, 1.05 eq.), $K_3PO_4$ (438.6 mg, 2.066 mmol, 2.0 eq.) copper iodide (157.4 mg, 0.826 mmol, 0.8 eq.) and trans-N,N'-dimethylcyclohexane-1,2-diamine (14.7 mg, 0.103 mmol, 0.1 eq.) were weighed out into a microwave vial. A stir bar was added, the vial was sealed and sparged with nitrogen. Then, 1,4-dioxane (5.2 mL) was added, and the mixture was heated to 100° C. for 22 hours under microwave irradiation. Then, the temperature was raised to 120° C. for 16 hours. The reaction mixture was cooled to ambient temperature, and sat. $NaHCO_3$ solution and DCM were added. The mixture was filtered through a hydrophobic frit, and the organic solvent was then evaporated. The crude remains were purified using silica gel chromatography to yield 180.0 mg (35%) of tert-butyl ((2R,3S)-2-benzyl-1-(1-(4-fluorophenyl)-1H-indazol-5-yl)-5-oxopyrrolidin-3-yl)carbamate.

Step 2: Tert-butyl ((2R,3S)-2-benzyl-1-(1-(4-fluorophenyl)-1H-indazol-5-yl)-5-oxopyrrolidin-3-yl)carbamate (180.0 mg, 0.360 mmol, 1.0 eq.) was dissolved in ethanol (3.6 mL) and the mixture was cooled to 0° C. Then, acetyl chloride (0.26 mL, 3.596 mmol, 10 eq.) was added, and the reaction mixture was stirred at ambient temperature for 16 hours. Then, acetyl chloride (0.26 mL, 3.596 mmol, 10 eq.) and a drop of water were added, and the mixture was stirred for another 24 hours. The reaction mixture was then evaporated to dryness to yield 93.0 mg (53%) of (4 S,5R)-4-amino-5-benzyl-1-(1-(4-fluorophenyl)-1H-indazol-5-yl)pyrrolidin-2-one (intermediate D8).

Step 1: Cis-5-(Cyclopropylmethyl)-4-((4-methoxybenzyl)amino)pyrrolidin-2-one (200.0 mg, 0.729 mmol, 1.0 eq.), 5-bromo-1-(4-fluorophenyl)indazole (318.3 mg, 1.093 mmol, 1.5 eq.), caesium carbonate (475.0 mg, 1.458 mmol, 2.0 eq.), Xantphos (63.2 mg, 0.109 mmol, 0.15 eq.), and $Pd_2dba_3$ (33.3 mg, 0.036 mol, 0.05 eq.) were weighed out into a microwave vial, a stir bar was added, the vial was sealed and purged with nitrogen. 1,4-dioxane (7.5 mL) was then added, and the mixture was heated to 90° C. for 48 h. The reaction mixture was then cooled to ambient temperature, was then filtered and the solvent was removed under reduced pressure. The crude remains were then purified via silica gel chromatography to yield 150.0 mg of cis-5-(cyclopropylmethyl)-1-(1-(4-fluorophenyl)-1H-indazol-5-yl)-4-((4-methoxybenzyl)amino)pyrrolidin-2-one.

Step 2: Cis-5-(cyclopropylmethyl)-1-(1-(4-fluorophenyl)-1H-indazol-5-yl)-4-((4-methoxybenzyl)amino)-pyrrolidin-2-one (118.0 mg, 0.244 mmol, 1.0 eq.) was dissolved in ethanol (23.6 mL) and ethyl acetate (23.6 mL). The mixture was then hydrogenated using flow hydrogenation (up to 10 bar $H_2$-pressure). The remains were evaporated to dryness to obtain 81.8 mg (92%) of cis-4-amino-5-(cyclopropylmethyl)-1-(1-(4-fluorophenyl)-1H-indazol-5-yl)pyrrolidin-2-one (intermediate D9).

The intermediates in Table 1 were synthesized in analogy to the examples described above, using the starting material specified below.

| Intermediate | Structure | In analogy to | Starting material |
| --- | --- | --- | --- |
| Intermediate D3 | 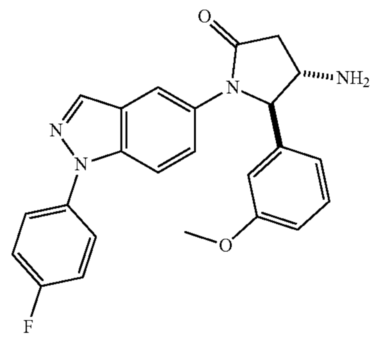 [SMILES: COc1cccc([C@@H]2[C@@H](N)CC(=O)N2c2ccc3c(cnn3-c3ccc(F)cc3)c2)c1] | Intermediate D2 | intermediate A16-Cbz |
| Intermediate D4 | 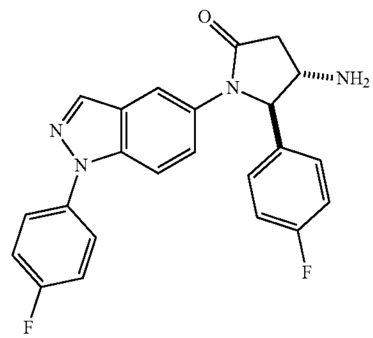 [SMILES: N[C@H]1CC(=O)N(c2ccc3c(cnn3-c3ccc(F)cc3)c2)[C@@H]1c1ccc(F)cc1] | Intermediate D2 | intermediate A8-Cbz |
| Intermediate D5 | 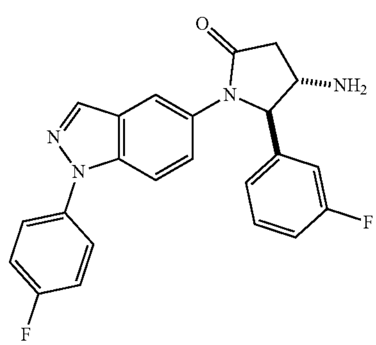 [SMILES: N[C@H]1CC(=O)N(c2ccc3c(cnn3-c3ccc(F)cc3)c2)[C@@H]1c1cccc(F)c1] | Intermediate D2 | intermediate A5-Cbz |
| Intermediate D7 | 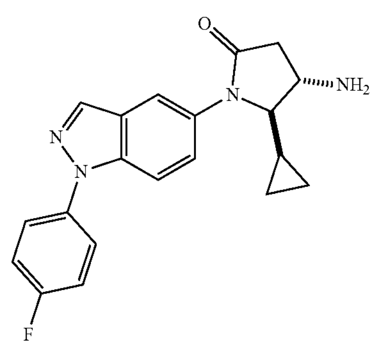 [SMILES: N[C@H]1CC(=O)N(c2ccc3c(cnn3-c3ccc(F)cc3)c2)[C@@H]1C1CC1] | Intermediate D1 | Intermediate A12-Boc |

EXAMPLE 1

N-(trans-2-(2,3-dihydrobenzo[b][1,4]dioxin-6-yl)-1-(1-(4-fluorophenyl)-1H-indazol-5-yl)-5-oxopyrrolidin-3-yl)-2,2-difluoropropanamide

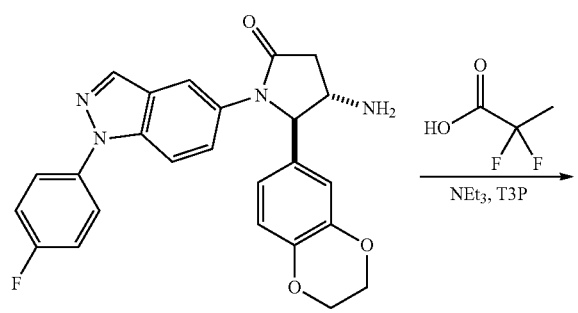

2,2-difluoropropanoic acid (8.6 mg, 0.078 mmol, 2.0 eq) was weighed out into a vial, followed by the addition of (trans)-4-amino-5-(2,3-dihydrobenzo[b][1,4]dioxin-6-yl)-1-(1-(4-fluorophenyl)-1H-indazol-5-yl)pyrrolidin-2-one (intermediate D1, 19.0 mg, 0.039 mmol, 1.0 eq) in dichloromethane (0.19 mL), followed by the addition of triethylamine (0.011 mL, 0.078 mmol, 2.0 eq) at ambient temperature. Propylphosphonic anhydride solution (≥50 wt. % in ethyl acetate, 0.046 mL, 0.078 mmol, 2.0 eq) was then added, and the reaction mixture was stirred overnight. After 16 hours, the reaction mixture was diluted with sat. $NaHCO_3$ solution and DCM. The resulting mixture was stirred for another 30 minutes, before being filtered through a hydrophobic frit. The solvent was removed under reduced pressure and the residue was purified by column chromatography and later HPLC to give example 1 (14.0 mg, 67%).

$^1$H NMR (DMSO-$d_6$) δ: 9.43 (d, 1H), 8.32 (d, 1H), 7.89 (d, 1H), 7.78-7.74 (m, 2H), 7.73 (d, 1H), 7.64 (dd, 1H), 7.46-7.35 (m, 2H), 6.87-6.74 (m, 3H), 5.22 (d, 1H), 4.30-4.20 (m, 1H), 4.19-4.15 (m, 4H), 3.09 (dd, 1H), 2.60 (dd, 1H), 2.07 (s, 1H), 1.79 (t, 3H).

EXAMPLE 2

2,2-difluoro-N-((2R,3S)-1-(1-(4-fluorophenyl)-1H-indazol-5-yl)-5-oxo-2-phenylpyrrolidin-3-yl)propanamide

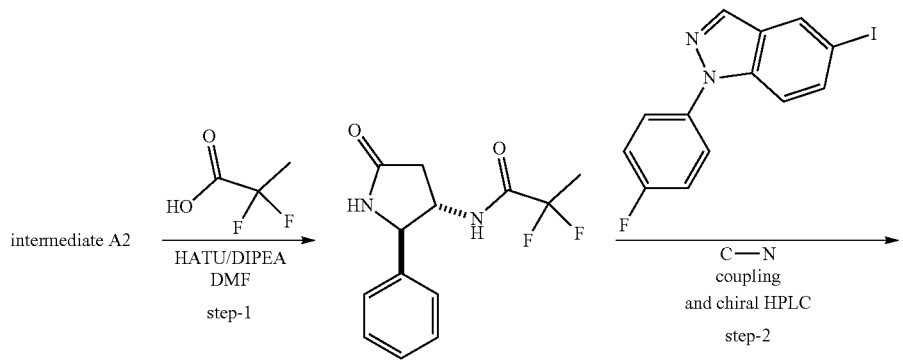

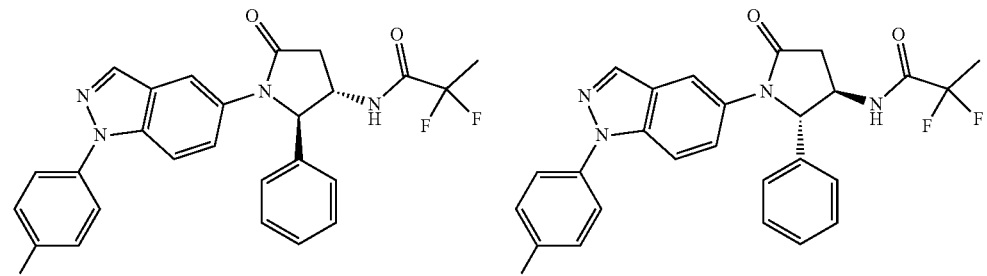

Step 1: To a stirred solution of intermediate A2 (1.0 g, 5.68 mmol, 1.0 eq) in DMF (20 mL), HATU (3.2 g, 8.52 mmol, 1.5 eq), DIPEA (4.9 mL, 28.40 mmol, 5.0 eq) and 2,2-difluoro-propionic acid (0.8 g, 7.38 mmol, 1.3 eq) were added. The reaction mixture was then stirred for 16 h at ambient temperature. After completion, the reaction mixture was diluted with EtOAc and was washed with ice cold water, sat. NaHCO$_3$ and sat. NH$_4$Cl solution. The combined organic layers were concentrated under reduced pressure to get the crude product which was purified by column chromatography (100-200 mesh silica gel; 2% MeOH-DCM; R$_f$-value-0.5) to afford trans-2,2-difluoro-N-(5-oxo-2-phenylpyrrolidin-3-yl)propanamide (1.4 g, 93%).

Step 2: A stirred solution of trans-2,2-difluoro-N-(5-oxo-2-phenylpyrrolidin-3-yl)propanamide (0.50 g, 1.86 mmol, 1.0 eq), 1-(4-fluorophenyl)-5-iodo-1H-indazole Flow Rate: 1.0 ml/min) and 2,2-difluoro-N-((2R,3S)-1-(1-(4-fluorophenyl)-1H-indazol-5-yl)-5-oxo-2-phenylpyrrolidin-3-yl)propanamide (0.05 g; RT=5.20 min; Column Nam: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 9.48 (d, 1H), 8.30 (d, 1H), 7.88 (d, 1H), 7.76-7.72 (m, 2H), 7.71 (d, 1H), 7.64 (dd, 1H), 7.42-7.34 (m, 4H), 7.32 (t, 2H), 7.26-7.22 (m, 1H), 5.32 (d, 1H), 4.34-4.25 (m, 1H), 3.11 (dd, 1H), 2.64 (dd, 1H), 1.79 (t, 3H).

EXAMPLE 4

2,2-difluoro-N-((2R,3S)-1-(1-(4-fluorophenyl)-1H-indazol-5-yl)-2-(2-methoxypyridin-4-yl)-5-oxopyrrolidin-3-yl)propanamide

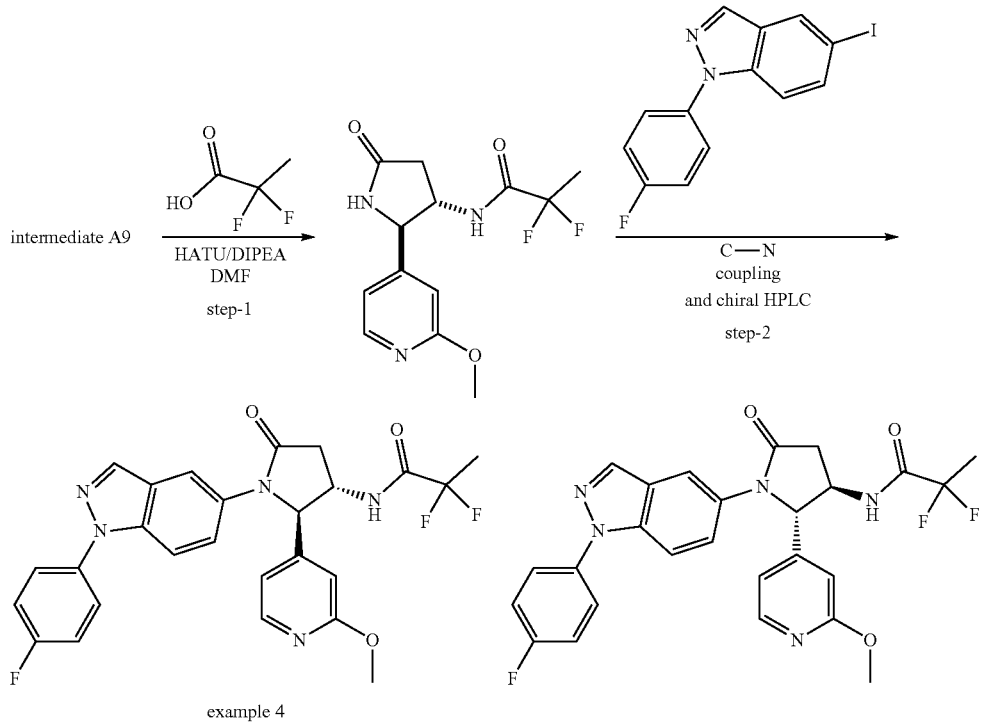

example 4

(0.75 g, 2.23 mmol, 1.2 eq) and K$_3$PO$_4$ (0.79 g, 3.73 mmol, 2.0 eq) in 1,4-dioxane (20 mL) was degassed with argon for 15 min. Then, trans-N,N'-dimethylcyclohexane-1,2-diamine (0.10 g, 0.75 mmol, 0.4 eq) and CuI (0.07 g, 0.37 mmol, 0.2 eq) were added and the reaction was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 50% EtOAc-Hexane; R$_f$-value-0.5) to afford the racemic product. Further enantiomer separation was done by chiral preparative HPLC to afford 2,2-difluoro-N-((2S,3R)-1-(1-(4-fluorophenyl)-1H-indazol-5-yl)-5-oxo-2-phenylpyrrolidin-3-yl)propanamide (0.06 g; RT=4.32 min; Column Name: Chiralpak IA (250×4.6 mm) 5 μm, Mobile Phase: Hexane/EA/EtOH/DEA: 50/25/25/0.1, Step 1: To a stirred solution of 2,2-difluoropropanoic acid (0.64 g, 5.79 mmol, 1.2 eq) in DMF (10 mL) HATU (3.60 g, 9.65 mmol, 2.0 eq), DIPEA (4.2 mL, 24.13 mmol, 5.0 eq) and intermediate A9 (1.00 g, 4.83 mmol, 1.0 eq) were added at 0° C. and the reaction mixture was then stirred at ambient temperature for 16 h. After completion of the reaction (monitored by TLC, TLC system 5% MeOH in DCM, Rf-0.3), the reaction mixture was diluted with EtOAc (25 mL), washed with ice cold water (3×25 mL), dried over Na$_2$SO$_4$ and concentrated to get the crude product which was purified by column chromatography (230-400 mesh silica gel; 0 to 2% MeOH-DCM) to afford trans-2,2-difluoro-N-(2-(2-methoxypyridin-4-yl)-5-oxopyrrolidin-3-yl)propanamide (0.76 g, 52%).

Step 2: A stirred solution of trans-2,2-difluoro-N-(2-(2-methoxypyridin-4-yl)-5-oxopyrrolidin-3-yl)propanamide (0.378 g, 1.263 mmol, 1.0 eq), 1-(4-fluorophenyl)-5-iodo-1H-indazole (0.512 g, 1.515 mmol, 1.2 eq) and K$_3$PO$_4$ (0.535 g, 2.526 mmol, 2.0 eq) in 1,4-dioxane (25 mL) was degassed with argon for 30 min. Then, trans-N,N'-dimethylcyclohexane-1,2-diamine (0.071 g, 0.505 mmol, 0.4 eq) and CuI (0.048 g, 0.253 mmol, 0.2 eq) were added and the reaction mixture was stirred for 16 h at 90° C. in a sealed tube. After completion of the reaction (monitored by TLC, TLC system 5% MeOH in DCM, Rf-0.1), the reaction mixture was filtered through a celite bed and the celite bed was washed 2-3 times with dioxane. The combined organic layers were concentrated under reduced pressure to get the crude product which was purified by column chromatography (230-400 mesh silica gel; 0 to 6% MeOH in DCM) to afford the racemic product. Further enantiomer separation was done by preparative chiral HPLC to afford pure 2,2-difluoro-N-((2S,3R)-1-(1-(4-fluorophenyl)-1H-indazol-5-yl)-2-(2-methoxypyridin-4-yl)-5-oxopyrrolidin-3-yl)propanamide (0.057 g, RT=6.16 min; Column Name: Chiralpak IA (250×4.6 mm) 5 µm, Mobile Phase: Hexane/EA/EtOH/DEA: 70/15/15/0.1, Flow Rate: 1.0 ml/min) and 2,2-difluoro-N-((2R,3S)-1-(1-(4-fluorophenyl)-1H-indazol-5-yl)-2-(2-methoxypyridin-4-yl)-5-oxopyrrolidin-3-yl)propanamide (0.047 g, RT=6.89 min; Column Name: Chiralpak IA (250×4.6 mm) 5 µm, Mobile Phase: Hexane/EA/EtOH/DEA: 70/15/15/0.1, Flow Rate: 1.0 ml/min).

$^1$H NMR (DMSO-d$_6$) δ: 9.51-9.49 (m, 1H), 8.32 (s, 1H), 8.09 (d, 1H), 7.89 (s, 1H), 7.77-7.72 (m, 3H), 7.67-7.64 (m, 1H), 7.42-7.37 (m, 2H), 7.00 (d, 1H), 6.76 (s, 1H), 5.33-5.32 (m, 1H), 4.31-4.29 (m, 1H), 3.76 (s, 3H), 3.14-3.07 (m, 1H), 2.67-2.62 (m, 1H), 1.84-1.74 (m, 3H).

EXAMPLE 5

N-(trans-2-(2,4-difluorophenyl)-1-(1-(4-fluorophenyl)-1H-indazol-5-yl)-5-oxopyrrolidin-3-yl)-2,2-difluoropropanamide

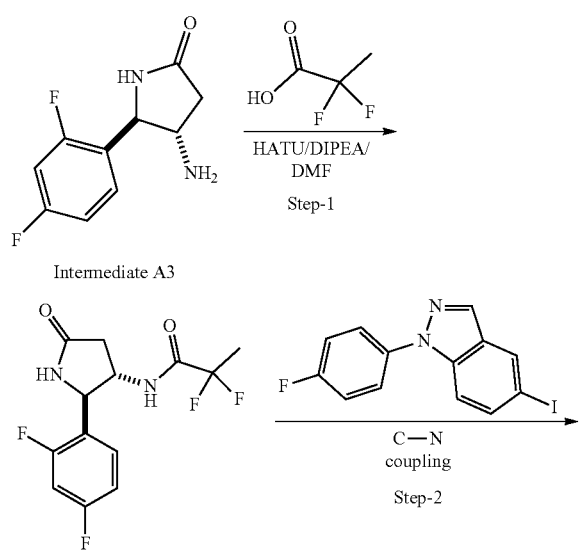

Intermediate A3

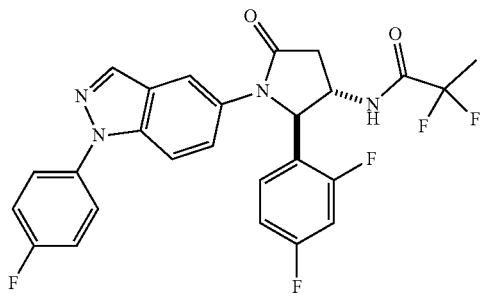

example 5

Step 1: A solution of intermediate A3 (0.85 g, 4.09 mmol, 1.0 eq) in DMF (12 mL) was treated with 2,2-difluoropropanoic acid (0.57 g, 5.21 mmol, 1.3 eq) in the presence of HATU (3.04 g, 8.01 mmol, 2.0 eq) and DIPEA (3.5 mL, 20.04 mmol, 2.0 eq) and this mixture was stirred at ambient temperature for 16 h. After ensuring complete consumption of starting material as evident from LCMS, the reaction mixture was partitioned between EtOAc and water. The organic extracts were washed with brine, dried and concentrated under reduced pressure to afford the crude product which was purified by flash column chromatography (230-400 mesh silica gel; 5% MeOH/EtOAc; R$_f$-value-0.4) to afford N-(trans-2-(2,4-difluorophenyl)-5-oxopyrrolidin-3-yl)-2,2-difluoropropanamide (0.70 g, 58%) as an off white solid.

Step 2: To a stirring solution of N-(trans-2-(2,4-difluorophenyl)-5-oxopyrrolidin-3-yl)-2,2-difluoropropanamide (0.25 g, 0.82 mmol, 1.0 eq) and 1-(4-fluorophenyl)-5-iodo-1H-indazole (0.28 g, 0.82 mmol, 1.0 eq) in 1,4-dioxane (4 mL), K$_3$PO$_4$ (0.35 g, 1.64 mmol, 2.0 eq), CuI (0.03 g, 0.16 mmol, 0.2 eq) and trans-N,N'-dimethylcyclohexane-1,2-diamine (0.05 g, 0.32 mmol, 0.4 eq) were added at ambient temperature under a nitrogen atmosphere and the mixture was degassed with a stream of nitrogen for 5 min. The resulting mixture was then heated to 90° C. for 16 h. The reaction mixture was then allowed to cool to ambient temperature, was filtered and concentrated to afford the crude product which was purified by flash column chromatography (230-400 mesh silica gel; 5% MeOH/EtOAc; R$_f$-value-0.4) to afford N-(trans-2-(2,4-difluorophenyl)-1-(1-(4-fluorophenyl)-1H-indazol-5-yl)-5-oxopyrrolidin-3-yl)-2,2-difluoropropanamide (0.15 g, 36%) as an off white solid.

$^1$H NMR (DMSO-d$_6$) δ: 9.42 (d, 1H), 8.33 (s, 1H), 7.8 (d, 1H), 7.76-7.71 (m, 3H), 7.51-7.45 (m, 2H), 7.4 (t, 2H), 7.22-7.17 (m, 1H), 7.02-6.98 (m, 1H), 5.50 (d, 1H), 4.49 (m, 1H), 3.15-3.08 (m, 1H), 2.70 (dd, 1H), 1.76 (t, 3H).

EXAMPLE 6

N-(trans-1-(1-(3,4-difluorophenyl)-1H-indazol-5-yl)-5-oxo-2-phenylpyrrolidin-3-yl)-2,2-difluoropropanamide

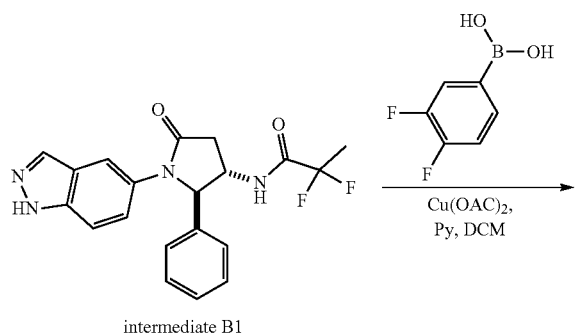

intermediate B1

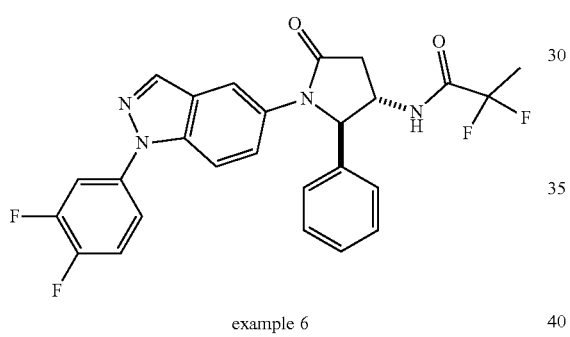

example 6

To a stirred solution of intermediate B1 (0.200 g, 0.521 mmol, 1.0 eq), (3,4-difluorophenyl)boronic acid (0.165 g, 1.042 mmol, 2.0 eq) and pyridine (0.1 mL, 1.042 mmol, 2.0 eq) in DCM (20 mL), was added Cu(OAc)$_2$ (0.142 g, 0.781 mmol, 1.5 eq) and the reaction mixture was stirred for 16 h at ambient temperature. After completion of the reaction (monitored by TLC, TLC system 5% MeOH in DCM, Rf-0.4), the solvent was removed under reduced pressure, and the residue was partitioned between DCM and water. The aqueous layer was extracted twice with DCM (2×50 mL). The combined organic layers were washed with brine, dried over Na$_2$SO$_4$, filtered and concentrated. The crude product was purified by preparative HPLC to afford N-(trans-1-(1-(3,4-difluorophenyl)-1H-indazol-5-yl)-5-oxo-2-phenylpyrrolidin-3-yl)-2,2-difluoropropanamide (0.051 g, 20%).

$^1$H NMR (DMSO-d$_6$) δ: 9.50-9.49 (m, 1H), 8.34 (s, 1H), 7.89-7.87 (m, 3H), 7.67-7.60 (m, 3H), 7.36-7.23 (m, 5H), 5.32 (s, 1H), 4.29-4.25 (m, 1H), 3.14-3.07 (m, 1H), 2.65-2.60 (m, 1H), 1.83-1.73 (m, 3H).

EXAMPLE 9

N-trans-(1-(1-(4-fluorophenyl)-1H-indazol-5-yl)-5-oxo-2-phenylpyrrolidin-3-yl)cyclopropanesulfonamide

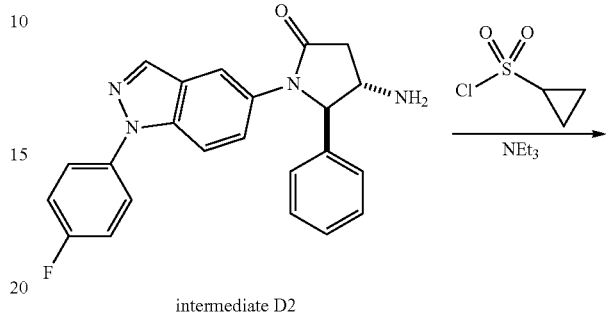

intermediate D2

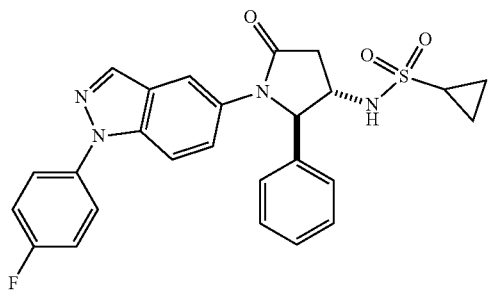

example 9

N-trans-(1-(1-(4-fluorophenyl)-1H-indazol-5-yl)-5-oxo-2-phenylpyrrolidin-3-yl)amine (intermediate D2, 144.0 mg, 0.373 mmol, 1.0 eq) was dissolved in DCM (2.0 mL), and the solution was cooled to 0° C. Triethylamine (0.31 mL, 2.236 mmol, 6.0 eq) was then added, followed by the dropwise addition of cyclopropanesulfonyl chloride (0.15 mL, 1.491 mmol, 4.0 eq). The reaction mixture was then allowed to warm to ambient temperature and was stirred for 72 hours. The reaction mixture was then diluted with water and DCM and was filtered through a hydrophobic frit. The solvent was removed under reduced pressure and the remains were purified via column chromatography to give example 9 (69.4 mg, 38%).

$^1$H NMR (DMSO-d$_6$) δ: 8.30 (s, 1H), 8.00 (d, 1H), 7.83 (d, 1H), 7.76-7.72 (m, 2H), 7.70 (d, 1H), 7.58 (dd, 1H), 7.42-7.35 (m, 4H), 7.32 (t, 2H), 7.26-7.21 (m, 1H), 5.31 (d, 1H), 4.01-3.92 (m, 1H), 3.15 (dd, 1H), 2.62 (dd, 1H), 2.53-2.45 (m, 1H), 0.96-0.87 (m, 2H), 0.87-0.78 (m, 2H).

EXAMPLE 12

N-((2R,3S)-2-(3-chlorophenyl)-1-(1-(4-fluorophenyl)-1H-indazol-5-yl)-5-oxopyrrolidin-3-yl)-2,2-difluoropropanamide

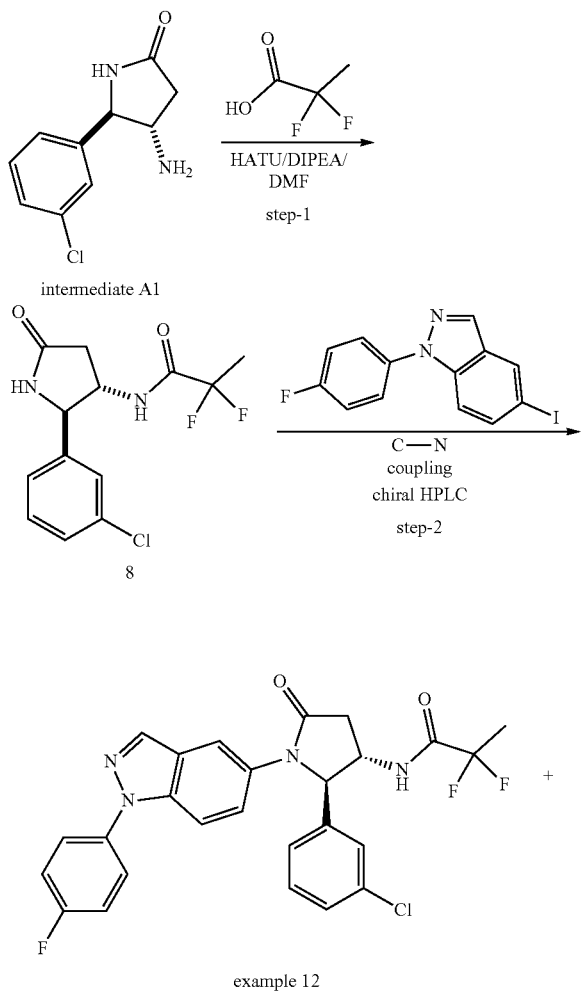

Step 1: To a stirred solution of intermediate A1 (0.25 g, 1.19 mmol, 1.0 eq) in DMF (10 mL), were added HATU (0.68 g, 1.78 mmol, 1.5 eq), DIPEA (1.0 mL, 5.95 mmol, 5.0 eq) and 2,2-difluoropropanoic acid (0.17 g, 1.54 mmol, 1.3 eq) and the reaction mixture was then stirred for 16 h at ambient temperature. After completion, the reaction mixture was diluted with EtOAc and was washed with ice cold water, sat. NaHCO$_3$ and sat. NH$_4$Cl solution. The combined organic layers were concentrated to get the crude product, which was purified by column chromatography (100-200 mesh silica gel; 2% MeOH-DCM; R$_f$-value-0.5) to afford N-(trans-2-(3-chlorophenyl)-5-oxopyrrolidin-3-yl)-2,2-difluoropropanamide (0.19 g, 53%).

Step 2: A stirred solution of N-(trans-2-(3-chlorophenyl)-5-oxopyrrolidin-3-yl)-2,2-difluoropropanamide (0.30 g, 0.99 mmol, 1 eq), 1-(4-fluorophenyl)-5-iodo-1H-indazole (0.40 g, 1.19 mmol, 1.2 eq) and K$_3$PO$_4$ (0.42 g, 1.98 mmol, 2.0 eq) in 1,4-dioxane (20 mL) was degassed with argon for 15 min. Then, trans-N,N'-dimethylcyclohexane-1,2-diamine (0.06 g, 0.40 mmol, 0.4 eq) and CuI (0.04 g, 0.20 mmol, 0.2 eq) were added and the reaction mixture was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 50% EtOAc-Hexane; R$_f$-value-0.5) to afford the racemic product. Further enantiomer separation was done by preparative chiral HPLC to afford N-((2S,3R)-2-(3-chlorophenyl)-1-(1-(4-fluorophenyl)-1H-indazol-5-yl)-5-oxopyrrolidin-3-yl)-2,2-difluoropropanamide (0.07 g; RT=5.32 min; Column Name: Chiralpak IA (250×4.6 mm) 5 μm, Mobile Phase: Hexane/EA/EtOH/DEA: 70/15/15/0.1, Flow Rate: 1.0 ml/min) and N-((2R,3S)-2-(3-chlorophenyl)-1-(1-(4-fluorophenyl)-1H-indazol-5-yl)-5-oxopyrrolidin-3-yl)-2,2-difluoropropanamide (0.06 g; RT=7.21 min; Column Name: Chiralpak IA (250×4.6 mm) 5 μm, Mobile Phase: Hexane/EA/EtOH/DEA: 70/15/15/0.1, Flow Rate: 1.0 ml/min).

$^1$H NMR (DMSO-d$_6$) δ: 9.48 (d, 1H), 8.32 (s, 1H), 7.89 (s, 1H), 7.77-7.71 (m, 3H), 7.64 (d, 1H), 7.46 (s, 1H), 7.39 (t, 2H), 7.34-7.28 (m, 3H), 5.35 (s, 1H), 4.30 (bs, 1H), 3.15-3.09 (m, 1H), 2.67-2.63 (m, 1H), 1.78 (t, 3H).

EXAMPLE 13

N-trans-(1-(1-(4-fluorophenyl)-1H-indazol-5-yl)-5-oxo-2-(4-fluorophenyl)pyrrolidin-3-yl)-1-methylcyclopropane-1-carboxamide

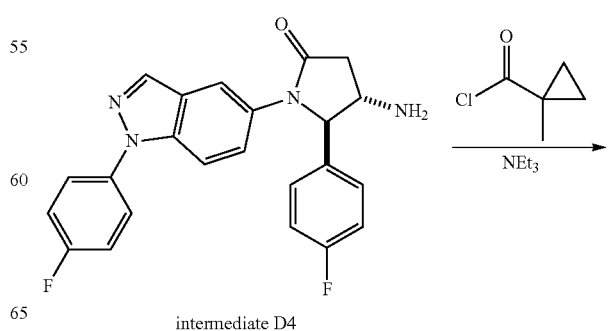

intermediate D4

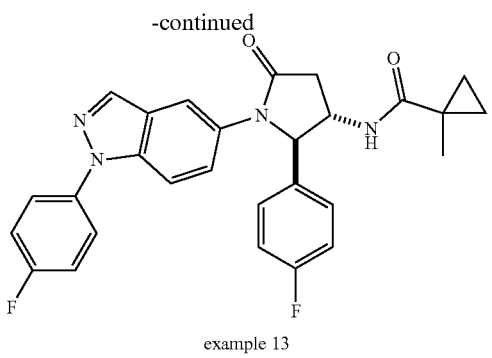

example 13

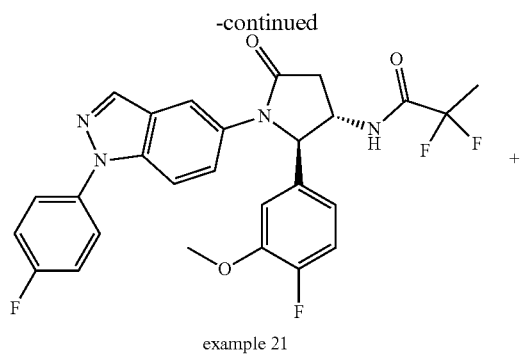

example 21

N-trans-(1-(1-(4-fluorophenyl)-1H-indazol-5-yl)-5-oxo-2-(4-fluorophenyl)pyrrolidin-3-yl)amine (intermediate D2, 50.0 mg, 0.124 mmol, 1.0 eq) was dissolved in dichloromethan (1.4 mL) under a nitrogen atmosphere, then triethylamine (0.035 mL, 0.247 mmol, 2.0 eq) was added. The mixture was stirred for ten minutes, before 1-methylcyclopropanecarbonyl chloride (0.03 mL, 0.247 mmol, 2.0 eq) was added. The reaction mixture was stirred at ambient temperature for 20 minutes, before sat. NaHCO$_3$ solution was added. The mixture was diluted with DCM, and was then filtered through a hydrophobic frit. The solvent was removed under reduced pressure and the remains were then purified by column chromatography and later HPLC to give example 13 (42.0 mg, 70%).

$^1$H NMR (DMSO-d$_6$) δ: 8.30 (d, 1H), 8.13 (d, 1H), 7.85 (d, 1H), 7.76-7.72 (m, 2H), 7.70 (d, 1H), 7.61 (dd, 1H), 7.44-7.35 (m, 4H), 7.16-7.08 (m, 2H), 5.26 (d, 1H), 4.27-4.19 (m, 1H), 3.02 (dd, 1H), 2.62 (dd, 1H), 1.31 (s, 3H), 1.06-0.94 (m, 2H), 0.56 (d, 2H)

EXAMPLE 20 AND EXAMPLE 21

2,2-difluoro-N-((2S,3R)-2-(4-fluoro-3-methoxyphenyl)-1-(1-(4-fluorophenyl)-1H-indazol-5-yl)-5-oxopyrrolidin-3-yl)propanamide and 2,2-difluoro-N-((2R,3 S)-2-(4-fluoro-3-methoxyphenyl)-1-(1-(4-fluorophenyl)-1H-indazol-5-yl)-5-oxopyrrolidin-3-yl)propanamide

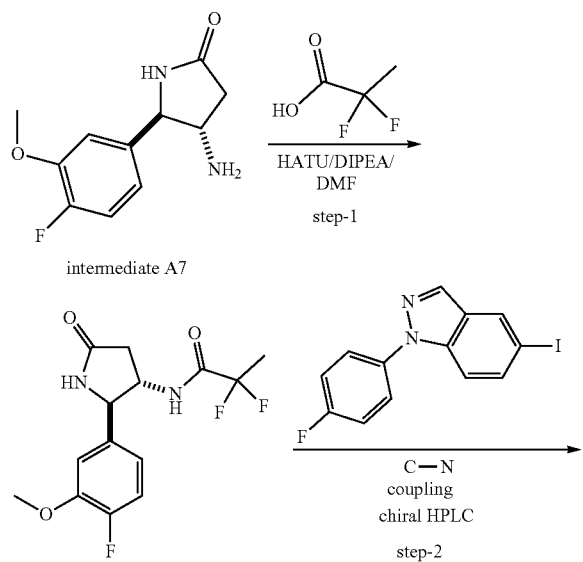

example 20

Step 1: To a stirred solution of intermediate A7 (3.12 g, 13.92 mmol, 1.0 eq) in DMF (30 mL) were added HATU (7.90 g, 20.89 mmol, 1.5 eq), DIPEA (12.0 mL, 69.64 mmol, 5.0 eq) and 2,2-difluoro-propionic acid (2.00 g, 18.10 mmol, 1.3 eq) and the reaction mixture was stirred for 16 h at ambient temperature. After completion, the reaction mixture was diluted with EtOAc and was washed with ice cold water, sat. NaHCO$_3$ and sat. NH$_4$Cl solution. The organic layer was concentrated to get the crude product which was purified by column chromatography (100-200 mesh silica gel; 2% MeOH-DCM; R$_f$-value-0.5) to afford 2,2-difluoro-N-(trans-2-(4-fluoro-3-methoxyphenyl)-5-oxopyrrolidin-3-yl)propanamide (3.50 g, 80%).

Step 2: A stirred solution of 2,2-difluoro-N-(trans-2-(4-fluoro-3-methoxyphenyl)-5-oxopyrrolidin-3-yl)propanamide (0.30 g, 0.95 mmol, 1.0 eq), 1-(4-fluorophenyl)-5-iodo-1H-indazole (0.38 g, 1.13 mmol, 1.2 eq) and K$_3$PO$_4$ (0.40 g, 1.89 mmol, 2.0 eq) in 1,4-dioxane (20 mL) was degassed with argon for 15 min. Then, trans-N,N'-dimethylcyclohexane-1,2-diamine (0.05 g, 0.38 mmol, 0.4 eq) and CuI (0.04 g, 0.19 mmol, 0.2 eq) were added and the reaction mixture was stirred for 16 h at 90° C. After completion, the reaction mixture was filtered through a celite bed and was washed 2-3 times with EtOAc. The combined organic layers were concentrated to get the crude product which was purified by column chromatography (100-200 mesh silica gel; 50% EtOAc-Hexane; R$_f$-value-0.5) to afford the racemic product. Further enantiomer separation was done by preparative chiral HPLC to afford 2,2-difluoro-N-((2S,3R)-2-(4-fluoro-3-methoxyphenyl)-1-(1-(4-fluorophenyl)-1H-indazol-5-yl)-5-oxopyrrolidin-3-yl)propanamide (0.12 g; RT=3.08 min; Column Name: Chiralpak IA Mobile Phase: MeOH) and 2,2-difluoro-N-((2R,3S)-2-(4-fluoro-3-methoxyphenyl)-1-(1-(4-fluorophenyl)-1H-indazol-5-yl)-5-oxo pyrrolidin-3-yl)propanamide (0.12 g; RT=3.78 min; Column Name: Chiralpak IA Mobile Phase: MeOH) as an off white solid.

¹H NMR (DMSO-d₆) δ: 9.45-9.43 (m, 1H), 8.31 (s, 1H), 7.87-7.86 (m, 1H), 7.77-7.71 (m, 3H), 7.63-7.60 (m, 1H), 7.42-7.37 (m, 2H), 7.20-7.17 (m, 1H), 7.13-7.08 (m, 1H), 6.87-6.84 (m, 1H), 5.29 (s, 1H), 4.35-4.28 (m, 1H), 3.78 (s, 3H), 3.13-3.07 (m, 1H), 2.67-2.61 (m, 1H), 1.83-1.78 (m, 3H).

EXAMPLE 24

2,2-difluoro-N-((2S,3R)-2-(2-fluorophenyl)-1-(1-(4-fluorophenyl)-1H-indazol-5-yl)-5-oxopyrrolidin-3-yl)propanamide and Example 33: 2,2-difluoro-N-((2R,3S)-2-(2-fluorophenyl)-1-(1-(4-fluorophenyl)-1H-indazol-5-yl)-5-oxopyrrolidin-3-yl)propanamide

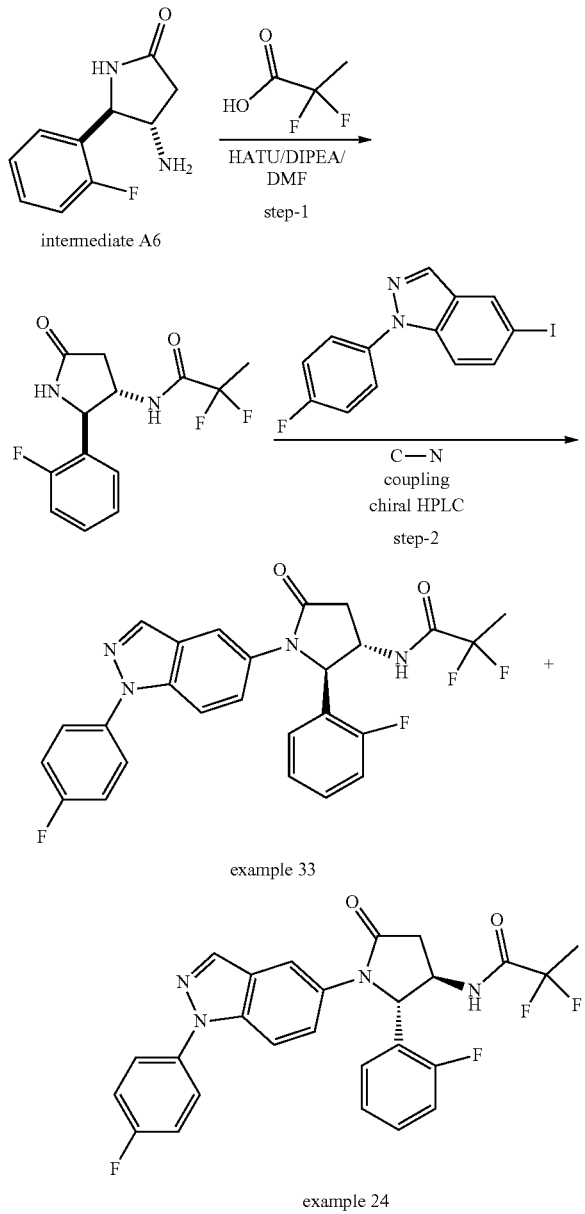

Starting from intermediate A6, example 24 and example 33 were synthesized in analogy to the synthetic procedure described for example 20 and example 21.

Enantiomer separation was done by preparative chiral HPLC to afford example 24 (0.07 g; RT=6.13 min; Column Name: Chiralpak IA (250×4.6 mm) 5 µm, Mobile Phase: Hexane/EA/EtOH/DEA: 70/15/15/0.1, Flow Rate: 1.0 ml/min) and example 33 (0.06 g; RT=10.12 min; Column Name: Chiralpak IA (250×4.6 mm) 5 µm, Mobile Phase: Hexane/EA/EtOH/DEA: 70/15/15/0.1, Flow Rate: 1.0 ml/min).

¹H NMR (DMSO-d₆) δ: 9.46-9.44 (m, 1H), 8.32 (s, 1H), 7.81 (s, 1H), 7.76-7.71 (m, 3H), 7.54-7.51 (m, 1H), 7.41-7.37 (m, 3H), 7.27-7.24 (m, 1H), 7.16-7.08 (m, 2H), 5.54-5.53 (m, 1H), 4.48-4.46 (m, 1H), 3.17-3.10 (m, 1H), 2.70-2.64 (m, 1H), 1.81-1.71 (m, 3H).

EXAMPLE 25

2,2-difluoro-N-(trans-1-(1-(3-fluorophenyl)-1H-indazol-5-yl)-5-oxo-2-phenylpyrrolidin-3-yl)propanamide

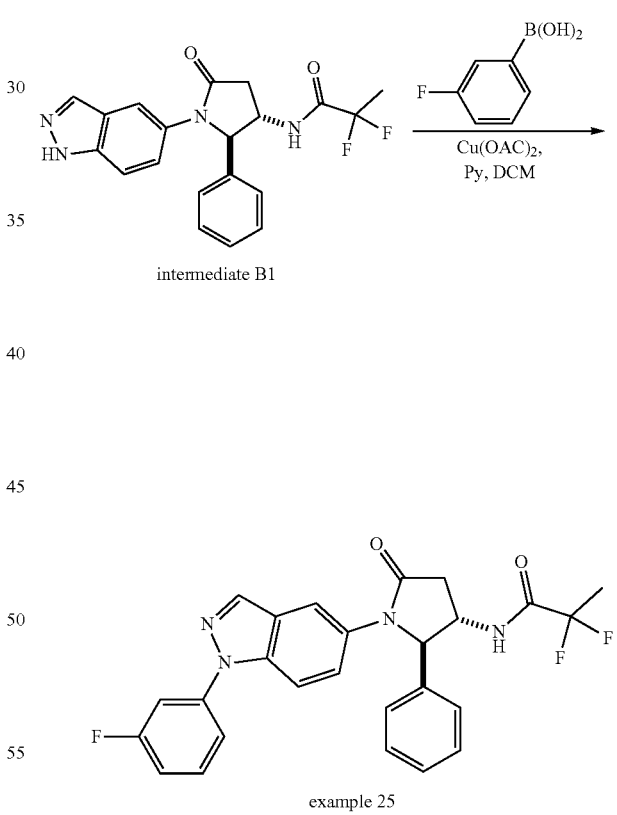

Starting from intermediate B1, example 25 was synthesized in analogy to the synthetic procedure described for example 6.

¹H NMR (DMSO-d₆) δ: 9.51-9.49 (m, 1H), 8.35 (s, 1H), 7.90 (s, 1H), 7.85-7.83 (m, 1H), 7.68-7.66 (m, 1H), 7.60-7.58 (m, 3H), 7.37-7.30 (m, 4H), 7.23-7.20 (m, 2H), 5.33-5.32 (m, 1H), 4.29-4.25 (m, 1H), 3.14-3.07 (m, 1H), 2.65-2.60 (m, 1H), 1.83-1.74 (m, 3H).

EXAMPLE 26

N-trans-(1-(1-(4-fluorophenyl)-1H-indazol-5-yl)-5-oxo2-(3,5-difluorophenyl)pyrrolidin-3-yl)-2,2-difluoropropanamide

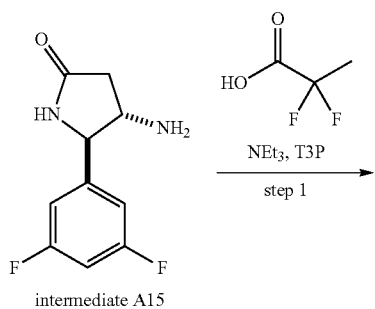

intermediate A15

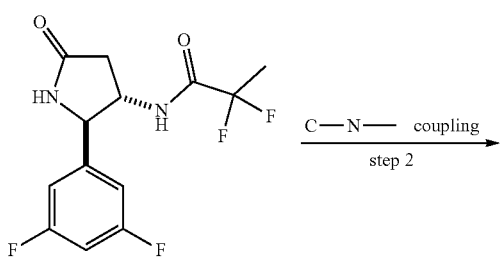

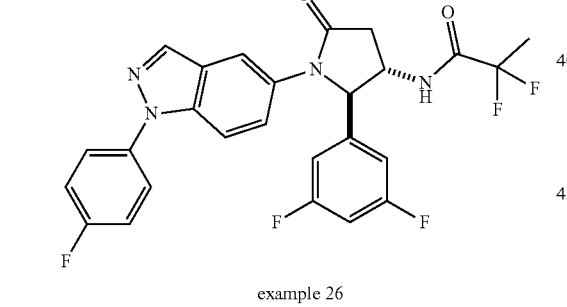

example 26

Step 1: 2,2-difluoropropanoic acid (383.9 mg, 3.488 mmol, 2.0 eq) was weighed out into a flask, a stir bar was added and the flask was sealed. The flask was purged with nitrogen, followed by the addition of DCM (2.0 mL) and triethylamine (0.49 mL, 3.488 mmol, 2.0 eq). Propylphosphonic anhydride solution (≥50 wt. % in ethyl acetate, 2.1 mL, 3.488 mmol, 2.0 eq) was added next, and the mixture was stirred for 10 minutes. Then, N-trans-(5-oxo-2-(3,5-difluorophenyl)pyrrolidin-3-yl)amine (intermediate 15, 370.1 mg, 1.744 mmol, 1.0 eq) was added in DCM (7 mL). The reaction mixture was stirred at ambient temperature for 16 hours. The reaction mixture was then diluted with water and EtOAc. The layers were separated, and the aqueous layer was extracted two more times with EtOAc. The combined organic layers were then washed with brine and dried over MgSO$_4$. The solvent was removed under reduced pressure and the remains were then purified via column chromatography to give trans-2,2-difluoro-N-(5-oxo-2-(3,5-difluorophenyl)pyrrolidin-3-yl)propanamide (466.8 mg, 88%) as a white solid.

Step 2: Trans-2,2-difluoro-N-(5-oxo-2-(3,5-difluorophenyl)pyrrolidin-3-yl)propanamide (47.0 mg, 0.154 mmol, 1.0 eq), potassium phosphate tribasic (65.6 mg, 0.309 mmol, 2.0 eq), copper iodide (5.9 mg, 0.031 mmol, 0.2 eq) and 1-(4-fluorophenyl)-5-iodo-indazole (62.7 mg, 0.185 mmol, 1.2 eq) are weighed out into a vial, the vial was sealed, a stir bar was added and the vial was purged with nitrogen. 1,4-dioxane (1.0 mL) was then added, followed by the addition of trans-cyclohexane-1,2-diamine (7.4 μL, 0.62 mmol, 0.4 eq). The reaction mixture was then heated to 110° C. for 16 hours. After that, the mixture was cooled to ambient temperature and was diluted with water and DCM. The mixture was filtered through a hydrophobic frit and the solvent was removed under reduced pressure. The remains were purified by column chromatography and later HPLC to give example 26 (14.4 mg, 18%).

$^1$H NMR (DMSO-d$_6$) δ: 9.45 (d, 1H), 8.33 (d, 1H), 7.92-7.88 (m, 1H), 7.79-7.72 (m, 3H), 7.64 (dd, 1H), 7.41 (t, 2H), 7.16-7.08 (m, 3H), 5.37 (d, 1H), 4.42-4.28 (m, 1H), 3.14 (dd, 1H), 2.67 (dd, 1H), 1.80 (t, 3H).

EXAMPLE 27

2,2-difluoro-N-(trans-5-oxo-2-phenyl-1-(1-phenyl-1H-indazol-5-yl)pyrrolidin-3-yl)propanamide

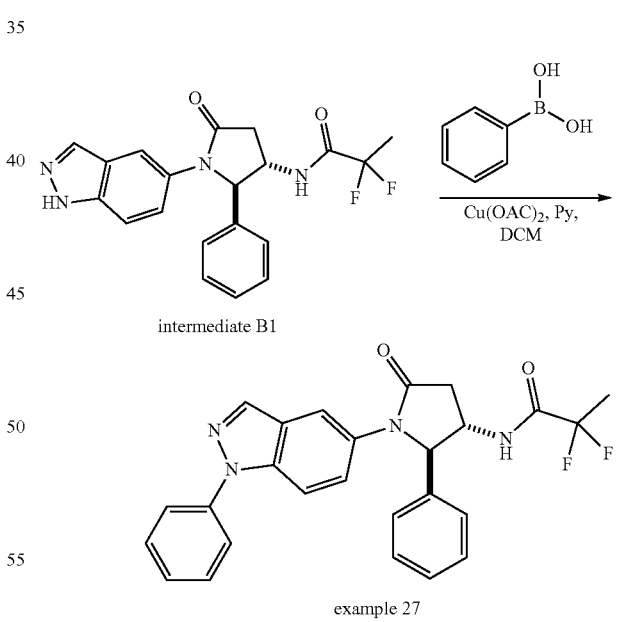

Starting from intermediate B1, example 27 was synthesized in analogy to the synthetic procedure described for example 6.

$^1$H NMR (DMSO-d$_6$) δ: 9.51-9.49 (m, 1H), 8.31 (s, 1H), 7.88 (s, 1H), 7.78-7.70 (m, 3H), 7.65-7.63 (m, 1H), 7.58-7.54 (m, 2H), 7.40-7.23 (m, 6H), 5.32 (s, 1H), 4.29-4.25 (m, 1H), 3.14-3.07 (m, 1H), 2.66-2.59 (m, 1H), 1.83-1.74 (m, 3H).

EXAMPLE 28

N-((2R,3S)-2-(2-fluorophenyl)-1-(1-(4-fluorophenyl)-1H-indazol-5-yl)-5-oxopyrrolidin-3-yl)cyclopropanecarboxamide

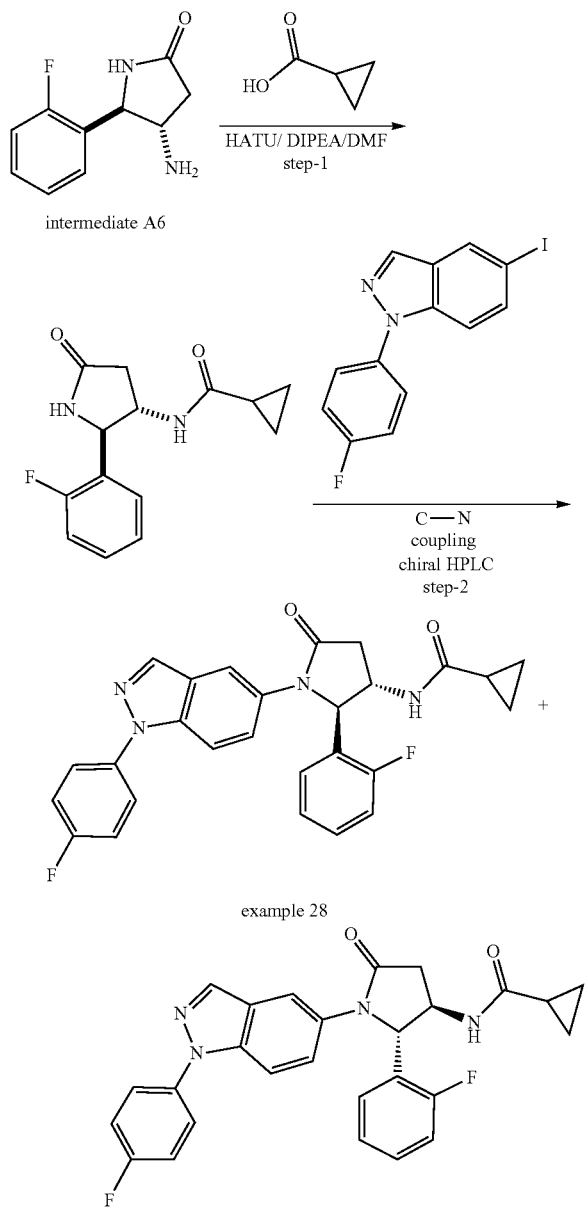

Step 1: To a stirred solution of cyclopropanecarboxylic acid (0.53 g, 6.18 mmol, 1.2 eq) in DMF (8.0 mL) was added HATU (4.00 g, 10.30 mmol, 2.0 eq), DIPEA (4.5 mL, 25.75 mmol, 5.0 eq) and intermediate A6 (1.00 g, 5.15 mmol, 1.0 eq) at 0° C. and the reaction mixture was then stirred at ambient temperature for 16 h. After completion of the reaction (monitored by TLC, TLC system 5% MeOH in DCM, Rf-0.3), the reaction mixture was diluted with EtOAc (25 mL) and was washed with ice cold water (3×25 mL), dried over $Na_2SO_4$ and concentrated under reduced pressure to get the crude product which was purified by column chromatography (230-400 mesh silica gel; 0 to 2% MeOH-DCM) to afford N-(trans-2-(2-fluorophenyl)-5-oxopyrrolidin-3-yl)cyclopropanecarboxamide (0.56 g, 41%).

Step 2: A stirred solution of N-(trans-2-(2-fluorophenyl)-5-oxopyrrolidin-3-yl)cyclopropanecarboxamide (0.250 g, 0.953 mmol, 1 eq), 1-(4-fluorophenyl)-5-iodo-1H-indazole (0.385 g, 1.140 mmol, 1.2 eq) and $K_3PO_4$ (0.404 g, 1.906 mmol, 2.0 eq) in 1,4-dioxane (10 mL) was degassed with argon for 30 min. Then, trans-N,N'-dimethylcyclohexane-1,2-diamine (0.054 g, 0.381 mmol, 0.4 eq) and CuI (0.036 g, 0.191 mmol, 0.2 eq) were added and the reaction mixture was stirred for 16 h at 90° C. in a sealed tube. After completion of the reaction (monitored by TLC, TLC system 5% methanol in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic product. Further enantiomer separation was done by preparative chiral HPLC to afford pure N-((2S,3R)-2-(2-fluorophenyl)-1-(1-(4-fluorophenyl)-1H-indazol-5-yl)-5-oxopyrrolidin-3-yl)cyclopropanecarboxamide (0.063 g, 14%; RT=7.76 min; Column Name: Chiralpak IA (250×4.6 mm) 5 µm, Mobile Phase: Hexane/EA/EtOH/DEA: 70/15/15/0.1, Flow Rate: 1.0 ml/min) and N-((2R,3S)-2-(2-fluorophenyl)-1-(1-(4-fluorophenyl)-1H-indazol-5-yl)-5-oxopyrrolidin-3-yl)cyclopropanecarboxamide (0.036 g, 8%; RT=10.73 min; Column Name: Chiralpak IA (250×4.6 mm) 5 µm, Mobile Phase: Hexane/EA/EtOH/DEA: 70/15/15/0.1, Flow Rate: 1.0 ml/min).

$^1$H NMR (DMSO-$d_6$) δ: 8.87-8.85 (m, 1H), 8.32 (s, 1H), 7.84 (s, 1H), 7.76-7.71 (m, 3H), 7.57-7.55 (m, 1H), 7.42-7.37 (m, 3H), 7.27-7.26 (m, 1H), 7.16-7.09 (m, 2H), 5.44 (s, 1H), 4.37-4.32 (m, 1H), 3.13-3.07 (m, 1H), 2.54 (s, 1H), 1.59-1.57 (m, 1H), 0.70-0.68 (m, 4H).

EXAMPLE 29

N-(trans-1-(1-(4-cyanophenyl)-1H-indazol-5-yl)-5-oxo-2-phenylpyrrolidin-3-yl)-2,2-difluoropropanamide

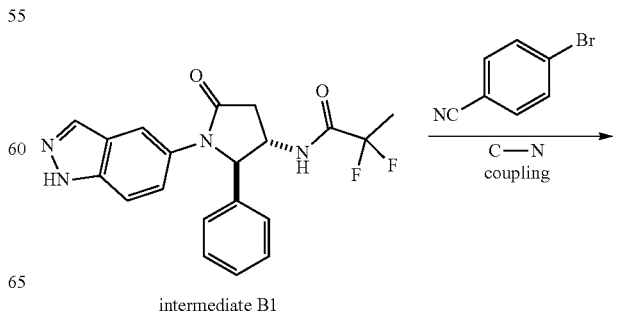

intermediate B1

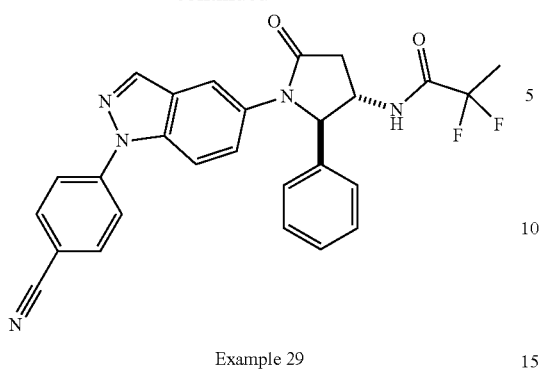

Example 29

A stirred solution of intermediate B1 (0.600 g, 1.563 mmol, 1.0 eq), 4-bromobenzonitrile (0.339 g, 1.875 mmol, 1.2 eq) and $K_3PO_4$ (0.662 g, 3.125 mmol, 2.0 eq) in 1,4-dioxane (30 mL) was degassed with argon for 30 min. Then, trans-N,N'-dimethylcyclohexane-1,2-diamine (0.088 g, 0.625 mmol, 0.4 eq) and CuI (0.060 g, 0.3125 mmol, 0.2 eq) were added and the reaction mixture was stirred for 16 h at 90° C. in a sealed tube. After completion of the reaction (monitored by TLC, TLC system 5% methanol in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) followed by further purification using preparative HPLC to afford pure N-(trans-1-(1-(4-cyanophenyl)-1H-indazol-5-yl)-5-oxo-2-phenylpyrrolidin-3-yl)-2,2-difluoropropanamide (0.22 g, 29%).

$^1$H NMR (DMSO-$d_6$) δ: 9.51-9.49 (m, 1H), 8.43 (s, 1H), 8.02-7.97 (m, 4H), 7.94-7.92 (m, 2H), 7.72-7.70 (m, 1H), 7.36-7.29 (m, 4H), 7.24-7.23 (m, 1H), 5.34 (s, 1H), 4.27 (bs, 1H), 3.15-3.08 (m, 1H), 2.65-2.60 (m, 1H), 1.83-1.73 (m, 3H).

EXAMPLE 30

N-(trans-1-(1-(3-cyanophenyl)-1H-indazol-5-yl)-5-oxo-2-phenylpyrrolidin-3-yl)-2,2-difluoropropanamide

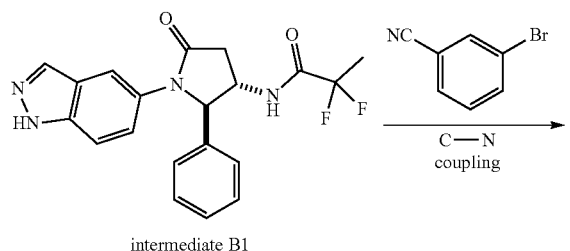

intermediate B1

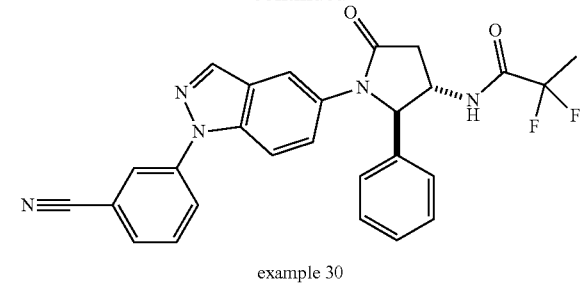

example 30

Starting from intermediate B1, example 30 was synthesized in analogy to the synthetic procedure described for example 29.

$^1$H NMR (DMSO-$d_6$) δ: 9.51-9.49 (m, 1H), 8.39 (s, 1H), 8.20 (s, 1H), 8.11-8.09 (m, 1H), 7.92-7.89 (m, 2H), 7.84-7.82 (m, 1H), 7.77-7.75 (m, 1H), 7.68-7.66 (m, 1H), 7.37-7.30 (m, 4H), 7.25-7.23 (m, 1H), 5.33 (s, 1H), 4.27 (bs, 1H), 3.14-3.08 (m, 1H), 2.65-2.60 (m, 1H), 1.83-1.73 (m, 3H).

EXAMPLE 34

N-((2R,3S)-2-(4-fluoro-3-methoxyphenyl)-1-(1-(4-fluorophenyl)-1H-indazol-5-yl)-5-oxopyrrolidin-3-yl)cyclopropanecarboxamide

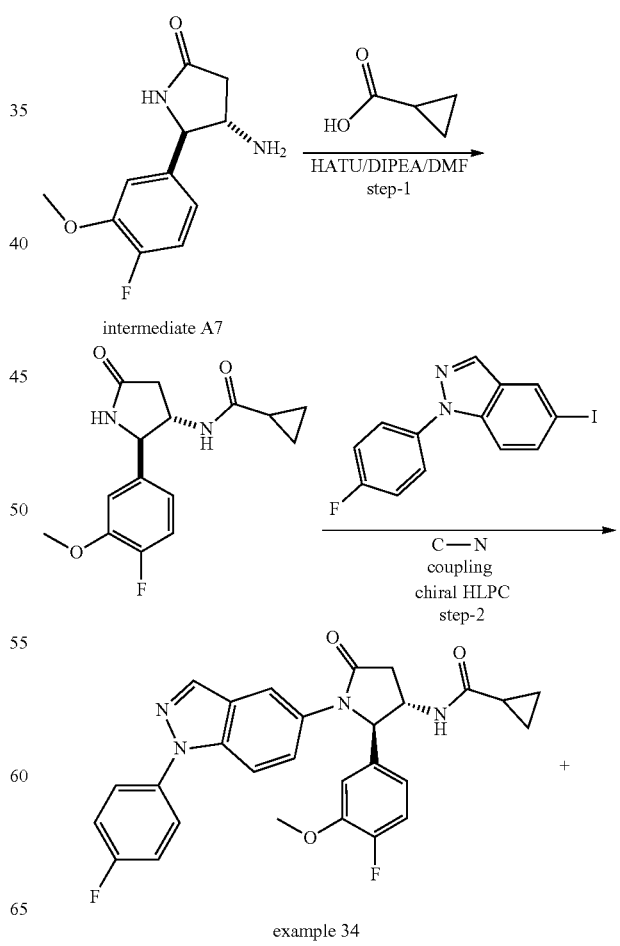

example 34

-continued

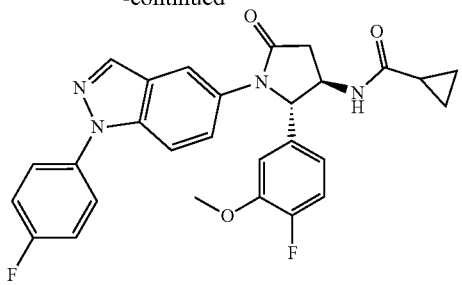

Step 1: To a stirred solution of intermediate A7 (0.70 g, 3.12 mmol, 1.0 eq) in DMF (30 mL) was added HATU (1.78 g, 4.68 mmol, 1.5 eq), DIPEA (2.7 mL, 15.62 mmol, 5.0 eq) and cyclopropanecarboxylic acid (0.34 g, 4.06 mmol, 1.3 eq) and the reaction mixture was stirred for 16 h at ambient temperature. After completion, the reaction mixture was diluted with EtOAc and was washed with ice cold water, sat. NaHCO$_3$ and sat. NH$_4$Cl solution. The combined organic layers were concentrated under reduced pressure to get the crude product which was purified by column chromatography (100-200 mesh silica gel; 2% MeOH-DCM; R$_f$-value-0.5) to afford N-(trans-2-(4-fluoro-3-methoxyphenyl)-5-oxopyrrolidin-3-yl)cyclopropanecarboxamide (0.70 g, 77%).

Step 2: A stirred solution of N-(trans-2-(4-fluoro-3-methoxyphenyl)-5-oxopyrrolidin-3-yl)cyclopropanecarboxamide (0.25 g, 0.86 mmol, 1.0 eq), 1-(4-fluorophenyl)-5-iodo-1H-indazole (0.35 g, 1.02 mmol, 1.2 eq) and K$_3$PO$_4$ (0.36 g, 1.71 mmol, 2.0 eq) in 1,4-dioxane (20 mL) was degassed with argon for 15 min. Then, trans-N,N'-dimethylcyclohexane-1,2-diamine (0.05 g, 0.34 mmol, 0.4 eq) and CuI (0.03 g, 0.17 mmol, 0.2 eq) were added and the reaction mixture was stirred for 16 h at 90° C. After completion, the reaction mixture was filtered through a celite bed and the celite bed was washed 2-3 times with EtOAc. The combined organic layers were concentrated to get the crude product which was purified by column chromatography (100-200 mesh silica gel; 5% MeOH-DCM; R$_f$-value-0.5) to afford the racemic product. Further enantiomer separation was done by preparative chiral HPLC chiral to afford N-((2S,3R)-2-(4-fluoro-3-methoxyphenyl)-1-(1-(4-fluorophenyl)-1H-indazol-5-yl)-5-oxopyrrolidin-3-yl)cyclopropanecarboxamide (0.07 g; RT=10.55 min; Column Name: Chiralpak ID (250×4.6 mm) 5 μm, Mobile Phase: Hexane/EtOH/DEA: 80/20/0.1, Flow Rate: 1.0 ml/min) and N-((2R,3S)-2-(4-fluoro-3-methoxyphenyl)-1-(1-(4-fluorophenyl)-1H-indazol-5-yl)-5-oxopyrrolidin-3-yl)cyclopropanecarboxamide (0.06 g; RT=13.05 min; Column Name: Chiralpak ID (250×4.6 mm) 5 μm, Mobile Phase: Hexane/EtOH/DEA: 80/20/0.1, Flow Rate: 1.0 ml/min).

$^1$H NMR (DMSO-d$_6$) δ: 8.87 (d, 1H), 8.31 (s, 1H), 7.90-7.89 (m, 1H), 7.77-7.72 (m, 3H), 7.69-7.66 (m, 1H), 7.42-7.38 (t, 2H), 7.19-7.16 (m, 1H), 7.14-7.09 (m, 1H), 6.86-6.83 (m, 1H), 5.23 (s, 1H), 4.18-4.17 (m, 1H), 3.79 (s, 3H), 3.11-3.05 (m, 1H), 2.44-2.43 (m, 1H), 1.61-1.58 (m, 1H), 0.74-0.69 (m, 4H).

EXAMPLE 38

2,2-difluoro-N-((2S,3R)-1-(1-(4-fluorophenyl)-1H-indazol-5-yl)-5-oxo-2-(o-tolyl)pyrrolidin-3-yl)propanamide and Example 72: 2,2-difluoro-N-((2R,3S)-1-(1-(4-fluorophenyl)-1H-indazol-5-yl)-5-oxo-2-(o-tolyl)pyrrolidin-3-yl)propanamide

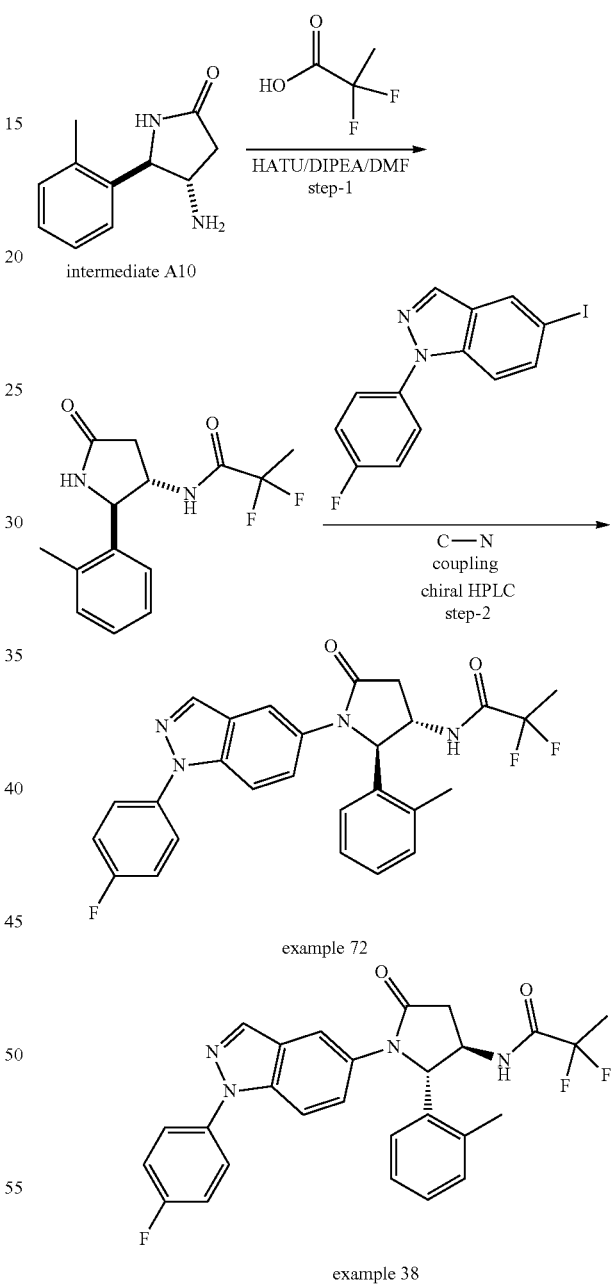

Starting from intermediate A10, example 38 and example 72 were synthesized in analogy to the synthetic procedure described for example 20 and example 21.

Enantiomer separation was done by preparative chiral HPLC to afford example 38 (0.07 g; RT=4.01 min; Column Name: Chiralpak IA (250×4.6 mm) 5 μm, Mobile Phase: Hexane/EA/EtOH/DEA:50/25/25/0.1, Flow Rate: 1.0 ml/min) and example 72 (0.06 g; RT=4.99 min; Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 9.63-9.61 (m, 1H), 8.32 (s, 1H), 7.87 (s, 1H), 7.76-7.71 (m, 3H), 7.64-7.62 (m, 1H), 7.41-7.37 (m, 2H), 7.16-7.13 (m, 4H), 5.54 (s, 1H), 4.27 (s, 1H), 3.17-3.10 (m, 1H), 2.38 (s, 3H), 1.83-1.73 (m, 3H).

EXAMPLE 39

N-((2S,3R)-1-(1-(4-fluorophenyl)-1H-indazol-5-yl)-5-oxo-2-phenylpyrrolidin-3-yl)cyclopropanecarboxamide and Example 65: N-((2R,3S)-1-(1-(4-fluorophenyl)-1H-indazol-5-yl)-5-oxo-2-phenyl pyrrolidin-3-yl)cyclopropanecarboxamide

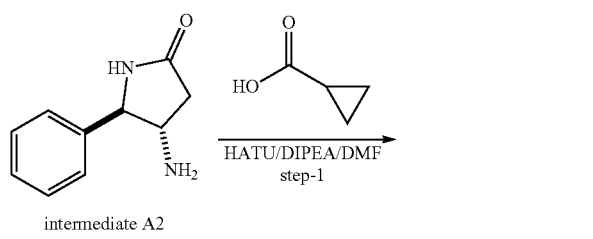

intermediate A2

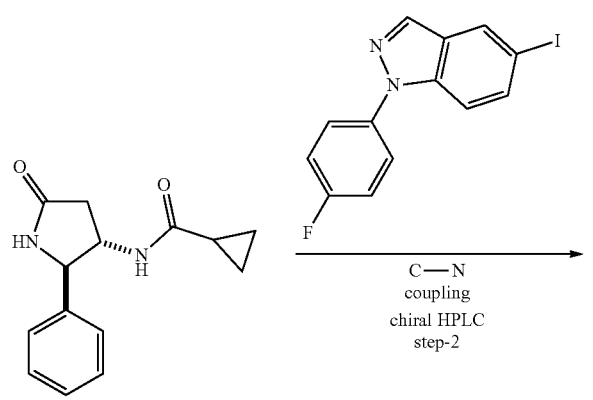

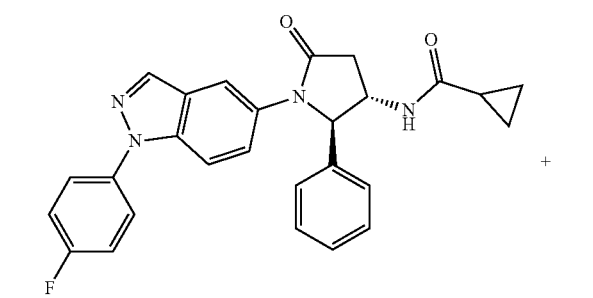

example 65

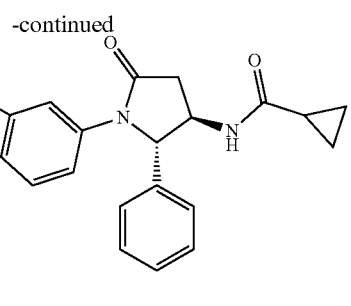

example 39

Step 1: To a stirred solution of cyclopropanecarboxylic acid (0.59 g, 6.818 mmol, 1.2 eq) in DMF (15 mL) was added HATU (4.32 g, 11.363 mmol, 2.0 eq), DIPEA (5.0 mL, 28.409 mmol, 5.0 eq) and intermediate A2 (1.00 g, 5.681 mmol, 1.0 eq) at 0° C. and the reaction mixture was then stirred at ambient temperature for 16 h. After completion of the reaction (monitored by TLC, TLC system 5% MeOH in DCM, Rf-0.3), the reaction mixture was diluted with EtOAc (35 mL) and was washed with ice cold water (3×25 mL), dried over Na$_2$SO$_4$ and concentrated under reduced pressure to get the crude product which was purified by column chromatography (230-400 mesh silica gel; 0 to 4% MeOH-DCM) to afford N-(trans-5-oxo-2-phenylpyrrolidin-3-yl)cyclopropanecarboxamide (0.45 g, 32%).

Step 2: A stirred solution of N-(trans-5-oxo-2-phenylpyrrolidin-3-yl)cyclopropanecarboxamide (0.450 g, 1.844 mmol, 1.0 eq), 1-(4-fluorophenyl)-5-iodo-1H-indazole (0.748 g, 2.213 mmol, 1.2 eq) and K$_3$PO$_4$ (0.781 g, 3.688 mmol, 2.0 eq) in 1,4-dioxane (30 mL) was degassed with argon for 30 min. Then, trans-N,N'-dimethylcyclohexane-1,2-diamine (0.104 g, 0.737 mmol, 0.4 eq) and CuI (0.070 g, 0.368 mmol, 0.2 eq) were added and the reaction mixture was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic product. Further enantiomer separation was done by preparative chiral HPLC to afford pure N-((2S, 3R)-1-(1-(4-fluorophenyl)-1H-indazol-5-yl)-5-oxo-2-phenylpyrrolidin-3-yl)cyclopropanecarboxamide (0.267 g, 32%; RT=5.56 min; Column Name: Chiralpak IA (250×4.6 mm) 5 μm, Mobile Phase: Hexane/Isopropanol/DCM/DEA: 70/15/15/0.1, Flow Rate: 1.0 ml/min) and N-((2R,3S)-1-(1-(4-fluorophenyl)-1H-indazol-5-yl)-5-oxo-2-phenylpyrrolidin-3-yl)cyclopropanecarboxamide (0.254 g, 30%; RT=7.13 min; Column Name: Chiralpak IA (250×4.6 mm) 5 μm, Mobile Phase: Hexane/Isopropanol/DCM/DEA: 70/15/15/0.1, Flow Rate: 1.0 ml/min).

$^1$H-NMR (DMSO-d$_6$) δ: 8.90 (s, 1H), 8.30 (s, 1H), 7.91 (s, 1H), 7.73-7.71 (d, 4H), 7.41-7.23 (m, 7H), 5.26 (s, 1H), 4.16-4.12 (m, 1H), 3.09-3.03 (m, 1H), 2.42-2.32 (d, 1H), 1.62-1.58 (m, 1H), 0.71-0.69 (m, 4H).

EXAMPLE 42

2,2-difluoro-N-((2S,3R)-2-(2-fluoro-5-methoxyphenyl)-1-(1-(4-fluorophenyl)-1H-indazol-5-yl)-5-oxopyrrolidin-3-yl)propanamide and Example 69: 2,2-difluoro-N-((2R,3S)-2-(2-fluoro-5-methoxyphenyl)-1-(1-(4-fluorophenyl)-1H-indazol-5-yl)-5-oxopyrrolidin-3-yl)propanamide

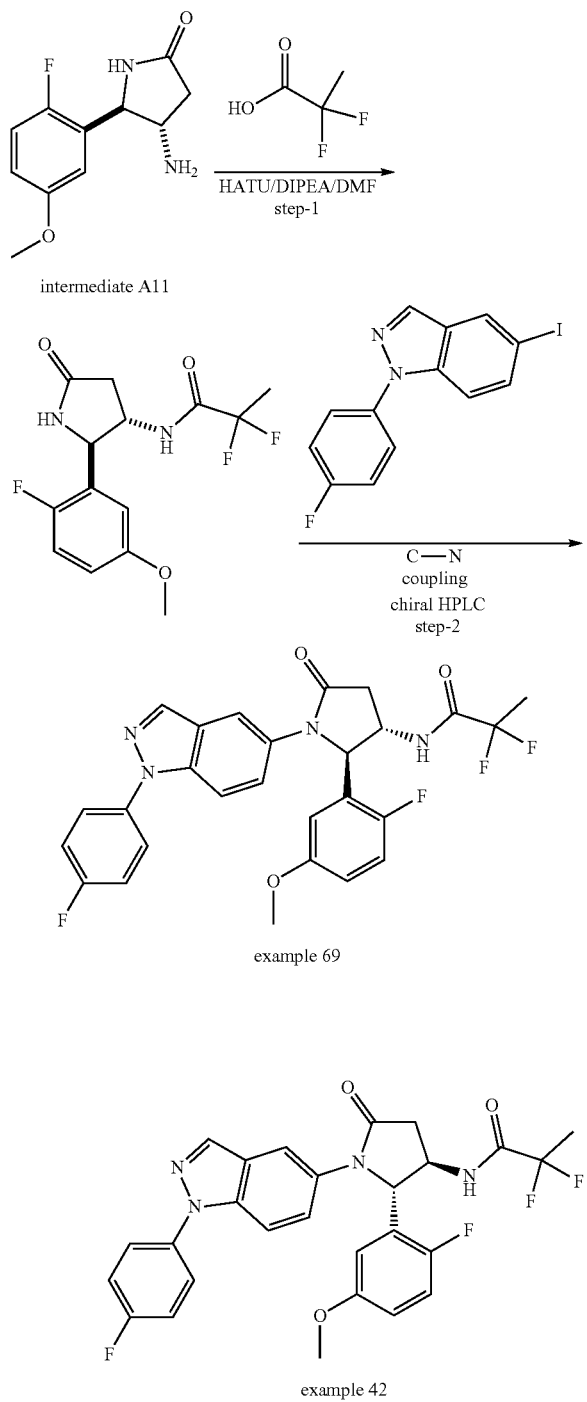

Starting from intermediate A11, example 42 and example 69 were synthesized in analogy to the synthetic procedure described for example 20 and example 21.

Enantiomer separation was done by preparative chiral HPLC to afford example 42 (0.07 g; RT=7.96 min; Column Name: Chiralpak ID (250×4.6 mm) 5 μm, Mobile Phase: EtOH, Flow Rate: 0.5 ml/min) and example 69 (0.06 g; RT=10.31 min; Column Name: Chiralpak ID (250×4.6 mm) 5 μm, Mobile Phase: EtOH, Flow Rate: 0.5 ml/min).

$^1$H NMR (DMSO-$d_6$): δ 9.42-9.40 (m, 1H), 8.34 (s, 1H), 7.81 (s, 1H), 7.77-7.72 (m, 3H), 7.54-7.51 (m, 1H), 7.42 (t, 2H), 7.08 (t, 1H), 6.92-6.90 (m, 1H), 6.80-6.77 (m, 1H), 5.51-5.50 (m, 1H), 4.49-4.48 (m, 1H), 3.64 (s, 3H), 3.16-3.09 (m, 1H), 2.69-2.64 (m, 1H), 1.81-1.71 (m, 3H).

EXAMPLE 43

N-((2S,3R)-2-(2-fluoro-5-methoxyphenyl)-1-(1-(4-fluorophenyl)-1H-indazol-5-yl)-5-oxopyrrolidin-3-yl)cyclopropanecarboxamide and Example 62: N-((2R,3S)-2-(2-fluoro-5-methoxyphenyl)-1-(1-(4-fluorophenyl)-1H-indazol-5-yl)-5-oxopyrrolidin-3-yl)cyclopropanecarboxamide

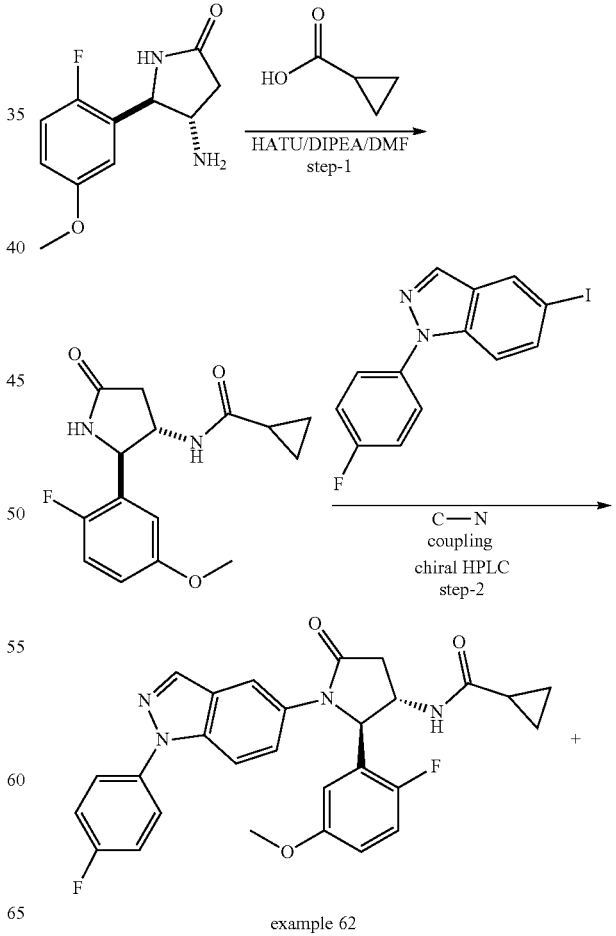

-continued

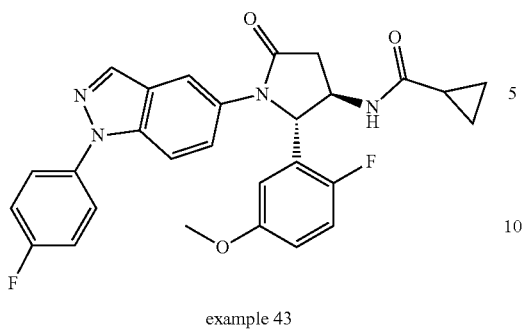

example 43

Starting from intermediate A11, example 43 and example 62 were synthesized in analogy to the synthetic procedure described for example 39 and example 65.

Enantiomer separation was done by preparative chiral HPLC to afford example 43 (0.07 g; RT=5.05 min; Column Name: Chiralpak ID (250×4.6 mm) 5 μm, Mobile Phase: Hexane/EA/EtOH/DEA: 50/25/25/0.1, Flow Rate: 1.0 ml/min) and example 62 (0.06 g; RT=7.12 min; Column Name: Chiralpak ID (250×4.6 mm) 5 μm, Mobile Phase: Hexane/EA/EtOH/DEA: 50/25/25/0.1, Flow Rate: 1.0 ml/min).

$^1$H NMR (DMSO-d$_6$) δ: 8.84-8.82 (m, 1H), 8.33 (s, 1H), 7.84 (s, 1H), 7.77-7.72 (m, 3H), 7.58-7.55 (m, 1H), 7.42 (t, 2H), 7.08 (t, 1H), 6.87-6.85 (m, 1H), 6.80-6.77 (m, 1H), 5.42 (s, 1H), 4.37-4.35 (m, 1H), 3.64 (s, 3H), 3.13-3.07 (m, 1H), 2.54-2.52 (m, 1H), 1.58-1.55 (m, 1H), 0.70-0.68 (m, 4H).

EXAMPLE 49

N-((2R,3S)-1-(1-(4-fluorophenyl)-1H-indazol-5-yl)-2-(2-methoxypyridin-4-yl)-5-oxopyrrolidin-3-yl)cyclopropanecarboxamide

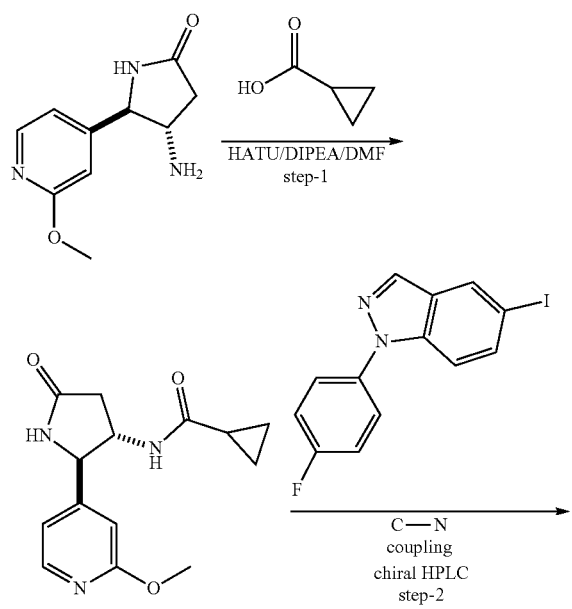

-continued

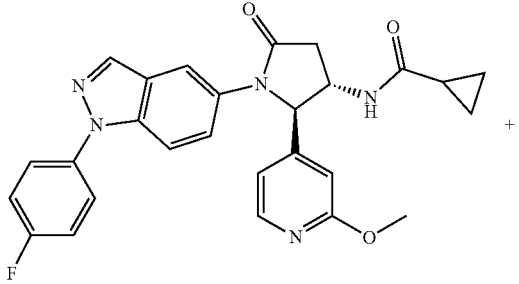

example 49

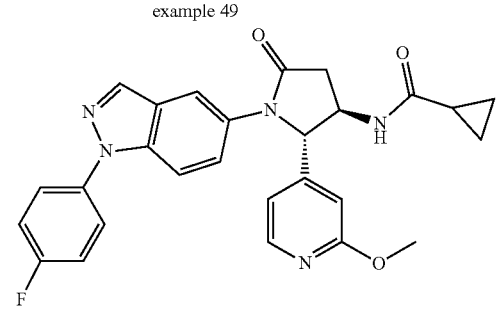

Step 1: To a stirred solution of cyclopropanecarboxylic acid (0.50 g, 5.79 mmol, 1.2 eq) in DMF (10 mL) was added HATU (3.60 g, 9.65 mmol, 2.0 eq), DIPEA (4.2 mL, 24.13 mmol, 5.0 eq) and intermediate A9 (1.00 g, 4.82 mmol, 1.0 eq) at 0° C. and the reaction mixture was then stirred at ambient temperature for 16 h. After completion of the reaction (monitored by TLC, TLC system 5% MeOH in DCM, Rf-0.3), the reaction mixture was diluted with EtOAc (25 mL) and was washed with ice cold water (3×25 mL), dried over Na$_2$SO$_4$ and concentrated under reduced pressure to get the crude product which was purified by column chromatography (230-400 mesh silica gel; 0 to 2% MeOH-DCM) to afford N-(trans-2-(2-methoxypyridin-4-yl)-5-oxopyrrolidin-3-yl)cyclopropanecarboxamide (0.88 g, 66%).

Step 2: A stirred solution of N-(trans-2-(2-methoxypyridin-4-yl)-5-oxopyrrolidin-3-yl)-cyclopropanecarboxamide (0.444 g, 1.612 mmol, 1.0 eq), 1-(4-fluorophenyl)-5-iodo-1H-indazole (0.654 g, 1.935 mmol, 1.2 eq) and K$_3$PO$_4$ (0.683 g, 3.224 mmol, 2.0 eq) in 1,4-dioxane (10 mL) was degassed with argon for 30 min. Then trans-N,N'-dimethylcyclohexane-1,2-diamine (0.092 g, 0.645 mmol, 0.4 eq) and CuI (0.062 g, 0.322 mmol, 0.2 eq) were added and the reaction mixture was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 6% MeOH in DCM) to afford the racemic product. Further enantiomer separation was done by preparative chiral HPLC to afford pure N-((2S,3R)-1-(1-(4-fluorophenyl)-1H-indazol-5-yl)-2-(2-methoxypyridin-4-yl)-5-oxopyrrolidin-3-yl)cyclopropanecarboxamide (0.042 g; RT=8.74 min; Column Name: Chiralpak IA (250×4.6 mm) 5 μm, Mobile Phase: Hexane/EA/EtOH/DEA: 70/15/15/0.1, Flow Rate: 1.0 ml/min) and N-((2R,3S)-1-(1-(4-fluorophenyl)-1H-indazol-5-yl)-2-(2-methoxypyridin-4- yl)-5-oxopyrrolidin-3-yl)cyclopropanecarboxamide (0.060 g; RT=7.54 min; Column Name: Chiralpak IA (250×4.6 mm) 5 μm, Mobile Phase: Hexane/EA/EtOH/DEA: 70/15/15/0.1, Flow Rate: 1.0 ml/min).

$^1$H NMR (DMSO-d$_6$): δ 8.92-8.91 (m, 1H), 8.32 (s, 1H), 8.10 (d, 1H), 7.92 (s, 1H), 7.77-7.71 (m, 4H), 7.42 (t, 2H), 7.00 (d, 1H), 6.73 (s, 1H), 5.25-5.24 (m, 1H), 4.18-4.14 (m, 1H), 3.77 (s, 3H), 3.11-3.04 (m, 1H), 2.45-2.44 (m, 1H), 1.59 (bs, 1H), 0.76-0.70 (m, 4H).

EXAMPLE 53

N-((2R,3S)-1-(1-(4-fluorophenyl)-1H-indazol-5-yl)-5-oxo-2-(o-tolyl)pyrrolidin-3-yl)cyclopropanecarboxamide

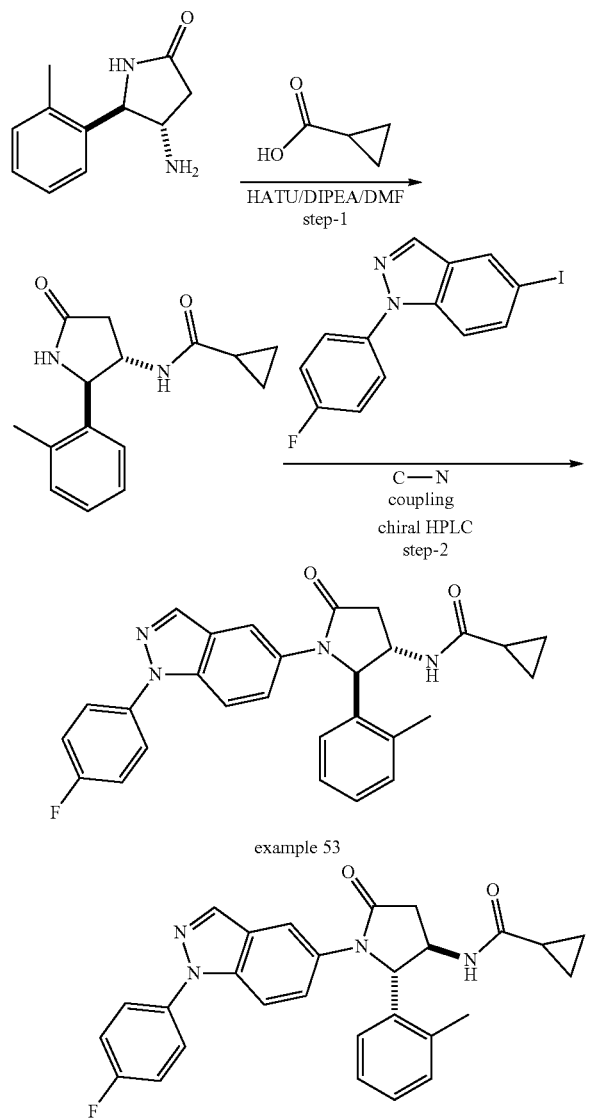

example 53

Starting from intermediate A10, example 53 was synthesized in analogy to the synthetic procedure described for example 28.

Enantiomer separation was done by preparative chiral HPLC to afford N-((2S,3R)-1-(1-(4-fluorophenyl)-1H-indazol-5-yl)-5-oxo-2-(o-tolyl)pyrrolidin-3-yl)cyclopropanecarboxamide (0.134 g, RT=4.48 min; Column Name: Chiralpak IA (250×4.6 mm) 5 μm, Mobile Phase: Hexane/EA/EtOH/DEA: 50/25/25/0.1, Flow Rate: 1.0 ml/min) and example 63 (0.077 g, RT=5.32 min; Column Name: Chiralpak IA (250×4.6 mm) 5 μm, Mobile Phase: Hexane/EA/EtOH/DEA: 50/25/25/0.1, Flow Rate: 1.0 ml/min).

$^1$H NMR (DMSO-d$_6$): δ 9.01 (d, 1H), 8.32 (s, 1H), 7.92 (s, 1H), 7.76-7.72 (m, 3H), 7.69-7.67 (m, 1H), 7.42-7.37 (m, 2H), 7.20-7.17 (m, 1H), 7.13-7.08 (m, 3H), 5.41 (s, 1H), 4.19-4.15 (m, 1H), 3.10-3.04 (m, 1H), 2.42-2.39 (m, 4H), 1.62-1.59 (m, 1H), 0.71-0.69 (m, 4H).

EXAMPLE 73

1-fluoro-N-((2R,3S)-1-(1-(4-fluorophenyl)-1H-indazol-5-yl)-5-oxo-2-phenylpyrrolidin-3-yl)cyclopropane-1-carboxamide

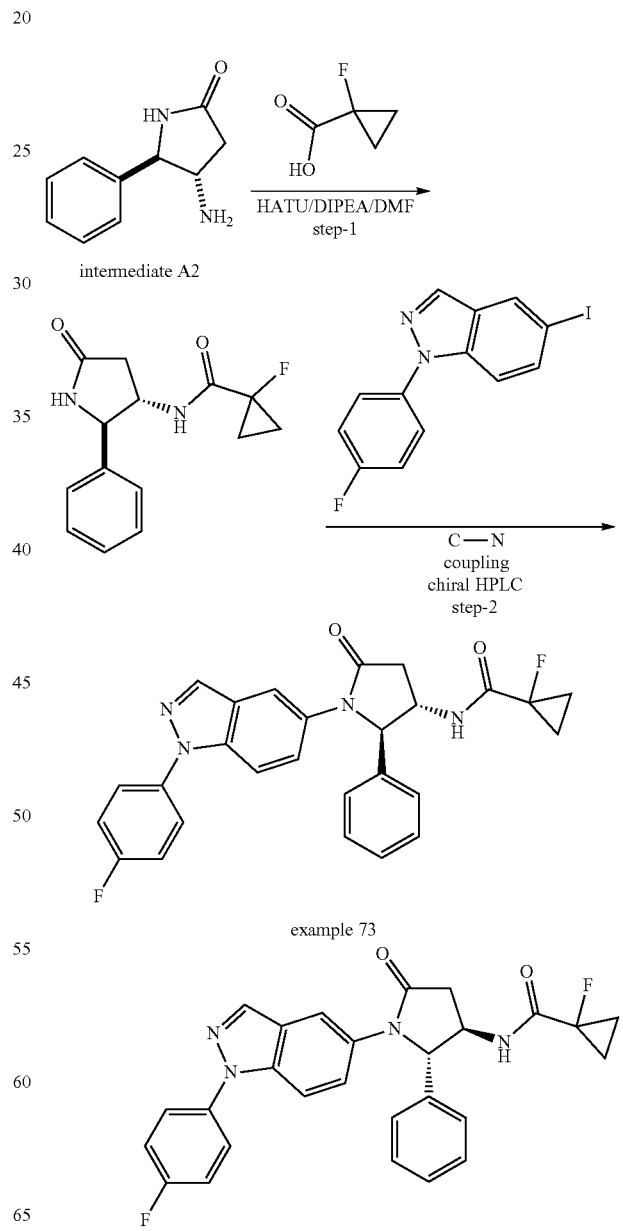

example 73

Starting from intermediate A2, example 73 was synthesized in analogy to the synthetic procedure described for example 28.

Enantiomer separation was done by preparative chiral HPLC to afford 1-fluoro-N-((2S,3R)-1-(1-(4-fluorophenyl)-1H-indazol-5-yl)-5-oxo-2-phenylpyrrolidin-3-yl)cyclopropane-1-carboxamide (0.07 g; RT=7.17 min; Column Name: Chiralpak IA (250×4.6 mm) 5 µm, Mobile Phase: Hexane/EA/EtOH/DEA: 70/15/15/0.1, Flow Rate: 1.0 ml/min) and example 73 (0.10 g; RT=10.00 min; Column Name: Chiralpak IA (250×4.6 mm) 5 µm, Mobile Phase: Hexane/EA/EtOH/DEA: 70/15/15/0.1, Flow Rate: 1.0 ml/min).

$^1$H NMR (DMSO-d$_6$): δ 9.20-9.18 (m, 1H), 8.30 (s, 1H), 7.87 (s, 1H), 7.76-7.63 (m, 4H), 7.41-7.28 (m, 6H), 7.23-7.21 (m, 1H), 5.36-5.35 (m, 1H), 4.35-4.31 (m, 1H), 3.10-3.03 (m, 1H), 2.67-2.62 (m, 1H), 1.34-1.30 (m, 2H), 1.21 (s, 2H).

EXAMPLE 74

N-((2R,3S)-1-(1-(4-fluorophenyl)-1H-indazol-5-yl)-5-oxo-2-phenylpyrrolidin-3-yl)-1-methylcyclopropane-1-carboxamide

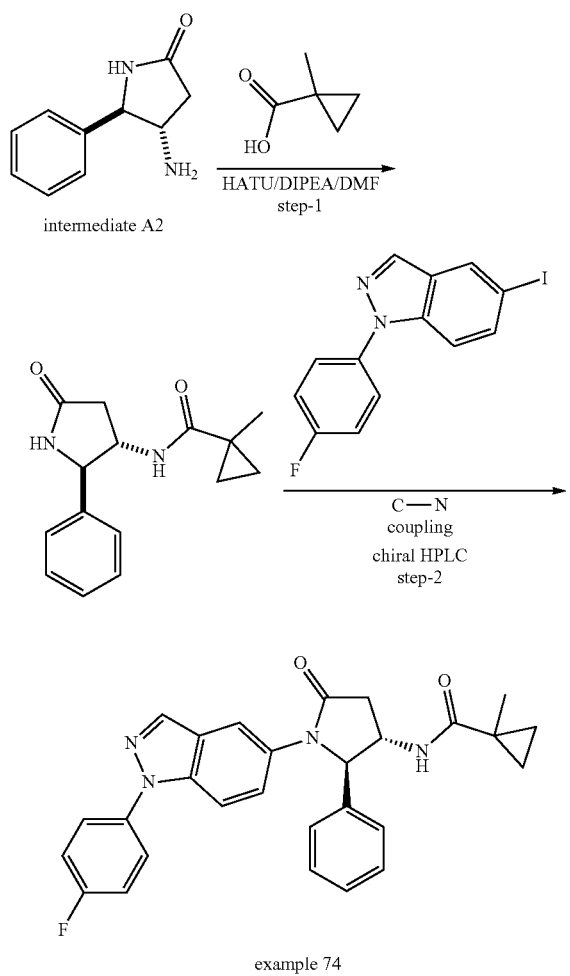

example 74

Starting from intermediate A2, example 74 was synthesized in analogy to the synthetic procedure described for example 28.

Enantiomer separation was done by preparative chiral HPLC to afford N-((2S,3R)-1-(1-(4-fluorophenyl)-1H-indazol-5-yl)-5-oxo-2-phenylpyrrolidin-3-yl)-1-methylcyclopropane-1-carboxamide (0.050 g; RT=4.75 min; Column Name: Chiralpak ID (250×4.6 mm) 5 µm, Mobile Phase: Hexane/EA/EtOH/DEA: 50/25/25/0.1, Flow Rate: 1.0 ml/min) and example 74 (0.063 g; RT=6.78 min; Column Name: Chiralpak ID (250×4.6 mm) 5 µm, Mobile Phase: Hexane/EA/EtOH/DEA: 50/25/25/0.1, Flow Rate: 1.0 ml/min).

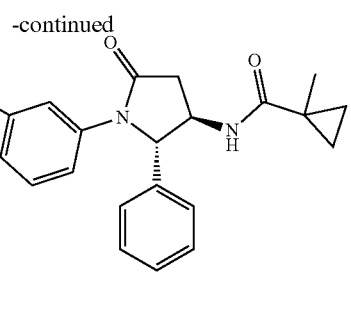

$^1$H NMR (DMSO-d$_6$): δ 8.30 (s, 1H), 8.18 (s, 1H), 7.87 (s, 1H), 7.73-7.66 (m, 4H), 7.39-7.21 (m, 7H), 5.25 (s, 1H), 4.20 (s, 1H), 3.19-3.01 (m, 1H), 2.61 (s, 1H), 1.30 (s, 3H), 1.00 (s, 2H), 0.55 (s, 2H).

EXAMPLE 75

N-(trans-1-(1-(4,4-difluorocyclohexyl)-1H-indazol-5-yl)-5-oxo-2-phenylpyrrolidin-3-yl)-2,2-difluoropropanamide

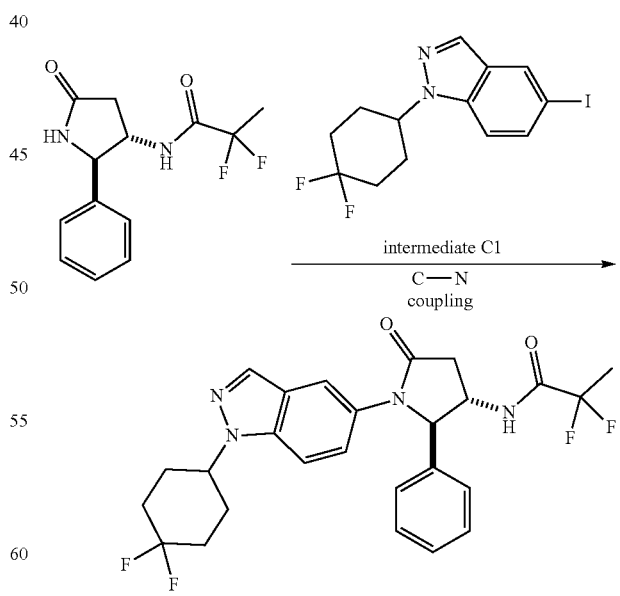

example 75

A stirred solution of 2,2-difluoro-N-(trans-5-oxo-2-phenylpyrrolidin-3-yl)propanamide (for synthesis see example 2, step 1) (0.20 g, 0.75 mmol, 1.0 eq), intermediate C1 (0.32 g, 0.90 mmol, 1.2 eq) and K$_3$PO$_4$ (0.32 g, 1.49 mmol, 2.0 eq) in 1,4-dioxane (20 mL) was degassed with argon for 30 min. Then, trans-N,N'-dimethylcyclohexane-1,2-diamine (0.04 g, 0.30 mmol, 0.4 eq) and CuI (0.03 g, 0.15 mmol, 0.2 eq) were added and the reaction was stirred for 16 h at 90° C. in a sealed tube. After completion of the reaction (monitored by TLC, TLC system 5% MeOH in DCM, Rf-0.5), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the desired N-(trans-1-(1-(4,4-difluorocyclohexyl)-1H-indazol-5-yl)-5-oxo-2-phenylpyrrolidin-3-yl)-2,2-difluoropropanamide (0.06 g, 15%).

$^1$H NMR (DMSO-d$_6$): δ 9.47-9.46 (m, 1H), 8.01 (s, 1H), 7.72 (s, 1H), 7.62-7.60 (m, 1H), 7.53-7.51 (m, 1H), 7.34-7.21 (m, 5H), 5.27 (s, 1H), 4.79 (s, 1H), 4.26 (s, 1H), 3.11-3.05 (m, 1H), 2.63-2.58 (m, 1H), 2.162.07 (m, 7H), 1.96 (s, 2H), 1.83-1.73 (m, 3H).

EXAMPLE 76

N-(trans-1-(1-(cyclohexyl)-1H-indazol-5-yl)-5-oxo-2-phenylpyrrolidin-3-yl)-2,2-difluoropropanamide

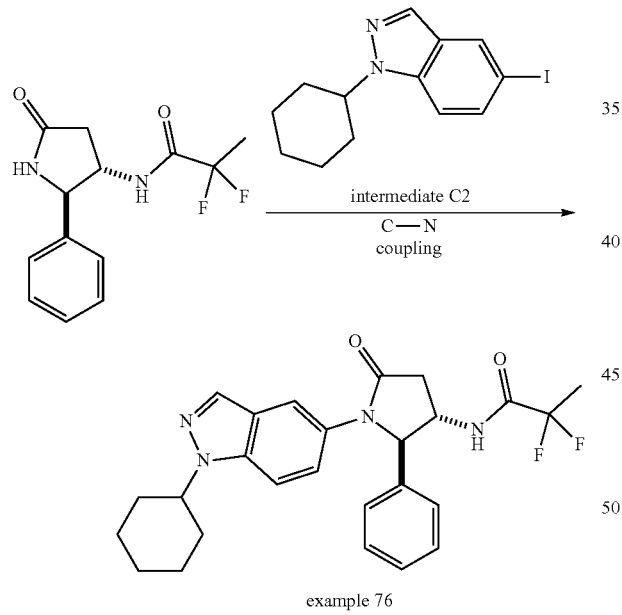

example 76

Starting from intermediate C2, example 76 was synthesized in analogy to the synthetic procedure described for example 75.

$^1$H NMR (DMSO-d$_6$) δ: 9.47-9.46 (m, 1H), 7.96 (s, 1H), 7.69 (s, 1H), 7.62-7.60 (m, 1H), 7.48-7.45 (m, 1H), 7.34-7.28 (m, 4H), 7.23-7.21 (m, 1H), 5.25 (s, 1H), 4.51-4.47 (m, 1H), 4.27-4.23 (m, 1H), 3.10-3.04 (m, 1H), 2.63-2.57 (m, 1H), 1.83-1.73 (m, 8H), 1.69-1.66 (m, 1H), 1.46-1.43 (m, 2H), 1.24-1.21 (m, 1H).

EXAMPLE 77

2,2-difluoro-N-(trans-2-(2-fluoro-5-methoxyphenyl)-1-(1-methyl-1H-indazol-5-yl)-5-oxopyrrolidin-3-yl)propanamide

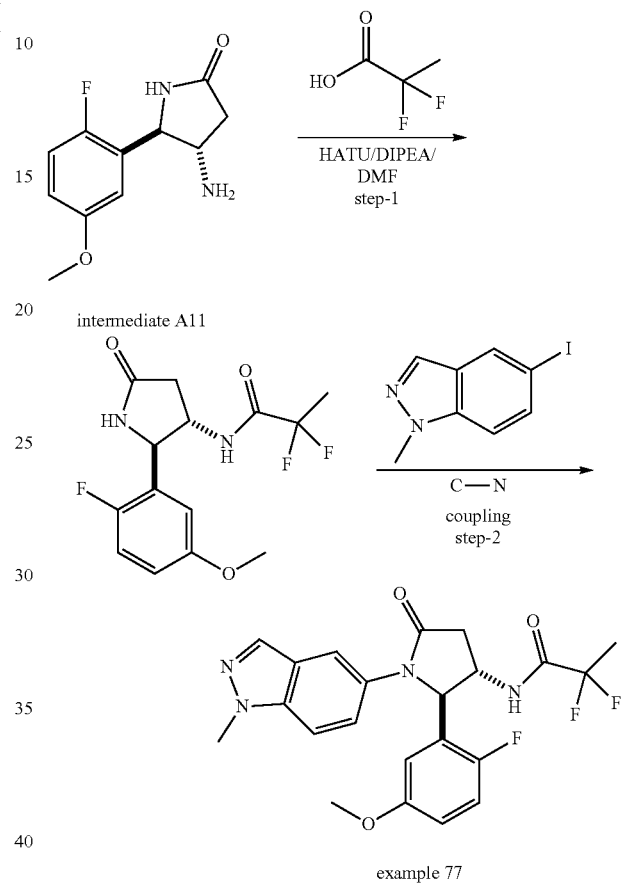

example 77

Step 1: To a stirred solution of 2,2-difluoropropanoic acid (0.35 g, 3.214 mmol, 1.2 eq) in DMF (8 mL) was added HATU (2.03 g, 5.357 mmol, 2.0 eq), DIPEA (2.4 mL, 13.392 mmol, 5.0 eq) and intermediate A11 (0.60 g, 2.678 mmol, 1.0 eq) at 0° C. and the reaction was stirred at ambient temperature for 16 h. After completion of the reaction (monitored by TLC, TLC system 5% MeOH in DCM, Rf-0.3), the reaction mixture was diluted with EtOAc (25 mL) and was washed with ice cold water (3×25 mL), dried over Na$_2$SO$_4$ and concentrated under reduced pressure to get the crude product which was purified by column chromatography (230-400 mesh silica gel; 0 to 2% MeOH-DCM) to afford 2,2-difluoro-N-(trans-2-(2-fluoro-5-methoxyphenyl)-5-oxopyrrolidin-3-yl)propanamide (0.60 g, 71%).

Step 2: A stirred solution of 2,2-difluoro-N-(trans-2-(2-fluoro-5-methoxyphenyl)-5-oxopyrrolidin-3-yl)propanamide (0.150 g, 0.474 mmol, 1.0 eq), 5-iodo-1-methyl-1H-indazole (0.146 g, 0.569 mmol, 1.2 eq) and K$_3$PO$_4$ (0.200 g, 0.949 mmol, 2.0 eq) in 1,4-dioxane (10 mL) was degassed with argon for 30 min. Then, trans-N,N'-dimethylcyclohexane-1,2-diamine (0.027 g, 0.189 mmol, 0.4 eq) and CuI (0.018 g, 0.095 mmol, 0.2 eq) were added and the reaction mixture was stirred for 16 h at 90° C. After completion, the reaction mixture was filtered through a celite bed and the celite bed was washed 2-3 times with EtOAc. The combined organic layers were concentrated to get the crude product which was purified by column chromatography (230-400 mesh silica gel; 3% MeOH-DCM; $R_f$-value-0.4) to afford 2,2-difluoro-N-(trans-2-(2-fluoro-5-methoxyphenyl)-1-(1-methyl-1H-indazol-5-yl)-5-oxopyrrolidin-3-yl)propanamide (0.059 g, 28%).

$^1$H NMR (DMSO-$d_6$) δ: 9.39-9.38 (m, 1H), 7.98 (s, 1H), 7.65 (s, 1H), 7.56-7.54 (m, 1H), 7.40-7.37 (m, 1H), 7.05-7.01 (m, 1H), 6.88-6.87 (m, 1H), 6.76-6.74 (m, 1H), 5.47 (s, 1H), 4.50-4.46 (m, 1H), 3.97 (s, 3H), 3.63 (s, 3H), 3.12-3.06 (m, 1H), 2.68-2.62 (m, 1H), 1.80-1.70 (m, 3H).

EXAMPLE 78

N-(trans-1-(1-(2,2-difluoroethyl)-1H-indazol-5-yl)-2-(2-fluoro-5-methoxyphenyl)-5-oxopyrrolidin-3-yl)-2,2-difluoropropanamide

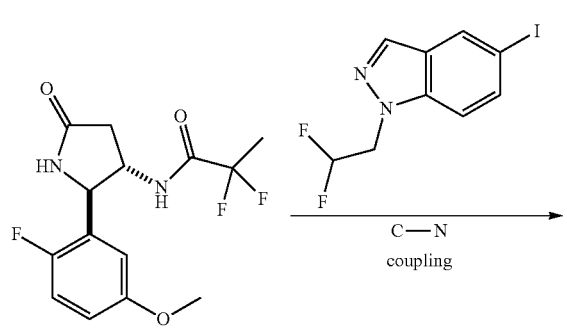

example 78

Starting from 1-(2,2-difluoroethyl)-5-iodo-1H-indazole and 2,2-difluoro-N-(trans-2-(2-fluoro-5-methoxyphenyl)-5-oxopyrrolidin-3-yl)propenamide (see example 77, step 1), example 78 was synthesized in analogy to the synthetic procedure described for example 75.

$^1$H NMR (DMSO-$d_6$) δ: 9.41-9.39 (m, 1H), 8.11 (s, 1H), 7.69-7.63 (m, 2H), 7.45-7.43 (m, 1H), 7.07-7.02 (m, 1H), 6.90 (s, 1H), 6.77 (s, 1H), 6.38 (s, 1H), 5.47 (s, 1H), 4.90 (t, 2H), 4.48 (s, 1H), 3.63 (s, 3H), 3.11-3.07 (m, 1H), 2.68-2.62 (m, 1H), 1.80-1.70 (m, 3H).

EXAMPLE 79

2,2-difluoro-N-(trans-1-(1-(2-fluorobenzyl)-1H-indazol-5-yl)-5-oxo-2-phenylpyrrolidin-3-yl)propanamide

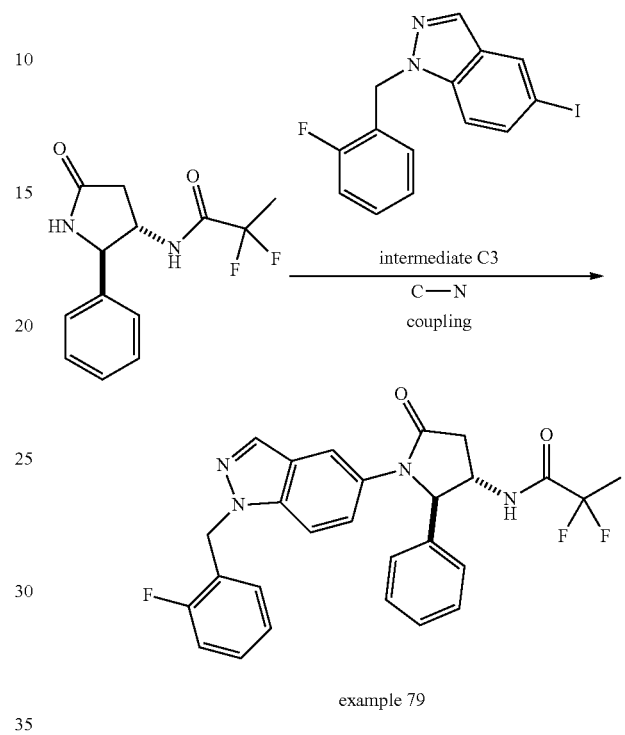

example 79

Starting from intermediate C3, example 79 was synthesized in analogy to the synthetic procedure described for example 75.

$^1$H NMR (DMSO-$d_6$) δ: 9.47-9.45 (m, 1H), 8.03 (s, 1H), 7.73 (s, 1H), 7.63-7.61 (m, 1H), 7.50-7.47 (m, 1H), 7.32-7.21 (m, 7H), 7.12-7.08 (m, 2H), 5.56 (s, 2H), 5.25 (s, 1H), 4.26-4.22 (s, 1H), 3.10-3.03 (m, 1H), 2.66-2.57 (m, 1H), 1.82-1.72 (m, 3H).

EXAMPLE 80

2,2-difluoro-N-(trans-1-(1-(3-fluorobenzyl)-1H-indazol-5-yl)-5-oxo-2-phenylpyrrolidin-3-yl)propanamide

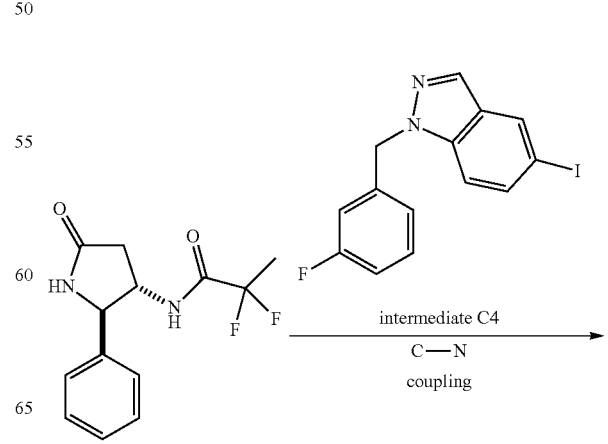

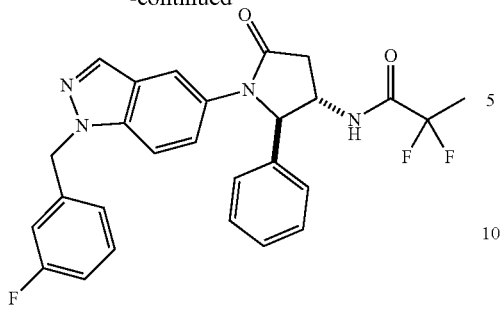

example 80

Starting from intermediate C4, example 80 was synthesized in analogy to the synthetic procedure described for example 75.

$^1$H NMR (DMSO-d$_6$) δ: 9.47-9.45 (m, 1H), 8.05 (s, 1H), 7.75 (s, 1H), 7.63-7.61 (m, 1H), 7.51-7.49 (m, 1H), 7.32-7.21 (m, 6H), 7.08-6.97 (m, 3H), 5.60 (s, 2H), 5.26 (s, 2H), 4.27-4.23 (m, 1H), 3.10-3.03 (m, 1H), 2.61-2.57 (m, 1H), 1.82-1.72 (m, 3H).

EXAMPLE 81

2,2-difluoro-N-(trans-1-(1-(4-fluorobenzyl)-1H-indazol-5-yl)-5-oxo-2-phenylpyrrolidin-3-yl)propanamide

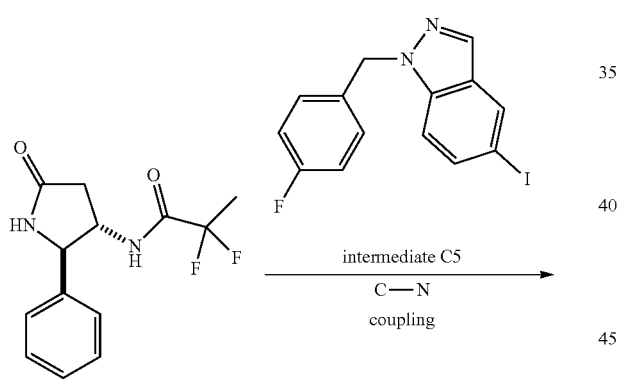

example 81

Starting from intermediate C5, example 81 was synthesized in analogy to the synthetic procedure described for example 75.

$^1$H NMR (DMSO-d$_6$) δ: 9.47-9.45 (m, 1H), 8.05 (s, 1H), 7.75 (s, 1H), 7.64-7.61 (m, 1H), 7.51-7.48 (m, 1H), 7.32-7.27 (m, 4H), 7.23-7.21 (m, 1H), 7.06-6.97 (m, 3H), 5.60 (s, 2H), 5.26 (s, 1H), 4.26-4.22 (s, 1H), 3.05-3.03 (m, 1H), 2.62-2.57 (m, 1H), 1.82-1.72 (m, 3H).

EXAMPLE 82

N-(trans-1-(1-(cyclopropylmethyl)-1H-indazol-5-yl)-5-oxo-2-phenylpyrrolidin-3-yl)-2,2-difluoropropanamide

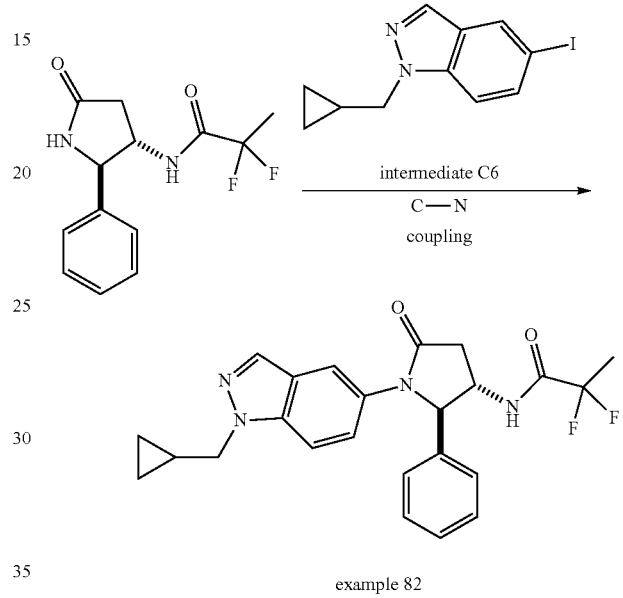

example 82

Starting from intermediate C6, example 82 was synthesized in analogy to the synthetic procedure described for example 75.

$^1$H NMR (DMSO-d$_6$) δ: 9.47-9.46 (m, 1H), 7.96 (s, 1H), 7.71 (s, 1H), 7.61-7.59 (m, 1H), 7.48-7.46 (m, 1H), 7.34-7.28 (m, 4H), 7.23-7.19 (m, 1H), 5.27-5.26 (m, 1H), 4.25-4.20 (m, 3H), 3.10-3.04 (m, 1H), 2.63-2.57 (m, 1H), 1.83-1.73 (m, 3H), 1.21-1.19 (m, 1H), 0.46-0.42 (m, 2H), 0.34-0.33 (m, 2H).

EXAMPLE 84

N-(trans-1-(1-((4,4-difluorocyclohexyl)methyl)-1H-indazol-5-yl)-5-oxo-2-phenylpyrrolidin-3-yl)-2,2-difluoropropanamide

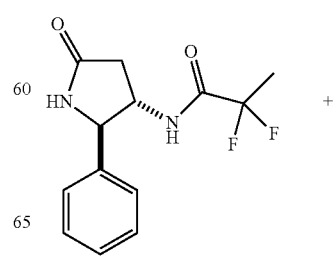 +

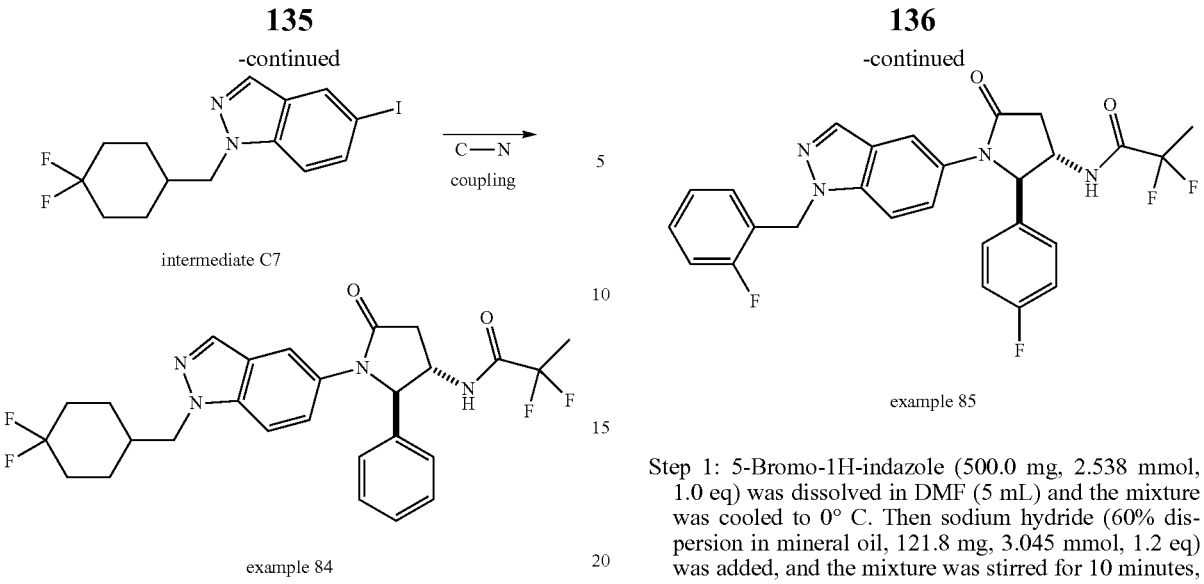

example 84

Starting from intermediate C7, example 84 was synthesized in analogy to the synthetic procedure described for example 75.

$^1$H NMR (DMSO-d$_6$): δ 9.48-9.46 (m, 1H), 7.99 (s, 1H), 7.70 (s, 1H), 7.63-7.61 (m, 1H), 7.50-7.48 (m, 1H), 7.33-7.22 (m, 5H), 5.26 (s, 1H), 4.26-4.24 (m, 3H), 3.10-3.04 (m, 1H), 2.66-2.57 (m, 1H), 1.95-1.93 (m, 3H), 1.83-1.66 (m, 5H), 1.51 (s, 2H), 1.26-1.23 (m, 2H).

EXAMPLE 85

2,2-difluoro-N-((trans)-1-(1-(2-fluorobenzyl)-1H-indazol-5-yl)-2-(4-fluorophenyl)-5-oxopyrrolidin-3-yl)propanamide

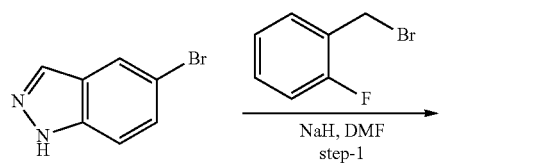

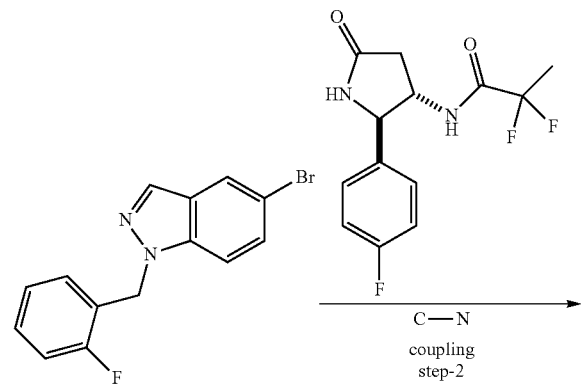

example 85

Step 1: 5-Bromo-1H-indazole (500.0 mg, 2.538 mmol, 1.0 eq) was dissolved in DMF (5 mL) and the mixture was cooled to 0° C. Then sodium hydride (60% dispersion in mineral oil, 121.8 mg, 3.045 mmol, 1.2 eq) was added, and the mixture was stirred for 10 minutes, followed by the addition of 1-(bromomethyl)-2-fluorobenzene (0.36 mL, 3.045 mmol, 1.2 eq). The mixture was warmed to ambient temperature overnight. The reaction mixture was quenched by the addition of water. The mixture was then extracted three times with EtOAc. The combined organic layers were washed with water, then with brine and were then dried over MgSO$_4$. The solvent was removed and the remains were purified via column chromatography. The desired compound was obtained in 60% yield (467.0 mg).

Step 2: 5-bromo-1-(2-fluorobenzyl)-1H-indazole (64.0 mg, 0.210 mmol, 1.2 eq), copper iodide (6.7 mg, 0.035 mmol, 0.2 eq), sodium iodide (52.4 mg, 0.349 mmol, 2.0 eq), 2,2-difluoro-N-[(trans)-2-(4-fluorophenyl)-5-oxo-pyrrolidin-3-yl]propanamide (50.0 mg, 0.175 mmol, 1.0 eq) and K$_3$PO$_4$ (74.2 mg, 0.349 mmol, 2.0 eq) are weighed out into a vial, a stir bar was added, the vial was sealed and was purged with nitrogen. 1,4-Dioxane (1.0 mL) was added, followed by trans-N,N'-dimethylcyclohexane-1,2-diamine (9.9 mg, 0.070 mmol, 0.4 eq). The mixture was heated to 110° C. for 16 hours. The mixture was cooled to ambient temperature and was then diluted with DCM and water. The mixture was filtered through a hydrophobic frit and was then purified via column chromatography to afford 2,2-difluoro-N-((trans)-1-(1-(2-fluorobenzyl)-1H-indazol-5-yl)-2-(4-fluorophenyl)-5-oxopyrrolidin-3-yl) propanamide (86.8 mg, 97%).

$^1$H NMR (DMSO-d$_6$) δ: 9.43 (d, 1H), 8.04 (d, 1H), 7.74 (d, 1H), 7.62 (d, 1H), 7.49 (dd, 1H), 7.42-7.37 (m, 2H), 7.36-7.29 (m, 1H), 7.21-7.15 (m, 1H), 7.15-7.06 (m, 4H), 5.63 (s, 2H), 5.28 (d, 1H), 4.34-4.22 (m, 1H), 3.07 (dd, 1H), 2.64 (dd, 1H), 1.78 (t, 3H).

EXAMPLE 86

2,2-difluoro-N-((trans)-1-(1-(4-fluorobenzyl)-1H-indazol-5-yl)-2-(4-fluorophenyl)-5-oxopyrrolidin-3-yl)propanamide

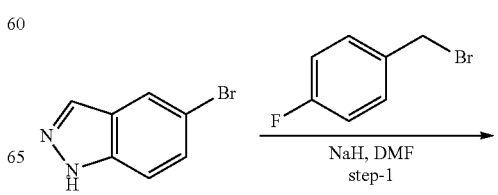

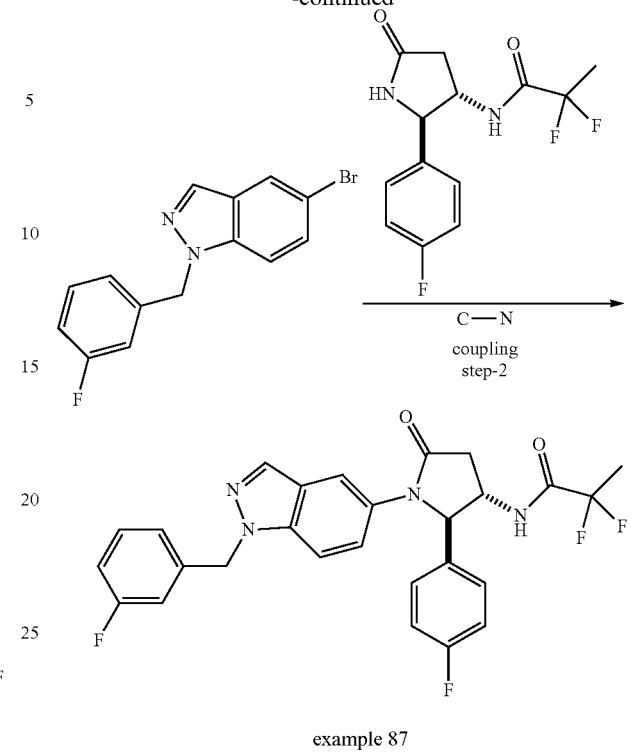

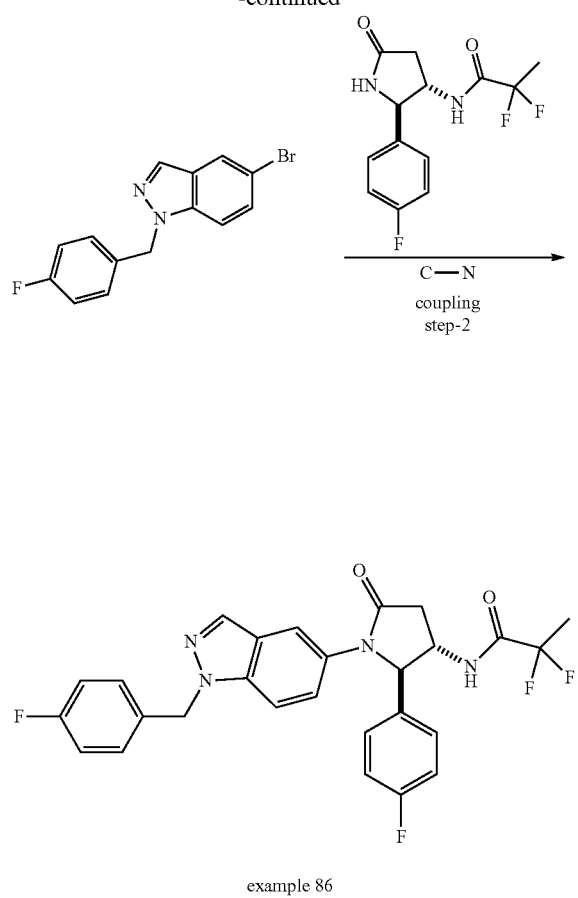

example 86

Example 86 was synthesized in analogy to the synthetic procedure described for example 85, substituting 1-(bromomethyl)-2-fluoro-benzene for 1-(bromomethyl)-4-fluorobenzene in step 1 (yield 56.4%) and 5-bromo-1-(2-fluorobenzyl)-1H-indazole for 5-bromo-1-(4-fluorobenzyl)-1H-indazole in step 2. Example 86 was obtained in 41% yield (36.6 mg).

$^1$H NMR (DMSO-d$_6$) δ: 9.42 (d, 1H), 8.04 (d, 1H), 7.72 (d, 1H), 7.63 (d, 1H), 7.46 (dd, 1H), 7.42-7.36 (m, 2H), 7.28-7.24 (m, 2H), 7.14-7.09 (m, 4H), 5.57 (s, 2H), 5.27 (d, 1H), 4.34-4.22 (m, 1H), 3.07 (dd, 1H), 2.63 (dd, 1H), 1.78 (t, 3H)

EXAMPLE 87

2,2-difluoro-N-((trans)-1-(1-(3-fluorobenzyl)-1H-indazol-5-yl)-2-(4-fluorophenyl)-5-oxopyrrolidin-3-yl)propanamide

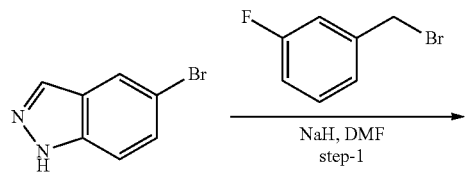

example 87

Example 87 was synthesized in analogy to the synthetic procedure described for example 85, substituting 1-(bromomethyl)-2-fluoro-benzene for 1-(bromomethyl)-3-fluorobenzene in step 1 (yield 67%) and 5-bromo-1-(2-fluorobenzyl)-1H-indazole for 5-bromo-1-(3-fluorobenzyl)-1H-indazole in step 2 and requiring additional purification of the final compound via HPLC. Example 87 was obtained in 43% yield (38.0 mg).

$^1$H NMR (DMSO-d$_6$) δ: 9.42 (d, 1H), 8.06 (d, 1H), 7.74 (d, 1H), 7.63 (d, 1H), 7.47 (dd, 1H), 7.40-7.37 (m, 2H), 7.35-7.30 (m, 1H), 7.14-7.10 (m, 2H), 7.09-7.05 (m, 1H), 7.03 6.99 (m, 2H), 5.61 (s, 2H), 5.27 (d, 1H), 4.33-4.23 (m, 1H), 3.07 (dd, 1H), 2.63 (dd, 1H), 1.78 (t, 3H)

EXAMPLE 89

N-(trans-1-(1-(4-fluorophenyl)-1H-indazol-5-yl)-5-oxo-2-ethylpyrrolidin-3-yl)-2,2-difluoropropanamide

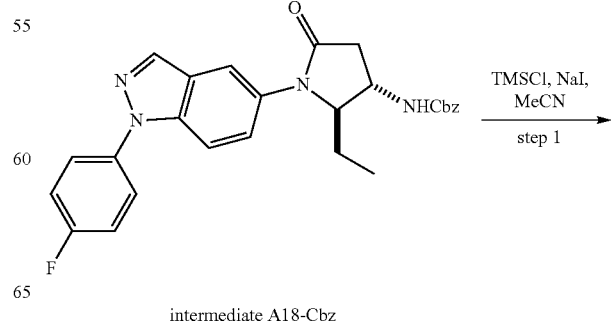

intermediate A18-Cbz

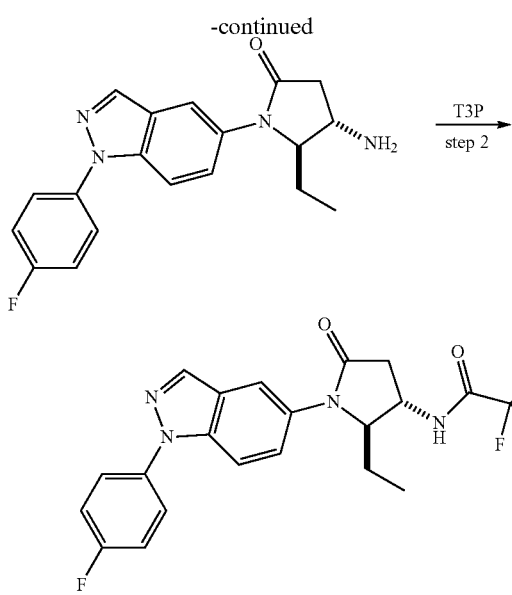

example 89

Step 1: Sodium iodide (304.5 mg, 2.032 mmol, 6.0 eq.) was weighed out into a microwave vial, a stir bar was added, the vial was sealed and sparged with nitrogen. Then trans-{1-[1-(4-Fluoro-phenyl)-1H-indazol-5-yl]-5-oxo-2-ethyl-pyrrolidin-3-yl}-carbamic acid benzyl ester (160.0 mg, 0.339 mmol, 1.0 eq.) in acetonitrile (8.0 mL) was added, followed by the addition of TMSCl (0.17 mL, 1.354 mmol, 4.0 eq.), and the resulting mixture was stirred at ambient temperature for 16 hours. Then ethanol (9.6 mL) was added and the resulting mixture was purified using a cationic exchange resin to obtain 170 mg of crude N-trans-(1-(1-(4-fluorophenyl)-1H-indazol-5-yl)-5-oxo-2-ethylpyrrolidin-3-yl)amine.

Step 2: 2,2-Difluoropropanoic acid (39.0 mg, 0.355 mmol, 1.5 eq.) was weighed out into a vial, a stir bar was added, the vial was sealed and purged with nitrogen. Then DCM (2.3 mL) was added, followed by the addition of T3P (≥50 wt. % in ethyl acetate, 0.28 mL, 2.0 eq.) and triethylamine (0.13 mL, 0.946 mmol, 4.0 eq.). The resulting reaction mixture was stirred for 10 minutes at ambient temperature. Then N-trans-(1-(1-(4-fluorophenyl)-1H-indazol-5-yl)-5-oxo-2-ethylpyrrolidin-3-yl)amine (80 mg of the 170 mg obtained in step 1) in DCM (2.3 mL) was added, and the reaction mixture was stirred at ambient temperature for 10 minutes. Then, sat. NaHCO₃ solution and more DCM was added, and the mixture was filtered through a hydrophobic frit. The organic layers was then evaporated under reduced pressure and the obtained crude material was purified via silica gel chromatography to obtain 45.0 mg of N-(trans-1-(1-(4-fluorophenyl)-1H-indazol-5-yl)-5-oxo-2-ethylpyrrolidin-3-yl)-2,2-difluoropropanamide.

$^1$H NMR (DMSO-$d_6$) δ: 9.33 (d, 1H), 8.39 (s, 1H), 7.92 (s, 1H), 7.86-7.77 (m, 3H), 7.59 (dd, 1H), 7.44 (t, 2H), 4.37-4.28 (m, 1H), 4.15 (dd, 1H), 3.01 (dd, 1H), 2.52-2.44 (m, 1H), 1.80 (t, 3H), 1.66-1.54 (m, 1H), 1.55-1.42 (m, 1H), 0.83 (t, 3H)

EXAMPLE 100

N-trans-(1-(1-(4-fluorophenyl)-1H-indazol-5-yl)-5-oxo-2-(5-chlorothiophen-2-yl)pyrrolidin-3-yl)cyclopropanesulfonamide

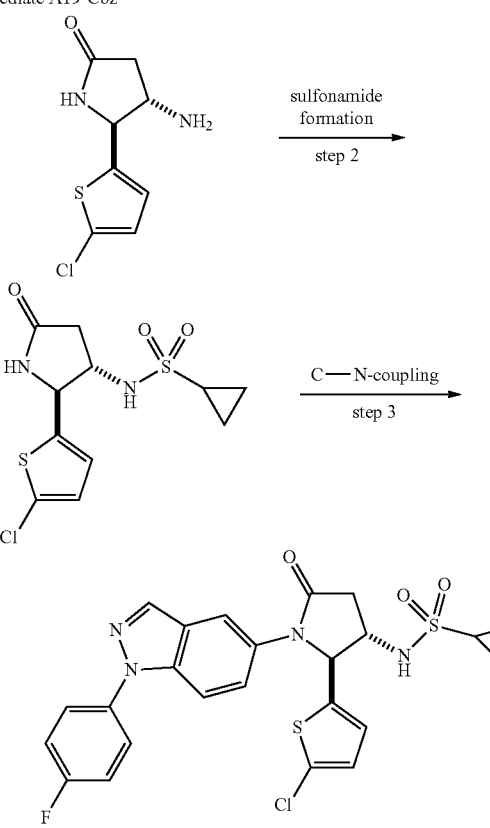

example 100

Step 1: A solution of benzyl (trans-2-(5-chlorothiophen-2-yl)-5-oxopyrrolidin-3-yl)carbamate (1.7 g, 4.845 mmol, 1.0 eq) in TFA (15 ml) was refluxed for 16 hours. After completion of the reaction (monitored by TLC, 5% of Methanol in DCM, Rf=0.1), the TFA was evaporated under reduced pressure and the obtained residue was dissolved in 10% DCM in MeOH (150 ml) and was washed with saturated aqueous NaHCO₃ (2×75 ml) and brine (50 ml). The organic layer was then dried over Na₂SO₄ and was concentrated under reduced pressure to obtain the crude product which was purified by column chromatography (230-400 mesh silica gel; 3-5% MeOH in DCM) to afford trans-4-amino-5-(5-chlorothiophen-2-yl)pyrrolidin-2-one (0.75 g, 71%) as a gummy liquid.

Step 2: To a stirred solution of trans-4-amino-5-(5-chlorothiophen-2-yl)pyrrolidin-2-one (220 mg, 1.015 mmol, 1.0 eq) in DCM (15 ml), DIPEA (0.3 ml, 1.522 mmol, 1.5 eq) and cyclopropane sulfonyl chloride (214 mg, 1.522 mmol, 1.5 eq) were added at 0° C. and the reaction was then stirred at ambient temperature for 16 hours. After completion of the reaction (monitored by TLC, TLC system 5% methanol in DCM, Rf-0.3), the solvent was removed under reduced pressure to obtain a residue, which was diluted with DCM (100 mL), washed with sodium bicarbonate solution (3×50 mL), dried over $Na_2SO_4$ and concentrated to obtain a residue. This residue was purified by column chromatography (230-400 mesh silica gel; 2 to 4% MeOH-DCM;) to afford N-(trans-2-(5-chlorothiophen-2-yl)-5-oxopyrrolidin-3-yl)cyclopropanesulfonamide (300 mg, 92%).

Step 3: A stirred solution of N-(trans-2-(5-chlorothiophen-2-yl)-5-oxopyrrolidin-3-yl)cyclopropanesulfonamide (150 mg, 0.467 mmol, 1.0 eq), 1-(4-fluorophenyl)-5-iodo-1H-indazole (205 mg, 0.607 mmol, 1.3 eq) and $K_3PO_4$ (198 mg, 0.935 mmol, 2.0 eq) in 1,4-dioxane (25 ml) was degassed with argon for 30 min. Then, trans-N,N'-dimethylcyclohexane-1,2-diamine (26.6 mg, 0.187 mmol, 0.4 eq) and CuI (17.8 mg, 0.0935 mmol, 0.2 eq) were added and the reaction was stirred for 16 hours at 90° C. in a sealed tube. After completion of the reaction (monitored by TLC, TLC system 5% methanol in DCM, Rf-0.4), the reaction mixture was concentrated under reduced pressure, diluted with ethyl acetate (100 mL), washed with water (2×75 mL), dried over $Na_2SO_4$ and concentrated under reduced pressure to get the crude product which was purified by HP LC to afford N-trans-(1-(1-(4-fluorophenyl)-1H-indazol-5-yl)-5-oxo-2-(5-chlorothiophen-2-yl)pyrrolidin-3-yl)cyclopropanesulfonamide_(47.5 mg, 17%).

$^1$H NMR (400 MHz, DMSO-$d_6$): δ 8.36 (s, 1H), 8.02 (d, 1H), 7.86 (bs, 1H), 7.79-7.74 (m, 3H), 7.56-7.53 (m, 1H), 7.43-7.39 (m, 2H), 7.03 (d, 1H), 6.93 (d, 1H), 5.48 (d, 1H), 4.07-4.05 (m, 1H), 3.20-3.14 (m, 1H), 2.67-2.58 (m, 2H), 0.99-0.85 (m, 4H).

EXAMPLE 101

N-(trans-2-phenyl-1-(1-(4-fluorophenyl)-1H-pyrazolo[3,4-b]pyridin-5-yl)-5-oxopyrrolidin-3-yl)-2,2-difluoropropanamide

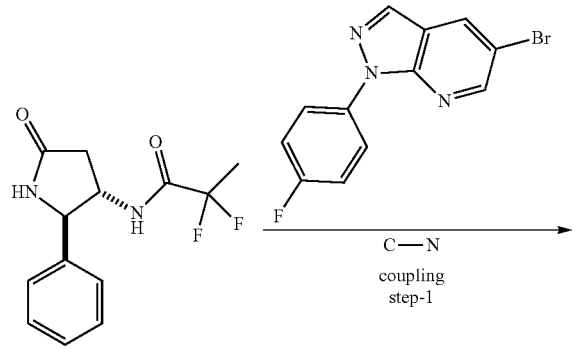

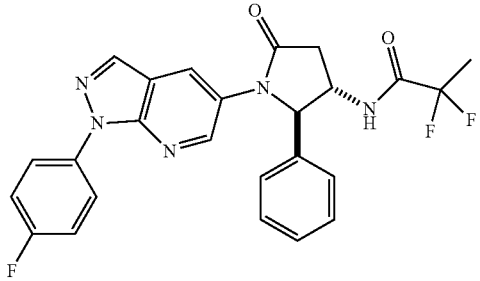

example 101

Step 1: Example 101 was prepared in analogy to example 102 using 5-bromo-1-(4-fluorophenyl)-1H-pyrazolo[3,4-b]pyridine instead of 5-bromo-1-(4-fluorophenyl)pyrazolo[3,4-c]pyridine. Yield: 46%.

$^1$H NMR (DMSO-$d_6$) δ: 9.48 (d, 1H), 8.75 (d, 1H), 8.43-8.35 (m, 2H), 8.24-8.15 (m, 2H), 7.42-7.36 (m, 4H), 7.32 (dd, 2H), 7.25 (d, 1H), 5.38 (d, 1H), 4.38 (tt, 1H), 3.15 (dd, 1H), 2.68 (dd, 1H), 1.79 (t, 3H).

EXAMPLE 102

N-(trans-2-phenyl-1-(1-(4-fluorophenyl)-1H-pyrazolo[3,4-c]pyridin-5-yl)-5-oxopyrrolidin-3-yl)-2,2-difluoropropanamide

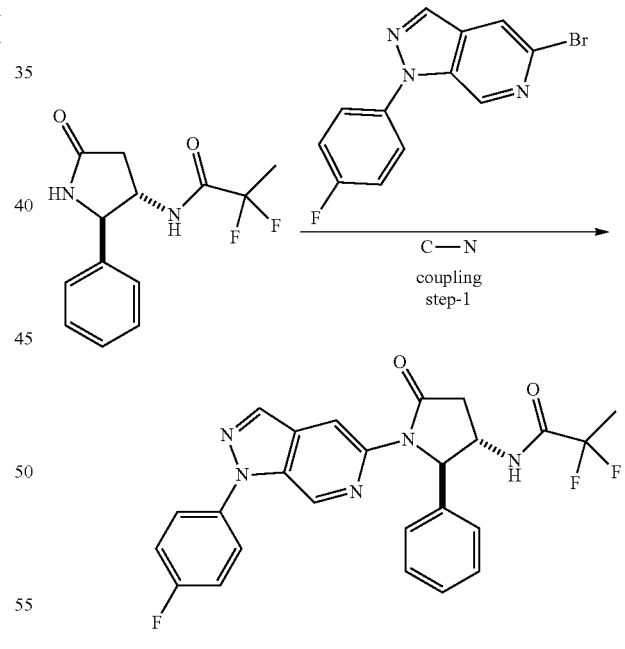

example 102

Step 1: 5-bromo-1-(4-fluorophenyl)pyrazolo[3,4-c]pyridine (65.3 mg, 0.224 mmol, 1.2 eq.), sodium iodide (55.9 mg, 0.373 mmol, 2.0 eq.), copper iodide (7.1 mg, 0.037 mmol, 0.2 eq.), trans-2,2-difluoro-N-(5-oxo-2-phenylpyrrolidin-3-yl)propanamide (50.0 mg, 0.186 mmol, 1.0 eq.) and potassium phosphate (79.1 mg, 0.373 mmol, 2.0 eq.) were weighed out into a vial, a stir bar was added, the vial was sealed and was purged with nitrogen. 1,4-Dioxane (1.0 mL) and trans-N,N'-dimethylcyclohexane-1,2-diamine (0.012 mL, 0.075 mmol, 0.4 eq.) were then added, and the mixture was heated to 110° C. for 16 hours. The mixture was cooled to ambient temperature and was diluted with DCM and water. The mixture was then filtered through a hydrophobic frit and the solvent was removed. The crude compound was then purified via MPLC and HPLC to yield 13.3 mg (15%) of example 102.

$^1$H NMR (DMSO-d$_6$) δ: 9.57 (d, 1H), 8.97 (d, 1H), 8.72 (d, 1H), 8.56 (d, 1H), 7.89-7.79 (m, 2H), 7.42-7.36 (m, 2H), 7.33-7.29 (m, 4H), 7.22 (td, 1H), 5.78 (d, 1H), 4.24 (t, 1H), 3.16 (dd, 1H), 2.69 (dd, 1H), 1.80 (t, 3H).

EXAMPLE 103

N-(trans-2-phenyl-1-(1-(4-fluorophenyl)-1H-pyrazolo[4,3-b]pyridin-5-yl)-5-oxopyrrolidin-3-yl)-2,2-difluoropropanamide

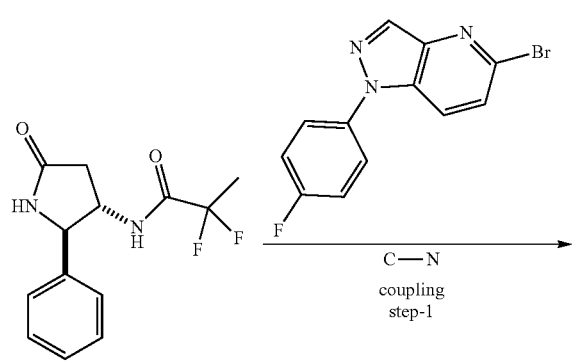

example 103

Step 1: Example 103 was prepared in analogy to example 102, using 5-bromo-1-(4-fluorophenyl)-1H-pyrazolo[4,3-b]pyridine instead of 5-bromo-1-(4-fluorophenyl)pyrazolo[3,4-c]pyridine. Yield: 61%.

$^1$H NMR (DMSO-d$_6$) δ: 9.59 (d, 1H), 8.54 (d, 1H), 8.39-8.31 (m, 2H), 7.84-7.75 (m, 2H), 7.43 (dd, 2H), 7.36-7.29 (m, 4H), 7.27-7.20 (m, 1H), 5.78 (d, 1H), 4.26 (ddd, 1H), 3.19 (dd, 1H), 2.68 (dd, 1H), 1.80 (t, 3H).

The examples in Table 2 were synthesized in analogy to Example 1 described above, using the appropriate carboxylic acid, acid chloride or sulfonyl chloride.

| Ex. # | Intermediate (INT) | Structure | Yield (%) | $^1$H NMR |
|---|---|---|---|---|
| 3 | INT D2 | 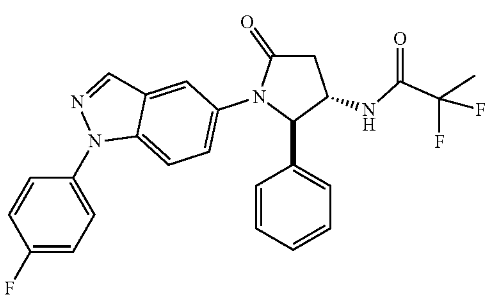 [SMILES: CC(F)(F)C(=O)N[C@H]1CC(=O)N(c2ccc3c(cnn3-c3ccc(F)cc3)c2)[C@@H]1c1ccccc1] | 35 | $^1$H NMR (DMSO-d$_6$) δ: 9.48 (d, 1H), 8.30 (d, 1H), 7.88 (d, 1H), 7.76-7.72 (m, 2H), 7.71 (d, 1H), 7.64 (dd, 1H), 7.42-7.34 (m, 4H), 7.32 (t, 2H), 7.26-7.22 (m, 1H), 5.32 (d, 1H), 4.34-4.25 (m, 1H), 3.11 (dd, 1H), 2.64 (dd, 1H), 1.79 (t, 3H) |
| 7 | INT D3 | 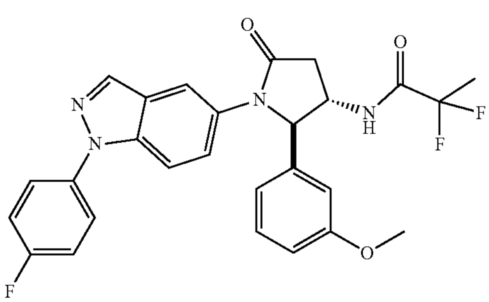 [SMILES: COc1cccc([C@@H]2[C@@H](NC(=O)C(C)(F)F)CC(=O)N2c2ccc3c(cnn3-c3ccc(F)cc3)c2)c1] | 28 | $^1$H NMR (DMSO-d$_6$) δ: 9.47 (d, 1H), 8.31 (d, 1H), 7.91-7.86 (m, 1H), 7.77-7.73 (m, 2H), 7.73-7.71 (m, 1H), 7.67-7.64 (m, 1H), 7.40 (tt, 2H), 7.23 (tt, 1H), 6.91 (dt, 2H), 6.82-6.79 (m, 1H), 5.30 (d, 1H), 4.33-4.26 (m, 1H), 3.70 (d, 3H), 3.11 (dd, 1H), 2.64 (dd, 1H), 1.79 (t, 3H) |

-continued

| Ex. # | Intermediate (INT) | Structure | Yield (%) | ¹H NMR |
|---|---|---|---|---|
| 8 | INT D2 | 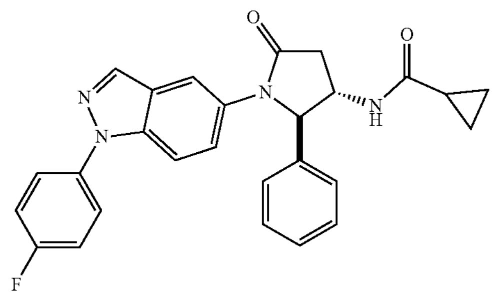 [SMILES: O=C(N[C@H]1CC(=O)N(c2ccc3c(cnn3-c3ccc(F)cc3)c2)[C@@H]1c1ccccc1)C1CC1] | 39 | ¹H NMR (DMSO-d$_6$) δ: 8.90 (d, 1H), 8.31 (s, 1H), 7.91 (s, 1H), 7.77-7.68 (m, 4H), 7.43-7.35 (m, 4H), 7.33 (t, 2H), 7.24 (td, 1H), 5.27 (d, 1H), 4.21-4.11 (m, 1H), 3.07 (ddd, 1H), 2.47 (dd, 1H), 1.65-1.57 (m, 1H), 0.80-0.67 (m, 4H) |
| 11 | INT D4 | 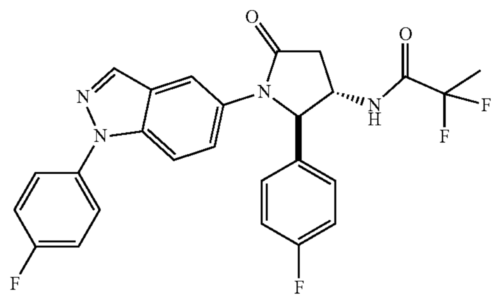 [SMILES: CC(F)(F)C(=O)N[C@H]1CC(=O)N(c2ccc3c(cnn3-c3ccc(F)cc3)c2)[C@@H]1c1ccc(F)cc1] | 78 | ¹H NMR (DMSO-d$_6$) δ: 9.46 (d, 1H), 8.31 (s, 1H), 7.87 (d, 1H), 7.77-7.72 (m, 2H), 7.71 (d, 1H), 7.61 (dd, 1H), 7.45-7.36 (m, 4H), 7.14 (t, 2H), 5.33 (d, 1H), 4.35-4.27 (m, 1H), 3.11 (dd, 1H), 2.66 (dd, 1H), 1.79 (t, 3H) |
| 14 | INT D5 | 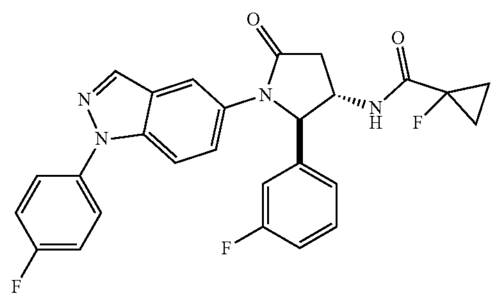 [SMILES: O=C1C[C@H](NC(=O)C2(F)CC2)[C@@H](c2cccc(F)c2)N1c1ccc2c(cnn2-c2ccc(F)cc2)c1] | 98 | ¹H NMR (DMSO-d$_6$) δ: 9.21-9.13 (m, 1H), 8.31 (d, 1H), 7.88 (dd, 1H), 7.76-7.73 (m, 2H), 7.73-7.68 (m, 1H), 7.68-7.56 (m, 1H), 7.42-7.37 (m, 2H), 7.34 (td, 1H), 7.28-7.13 (m, 2H), 7.13-6.99 (m, 1H), 5.38 (d, 1H), 4.43-4.32 (m, 1H), 3.09 (dd, 1H), 2.69 (dd, 1H), 1.37-1.30 (m, 2H), 1.30-1.13 (m, 2H) |
| 15 | INT D5 | 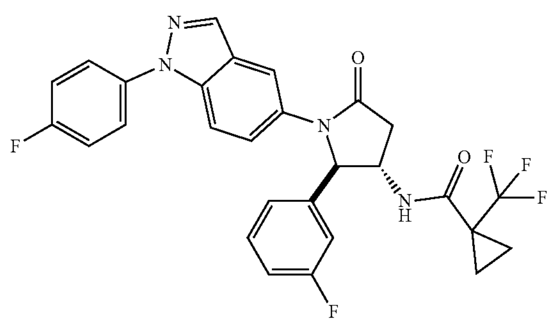 [SMILES: O=C1C[C@H](NC(=O)C2(C(F)(F)F)CC2)[C@@H](c2cccc(F)c2)N1c1ccc2c(cnn2-c2ccc(F)cc2)c1] | 50 | ¹H NMR (DMSO-d$_6$) δ: 8.50 (d, 1H), 8.30 (d, 1H), 7.86 (d, 1H), 7.76-7.69 (m, 3H), 7.61 (dd, 1H), 7.41-7.37 (m, 2H), 7.36-7.28 (m, 1H), 7.23-7.14 (m, 2H), 7.08-6.99 (m, 1H), 5.27 (d, 1H), 4.38-4.19 (m, 1H), 3.06 (dd, 1H), 2.63-2.55 (m, 1H), 1.42-1.31 (m, 2H), 1.32-1.22 (m, 2H) |
| 17 | INT D3 | 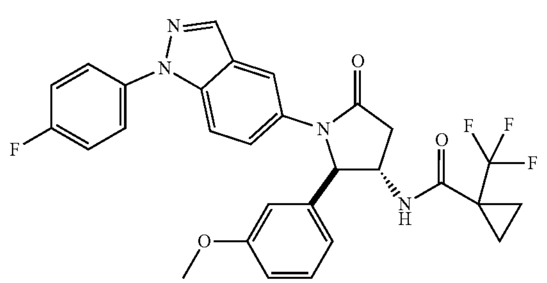 [SMILES: COc1cccc([C@@H]2[C@@H](NC(=O)C3(C(F)(F)F)CC3)CC(=O)N2c2ccc3c(cnn3-c3ccc(F)cc3)c2)c1] | 57 | ¹H NMR (DMSO-d$_6$) δ: 8.48 (d, 1H), 8.31 (s, 1H), 7.88 (s, 1H), 7.78-7.73 (m, 2H), 7.72 (d, 1H), 7.64 (d, 1H), 7.40 (t, 2H), 7.23 (t, 1H), 6.92-6.87 (m, 2H), 6.79 (d, 1H), 5.23 (d, 1H), 4.30-4.21 (m, 1H), 3.70 (s, 3H), 3.05 (dd, 1H), 2.56 (dd, 1H), 1.49-1.36 (m, 2H), 1.34-1.19 (m, 2H) |

-continued

| Ex. # | Intermediate (INT) | Structure | Yield (%) | ¹H NMR |
|---|---|---|---|---|
| 19 | INT D5 | 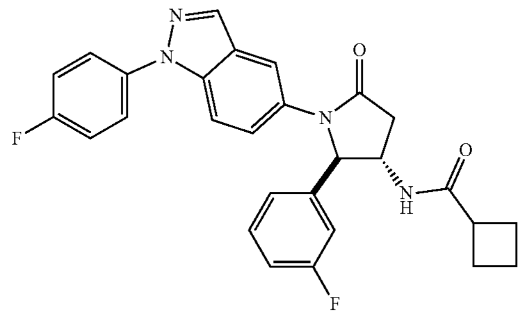 [SMILES: O=C(N[C@H]1CC(=O)N(c2ccc3c(cnn3-c3ccc(F)cc3)c2)[C@@H]1c1cccc(F)c1)C1CCC1] | 100 | ¹H NMR (DMSO-d$_6$) δ: 8.45 (d, 1H), 8.31 (d, 1H), 7.91 (d, 1H), 7.79-7.64 (m, 4H), 7.43-7.33 (m, 3H), 7.21 (dd, 2H), 7.10-7.03 (m, 1H), 5.27 (d, 1H), 4.20-4.13 (m, 1H), 3.12-3.02 (m, 2H), 2.47 (dd, 1H), 2.22-2.11 (m, 2H), 2.07-2.02 (m, 2H), 1.95-1.87 (m, 1H), 1.83-1.75 (m, 1H) |
| 23 | INT D3 | 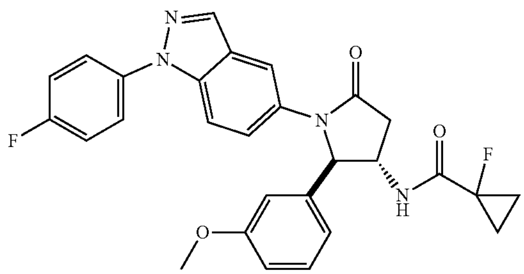 [SMILES: COc1cccc([C@@H]2[C@@H](NC(=O)C3(F)CC3)CC(=O)N2c2ccc3c(cnn3-c3ccc(F)cc3)c2)c1] | 100 | ¹H NMR (DMSO-d$_6$) δ: 9.15 (d, 1H), 8.25 (s, 1H), 7.86 (d, 1H), 7.73-7.69 (m, 2H), 7.68-7.61 (m, 2H), 7.34 (t, 2H), 7.19 (t, 1H), 6.94-6.88 (m, 2H), 6.76 (dd, 1H), 5.33 (d, 1H), 4.41-4.33 (m, 1H), 3.06 (dd, 1H), 2.66 (dd, 1H), 1.33-1.26 (m, 2H), 1.23-1.17 (m, 2H) |
| 31 | INT D6 | 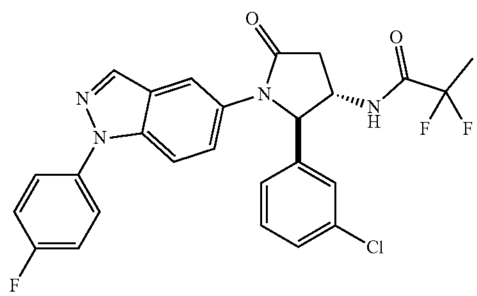 [SMILES: CC(F)(F)C(=O)N[C@H]1CC(=O)N(c2ccc3c(cnn3-c3ccc(F)cc3)c2)[C@@H]1c1cccc(Cl)c1] | 42 | ¹H NMR (DMSO-d$_6$) δ: 8.32 (d, 1H), 7.93-7.86 (m, 1H), 7.80-7.69 (m, 3H), 7.66-7.63 (m, 1H), 7.47-7.46 (m, 1H), 7.40 (t, 2H), 7.37-7.27 (m, 4H), 5.35 (d, 1H), 4.36-4.28 (m, 1H), 3.13 (dd, 1H), 2.67 (dd, 1H), 1.80 (t, 3H) |
| 32 | INT D6 | 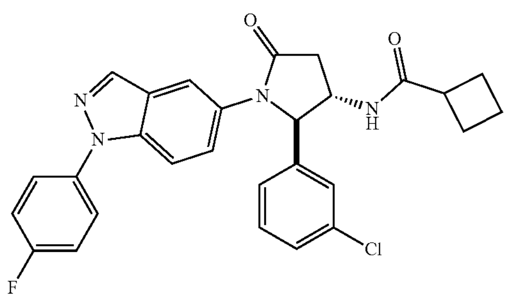 [SMILES: O=C(N[C@H]1CC(=O)N(c2ccc3c(cnn3-c3ccc(F)cc3)c2)[C@@H]1c1cccc(Cl)c1)C1CCC1] | 69 | ¹H NMR (DMSO-d$_6$) δ: 8.45 (d, 1H), 8.31 (d, 1H), 7.91 (d, 1H), 7.78-7.70 (m, 3H), 7.67 (dd, 1H), 7.46 (d, 1H), 7.45-7.35 (m, 2H), 7.34 (d, 1H), 7.33-7.27 (m, 2H), 5.26 (d, 1H), 4.18-4.14 (m, 1H), 3.11-3.02 (m, 2H), 2.48 (dd, 1H), 2.23-2.11 (m, 2H), 2.11-2.02 (m, 2H), 1.96-1.87 (m, 1H), 1.83-1.74 (m, 1H) |
| 36 | INT D7 | 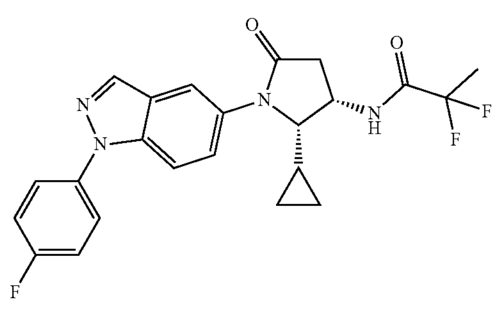 [SMILES: CC(F)(F)C(=O)N[C@H]1CC(=O)N(c2ccc3c(cnn3-c3ccc(F)cc3)c2)[C@H]1C1CC1] | 74 | ¹H NMR (DMSO-d$_6$) δ: 9.19 (d, 1H), 8.38 (d, 1H), 7.86 (d, 1H), 7.84-7.75 (m, 3H), 7.49 (dd, 1H), 7.44 (t, 2H), 4.82 (p, 1H), 3.63 (dd, 1H), 2.84-2.70 (m, 2H), 1.80 (t, 3H), 0.92-0.80 (m, 1H), 0.38-0.24 (m, 1H), 0.22-0.15 (m, 1H), 0.02--0.07 (m, 1H), −0.24 (dt, 1H) |

-continued

| Ex. # | Intermediate (INT) | Structure | Yield (%) | ¹H NMR |
|---|---|---|---|---|
| 45 | INT D4 | | 84 | ¹H NMR (DMSO-d$_6$) δ: 8.94 (dd, 1H), 8.30 (dd, 1H), 7.88 (dd, 1H), 7.76-7.72 (m, 2H), 7.72-7.70 (m, 1H), 7.63 (ddd, 1H), 7.43-7.37 (m, 4H), 7.14 (td, 2H), 5.26 (dd, 1H), 4.98-4.70 (m, 1H), 4.22-4.16 (m, 1H), 3.18-3.00 (m, 1H), 2.61-2.41 (m, 1H), 1.98-1.70 (m, 1H), 1.62-1.54 (m, 1H), 1.11-0.99 (m, 1H) |
| 46 | INT D3 | 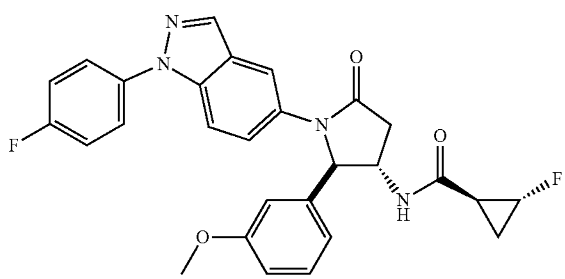 [SMILES: COc1cccc([C@@H]2[C@@H](NC(=O)[C@@H]3C[C@H]3F)CC(=O)N2c2ccc3c(cnn3-c3ccc(F)cc3)c2)c1] | 38 | ¹H NMR (DMSO-d$_6$) δ: 9.08 (d, 1H), 8.31 (d, 1H), 7.94-7.89 (m, 1H), 7.79-7.67 (m, 4H), 7.44-7.36 (m, 2H), 7.24 (t, 1H), 6.94-6.88 (m, 2H), 6.83-6.76 (m, 1H), 5.24 (d, 1H), 4.92-4.73 (m, 1H), 4.21-4.11 (m, 1H), 3.70 (s, 3H), 3.09 (dd, 1H), 2.48 (dd, 1H), 2.17-2.10 (m, 1H), 1.47-1.37 (m, 1H), 1.22-1.15 (m, 1H) |
| 48 | INT D7 | 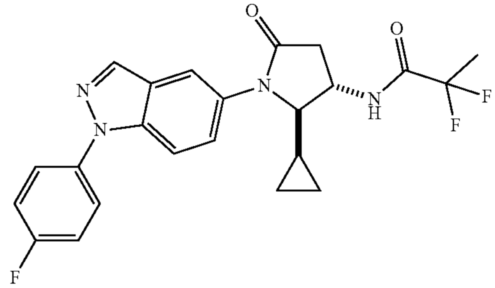 [SMILES: CC(F)(F)C(=O)N[C@H]1CC(=O)N(c2ccc3c(cnn3-c3ccc(F)cc3)c2)[C@@H]1C1CC1] | 61 | ¹H NMR (DMSO-d$_6$) δ: 9.26 (d, 1H), 8.40 (d, 1H), 7.88 (dd, 1H), 7.88-7.78 (m, 3H), 7.50 (dd, 1H), 7.45 (t, 2H), 4.43-4.14 (m, 1H), 3.46 (dd, 1H), 3.03 (dd, 1H), 2.47 (dd, 1H), 1.80 (t, 3H), 1.11-0.94 (m, 1H), 0.40-0.34 (m, 1H), 0.31-0.18 (m, 2H), −0.01--0.09 (m, 1H) |
| 52 | INT D5 | 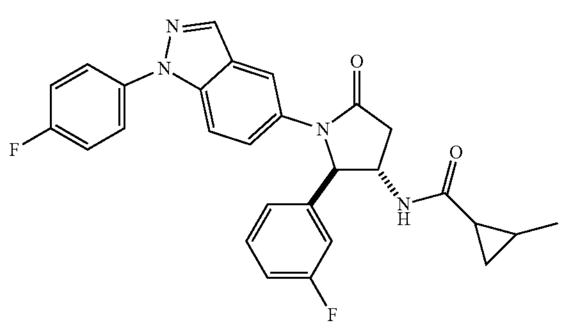 [SMILES: CC1CC1C(=O)N[C@H]1CC(=O)N(c2ccc3c(cnn3-c3ccc(F)cc3)c2)[C@@H]1c1cccc(F)c1] | 80 | ¹H NMR (DMSO-d$_6$) δ: 8.82 (t, 1H), 8.31 (d, 1H), 7.93 (d, 1H), 7.80-7.65 (m, 4H), 7.43-7.31 (m, 3H), 7.25-7.17 (m, 2H), 7.11-7.03 (m, 1H), 5.39-5.17 (m, 1H), 4.28-4.01 (m, 1H), 3.10 (dd, 1H), 2.49-2.43 (m, 1H), 1.38-1.31 (m, 1H), 1.26-1.11 (m, 3H), 1.09-1.03 (m, 3H), 0.99-0.90 (m, 1H), 0.60-0.52 (m, 1H) |

-continued
| Ex. # | Intermediate (INT) | Structure | Yield (%) | ¹H NMR |
|---|---|---|---|---|
| 54 | INT D4 | 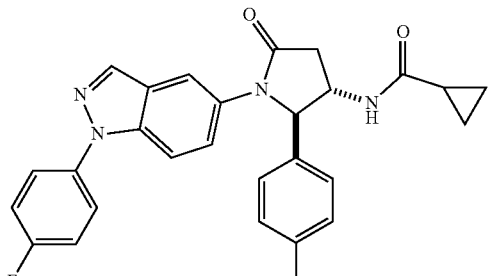 | 71 | ¹H NMR (DMSO-d₆) δ: 8.88 (d, 1H), 8.31 (s, 1H), 7.90 (d, 1H), 7.79-7.69 (m, 3H), 7.67 (dd, 1H), 7.44-7.36 (m, 4H), 7.14 (t, 2H), 5.27 (d, 1H), 4.20-4.13 (m, 1H), 3.08 (dd, 1H), 2.51-2.44 (m, 1H), 1.65-1.57 (m, 1H), 0.79-0.68 (m, 4H) |
| 55 | INT D3 | 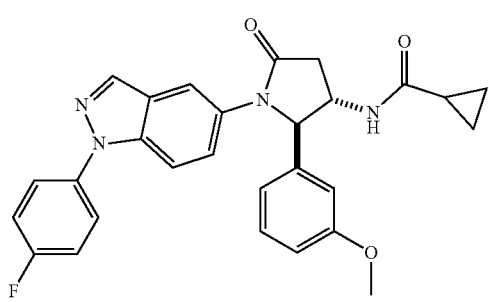 [SMILES: COc1cccc([C@@H]2[C@@H](NC(=O)C3CC3)CC(=O)N2c2ccc3c(cnn3-c3ccc(F)cc3)c2)c1] | 84 | ¹H NMR (DMSO-d₆) δ: 8.88 (d, 1H), 8.31 (s, 1H), 7.95-7.89 (m, 1H), 7.78-7.69 (m, 4H), 7.44-7.36 (m, 2H), 7.29-7.20 (m, 1H), 6.94-6.89 (m, 2H), 6.82-6.80 (m, 1H), 5.24 (d, 1H), 4.19-4.13 (m, 1H), 3.70 (d, 3H), 3.07 (dd, 1H), 2.46 (dd, 1H), 1.67-1.57 (m, 1H), 0.80-0.68 (m, 4H) |
| 56 | INT D4 | 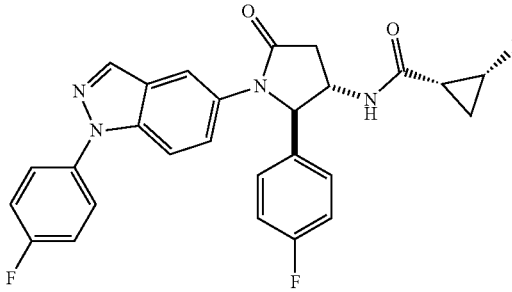 | 89 | ¹H NMR (DMSO-d₆) δ: 8.94 (dd, 1H), 8.31 (dd, 1H), 7.87 (dd, 1H), 7.76-7.70 (m, 3H), 7.63 (ddd, 1H), 7.46-7.30 (m, 4H), 7.14 (td, 2H), 5.26 (dd, 1H), 4.84 (dtd, 1H), 4.22-4.16 (m, 1H), 3.12-3.06 (m, 1H), 2.48 (t, 1H), 1.87-1.80 (m, 1H), 1.62-1.53 (m, 1H), 1.10-1.04 (m, 1H) |
| 61 | INT D5 | 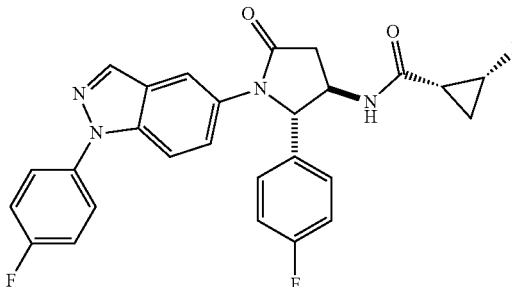 | 72 | ¹H NMR (DMSO-d₆) δ: 8.90 (d, 1H), 8.30 (s, 1H), 7.91 (d, 1H), 7.78-7.65 (m, 4H), 7.43-7.29 (m, 3H), 7.25-7.17 (m, 2H), 7.09-7.02 (m, 1H), 5.29 (d, 1H), 4.22-4.16 (m, 1H), 3.10 (dd, 1H), 2.53-2.46 (m, 1H), 1.66-1.56 (m, 1H), 0.80-0.66 (m, 4H) |

-continued

| Ex. # | Intermediate (INT) | Structure | Yield (%) | ¹H NMR |
|---|---|---|---|---|
| 63 | INT D3 | | 53 | ¹H NMR (DMSO-d₆) δ: 8.94 (dd, 1H), 8.32 (dd, 1H), 7.91 (dd, 1H), 7.77-7.63 (m, 4H), 7.43-7.38 (m, 2H), 7.24 (t, 1H), 6.93-6.87 (m, 2H), 6.81 (ddd, 1H), 5.24 (dd, 1H), 4.93-4.74 (m, 1H), 4.25-4.10 (m, 1H), 3.70 (s, 3H), 3.11-3.05 (m, 1H), 2.47 (dt, 1H), 1.87-1.80 (m, 1H), 1.63-1.54 (m, 1H), 1.11-1.03 (m, 1H) |
| 67 | INT D6 | 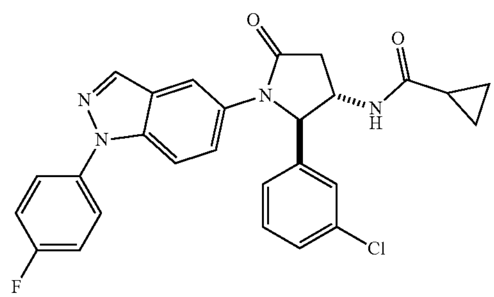 [SMILES: O=C(N[C@H]1CC(=O)N(c2ccc3c(cnn3-c3ccc(F)cc3)c2)[C@@H]1c1cccc(Cl)c1)C1CC1] | 59 | ¹H NMR (DMSO-d₆) δ: 8.90 (d, 1H), 8.32 (d, 1H), 7.92 (d, 1H), 7.79-7.71 (m, 3H), 7.72-7.67 (m, 1H), 7.45 (d, 1H), 7.44-7.36 (m, 2H), 7.38-7.32 (m, 1H), 7.33-7.28 (m, 2H), 5.28 (d, 1H), 4.21-4.14 (m, 1H), 3.10 (dd, 1H), 2.51-2.45 (m, 1H), 1.65-1.57 (m, 1H), 0.80-0.69 (m, 4H) |
| 68 | INT D5 | 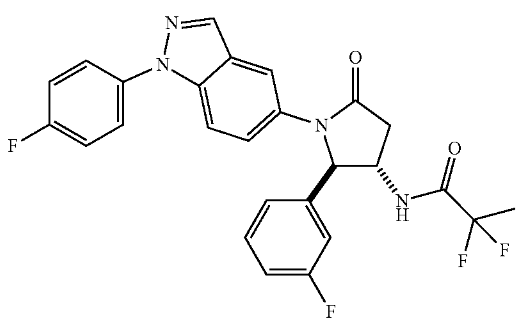 [SMILES: CC(F)(F)C(=O)N[C@H]1CC(=O)N(c2ccc3c(cnn3-c3ccc(F)cc3)c2)[C@@H]1c1cccc(F)c1] | 93 | ¹H NMR (DMSO-d₆) δ: 9.48 (d, 1H), 8.30 (d, 1H), 7.88 (d, 1H), 7.78-7.66 (m, 3H), 7.62 (dd, 1H), 7.44-7.27 (m, 3H), 7.26-7.16 (m, 2H), 7.05 (td, 1H), 5.35 (d, 1H), 4.38-4.29 (m, 1H), 3.12 (dd, 1H), 2.66 (ddd, 1H), 1.78 (t, 3H) |
| 70 | INT D4 | 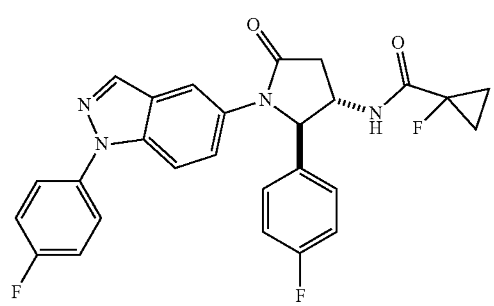 [SMILES: O=C1C[C@H](NC(=O)C2(F)CC2)[C@@H](c2ccc(F)cc2)N1c1ccc2c(cnn2-c2ccc(F)cc2)c1] | 82 | ¹H NMR (DMSO-d₆) δ: 9.15 (d, 1H), 8.31 (s, 1H), 7.86 (d, 1H), 7.77-7.73 (m, 2H), 7.71 (d, 1H), 7.62 (dd, 1H), 7.45-7.37 (m, 4H), 7.16-7.09 (m, 2H), 5.37 (d, 1H), 4.41-4.30 (m, 1H), 3.07 (dd, 1H), 2.69 (dd, 1H), 1.39-1.24 (m, 2H), 1.26-1.14 (m, 2H) |

| Ex. # | Intermediate (INT) | Structure | Yield (%) | ¹H NMR |
|---|---|---|---|---|
| 71 | INT D4 | 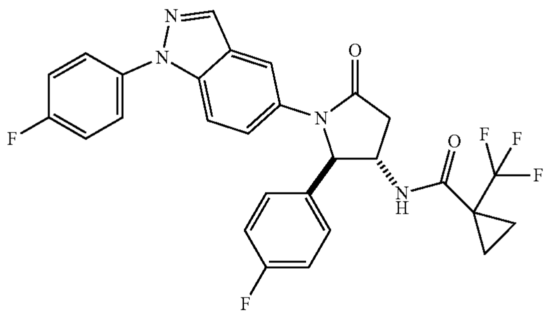 [SMILES: O=C1C[C@H](NC(=O)C2(C(F)(F)F)CC2)[C@@H](c2ccc(F)cc2)N1c1ccc2c(cnn2-c2ccc(F)cc2)c1] | 44 | ¹H NMR (DMSO-d$_6$) δ: 8.47 (d, 1H), 8.31 (d, 1H), 7.86 (d, 1H), 7.77-7.73 (m, 2H), 7.71 (d, 1H), 7.61 (dd, 1H), 7.43-7.36 (m, 4H), 7.13 (td, 2H), 5.25 (d, 1H), 4.30-4.22 (m, 1H), 3.05 (dd, 1H), 2.58 (dd, 1H), 1.40 (d, 2H), 1.30-1.22 (m, 2H) |
| 88 | INT D8 | 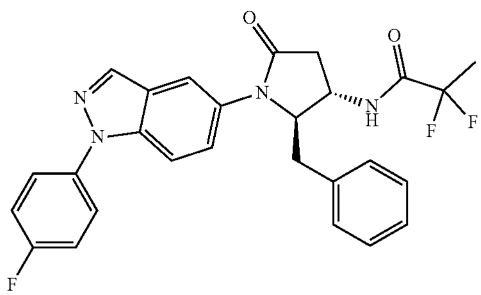 [SMILES: CC(F)(F)C(=O)N[C@H]1CC(=O)N(c2ccc3c(cnn3-c3ccc(F)cc3)c2)[C@@H]1Cc1ccccc1] | 46 | ¹H NMR (600 MHz, DMSO-d$_6$) 9.22 (d, 1H), 8.43 (d, 1H), 8.11-8.04 (m, 1H), 7.91-7.78 (m, 3H), 7.78-7.70 (m, 1H), 7.50-7.40 (m, 2H), 7.31-7.22 (m, 2H), 7.25-7.17 (m, 1H), 7.17-7.11 (m, 2H), 4.67-4.59 (m, 1H), 4.35-4.26 (m, 1H), 2.95-2.81 (m, 2H), 2.63-2.54 (m, 1H), 2.34-2.24 (m, 1H), 1.69 (t, J = 19.5 Hz, 3H). |
| 90 | INT D9 | 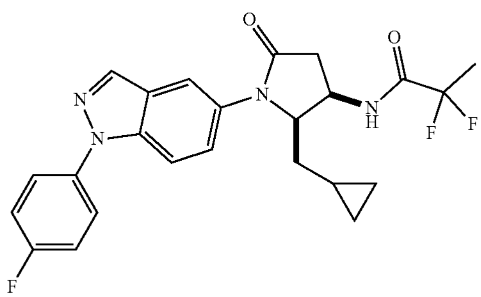 [SMILES: CC(F)(F)C(=O)N[C@@H]1CC(=O)N(c2ccc3c(cnn3-c3ccc(F)cc3)c2)[C@@H]1CC1CC1] | 46 | ¹H NMR (DMSO-d$_6$) δ: 9.25 (d, 1H), 8.38 (d, 1H), 7.90 (dd, 1H), 7.84-7.77 (m, 3H), 7.56 (dd, 1H), 7.46-7.40 (m, 2H), 4.90-4.76 (m, 1H), 4.58 (ddd, 1H), 2.82 (dd, 1H), 2.66 (dd, 1H), 1.80 (t, 3H), 1.53 (ddd, 1H), 1.09 (ddd, 1H), 0.48 (dtt, 1H), 0.36-0.18 (m, 2H), −0.09--0.20 (m, 2H). |
| 91 | INT D2-ent1 | 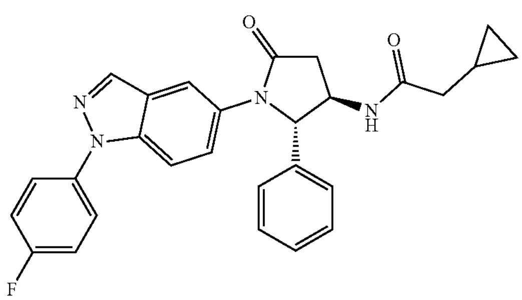 [SMILES: O=C(CC1CC1)N[C@@H]1CC(=O)N(c2ccc3c(cnn3-c3ccc(F)cc3)c2)[C@H]1c1ccccc1] | 86 | ¹H NMR (DMSO-d$_6$) δ: 8.56 (d, 1H), 8.30 (s, 1H), 7.89 (d, 1H), 7.76-7.69 (m, 3H), 7.64 (dd, 1H), 7.43-7.28 (m, 6H), 7.27-7.20 (m, 1H), 5.26 (d, 1H), 4.16 (tt, 1H), 3.06 (dd, 1H), 2.46 (dd, 1H), 2.12-2.03 (m, 3H), 1.00 (tt, 1H), 0.45 (ddt, 2H), 0.15 (dt, 2H). |
| 92 | INT D2-ent2 | 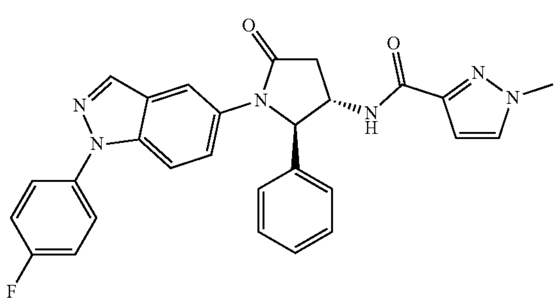 [SMILES: Cn1ccc(C(=O)N[C@H]2CC(=O)N(c3ccc4c(cnn4-c4ccc(F)cc4)c3)[C@@H]2c2ccccc2)n1] | 67 | ¹H NMR (DMSO-d$_6$) δ: 8.89 (d, 1H), 8.29 (d, 1H), 7.86 (dd, 1H), 7.78 (d, 1H), 7.76-7.72 (m, 2H), 7.69 (dt, 1H), 7.62 (dd, 1H), 7.43-7.35 (m, 4H), 7.30 (t, 2H), 7.25-7.18 (m, 1H), 6.64 (d, 1H), 5.42 (d, 1H), 4.47 (ddt, 1H), 3.93 (s, 3H), 3.06 (dd, 1H), 2.73 (dd, 1H). |

-continued
| Ex. # | Intermediate (INT) | Structure | Yield (%) | 1H NMR |
|---|---|---|---|---|
| 93 | INT D2-ent2 | 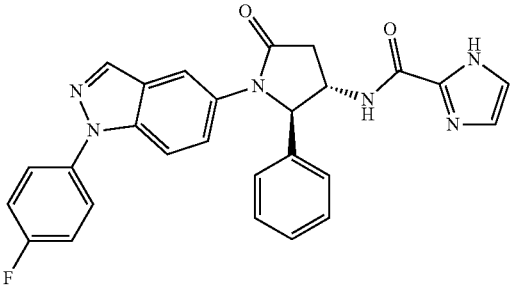 [SMILES: O=C(N[C@H]1CC(=O)N(c2ccc3c(cnn3-c3ccc(F)cc3)c2)[C@@H]1c1ccccc1)c1ncc[nH]1] | 24 | 1H NMR (DMSO-d$_6$) δ: 9.21 (d, 1H), 8.29 (d, 1H), 7.84 (d, 1H), 7.76-7.71 (m, 2H), 7.69 (d, 1H), 7.60 (dd, 1H), 7.43-7.36 (m, 4H), 7.31-7.27 (m, 3H), 7.23-7.18 (m, 1H), 7.09 (s, 1H), 5.45 (d, 1H), 4.50 (tt, 1H), 3.07 (dd, 1H), 2.77 (dd, 1H). |
| 94 | INT D2-ent2 | 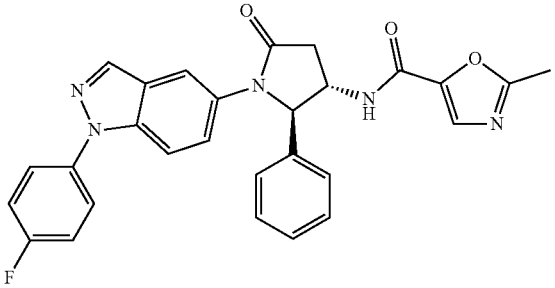 [SMILES: Cc1ncc(C(=O)N[C@H]2CC(=O)N(c3ccc4c(cnn4-c4ccc(F)cc4)c3)[C@@H]2c2ccccc2)o1] | 27 | 1H NMR (600 MHz, DMSO-d$_6$) δ 9.27 (d, 1H), 8.30 (s, 1H), 7.92 (d, 1H), 7.78-7.66 (m, 5H), 7.44-7.37 (m, 4H), 7.36-7.30 (m, 2H), 7.27-7.21 (m, 1H), 5.40 (d, 1H), 4.43-4.36 (m, 1H), 3.15 (dd, 1H), 2.65 (dd, 1H), 2.50 (s, 3H). |
| 95 | INT D2-ent2 | 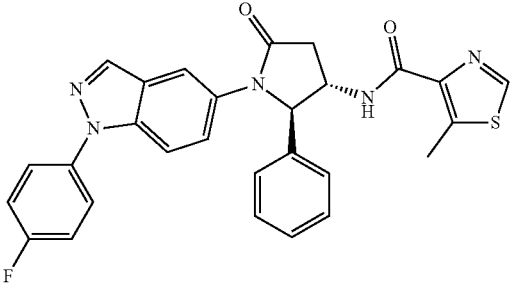 [SMILES: Cc1scnc1C(=O)N[C@H]1CC(=O)N(c2ccc3c(cnn3-c3ccc(F)cc3)c2)[C@@H]1c1ccccc1] | 54 | 1H NMR (DMSO-d$_6$) δ: 9.07 (s, 1H), 9.03 (d, 1H), 8.30 (s, 1H), 7.91 (s, 1H), 7.78-7.64 (m, 4H), 7.44-7.37 (m, 4H), 7.34 (t, 2H), 7.24 (t, 1H), 5.41 (d, 1H), 4.40 (dt, 1H), 3.13 (dd, 1H), 2.66 (dd, 1H), 2.62 (s, 3H). |
| 96 | INT D2-ent2 | 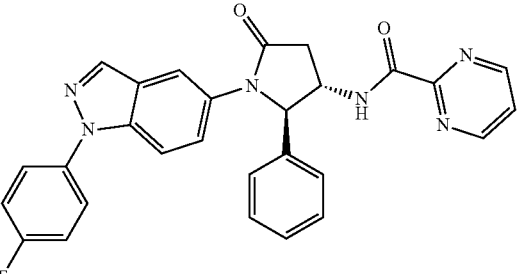 | 53 | 1H NMR (600 MHz, DMSO-d$_6$) δ 9.68 (d, 1H), 8.99 (d, 1H), 8.29 (d, 1H), 7.88 (d, 1H), 7.77-7.67 (m, 4H), 7.66-7.61 (m, 1H), 7.43-7.35 (m, 4H), 7.31 (t, 2H), 7.25-7.19 (m, 1H), 5.50 (d, 1H), 4.54 (tt, 4.6 Hz, 1H), 3.17-3.10 (m, 1H), 2.82-2.75 (m, 1H). |
| 97 | INT D2-ent2 | 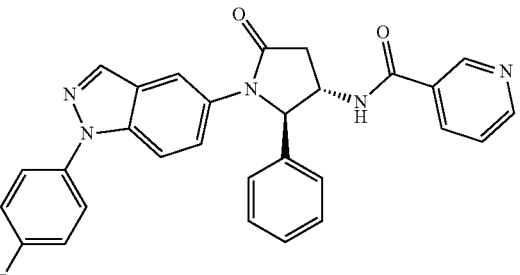 | 44 | 1H NMR (DMSO-d$_6$) δ: 9.39 (d, 1H), 9.10 (dd, 1H), 8.74 (dd, 1H), 8.32-8.25 (m, 2H), 7.94 (t, 1H), 7.77-7.70 (m, 4H), 7.55 (ddd, 1H), 7.46-7.32 (m, 6H), 7.26 (td, 1H), 5.46 (d, 1H), 4.44 (ddd, 1H), 3.19 (dd, 1H), 2.69 (dd, 1H). |

| Ex. # | Intermediate (INT) | Structure | Yield (%) | $^1$H NMR |
|---|---|---|---|---|
| 98 | INT D2-ent2 | 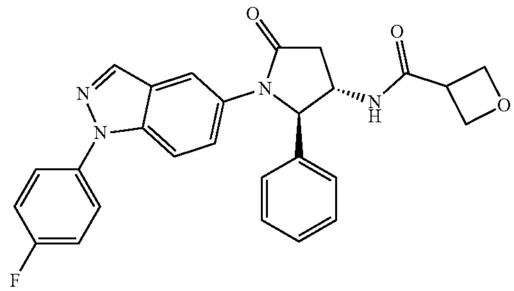 [SMILES: O=C(N[C@H]1CC(=O)N(c2ccc3c(cnn3-c3ccc(F)cc3)c2)[C@@H]1c1ccccc1)C1COC1] | 75 | $^1$H NMR (DMSO-$d_6$) δ: 8.73 (d, 1H), 8.30 (d, 1H), 7.92 (d, 1H), 7.76-7.73 (m, 2H), 7.71 (d, 1H), 7.68 (dd, 1H), 7.42-7.37 (m, 4H), 7.34 (t, 2H), 7.27-7.22 (m, 1H), 5.29 (d, 1H), 4.75-4.60 (m, 4H), 4.19 (tt, 1H), 3.89-3.74 (m, 1H), 3.12-3.06 (m, 1H), 2.45 (dd, 1H). |

The examples in Table 3 were synthesized in analogy to the Example 9 described above, using the appropriate carboxylic acid, acid chloride or sulfonyl chloride.

| Ex. # | Intermediate (INT) | Structure | Yield (%) | $^1$H NMR |
|---|---|---|---|---|
| 10 | INT D3 | 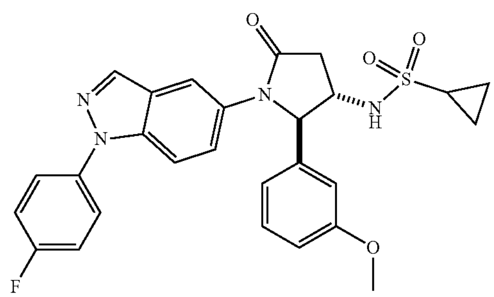 [SMILES: COc1cccc([C@@H]2[C@@H](NS(=O)(=O)C3CC3)CC(=O)N2c2ccc3c(cnn3-c3ccc(F)cc3)c2)c1] | 42 | $^1$H NMR (DMSO-$d_6$) δ: 8.32 (s, 1H), 7.99 (d, 1H), 7.85 (s, 1H), 7.77-7.73 (m, 2H), 7.72 (d, 1H), 7.60 (dd, 1H), 7.40 (t, 2H), 7.24 (t, 1H), 6.95-6.90 (m, 2H), 6.84-6.79 (m, 1H), 5.29 (d, 1H), 4.00-3.93 (m, 1H), 3.70 (s, 3H), 3.15 (dd, 1H), 2.60 (dd, 1H), 2.53-2.47 (m, 1H), 0.98-0.88 (m, 2H), 0.88-0.81 (m, 2H) |
| 37 | INT D6 | 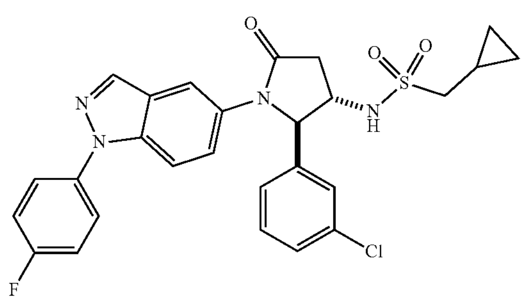 [SMILES: O=C1C[C@H](NS(=O)(=O)CC2CC2)[C@@H](c2cccc(Cl)c2)N1c1ccc2c(cnn2-c2ccc(F)cc2)c1] | 55 | $^1$H NMR (DMSO-$d_6$) δ: 8.32 (s, 1H), 8.01 (d, 1H), 7.87 (d, 1H), 7.79-7.70 (m, 3H), 7.61 (dd, 1H), 7.47-7.43 (m, 1H), 7.44-7.28 (m, 5H), 5.34 (d, 1H), 4.02-3.97 (m, 1H), 3.13 (dd, 1H), 2.91 (d, 2H), 2.59 (dd, 1H), 0.98-0.89 (m, 1H), 0.57-0.48 (m, 2H), 0.31-0.23 (m, 2H) |
| 51 | INT D4 | 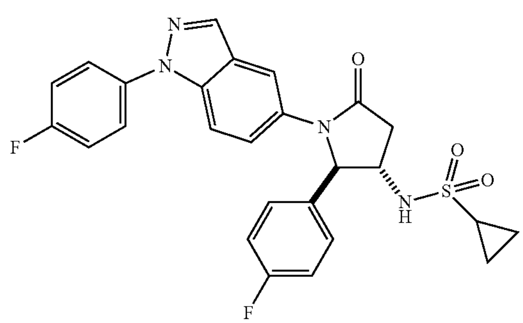 [SMILES: O=C1C[C@H](NS(=O)(=O)C2CC2)[C@@H](c2ccc(F)cc2)N1c1ccc2c(cnn2-c2ccc(F)cc2)c1] | 80 | $^1$H NMR (DMSO-$d_6$) δ: 8.31 (s, 1H), 7.98 (d, 1H), 7.82 (s, 1H), 7.78-7.67 (m, 3H), 7.55 (dd, 1H), 7.46-7.36 (m, 4H), 7.14 (t, 2H), 5.30 (d, 1H), 4.01-3.93 (m, 1H), 3.15 (dd, 1H), 2.63 (dd, 1H), 2.51-2.45 (m, 1H), 0.98-0.88 (m, 2H), 0.88-0.79 (m, 2H) |

-continued

| Ex. # | Intermediate (INT) | Structure | Yield (%) | ¹H NMR |
|---|---|---|---|---|
| 99 | INT D2-ent2 | 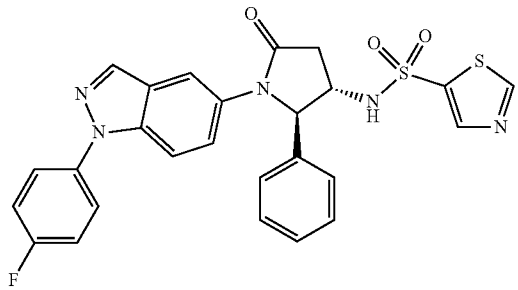 [SMILES: O=C1C[C@H](NS(=O)(=O)c2cncs2)[C@@H](c2ccccc2)N1c1ccc2c(cnn2-c2ccc(F)cc2)c1] | 35 | ¹H NMR (DMSO-$d_6$) δ: 9.35 (t, 1H), 8.30 (t, 1H), 8.26 (d, 1H), 7.79 (dd, 1H), 7.76-7.66 (m, 3H), 7.53 (dt, 1H), 7.43-7.35 (m, 2H), 7.30-7.18 (m, 6H), 5.27 (d, 1H), 3.90-3.84 (m, 1H), 2.99 (dd, 1H), 2.45-2.38 (m, 1H) |

The examples in Table 4 were synthesized in analogy to the Example 13 described above, using the appropriate carboxylic acid, acid chloride or sulfonyl chloride.

| Ex. # | Intermediate (INT) | Structure | Yield (%) | ¹H NMR |
|---|---|---|---|---|
| 16 | INT D5 | 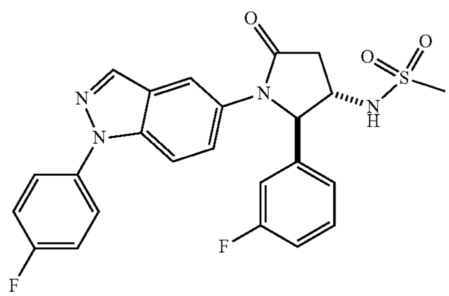 [SMILES: CS(=O)(=O)N[C@H]1CC(=O)N(c2ccc3c(cnn3-c3ccc(F)cc3)c2)[C@@H]1c1cccc(F)c1] | 21 | ¹H NMR (DMSO-$d_6$) δ: 8.31 (d, 1H), 7.85 (d, 1H), 7.78-7.66 (m, 3H), 7.58 (dd, 1H), 7.43-7.29 (m, 3H), 7.24-7.18 (m, 2H), 7.10-7.01 (m, 1H), 5.32 (d, 1H), 4.02-3.96 (m, 1H), 3.14 (dd, 1H), 2.87 (s, 3H), 2.58 (dd, 1H) |
| 18 | INT D5 | 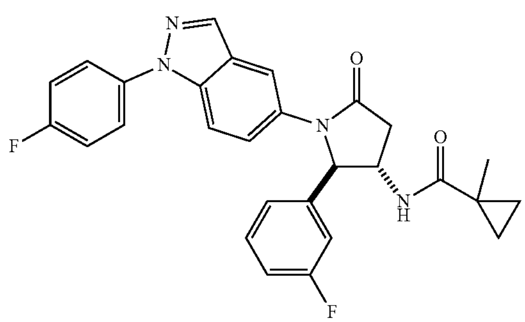 [SMILES: CC1(C(=O)N[C@H]2CC(=O)N(c3ccc4c(cnn4-c4ccc(F)cc4)c3)[C@@H]2c2cccc(F)c2)CC1] | 100 | ¹H NMR (DMSO-$d_6$) δ: 8.31 (d, 1H), 8.19-8.13 (m, 1H), 7.89 (t, 1H), 7.79-7.63 (m, 4H), 7.44-7.31 (m, 3H), 7.25-7.16 (m, 2H), 7.09-7.01 (m, 1H), 5.31-5.26 (m, 1H), 4.28-4.20 (m, 1H), 3.05 (ddd, 1H), 2.67-2.59 (m, 1H), 1.32 (d, 3H), 1.07-0.96 (m, 2H), 0.59-0.54 (m, 2H) |
| 22 | INT D3 | 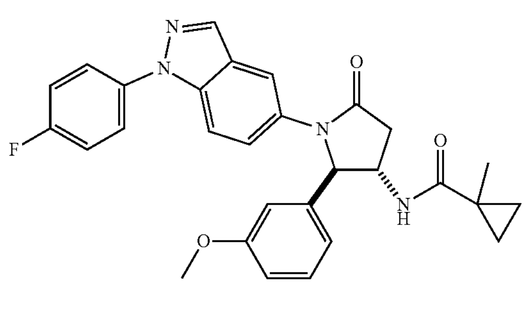 [SMILES: COc1cccc([C@@H]2[C@@H](NC(=O)C3(C)CC3)CC(=O)N2c2ccc3c(cnn3-c3ccc(F)cc3)c2)c1] | 23 | ¹H NMR (DMSO-$d_6$) δ: 8.31 (d, 1H), 8.13 (d, 1H), 7.88 (d, 1H), 7.77-7.74 (m, 2H), 7.72 (d, 1H), 7.66 (dd, 1H), 7.44-7.37 (m, 2H), 7.22 (t, 1H), 6.93-6.87 (m, 2H), 6.79 (ddd, 1H), 5.24 (d, 1H), 4.24-4.19 (m, 1H), 3.70 (s, 3H), 3.01 (dd, 1H), 2.59 (dd, 1H), 1.31 (s, 3H), 1.04-0.97 (m, 2H), 0.60-0.54 (m, 2H) |

| Ex. # | Intermediate (INT) | Structure | Yield (%) | 1H NMR |
|---|---|---|---|---|
| 66 | INT D5 | 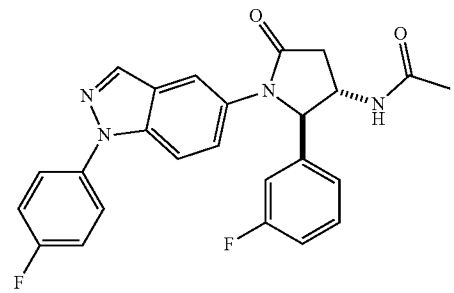 [SMILES: CC(=O)N[C@H]1CC(=O)N(c2ccc3c(cnn3-c3ccc(F)cc3)c2)[C@@H]1c1cccc(F)c1] | 39 | 1H NMR (DMSO-$d_6$) δ: 8.69 (d, 1H), 8.30 (d, 1H), 7.91 (d, 1H), 7.79-7.68 (m, 3H), 7.66 (dd, 1H), 7.43-7.29 (m, 3H), 7.25-7.16 (m, 2H), 7.09-7.02 (m, 1H), 5.29 (d, 1H), 4.20-4.13 (m, 1H), 3.09 (dd, 1H), 2.45 (dd, 1H), 1.90 (s, 3H) |

GRE Agonist

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)
25 mL of 7.5% Sodium Bicarbonate (LONZA cat. No BE17-613E)
6.5 mL of 1 M Hepes (LONZA cat. No: BE17-737E)
5 mL of 100× Penicillin/Streptomycin (LONZA cat. No DE17-602E)
50 mL of Fetal Bovine Serum (Euroclone cat. No ECS 0180L)
0.25 mL of 10 mg/mL Puromycin (InvivoGen cat.: ant-pr-1)
0.5 mL of 100 mg/mL Zeocin (InvivoGen cat.: ant-m-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 30 µl Opti-MEM (GIBCO, cat. #31985062) as assay buffer. To test the compounds an 8-point half-log compound dilution curve was generated in 100% DMSO starting from a 2 mM stock and compounds were then diluted 1:50 in Opti-MEM. 10 µl of compounds were then added to the wells containing 30 µl Opti-MEM resulting in a final assay concentration range from 10 µM to 0.003 µM in 0.5% DMSO. Compounds were tested at 8 concentrations in quadruplicate data points. Cells were incubated for 6 hour with compounds and beclometasone (Sigma, cat. #Y0000351) as control compound at 37° C., 5% $CO_2$ and 95% humidity in a total volume of 40 µl. Finally, cells were lysed with 20 W of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:

% effect=((compound−min)/(max−min))×100

[min=Opti-MEM only, max=beclometasone]

To calculate EC50, max, min and slope factor for each compound a concentration response curve was fitted by plotting % effect versus compound concentration using a 4 parameter logistic equation:

$y = A + (B-A)/(1+((10C)/x)D)$

[A=min y, B=max y, C=log $EC_{50}$, D=slope]

GRE Antagonist

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)

25 mL of 7.5% Sodium Bicarbonate (LONZA cat. No BE17-613E)
6.5 mL of 1 M Hepes (LONZA cat. No: BE17-737E)
5 mL of 100× Penicillin/Streptomycin (LONZA cat. No DE17-602E)
50 mL of Fetal Bovine Serum (Euroclone cat. No ECS 0180L)
0.25 mL of 10 mg/mL Puromycin (InvivoGen cat.: ant-pr-1)
0.5 mL of 100 mg/mL Zeocin (InvivoGen cat.: ant-m-1)

Cryo-preserved CHO-Gal4/GR cells were suspended in complete medium and 5000 cells/25 μl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 20 μl Opti-MEM (GIBCO, cat. #31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 μl of compounds were then added to the wells containing 20 μl Opti-MEM and incubated for 10 min. After this pre-incubation 10 μl of the reference agonist beclometasone (Sigma, cat. #Y0000351) at an EC50 of 2.5 nM were added resulting in a final assay concentration range from 10 μM to 0.003 μM in 0.5% DMSO in a total volume of 40 μl. Compounds were tested at 8 concentrations in quadruplicate data points. Cells were incubated for 6 hour with compounds and mifepristone as control compound (Sigma, cat. #M8046) at 37° C., 5% $CO_2$ and 95% humidity. Finally, cells were lysed with 20 μl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:

% effect=((compound−min)/(max−min))×−100

[min=Opti-MEM only, max=mifepristone]

To calculate IC50, max, min and slope factor for each compound a concentration response curve was fitted by plotting % effect versus compound concentration using a 4 parameter logistic equation:

$y = A + (B-A)/(1+((10C)/x)D)$

[A=min y, B=max y, C=log $IC_{50}$, D=slope]

TABLE 5

| Cpd # | IC50 or EC50<br>A <100 nM<br>B = 100 nM-1 μM,<br>C = 1 μM-15 μM |
|---|---|
| 1 | A |
| 2 | A |
| 4 | A |
| 5 | A |
| 7 | A |
| 8 | A |
| 9 | B |
| 10 | B |
| 12 | A |
| 13 | A |
| 14 | A |
| 15 | A |
| 16 | A |
| 17 | A |
| 18 | A |
| 19 | A |
| 20 | B |

TABLE 5-continued

| Cpd # | IC50 or EC50<br>A <100 nM<br>B = 100 nM-1 μM,<br>C = 1 μM-15 μM |
|---|---|
| 21 | A |
| 22 | A |
| 24 | B |
| 25 | B |
| 26 | A |
| 27 | A |
| 28 | A |
| 29 | B |
| 30 | B |
| 31 | A |
| 32 | A |
| 34 | A |
| 36 | B |
| 37 | B |
| 38 | B |
| 39 | B |
| 42 | C |
| 43 | C |
| 44 | C |
| 45 | A |
| 46 | A |
| 47 | B |
| 48 | B |
| 49 | B |
| 51 | A |
| 52 | A |
| 53 | A |
| 54 | A |
| 55 | A |
| 56 | A |
| 61 | A |
| 62 | A |
| 63 | A |
| 65 | A |
| 66 | A |
| 67 | A |
| 75 | B |
| 76 | B |
| 77 | C |
| 78 | C |
| 79 | A |
| 80 | A |
| 81 | A |
| 82 | B |
| 85 | B |
| 86 | A |
| 87 | B |
| 88 | A |
| 89 | A |
| 90 | C |
| 91 | C |
| 92 | A |
| 93 | A |
| 94 | A |
| 95 | A |
| 96 | B |
| 97 | B |
| 98 | B |
| 99 | A |
| 100 | B |
| 101 | A |
| 102 | B |
| 103 | B |

The invention claimed is:
1. A compound according to general formula (I),

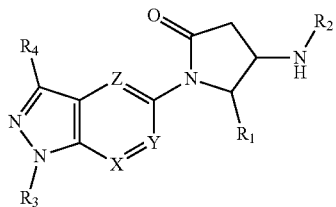

wherein
R$_1$ represents —C$_{1-10}$-alkyl; —C$_{3-10}$-cycloalkyl; —C$_{1-6}$-alkylene-C$_{3-10}$-cycloalkyl; 3 to 7 membered heterocycloalkyl; —C$_{1-6}$-alkylene-(3 to 7 membered heterocycloalkyl); aryl; —C$_{1-6}$-alkylene-aryl; 5 or 6-membered heteroaryl; or —C$_{1-6}$-alkylene-(5 or 6-membered heteroaryl);
R$_2$ represents —C(=O)—C$_{1-10}$-alkyl; —C(=O)—C$_{3-10}$-cycloalkyl; —C(=O)—C$_{1-6}$-alkylene-C$_{3-10}$-cycloalkyl; —C(=O)-(3 to 7 membered heterocycloalkyl); —C(=O)—C$_{1-6}$-alkylene-(3 to 7 membered heterocycloalkyl); —C(=O)-aryl; —C(=O)—C$_{1-6}$-alkylene-aryl; —C(=O)-(5 or 6-membered heteroaryl); —C(=O)—C$_{1-6}$-alkylene-(5 or 6-membered heteroaryl); —S(=O)$_{1-2}$—C$_{1-10}$-alkyl; —S(=O)$_{1-2}$—C$_{3-10}$-cycloalkyl; —S(=O)$_{1-2}$—C$_{1-6}$-alkylene-C$_{3-10}$-cycloalkyl; —S(=O)$_{1-2}$-(3 to 7 membered heterocycloalkyl); —S(=O)$_{1-2}$—C$_{1-6}$-alkylene-(3 to 7 membered heterocycloalkyl); —S(=O)$_{1-2}$-aryl; —S(=O)$_{1-2}$—C$_{1-6}$-alkylene-aryl; —S(=O)$_{1-2}$-(5 or 6-membered heteroaryl); or —S(=O)$_{1-2}$—C$_{1-6}$-alkylene-(5 or 6-membered heteroaryl);
R$_3$ represents —C$_{1-10}$-alkyl; —C$_{3-10}$-cycloalkyl; —C$_{1-6}$-alkylene-C$_{3-10}$-cycloalkyl; aryl; —C$_{1-6}$-alkylene-aryl; —C(=O)—C$_{1-10}$-alkyl; —C(=O)—C$_{3-10}$-cycloalkyl; —C(=O)—C$_{1-6}$-alkylene-C$_{3-10}$-cycloalkyl; —C(=O)-aryl; —C(=O)—C$_{1-6}$-alkylene-aryl; —S(=O)$_{1-2}$—C$_{1-10}$-alkyl; —S(=O)$_{1-2}$—C$_{3-10}$-cycloalkyl; —S(=O)$_{1-2}$—C$_{1-6}$-alkylene-C$_{3-10}$-cycloalkyl; —S(=O)$_{1-2}$-aryl; or —S(=O)$_{1-2}$—C$_{1-6}$-alkylene-aryl;
R$_4$ represents —H; —F; —Cl; —Br; —I; —CN; —CH$_3$; —CF$_3$; —CF$_2$H; —CFH$_2$ or cyclopropyl;
X represents N or CR$_5$; wherein R$_5$ represents —H; —F; —Cl; —Br; —I; —CN; —C$_{1-10}$-alkyl or —C$_{3-10}$-cycloalkyl;
Y represents N or CR$_6$; wherein R$_6$ represents —H; —F; —Cl; —Br; —I; —CN; —C$_{1-10}$-alkyl or —C$_{3-10}$-cycloalkyl;
Z represents N or CR$_7$; wherein R$_7$ represents —H; —F; —Cl; —Br; —I; —CN; —C$_{1-10}$-alkyl or —C$_{3-10}$-cycloalkyl;
wherein —C$_{1-10}$-alkyl, —C$_{1-4}$-alkyl and —C$_{1-6}$-alkylene- in each case independently from one another is linear or branched, saturated or unsaturated;
wherein —C$_{1-10}$-alkyl, —C$_{1-4}$-alkyl, —C$_{1-6}$-alkylene-, —C$_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C(=O)—C$_{1-6}$-alkyl; —C(=O)—OH; —C(=O)—OC$_{1-6}$-alkyl; —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C(=O)—C$_{1-6}$-alkyl; —O—C(=O)—O—C$_{1-6}$-alkyl; —O—(CO)—NH(C$_{1-6}$-alkyl); —O—C(=O)—N(C$_{1-6}$-alkyl)$_2$; —O—S(=O)$_2$—NH$_2$; —O—S(=O)$_2$—NH(C$_{1-6}$-alkyl); —O—S(=O)$_2$—N(C$_{1-6}$-alkyl)$_2$; —NH$_2$; —NH(C$_{1-6}$-alkyl); —N(C$_{1-6}$-alkyl)$_2$; —NH—C(=O)—C$_{1-6}$-alkyl; —NH—C(=O)—O—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—C$_{1-6}$-alkyl; —N(C$_{1-6}$-alkyl)-C(=O)—O—C$_{1-6}$-alkyl; —N(C$_{1-6}$-alkyl)-C(=O)—NH$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$OH; NH—S(=O)$_2$—C$_{1-6}$-alkyl; —NH—S(=O)$_2$—O—C$_{1-6}$-alkyl; —NH—S(=O)$_2$—NH$_2$; —NH—S(=O)$_2$—NH(C$_{1-6}$-alkyl); —NH—S(=O)$_2$N(C$_{1-6}$-alkyl)$_2$; —N(C$_{1-6}$-alkyl)-S(=O)$_2$—OH; —N(C$_{1-6}$-alkyl)-S(=O)$_2$—C$_{1-6}$-alkyl; —N(C$_{1-6}$-alkyl)-S(=O)$_2$—O—C$_{1-6}$-alkyl; —N(C$_{1-6}$-alkyl)-S(=O)$_2$—NH$_2$; —N(C$_{1-6}$-alkyl)-S(=O)$_2$—NH(C$_{1-6}$-alkyl); —N(C$_{1-6}$-alkyl)-S(=O)$_2$—N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —S(=O)$_2$—OH; —S(=O)$_2$—O—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; 3 to 6-membered heterocycloalkyl; phenyl; 5 or 6-membered heteroaryl; —O—C$_{3-6}$-cycloalkyl; —O-(3 to 6-membered heterocycloalkyl); —O-phenyl; —O-(5 or 6-membered heteroaryl); —C(=O)—C$_{3-6}$-cycloalkyl; —C(=O)-(3 to 6-membered heterocycloalkyl); —C(=O)-phenyl; —C(=O)-(5 or 6-membered heteroaryl); —S(=O)$_2$-(C$_{3-6}$-cycloalkyl); —S(=O)$_2$-(3 to 6-membered heterocycloalkyl); —S(=O)$_2$-phenyl or —S(=O)$_2$-(5 or 6-membered heteroaryl);
wherein aryl and 5 or 6-membered heteroaryl in each case independently from one another are unsubstituted or mono- or polysubstituted with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C$_{1-4}$-alkylene-CF$_3$; —C$_{1-4}$-alkylene-CF$_2$H; —C$_{1-4}$-alkylene-CFH$_2$; —C(=O)—C$_{1-6}$-alkyl; —C(=O)—OH; —C(=O)—OC$_{1-6}$-alkyl; —C(=O)—NH(OH); —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —NH$_2$; —NH(C$_{1-6}$-alkyl); —N(C$_{1-6}$-alkyl) 2; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S—C$_{1-6}$-alkyl; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; 3 to 6-membered heterocycloalkyl; —C$_{1-4}$-alkylene-(3 to 6-membered heterocycloalkyl); phenyl or 5 or 6-membered heteroaryl;
in the form of the free compound or a physiologically acceptable salt thereof.
2. The compound according to claim 1, wherein
X represents CR$_5$, Y represents CR$_6$; and Z represents CR$_7$; or X represents N, Y represents CR$_6$; and Z represents CR$_7$; or X represents CR$_5$, Y represents N; and Z represents CR$_7$; or X represents CR$_5$, Y represents CR$_6$; and Z represents N; or X represents N, Y represents N; and Z represents CR$_7$; or X represents N, Y represents CR$_6$; and Z represents N; or X represents CR$_5$, Y represents N; and Z represents N; or X represents N, Y represents N; and Z represents N.

3. The compound according to claim 2, wherein optionally present R$_5$ represents —H; optionally present R$_6$ represents —H; and/or optionally present R$_7$ represents —H.

4. The compound according to claim 1, wherein
R$_1$ represents —C$_{3-10}$-cycloalkyl; —C$_{1-6}$-alkylene-C$_{3-10}$-cycloalkyl; aryl; or 5 or 6-membered heteroaryl.

5. The compound according to claim 1, wherein
R$_2$ represents —C(=O)—C$_{1-10}$-alkyl; —C(=O)—C$_{3-10}$-cycloalkyl; —C(=O)—C$_{1-6}$-alkylene-C$_{3-10}$-cycloalkyl; —C(=O)-(3 to 7 membered heterocycloalkyl); —C(=O)-(5 or 6-membered heteroaryl); —S(=O)$_2$—C$_{1-10}$-alkyl; —S(=O)$_2$—C$_{3-10}$-cycloalkyl; —S(=O)$_2$—C$_{1-6}$-alkylene-C$_{3-10}$-cycloalkyl; or —S(=O)$_2$-(5 or 6-membered heteroaryl).

6. The compound according to claim 1, wherein
R$_3$ represents —C$_{1-10}$-alkyl; —C$_{3-10}$-cycloalkyl; —C$_{1-6}$-alkylene-C$_{3-10}$-cycloalkyl; aryl; —C$_{1-6}$-alkylene-aryl.

7. The compound according to claim 1, wherein
R$_4$ represents —H.

8. The compound according to claim 1, wherein
R$_1$ represents
cyclopropyl, unsubstituted;
—CH$_2$-cyclopropyl, unsubstituted;
phenyl, unsubstituted or mono- or disubstituted with substituents independently of one another selected from the group consisting of —F, —Cl, —Br, —CH$_3$, —CF$_3$, —CN, cyclopropyl and —OCH$_3$, wherein phenyl is optionally annealed to a dioxolane ring by a substituent —O—CH$_2$CH$_2$—O—; or
pyridyl, unsubstituted or mono- or disubstituted with substituents independently of one another selected from the group consisting of —F, —Cl, —Br, —CH$_3$, —CF$_3$, —CN, and —OCH$_3$.

9. The compound according to claim 1, wherein
R$_2$ represents
—C(=O)—C$_{1-10}$-alkyl, unsubstituted or mono- or disubstituted with substituents independently of one another selected from the group consisting of —F, —Cl, and —Br;
—C(=O)-cyclopropyl, unsubstituted or mono- or disubstituted with substituents independently of one another selected from the group consisting of —F, —Cl, —Br, —CH$_3$, —CF$_3$, —CN, and —OCH$_3$;
—C(=O)-cyclobutyl, unsubstituted or mono- or disubstituted with substituents independently of one another selected from the group consisting of —F, —Cl, —Br, —CH$_3$, —CF$_3$, —CN and —OCH$_3$;
—C(=O)-2-tetrahydrofuranyl, unsubstituted;
—C(=O)-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$;
—S(=O)$_2$—C$_{1-10}$-alkyl, unsubstituted;
—S(=O)$_2$-cyclopropyl, unsubstituted;
—S(=O)$_2$—CH$_2$-cyclopropyl, unsubstituted; or
—S(=O)$_2$-(5- to 6-membered heteroaryl), wherein said 5- to 6-membered heteroaryl is selected from the group consisting of thiazolyl, pyrazolyl, oxazolyl and 1-oxa-2,4-diazolyl, 1,2,5-oxadiazolyl, isoxazolyl, isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

10. The compound according to claim 1, wherein
R$_3$ represents
—C$_{1-10}$-alkyl, unsubstituted or mono- or disubstituted with substituents independently of one another selected from the group consisting of —F, —Cl, and —Br;
cyclohexyl, unsubstituted or mono- or disubstituted with substituents independently of one another selected from the group consisting of —F, —Cl, and —Br;
—CH$_2$-cyclopropyl, unsubstituted;
—CH$_2$-cyclohexyl, unsubstituted or mono- or disubstituted with substituents independently of one another selected from the group consisting of —F, —Cl, and —Br;
phenyl, unsubstituted or mono- or disubstituted with substituents independently of one another selected from the group consisting of —F, —Cl, —Br, —CH$_3$, —CF$_3$, —CN, and —OCH$_3$; or
—CH$_2$-phenyl, unsubstituted or mono- or disubstituted with substituents independently of one another selected from the group consisting of —F, —Cl, —Br, —CH$_3$, —CF$_3$, —CN, and —OCH$_3$.

11. The compound according to claim 1, wherein
R$_1$ represents phenyl, unsubstituted or mono- or disubstituted with substituents independently of one another selected from the group consisting of —F, —Cl, —Br, —CH$_3$, —CF$_3$, —CN, cyclopropyl and —OCH$_3$; and/or
R$_2$ represents —C(=O)—C$_{1-6}$-alkyl; —C(=O)-cyclopropyl; or —C(=O)-cyclobutyl, unsubstituted or mono- or disubstituted with substituents independently of one another selected from the group consisting of —F, —Cl, and —Br; and/or
R$_3$ represents fluoro-phenyl.

12. The compound according to claim 1 selected from the group consisting of
1  2,2-difluoro-N-[rac-(2R,3S)-2-(2,3-dihydro-1,4-benzodioxin-6-yl)-1-[1-(4-fluorophenyl)indazol-5-yl]-5-oxo-pyrrolidin-3-yl]propanamide
2  2,2-difluoro-N-[(2R,3S)-1-[1-(4-fluorophenyl)indazol-5-yl]-5-oxo-2-phenyl-pyrrolidin-3-yl]propanamide
3  2,2-difluoro-N-[rac-(2R,3S)-1-[1-(4-fluorophenyl)indazol-5-yl]-5-oxo-2-phenyl-pyrrolidin-3-yl]propanamide
4  2,2-difluoro-N-[(2R,3S)-1-[1-(4-fluorophenyl)indazol-5-yl]-2-(2-methoxy-4-pyridyl)-5-oxo-pyrrolidin-3-yl]propanamide
5  2,2-difluoro-N-[rac-(2R,3S)-2-(2,4-difluorophenyl)-1-[1-(4-fluorophenyl)indazol-5-yl]-5-oxo-pyrrolidin-3-yl]propanamide 6   2,2-difluoro-N-[rac-(2R,3S)-1-[1-(3,4-difluorophenyl)indazol-5-yl]-5-oxo-2-phenyl-pyrrolidin-3-yl]propanamide
7   2,2-difluoro-N-[rac-(2R,3S)-1-[1-(4-fluorophenyl)indazol-5-yl]-2-(3-methoxyphenyl)-5-oxo-pyrrolidin-3-yl]propanamide
8   N-[rac-(2R,3S)-1-[1-(4-fluorophenyl)indazol-5-yl]-5-oxo-2-phenyl-pyrrolidin-3-yl]cyclopropanecarboxamide
9   N-[rac-(2R,3S)-1-[1-(4-fluorophenyl)indazol-5-yl]-5-oxo-2-phenyl-pyrrolidin-3-yl]cyclopropanesulfonamide
10  N-[rac-(2R,3S)-1-[1-(4-fluorophenyl)indazol-5-yl]-2-(3-methoxyphenyl)-5-oxo-pyrrolidin-3-yl]cyclopropanesulfonamide
11  2,2-difluoro-N-[rac-(2R,3S)-2-(4-fluorophenyl)-1-[1-(4-fluorophenyl)indazol-5-yl]-5-oxo-pyrrolidin-3-yl]propanamide
12  N-[(2R,3S)-2-(3-chlorophenyl)-1-[1-(4-fluorophenyl)indazol-5-yl]-5-oxo-pyrrolidin-3-yl]-2,2-difluoro-propanamide
13  1-methyl-N-[rac-(2R,3S)-2-(4-fluorophenyl)-1-[1-(4-fluorophenyl)indazol-5-yl]-5-oxo-pyrrolidin-3-yl]cyclopropanecarboxamide
14  1-fluoro-N-[rac-(2R,3S)-2-(3-chlorophenyl)-1-[1-(4-fluorophenyl)indazol-5-yl]-5-oxo-pyrrolidin-3-yl]cyclopropanecarboxamide
15  N-[rac-(2R,3S)-2-(3-fluorophenyl)-1-[1-(4-fluorophenyl)indazol-5-yl]-5-oxo-pyrrolidin-3-yl]-1-(trifluoromethyl)cyclopropanecarboxamide
16  N-[rac-(2R,3S)-2-(3-fluorophenyl)-1-[1-(4-fluorophenyl)indazol-5-yl]-5-oxo-pyrrolidin-3-yl]methanesulfonamide
17  N-[rac-(2R,3S)-1-[1-(4-fluorophenyl)indazol-5-yl]-2-(3-methoxyphenyl)-5-oxo-pyrrolidin-3-yl]-1-(trifluoromethyl)cyclopropanecarboxamide
18  1-methyl-N-[rac-(2R,3S)-2-(3-fluorophenyl)-1-[1-(4-fluorophenyl)indazol-5-yl]-5-oxo-pyrrolidin-3-yl]cyclopropanecarboxamide
19  N-[rac-(2R,3S)-2-(3-fluorophenyl)-1-[1-(4-fluorophenyl)indazol-5-yl]-5-oxo-pyrrolidin-3-yl]cyclobutanecarboxamide
20  2,2-difluoro-N-[(2S,3R)-2-(4-fluoro-3-methoxy-phenyl)-1-[1-(4-fluorophenyl)indazol-5-yl]-5-oxo-pyrrolidin-3-yl]propanamide
21  2,2-difluoro-N-[(2R,3S)-2-(4-fluoro-3-methoxy-phenyl)-1-[1-(4-fluorophenyl)indazol-5-yl]-5-oxo-pyrrolidin-3-yl]propanamide
22  1-methyl-N-[rac-(2R,3S)-1-[1-(4-fluorophenyl)indazol-5-yl]-2-(3-methoxyphenyl)-5-oxo-pyrrolidin-3-yl]cyclopropanecarboxamide
23  1-fluoro-N-[rac-(2R,3S)-1-[1-(4-fluorophenyl)indazol-5-yl]-2-(3-methoxyphenyl)-5-oxo-pyrrolidin-3-yl]cyclopropanecarboxamide
24  2,2-difluoro-N-[(2S,3R)-2-(2-fluorophenyl)-1-[1-(4-fluorophenyl)indazol-5-yl]-5-oxo-pyrrolidin-3-yl]propanamide
25  2,2-difluoro-N-[rac-(2R,3S)-1-[1-(3-fluorophenyl)indazol-5-yl]-5-oxo-2-phenyl-pyrrolidin-3-yl]propanamide
26  2,2-difluoro-N-[rac-(2R,3S)-2-(3,5-difluorophenyl)-1-[1-(4-fluorophenyl)indazol-5-yl]-5-oxo-pyrrolidin-3-yl]propanamide
27  2,2-difluoro-N-[rac-(2R,3S)-5-oxo-2-phenyl-1-(1-phenylindazol-5-yl)pyrrolidin-3-yl]propanamide
28  N-[(2R,3S)-2-(2-fluorophenyl)-1-[1-(4-fluorophenyl)indazol-5-yl]-5-oxo-pyrrolidin-3-yl]cyclo-propanecarboxamide
29  2,2-difluoro-N-[rac-(2R,3S)-1-[1-(4-cyanophenyl)indazol-5-yl]-5-oxo-2-phenyl-pyrrolidin-3-yl]propanamide
30  2,2-difluoro-N-[rac-(2R,3S)-1-[1-(3-cyanophenyl)indazol-5-yl]-5-oxo-2-phenyl-pyrrolidin-3-yl]propanamide
31  2,2-difluoro-N-[rac-(2R,3S)-2-(3-chlorophenyl)-1-[1-(4-fluorophenyl)indazol-5-yl]-5-oxo-pyrrolidin-3-yl]propanamide
32  N-[rac-(2R,3S)-2-(3-chlorophenyl)-1-[1-(4-fluorophenyl)indazol-5-yl]-5-oxo-pyrrolidin-3-yl]cyclobutanecarboxamide
33  2,2-difluoro-N-[(2R,3S)-2-(2-fluorophenyl)-1-[1-(4-fluorophenyl)indazol-5-yl]-5-oxo-pyrrolidin-3-yl]propanamide
34  N-[(2R,3S)-2-(4-fluoro-3-methoxy-phenyl)-1-[1-(4-fluorophenyl)indazol-5-yl]-5-oxo-pyrrolidin-3-yl]cyclopropanecarboxamide
36  2,2-difluoro-N-[rac-(2S,3S)-2-cyclopropyl-1-[1-(4-fluorophenyl)indazol-5-yl]-5-oxo-pyrrolidin-3-yl]propanamide
37  1-cyclopropyl-N-[rac-(2R,3S)-2-(3-chlorophenyl)-1-[1-(4-fluorophenyl)indazol-5-yl]-5-oxo-pyrrolidin-3-yl]methanesulfonamide
38  2,2-difluoro-N-[(2S,3R)-1-[1-(4-fluorophenyl)indazol-5-yl]-2-(o-tolyl)-5-oxo-pyrrolidin-3-yl]propanamide
39  N-[(2S,3R)-1-[1-(4-fluorophenyl)indazol-5-yl]-5-oxo-2-phenyl-pyrrolidin-3-yl]cyclopropanecarboxamide
42  2,2-difluoro-N-[(2S,3R)-2-(2-fluoro-5-methoxy-phenyl)-1-[1-(4-fluorophenyl)indazol-5-yl]-5-oxo-pyrrolidin-3-yl]propanamide
43  N-[(2S,3R)-2-(2-fluoro-5-methoxy-phenyl)-1-[1-(4-fluorophenyl)indazol-5-yl]-5-oxo-pyrrolidin-3-yl]cyclopropanecarboxamide
45  1:1 mixture of (1S,2S)-2-fluoro-N-[(2R,3S)-2-(4-fluorophenyl)-1-[1-(4-fluorophenyl)indazol-5-yl]-5-oxo-pyrrolidin-3-yl]cyclopropanecarboxamide and (1S,2S)-2-fluoro-N-[(2S,3R)-2-(4-fluorophenyl)-1-[1-(4-fluorophenyl)indazol-5-yl]-5-oxo-pyrrolidin-3-yl]cyclopropanecarboxamide
46  rac-(1S,2R)-2-fluoro-N-[rac-(2R,3S)-1-[1-(4-fluorophenyl)indazol-5-yl]-2-(3-methoxyphenyl)-5-oxo-pyrrolidin-3-yl]cyclopropanecarboxamide
48  2,2-difluoro-N-[rac-(2S,3R)-2-cyclopropyl-1-[1-(4-fluorophenyl)indazol-5-yl]-5-oxo-pyrrolidin-3-yl]propanamide
49  N-[(2R,3S)-1-[1-(4-fluorophenyl)indazol-5-yl]-2-(2-methoxy-4-pyridyl)-5-oxo-pyrrolidin-3-yl]cyclopropanecarboxamide
51  N-[rac-(2R,3S)-2-(4-fluorophenyl)-1-[1-(4-fluorophenyl)indazol-5-yl]-5-oxo-pyrrolidin-3-yl]cyclopropanesulfonamide
52  2-methyl-N-[rac-(2R,3S)-2-(3-fluorophenyl)-1-[1-(4-fluorophenyl)indazol-5-yl]-5-oxo-pyrrolidin-3-yl]cyclopropanecarboxamide
53  N-[(2R,3S)-1-[1-(4-fluorophenyl)indazol-5-yl]-2-(o-tolyl)-5-oxo-pyrrolidin-3-yl]cyclopropanecarboxamide
54  N-[rac-(2R,3S)-2-(4-fluorophenyl)-1-[1-(4-fluorophenyl)indazol-5-yl]-5-oxo-pyrrolidin-3-yl]cyclopropanecarboxamide
55  N-[rac-(2R,3S)-1-[1-(4-fluorophenyl)indazol-5-yl]-2-(3-methoxyphenyl)-5-oxo-pyrrolidin-3-yl]cyclopropanecarboxamide 56 1:1 mixture of (1R,2R)-2-fluoro-N-[(2R,3S)-2-(4-fluorophenyl)-1-[1-(4-fluorophenyl)indazol-5-yl]-5-oxo-pyrrolidin-3-yl]cyclopropanecarboxamide and (1R,2R)-2-fluoro-N-[(2S,3R)-2-(4-fluorophenyl)-1-[1-(4-fluorophenyl)indazol-5-yl]-5-oxo-pyrrolidin-3-yl]cyclopropanecarboxamide 61 N-[rac-(2R,3S)-2-(3-fluorophenyl)-1-[1-(4-fluorophenyl)indazol-5-yl]-5-oxo-pyrrolidin-3-yl]cyclopropanecarboxamide 62 N-[(2R,3S)-2-(2-fluoro-5-methoxy-phenyl)-1-[1-(4-fluorophenyl)indazol-5-yl]-5-oxo-pyrrolidin-3-yl]cyclopropanecarboxamide 63 1:1 mixture of (1R,2R)-2-fluoro-N-[(2R,3S)-1-[1-(4-fluorophenyl)indazol-5-yl]-2-(3-methoxyphenyl)-5-oxo-pyrrolidin-3-yl]cyclopropanecarboxamide and (1R,2R)-2-fluoro-N-[(2S,3R)-1-[1-(4-fluorophenyl)indazol-5-yl]-2-(3-methoxyphenyl)-5-oxo-pyrrolidin-3-yl]cyclopropanecarboxamide 65 N-[(2R,3S)-1-[1-(4-fluorophenyl)indazol-5-yl]-5-oxo-2-phenyl-pyrrolidin-3-yl]cyclopropanecarboxamide 66 N-[rac-(2R,3S)-2-(3-fluorophenyl)-1-[1-(4-fluorophenyl)indazol-5-yl]-5-oxo-pyrrolidin-3-yl]acetamide 67 N-[rac-(2R,3S)-2-(3-chlorophenyl)-1-[1-(4-fluorophenyl)indazol-5-yl]-5-oxo-pyrrolidin-3-yl]cyclopropanecarboxamide 68 2,2-difluoro-N-[rac-(2R,3S)-2-(3-fluorophenyl)-1-[1-(4-fluorophenyl)indazol-5-yl]-5-oxo-pyrrolidin-3-yl]propanamide 69 2,2-difluoro-N-[(2R,3S)-2-(2-fluoro-5-methoxy-phenyl)-1-[1-(4-fluorophenyl)indazol-5-yl]-5-oxo-pyrrolidin-3-yl]propanamide 70 1-fluoro-N-[rac-(2R,3S)-2-(4-fluorophenyl)-1-[1-(4-fluorophenyl)indazol-5-yl]-5-oxo-pyrrolidin-3-yl]cyclopropanecarboxamide 71 N-[rac-(2R,3S)-2-(4-fluorophenyl)-1-[1-(4-fluorophenyl)indazol-5-yl]-5-oxo-pyrrolidin-3-yl]-1-(trifluoromethyl)cyclopropanecarboxamide 72 2,2-difluoro-N-[(2R,3S)-1-[1-(4-fluorophenyl)indazol-5-yl]-2-(o-tolyl)-5-oxo-pyrrolidin-3-yl]propanamide 73 1-fluoro-N-[(2R,3S)-1-[1-(4-fluorophenyl)indazol-5-yl]-5-oxo-2-phenyl-pyrrolidin-3-yl]cyclopropanecarboxamide 74 N-[(2R,3S)-1-[1-(4-fluorophenyl)indazol-5-yl]-5-oxo-2-phenyl-pyrrolidin-3-yl]-1-methyl-cyclopropanecarboxamide 75 2,2-difluoro-N-[rac-(2R,3S)-1-[1-(4,4-difluorocyclohexyl)indazol-5-yl]-5-oxo-2-phenyl-pyrrolidin-3-yl]propanamide 76 2,2-difluoro-N-[rac-(2R,3S)-1-(1-cyclohexylindazol-5-yl)-5-oxo-2-phenyl-pyrrolidin-3-yl]propanamide 77 2,2-difluoro-N-[rac-(2R,3S)-2-(2-fluoro-5-methoxyphenyl)-1-(1-methylindazol-5-yl)-5-oxo-pyrrolidin-3-yl]propanamide 78 2,2-difluoro-N-[rac-(2R,3S)-1-[1-(2,2-difluoroethyl)indazol-5-yl]-2-(2-fluoro-5-methoxy-phenyl)-5-oxo-pyrrolidin-3-yl]propanamide 79 2,2-difluoro-N-[rac-(2R,3S)-1-[1-[(2-fluorophenyl)methyl]indazol-5-yl]-5-oxo-2-phenyl-pyrrolidin-3-yl]propanamide 80 2,2-difluoro-N-[rac-(2R,3S)-1-[1-[(3-fluorophenyl)methyl]indazol-5-yl]-5-oxo-2-phenyl-pyrrolidin-3-yl]propanamide 81 2,2-difluoro-N-[rac-(2R,3S)-1-[i-[(4-fluorophenyl)methyl]indazol-5-yl]-5-oxo-2-phenyl-pyrrolidin-3-yl]propanamide 82 2,2-difluoro-N-[rac-(2R,3S)-1-[1-(cyclopropylmethyl)indazol-5-yl]-5-oxo-2-phenyl-pyrrolidin-3-yl]propanamide 84 2,2-difluoro-N-[rac-(2R,3S)-1-[1-[(4,4-difluorocyclohexyl)methyl]indazol-5-yl]-5-oxo-2-phenyl-pyrrolidin-3-yl]propanamide 85 2,2-difluoro-N-[rac-(2R,3S)-2-(4-fluorophenyl)-1-[1-[(2-fluorophenyl)methyl]indazol-5-yl]-5-oxo-pyrrolidin-3-yl]propanamide 86 2,2-difluoro-N-[rac-(2R,3S)-2-(4-fluorophenyl)-1-[1-[(4-fluorophenyl)methyl]indazol-5-yl]-5-oxo-pyrrolidin-3-yl]propanamide 87 2,2-difluoro-N-[rac-(2R,3S)-2-(4-fluorophenyl)-1-[1-[(3-fluorophenyl)methyl]indazol-5-yl]-5-oxo-pyrrolidin-3-yl]propanamide 88 N-[(2R,3S)-2-benzyl-1-(1-(4-fluorophenyl)-1H-indazol-5-yl)-5-oxopyrrolidin-3-yl]-2,2-difluoropropanamide 89 2,2-difluoro-N-[rac-(2R,3S)-2-ethyl-1-[1-(4-fluorophenyl)indazol-5-yl]-5-oxopyrrolidin-3-yl]propanamide 90 2,2-difluoro-N-[rac-(2R,3R)-2-(cyclopropylmethyl)-1-[1-(4-fluorophenyl)indazol-5-yl]-5-oxopyrrolidin-3-yl]propanamide 91 2-cyclopropyl-N-[(2S,3R)-1-(1-(4-fluorophenyl)-1H-indazol-5-yl)-5-oxo-2-phenylpyrrolidin-3-yl]acetamide 92 N-[(2R,3S)-1-(1-(4-fluorophenyl)-1H-indazol-5-yl)-5-oxo-2-phenylpyrrolidin-3-yl]-1-methyl-1H-pyrazole-3-carboxamide 93 N-[(2R,3S)-1-(1-(4-fluorophenyl)-1H-indazol-5-yl)-5-oxo-2-phenylpyrrolidin-3-yl]-1H-imidazole-2-carboxamide 94 N-[(2R,3S)-1-(1-(4-fluorophenyl)-1H-indazol-5-yl)-5-oxo-2-phenylpyrrolidin-3-yl]-2-methyloxazole-5-carboxamide 95 N-[(2R,3S)-1-(1-(4-fluorophenyl)-1H-indazol-5-yl)-5-oxo-2-phenylpyrrolidin-3-yl]-5-methylthiazole-4-carboxamide 96 N-[(2R,3S)-1-(1-(4-fluorophenyl)-1H-indazol-5-yl)-5-oxo-2-phenylpyrrolidin-3-yl]pyrimidine-2-carboxamide 97 N-[(2R,3S)-1-(1-(4-fluorophenyl)-1H-indazol-5-yl)-5-oxo-2-phenylpyrrolidin-3-yl]nicotinamide 98 N-[(2R,3S)-1-(1-(4-fluorophenyl)-1H-indazol-5-yl)-5-oxo-2-phenylpyrrolidin-3-yl]oxetane-3-carboxamide 99 N-[(2R,3S)-1-(1-(4-fluorophenyl)-1H-indazol-5-yl)-5-oxo-2-phenylpyrrolidin-3-yl]thiazole-5-sulfonamide 100 N-[rac-(2R,3R)-2-(5-chlorothiophen-2-yl)-1-[1-(4-fluorophenyl)indazol-5-yl]-5-oxopyrrolidin-3-yl]cyclopropanesulfonamide 101 2,2-difluoro-N-[rac-(2R,3S)-1-[1-(4-fluorophenyl)pyrazolo[3,4-b]pyridin-5-yl]-5-oxo-2-phenylpyrrolidin-3-yl]propanamide 102 2,2-difluoro-N-[rac-(2R,3S)-1-[1-(4-fluorophenyl)pyrazolo[3,4-c]pyridin-5-yl]-5-oxo-2-phenylpyrrolidin-3-yl]propanamide 103 2,2-difluoro-N-[rac-(2R,3S)-1-[1-(4-fluorophenyl)pyrazolo[4,3-b]pyridin-5-yl]-5-oxo-2-phenylpyrrolidin-3-yl]propanamide in each case in the form of the free compound or a physiologically acceptable salt thereof.

13. A pharmaceutical dosage form comprising a compound according to claim 1.

14. A method for treatment and/or prophylaxis of pain and/or inflammation in a subject, comprising a step of administering to the subject a compound according to claim 1.

15. The method according to claim 14 for the treatment and/or prophylaxis of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

16. A compound according to general formula (I),

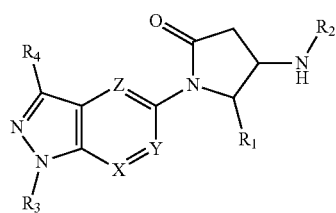

(I)

wherein
- $R_1$ represents —$C_{1-10}$-alkyl; —$C_{3-10}$-cycloalkyl; —$C_{1-6}$-alkylene-$C_{3-10}$-cycloalkyl; aryl; or —$C_{1-6}$-alkylene-aryl;
- $R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-aryl; —C(=O)—$C_{1-6}$-alkylene-aryl; —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-aryl; or —S(=O)$_{1-2}$—$C_{1-6}$-alkylene-aryl;
- $R_3$ represents —$C_{1-10}$-alkyl; —$C_{3-10}$-cycloalkyl; —$C_{1-6}$-alkylene-$C_{3-10}$-cycloalkyl; aryl; —$C_{1-6}$-alkylene-aryl; —C(=O)—$C_{1-10}$-alkyl; —C(=O)—$C_{3-10}$-cycloalkyl; —C(=O)—C1-6-alkylene-$C_{3-10}$-cycloalkyl; —C(=O)-aryl; —C(=O)—$C_{1-6}$-alkylene-aryl; —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-aryl; or —S(=O)$_{1-2}$—$C_{1-6}$-alkylene-aryl;
- $R_4$ represents —H; —F; —Cl; —Br; —I; —CN; —$CH_3$; —$CF_3$; —$CF_2H$; —$CFH_2$ or cyclopropyl;
- X represents $CR_5$; wherein $R_5$ represents —H; —F; —Cl; —Br; —I; —CN; —$C_{1-10}$-alkyl or —$C_{3-10}$-cycloalkyl;
- Y represents $CR_6$; wherein $R_6$ represents —H; —F; —Cl; —Br; —I; —CN; —$C_{1-10}$-alkyl or —$C_{3-10}$-cycloalkyl;
- Z represents $CR_7$; wherein $R_7$ represents —H; —F; —Cl; —Br; —I; —CN; —$C_{1-10}$-alkyl or —$C_{3-10}$-cycloalkyl;

wherein —$C_{1-10}$-alkyl, —$C_{1-4}$-alkyl and —$C_{1-6}$-alkylene- in each case independently from one another is linear or branched, saturated or unsaturated;

wherein —$C_{1-10}$-alkyl, —$C_{1-4}$-alkyl, —$C_{1-6}$-alkylene-, and —$C_{3-10}$-cycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; phenyl; —O—$C_{3-6}$-cycloalkyl; —O-phenyl; —C(=O)—$C_{3-6}$-cycloalkyl; —C(=O)-phenyl; —S(=O)$_2$—($C_{3-6}$-cycloalkyl); and —S(=O)$_2$-phenyl;

wherein aryl is unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)—O$C_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —$NH_2$; —NH($C_{1-6}$-alkyl); —N($C_{1-6}$-alkyl)$_2$; —NH—C(=O)—$C_{1-6}$-alkyl; —N($C_{1-6}$-alkyl)-C(=O)—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$—$C_{1-6}$-alkyl; —$SCF_3$; —S(=O)—$C_{1-6}$-alkyl; —S(=O)$_2$—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; —$C_{1-4}$-alkylene-$C_{3-6}$-cycloalkyl; and phenyl;

in the form of the free compound or a physiologically acceptable salt thereof.

17. A pharmaceutical dosage form comprising a compound according to claim 16.

18. A method for treatment and/or prophylaxis of pain and/or inflammation in a subject, comprising a step of administering to the subject a compound according to claim 16.

19. The method according to claim 18 for the treatment and/or prophylaxis of asthma, rheumatoid arthritis, inflammatory bowel disease, chronic obstructive pulmonary disease, acute respiratory distress syndrome, cystic fibrosis, osteoarthritis, polymyalgia rheumatica, giant cell arteritis, Sjögren syndrome, Duchenne muscular dystrophy, vasculitis, Behçet's disease, ulcerative colitis and/or Crohn's disease.

* * * * *